(12) United States Patent
Kerns et al.

(10) Patent No.: US 7,858,796 B2
(45) Date of Patent: *Dec. 28, 2010

(54) CHEMICAL COMPOUNDS

(75) Inventors: Jeffrey K. Kerns, King of Prussia, PA (US); Michael Lindenmuth, King of Prussia, PA (US); Xichen Lin, King of Prussia, PA (US); Hong Nie, King of Prussia, PA (US); Sonia M. Thomas, King of Prussia, PA (US)

(73) Assignee: Glaxo Group Limited, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/575,416

(22) PCT Filed: Sep. 21, 2005

(86) PCT No.: PCT/US2005/033752

§ 371 (c)(1),
(2), (4) Date: Mar. 16, 2007

(87) PCT Pub. No.: WO2006/034317

PCT Pub. Date: Mar. 30, 2006

(65) Prior Publication Data

US 2007/0254873 A1  Nov. 1, 2007

Related U.S. Application Data

(60) Provisional application No. 60/611,761, filed on Sep. 21, 2004, provisional application No. 60/695,454, filed on Jun. 30, 2005.

(51) Int. Cl.
*C07D 401/00* (2006.01)
(52) U.S. Cl. ...................................... 546/201
(58) Field of Classification Search .................. 546/201
See application file for complete search history.

(56) References Cited

U.S. PATENT DOCUMENTS

| | | | |
|---|---|---|---|
| 4,775,761 A | 10/1988 | Strupczewski | |
| 5,256,673 A | 10/1993 | Böttcher et al. | |
| 5,330,986 A * | 7/1994 | Shutske | 514/252.19 |
| 6,245,799 B1 | 6/2001 | Asselin et al. | |
| 2002/0147189 A1 | 10/2002 | Cai et al. | |
| 2002/0161004 A1 | 10/2002 | Browner et al. | |
| 2003/0022898 A1 | 1/2003 | Burke et al. | |

FOREIGN PATENT DOCUMENTS

| | | |
|---|---|---|
| DE | 3342632 | 6/1985 |
| DE | 19500689 | 7/1996 |
| DE | 19807993 | 9/1999 |
| DE | 19928424 | 12/2000 |
| DE | 10112151 | 9/2002 |
| DE | 10259244 | 7/2004 |
| EP | 279263 | 8/1993 |
| EP | 610134 | 8/1994 |
| EP | 416609 | 1/1997 |
| EP | 0812826 | 12/1997 |
| EP | 1077213 | 2/2001 |
| EP | 1134221 | 9/2001 |
| EP | 1209158 | 5/2002 |
| WO | WO9917773 | 4/1999 |
| WO | WO0130774 | 5/2001 |
| WO | WO0134598 | 5/2001 |
| WO | WO0158890 | 8/2001 |
| WO | WO0168648 | 9/2001 |
| WO | WO0183472 | 11/2001 |
| WO | WO0187298 | 11/2001 |
| WO | WO0198290 | 12/2001 |
| WO | WO0214317 | 2/2002 |
| WO | WO0216353 | 2/2002 |
| WO | WO0224679 | 3/2002 |
| WO | WO0228860 | 3/2002 |
| WO | WO0230353 | 4/2002 |
| WO | WO0230423 | 4/2002 |

(Continued)

OTHER PUBLICATIONS

C. G. Wermuth. *The Practice of Medicinal Chemistry*, Academic Press, pp. 203-214 (1996).

(Continued)

*Primary Examiner*—Nizal S Chandrakumar
(74) *Attorney, Agent, or Firm*—Nora Stein-Fernandez; Theodore R. Furman

(57) ABSTRACT

The invention is directed to novel indole carboxamide derivatives. Specifically, the invention is directed to compounds according to formula I:

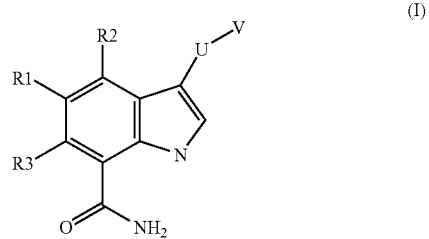

where R1, R2, R3, U and V are defined below and to pharmaceutically acceptable salts thereof.

The compounds of the invention are inhibitors of IKK2 and can be useful in the treatment of disorders associated with inappropriate IKK2 (also known as IKKβ) activity, such as rheumatoid arthritis, asthma, and COPD (chronic obstructive pulmonary disease). Accordingly, the invention is further directed to pharmaceutical compositions comprising a compound of the invention. The invention is still further directed to methods of inhibiting IKK2 activity and treatment of disorders associated therewith using a compound of the invention or a pharmaceutical composition comprising a compound of the invention.

32 Claims, No Drawings

FOREIGN PATENT DOCUMENTS

| | | |
|---|---|---|
| WO | WO0241843 | 5/2002 |
| WO | WO0244153 | 6/2002 |
| WO | WO0246171 | 6/2002 |
| WO | WO02051837 | 7/2002 |
| WO | WO02060386 | 8/2002 |
| WO | WO02094265 | 11/2002 |
| WO | WO02094322 | 11/2002 |
| WO | WO02094813 | 11/2002 |
| WO | WO03070706 | 1/2003 |
| WO | WO03010158 | 2/2003 |
| WO | WO03010163 | 2/2003 |
| WO | WO03022898 | 3/2003 |
| WO | WO03024935 | 3/2003 |
| WO | WO03024936 | 3/2003 |
| WO | WO03027075 | 4/2003 |
| WO | WO03035625 | 5/2003 |
| WO | WO03037886 | 5/2003 |
| WO | WO03084959 | 10/2003 |
| WO | WO03095430 | 11/2003 |
| WO | WO03103661 | 12/2003 |
| WO | WO2004019935 | 3/2004 |
| WO | WO2004022553 | 3/2004 |
| WO | WO2004024730 | 3/2004 |
| WO | WO2004024732 | 3/2004 |
| WO | WO2004024736 | 3/2004 |
| WO | WO2004075846 | 9/2004 |
| WO | WO2004089913 | 10/2004 |
| WO | WO2004106293 | 12/2004 |
| WO | WO2005012283 | 2/2005 |
| WO | WO2005035537 | 4/2005 |
| WO | WO 2005/067923 A1 | 7/2005 |
| WO | WO2005067923 | 7/2005 |
| WO | WO2007/005534 | 1/2007 |

OTHER PUBLICATIONS

Abstract No. 98323-88-7 (Sep. 29, 1985).

Abstract No. 98323-88-7 (Sep. 29, 1985).

Aupperle et al., "NF-κB Regulation by IκB Kinase in Primary Fibroblast-Like Synoviocytes" *J. Immunology* (1999) 163:427-433.

Aupperle et al., "NF-κB Regulation by IκB Kinase-2 in Rheumatoid Arthritis Synoviocytes" *J. Immunology* (2001) 166:31496-31501.

Breton et al., "The Natural Product Hymenialdisine Inhibits Interleukin-8 Production in U937 Cells by Inhibition of Nuclear Factor-κB" *JPET* (1997) 282(1):459-466.

Burke et al., "BMS-345541 Is a Highly Selective Inhibitor of IκB Kinase That Binds at an Allosteric Site of the Enzyme and Blocks NF-κB-dependent Transcription in Mice" *J. Biol Chem.* (2003) 278:1450-1456.

Guttridge et al., "NF-κB-Induced Loss of *MyoD* Messenger RNA: Possible Role in Muscle Decay and Cachexia" *Science* (2000) 289:2363-2365.

Murata et al., "Discovery of novel and selective IKK-β serine-threonine protein kinase inhibitors. Part 1." *Bioorg. Med. Chem. Letter* (2003) 13:913-198.

Murata et al., "Synthesis and structure—activity relationships of novel IKK-β inhibitors. Part 2: Improvement of in vitro activity" *Bioorg. Med. Chem. Letter* (2004) 14(15):4013-4017 and "Synthesis and structure—activity relationships of novel IKK-β inhibitors. Part 3: Orally active anti-inflammatory agents," *Bioorg. Med. Chem. Letter* (2004) 14(15):4019-4022.

Peet et al., "IκB Kinases α and β Show a Random Sequential Kinetic Mechanism and Are Inhibited by Staurosporine and Quercetin" *J. Biol. Chem.* (1999) 274:32655-32661.

Pierce, et al., "Novel Inhibitors of Cytokine-induced IκBα Phosphorylation and Endothelial Cell Adhesion Molecule Expression Show Anti-inflammatory Effects in Vivo" *J. Biol. Chem.* (1997) 272:21096-21103.

Roshak, et al., "Inhibition of NFκB-Mediated Interleukin-1β Stimulated Prostaglandin $E_2$ Formation by the Marine Natural Product Hymenialdisine" *JPET* (1997) 283(2):955-961.

Roshak, et al., "Manipulation of Distinct NFκB Proteins Alters Interleukin-1β-induced Human Rheumatoid Synovial Fibroblast Prostaglandin $E_2$ Formation" *J. Biol. Chem.* (1996) 271:31496-31501.

Sullivan et al., "2-Chloro-4-(trifluoromethyl)pyrimidine-5-N-(3', 5'-bis(trifluoromethyl)phenyl)-carboxamide: A Potent Inhibitor of NF-κB- and AP-1-Mediated Gene Expression Identified Using Solution-Phase Combinatorial Chemistry" *J. Med. Chem.* (1998) 41:413-419.

Tak et al., "Inhibitor of nuclear factor κB kinase β is a key regulator of synovial inflammation" *Arthritis and Rheumatism* (2001) 44(8):1897-1907.

Wahl et al., "Sulfasalazine: a potent and specific inhibitor of nuclear factor kappa B" *J. Clin. Invest.*(1998) 101(5):1163-1174.

Wisniewski et al., "Assay for IκB Kinases Using an in Vivo Biotinylated IκB Protein Substrate" *Analytical Biochem.* (1999) 274:220-228.

\* cited by examiner

CHEMICAL COMPOUNDS

This application is a 371 of International Application No. PCT/US2005/033752, filed 21 Sep. 2005, which claims priority of U.S. Provisional Application Nos. 60/695,454, filed 30 Jun. 2005, and 60/611,761, filed 21 Sep. 2004.

FIELD OF THE INVENTION

The invention is directed to certain indole carboxamide compounds, which are inhibitors of kinase activity. More specifically, the compounds are IKK2 inhibitors. These compounds are useful in the treatment of disorders associated with inappropriate IKK2 (also known as IKKβ) activity, in particular in the treatment and prevention of disorders mediated by IKK2 mechanisms including inflammatory and tissue repair disorders. Such disorders include rheumatoid arthritis, asthma, and GOPD (chronic obstructive pulmonary disease).

BACKGROUND OF THE INVENTION

An important large family of enzymes is the protein kinase enzyme family. Currently, there are about 500 different known protein kinases. However, because three to four percent of the human genome is a code for the formation of protein kinases, there may be many thousands of distinct and separate kinases in the human body. Protein kinases serve to catalyze the phosphorylation of an amino acid side chain in various proteins by the transfer of the γ-phosphate of the ATP-$Mg^{2+}$ complex to said amino acid side chain. These enzymes control the majority of the signaling processes inside cells, thereby governing cell function, growth, differentiation and destruction (apoptosis) through reversible phosphorylation of the *hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied family of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The serine/threonine kinases (PSTK), includes cyclic AMP- and cyclic GMP-dependent protein kinases, calcium and phospholipid dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. Much work is also under progress to identify modulators of tyrosine kinases as well.

Nuclear factor κB (NF-κB) belongs to a family of closely related dimeric transcription factor complexes composed of various combinations of the Rel/NF-κB family of polypeptides. The family consists of five individual gene products in mammals, RelA (p65), NF-κB1 (p50/p105), NF-κB2 (p49/p100), c-Rel, and RelB, all of which can form hetero- or homodimers. These proteins share a highly homologous 300 amino acid "Rel homology domain" which contains the DNA binding and dimerization domains. At the extreme C-terminus of the Rel homology domain is a nuclear translocation sequence important in the transport of NF-κB from the cytoplasm to the nucleus. In addition, p65 and cRel possess potent transactivation domains at their C-terminal ends.

The activity of NF-κB is regulated by its interaction with a member of the inhibitor IκB family of proteins. This interaction effectively blocks the nuclear localization sequence on the NF-κB proteins, thus preventing migration of the dimer to the nucleus. A wide variety of stimuli activate NF-κB through what are likely to be multiple signal transduction pathways. Included are bacterial products (LPS), some viruses (HIV-1, HTLV-1), inflammatory cytokines (TNFα, IL-1), environmental and oxidative stress and DNA damaging agents. Apparently common to all stimuli however, is the phosphorylation and subsequent degradation of IκB. IκB is phosphorylated on two N-terminal serines by the recently identified IκB kinases (IKK-α and IKK-β). IKK-β is also known as IKK2. Site-directed mutagenesis studies indicate that these phosphorylations are critical for the subsequent activation of NF-κB in that once phosphorylated the protein is flagged for degradation via the ubiquitin-proteasome pathway. Free from IκB, the active NF-κB complexes are able to translocate to the nucleus where they bind in a selective manner to preferred gene-specific enhancer sequences. Included in the genes regulated by NF-κB are a number of cytokines and chemokines, cell adhesion molecules, acute phase proteins, immunoreguatlory proteins, eicosanoid metabolizing enzymes and anti-apoptotic genes.

It is well-known that NF-κB plays a key role in the regulated expression of a large number of pro-inflammatory mediators including cytokines such as TNF, IL-1β, IL-6 and IL-8, cell adhesion molecules, such as ICAM and VCAM, and inducible nitric oxide synthase (iNOS). Such mediators are known to play a role in the recruitment of leukocytes at sites of inflammation and in the case of iNOS, may lead to organ destruction in some inflammatory and autoimmune diseases.

The importance of NF-κB in inflammatory disorders is further strengthened by studies of airway inflammation including asthma, in which NF-κB has been shown to be activated. This activation may underlie the increased cytokine production and leukocyte infiltration characteristic of these disorders. In addition, inhaled steroids are known to reduce airway hyperresponsiveness and suppress the inflammatory response in asthmatic airways. In light of the recent findings with regard to glucocorticoid inhibition of NF-κB, one may speculate that these effects are mediated through an inhibition of NF-κB.

Further evidence for a role of NF-κB in inflammatory disorders comes from studies of rheumatoid synovium. Although NF-κB is normally present as an inactive cytoplasmic complex, recent immunohistochemical studies have indicated that NF-κB is present in the nuclei, and hence active, in the cells comprising rheumatoid synovium. Furthermore, NF-κB has been shown to be activated in human synovial cells in response to stimulation with TNF-α or IL-1β. Such a distribution may be the underlying mechanism for the increased cytokine and eicosanoid production characteristic of this tissue. See Roshak, A. K., et al., *J. Biol. Chem.*, 271, 31496-31501 (1996). Expression of IKK-β has been shown in synoviocytes of rheumatoid arthritis patients and gene transfer studies have demonstrated the central role of IKK-β in stimulated inflammatory mediator production in these cells. See Aupperele et al. *J. Immunology* 1999. 163:427-433 and Aupperle et al. *J. Immunology* 2001; 166:2705-11. More recently, the intra-articular administration of a wild type IKK-β adenoviral construct was shown to cause paw swelling while intra-articular administration of dominant-negative IKKβ inhibited adjuvant-induced arthritis in rat. See Tak et al. *Arthritis and Rheumatism* 2001, 44:1897-1907.

The NF-κB/Rel and IκB proteins are also likely to play a key role in neoplastic transformation and metastasis. Family members are associated with cell transformation in vitro and in vivo as a result of overexpression, gene amplification, gene rearrangements or translocations. In addition, rearrangement and/or amplification of the genes encoding these proteins are seen in 20-25% of certain human lymphoid tumors. Further, NF-κB is activated by oncogenic ras, the most common defect in human tumors and blockade of NF-κB activation inhibits ras mediated cell transformation. In addition, a role for NF-κB in the regulation of apoptosis has been reported strengthening the role of this transcription factor in the regulation of tumor cell proliferation. TNF, ionizing radiation and DNA damaging agents have all been shown to activate NF-κB which in turn leads to the upregulated expression of several anti-apoptotic proteins. Conversely, inhibition of NF-κB has been shown to enhance apoptotic-killing by these agents in several tumor cell types. As this likely represents a major mechanism of tumor cell resistance to chemotherapy, inhibitors of NF-□B activation may be useful chemotherapeutic agents as either single agents or adjunct therapy. Recent reports have implicated NF-κB as an inhibitor of skeletal cell differentiation as well as a regulator of cytokine-induced muscle wasting (Guttridge et al. *Science;* 2000; 289: 2363-2365.) further supporting the potential of NFκB inhibitors as novel cancer therapies.

Several NF-κB inhibitors are described in C. Vahl, et al. *J. Clin. Invest.* 101 (5), 1163-1174 (1998), R. W. Sullivan, et al. *J. Med. Chem.* 41, 413-419 (1998), J. W. Pierce, et al. *J. Biol. Chem.* 272, 21096-21103 (1997).

The marine natural product hymenialdisine is known to inhibit NF-κB. Roshak, A., et al., *JPET,* 283, 955-961 (1997). Breton, J. J and Chabot-Fletcher, M. C., *JPET,* 282, 459-466 (1997).

Additionally, patent applications have been filed on aminothiophene inhibitors of the IKK2, see Callahan, et al., WO 2002030353; Baxter, et al., WO 2001058890, Faull, et al., WO 2003010158; Griffiths, et al., WO2003010163; Fancelli, et al., WO 200198290; imidazole inhibitors of IKK2, see Callahan, et al., WO 200230423; anilinophenylpyrimidine inhibitors of IKK2, see Kois, et al., WO 2002046171; β-carboline inhibitors of IKK2, see Ritzeler, et al, WO 2001068648, Ritzeler, et al, EP 1134221; Nielsch, et al. DE 19807993; Ritzeler, et al., EP 1209158; indole inhibitors of IKK2, see Ritzeler, et al., WO 2001030774; benzimidazole inhibitors of the IKK2, see Ritzeler, et al., DE 19928424; Ritzeler et al, WO 2001000610; aminopyridine inhibitors of IKK2, see Lowinger, et al, WO 2002024679; Murata, et al, WO 2002024693; Murata, et al., WO 2002044153; pyrazolaquinazoline inhibitors of IKK2, see Beaulieu, et al., WO 2002028860; Burke et al, WO 2002060386, Burke, et al. US 20030022898; quinoline inhibitors of IKK2, Browner, et al., WO2002041843, Browner, et al., US 20020161004 and pyridylcyanoguanidine inhibitors of IKK2, see Bjorkling, et al., WO 2002094813, Binderup et al, WO 2002094322 and Madsen, et al., WO 200294265. The natural products staurosporine, quercetin, K252a and K252b have been shown to be IKK2 inhibitors, see Peet, G. W. and Li, J. J. *Biol. Chem.*, 274, 32655-32661 (1999) and Wisniewski, D., et al., *Analytical Biochem.* 274, 220-228 (1999). Synthetic inhibitors of IKK2 have also been described, see Burke, et al. *J. Biol. Chem.*, 278, 1450-1456 (2003) and Murata, et al., *Bioorg. Med. Chem. Lett.*, 13, 913-198 (2003) have described IKK2 inhibitors.

Thus, attempts have been made to prepare compounds that inhibit IKK2 activity and a number of such compounds have been disclosed in the art. However, in view of the number of pathological responses that are mediated by IKK2, there remains a continuing need for inhibitors of IKK2 which can be used in the treatment of a variety of conditions.

The present inventors have discovered novel indole carboxamide compounds, which are inhibitors of kinase activity, in particular inappropriate IKK2 activity. Such indole carboxamide derivatives are therefore useful in the treatment of disorders associated with inappropriate kinase, in particular inappropriate IKK2 activity in particular in the treatment and prevention of disease states mediated by IKK2 mechanisms including inflammatory and tissue repair disorders, particularly rheumatoid arthritis, inflammatory bowel disease, asthma and COPD (chronic obstructive pulmonary disease); osteoarthritis, osteoporosis and fibrotic diseases; dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restonosis, diabetes, glomerulonephritis, cancer, including Hodgkins disease, cachexia, inflammation associated with infection and certain viral infections, including acquired immune deficiency syndrome (AIDS), adult respiratory distress syndrome, and Ataxia Telangiestasia.

SUMMARY OF THE INVENTION

The invention is directed to novel indole carboxamide derivatives. Specifically, the invention is directed to compounds according to formula (I):

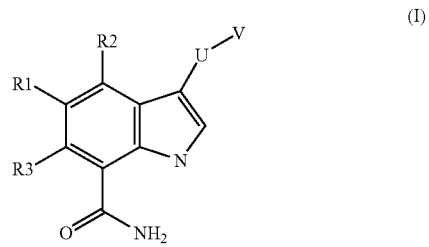

where R1, R2, R3, U and V are defined below and to pharmaceutically acceptable salts thereof.

The compounds of the invention are inhibitors of IKK2 and can be useful in the treatment of disorders associated with inappropriate IKK2 (also known as IKKβ) activity, such as rheumatoid arthritis, asthma, and COPD (chronic obstructive pulmonary disease). Accordingly, the invention is further directed to pharmaceutical compositions comprising a compound of the invention. The invention is still further directed to methods of inhibiting IKK2 activity and treatment of disorders associated therewith using a compound of the invention or a pharmaceutical composition comprising a compound of the invention.

DETAILED DESCRIPTION OF THE INVENTION

The invention is directed to compounds according to formula (I):

where:

R1 is H, halogen, or a group —YZ;

R2 is H, fluoro, or chloro;

R3 is H, fluoro, or chloro;

Y is a bond, $C_1$-$C_6$ alkylene, $C_2$-$C_6$ alkenylene, or $C_2$-$C_6$ alkynylene;

Z is optionally substituted aryl or optionally substituted heteroaryl, where said aryl and heteroaryl are optionally substituted with one to three substituents independently selected from the group consisting of: halo, —CN, —N(Rb)SO$_2$Re, —N(Rb)C(O)Ra, —C(O)NRaRb, —C(O)NRfRg, —C(O)H, —SO$_2$Ri, —N RaRb, —SO$_2$NRaRb, —SO$_2$NRfRg, —ORc, —N(Rb)C(O)NRaRb, —N(Rb)C(O)NRfRg, —N(Rb)C(O)ORd, $C_1$-$C_6$ alkyl, $C_1$-$C_6$ alkyl substituted with one to three substituents independently selected from the group consisting of: —NRaRb, $C_3$-$C_6$ cycloalkyl, phenyl, —ORc, heterocycloalkyl, and heterocycloalkyl substituted with OH, —C(O)NH$_2$, or one or two $C_1$-$C_6$ alkyl groups; $C_1$-$C_6$ haloalkyl, $C_1$-$C_6$ haloalkyl substituted with one to three substituents independently selected from the group consisting of —NRaRb, $C_3$-$C_6$ cycloalkyl, phenyl, heterocycloalkyl, and heterocycloalkyl substituted with one or two $C_1$-$C_6$ alkyl groups; heterocycloalkyl and heterocycloalkyl substituted with one or two $C_1$-$C_6$ alkyl groups;

U is a bond, $C_1$-$C_6$ alkylene or $C_2$-$C_6$ alkenylene;

V is phenyl, 5 or 6 membered heteroaryl, 5-7 membered heterocycloalkyl, $C_5$-$C_7$cycloalkyl, or $C_5$-$C_7$cycloalkenyl, each of which is substituted by —N(Rb)S(O)$_m$R4, —S(O)$_m$N(Rb)R4, or —S(O)$_m$R4;

m is 1 or 2;

R4 is the group —X—R5;

X is a bond, $C_1$-$C_6$ alkylene, $C_2$-$C_6$ alkenylene, $C_2$-$C_6$ alkynylene, aryl, $C_1$-$C_6$ alkylene-aryl, heteroaryl, $C_1$-$C_6$ alkylene-heteroaryl, heterocycloalkyl, $C_1$-$C_6$ alkylene-heterocycloalkyl, $C_4$-$C_7$cycloalkyl, $C_1$-$C_6$ alkylene-$C_4$-$C_7$cycloalkyl, $C_5$-$C_7$cycloalkenyl, or $C_1$-$C_6$ alkylene-$C_5$-$C_7$cycloalkenyl;

R5 is —NRaRb, —ORj, optionally substituted heterocycloalkyl, or optionally substituted heteroaryl, where said optionally substituted heterocycloalkyl and optionally substituted heteroaryl are optionally substituted with one to three substituents independently selected from the group consisting of: halo, heteroaryl, oxo, —CN, —C(O)Ra, —N(Rb)SO$_2$Re, —N(Rb)C(O)Ra, —NRaRb, —C(O)NRaRb, —C(O)NRfRg, —SO$_2$NRaRb, —SO$_2$NRfRg, —ORc, —C(O)ORc, —N(Rb)C(O)NRaRb, —N(Rb)C(O)NRfRg, —N(Rb)C(O)ORd, $C_1$-$C_6$ alkyl, $C_1$-$C_6$ alkyl substituted with one to three substituents independently selected from the group consisting of: —NRaRb, —ORc, —C(O)NRaRb, —C(O)Rc, $C_3$-$C_6$ cycloalkyl, heterocycloalkyl, and phenyl; $C_1$-$C_6$ haloalkyl, $C_1$-$C_6$ haloalkyl substituted with one to three substituents independently selected from the group consisting of: —NRaRb, —ORc, —C(O)NRaRb, $C_3$-$C_6$ cycloalkyl, heterocycloalkyl, and phenyl; heterocycloalkyl, heterocycloalkyl substituted with one to three substituents independently selected from the group consisting of: $C_1$-$C_6$ alkyl, halo, —ORc, haloalkyl, CN, and —SO$_2$Ri; phenyl, and phenyl substituted with one to three substituents independently selected from the group consisting of: halo, —ORc, haloalkyl, —CN, and —SO$_2$Ri;

each Ra is independently selected from the group consisting of: H, —ORh, $C_2$-$C_6$ alkenyl, $C_2$-$C_6$ alkynyl, $C_1$-$C_6$ alkyl, $C_1$-$C_6$ alkyl substituted with one to three substituents independently selected from the group consisting of: halo, —CN, —C(O)NH$_2$, —NRkRk, —SO$_2$Ri, —N(Rb)SO$_2$Re, —C(O)ORb, —N(Rb)C(O)Rb, —ORc, —SRc, $C_3$-$C_7$ cycloalkyl, $C_1$-$C_6$ haloalkyl, heterocycloalkyl, phenyl, phenolyl, and heteroaryl; phenyl, phenyl substituted with one to three substituents independently selected from the group consisting of: halo, oxo, $C_1$-$C_6$ alkyl, $C_1$-$C_6$ haloalkyl, NH$_2$, heteroaryl, —ORc, and —NRfRg; heteroaryl, heteroaryl substituted with one to three substituents independently selected from the group consisting of: halo, oxo, $C_1$-$C_6$ alkyl, $C_1$-$C_6$ haloalkyl, NH$_2$, heteroaryl, —ORc, and —NRfRg; $C_3$-$C_7$ cycloalkyl, $C_3$-$C_7$ cycloalkyl substituted with one to three substituents independently selected from the group consisting of: halo, oxo, $C_1$-$C_6$ alkyl, $C_1$-$C_6$ haloalkyl, NH$_2$, heteroaryl, —ORc, and —NRfRg; heterocycloalkyl, and heterocycloalkyl substituted with one to three substituents independently selected from the group consisting of: halo, oxo, $C_1$-$C_6$ alkyl, —CH$_2$C(O)Rb, $C_1$-$C_6$ haloalkyl, —C(O)ORb, NH$_2$, heteroaryl, —ORc, and NRfRg;

each Rb is independently selected from the group consisting of: H, $C_1$-$C_6$ alkyl, $C_1$-$C_6$ alkyl substituted with one —ORc, and $C_3$-$C_7$ cycloalkyl;

each Rc is independently selected from the group consisting of: H, $C_1$-$C_6$ alkyl, $C_1$-$C_6$ alkyl substituted with one to three substituents independently selected from the group consisting of: OH, $C_3$-$C_6$ cycloalkyl, phenyl, heterocycloalkyl, and heteroaryl; $C_1$-$C_6$ haloalkyl, $C_1$-$C_6$ haloalkyl substituted with one to three substituents independently selected from the group consisting of: OH, $C_3$-$C_6$ cycloalkyl, phenyl, heterocycloalkyl, and heteroaryl; $C_3$-$C_7$ cycloalkyl, $C_3$-$C_7$ cycloalkyl substituted with one to three $C_1$-$C_3$ alkyl groups; heterocycloalkyl, heterocycloalkyl substituted with one to three $C_1$-$C_3$ alkyl groups; aryl, aryl substituted with one to three substituents independently selected from the group consisting of: halo, $C_1$-$C_3$ alkyl, $C_1$-$C_3$ haloalkyl, and OH; heteroaryl, and heteroaryl substituted with one to three substituents independently selected from the group consisting of: halo, $C_1$-$C_3$ alkyl, $C_1$-$C_3$ haloalkyl, and OH;

each Rd is independently an optionally substituted $C_1$-$C_3$ alkyl, where said $C_1$-$C_3$ alkyl is optionally substituted with one to three substituents selected from the group consisting of: $C_3$-$C_6$ cycloalkyl, heterocycloalkyl, optionally substituted phenyl, and optionally substituted heteroaryl; where said phenyl and heteroaryl are optionally substituted with one to three substituents selected from the group consisting of: halo, $C_1$-$C_6$ alkyl and $C_3$-$C_6$ cycloalkyl;

each Re is independently selected from the group consisting of: $C_1$-$C_6$ alkyl, $C_1$-$C_6$ alkyl substituted with one substituent selected from the group consisting of: phenyl, heteroaryl, heterocycloalkyl, and NRaRb; phenyl, phenyl substituted with one to three substituents selected from the group consisting of: halo, CN, $C_1$-$C_6$ alkyl, $C_1$-$C_6$ haloalkyl, and ORh; heteroaryl, heteroaryl substituted with one to three substituents selected from the group consisting of: halo, CN, $C_1$-$C_6$ alkyl, $C_1$-$C_6$ haloalkyl, and —ORh; $C_5$-$C_7$ cycloalkyl, $C_5$-$C_7$ cycloalkyl substituted with one to three substituents selected from the group consisting of: halo, $C_1$-$C_6$ alkyl, and $C_3$-$C_6$ cycloalkyl; heterocycloalkyl, and heterocycloalkyl substituted with one to three substituents selected from the group consisting of: halo, $C_1$-$C_6$ alkyl, and $C_3$-$C_6$ cycloalkyl;

Rf and Rg taken together with the nitrogen atom to which they are attached form a ring having from 5 to 7 member atoms wherein said ring optionally contains one additional heteroatom as a member atom, said ring is saturated or unsaturated but not aromatic, and said ring is optionally substituted with one or two $C_1$-$C_3$ alkyl substituents;

each Rh is independently selected from the group consisting of: H, $C_1$-$C_6$ alkyl, and $C_1$-$C_6$ haloalkyl;

each Ri is independently selected from the group consisting of: $C_1$-$C_3$ alkyl and phenyl;

Rj is selected from the group consisting of H, optionally substituted $C_1$-$C_6$ alkyl, $C_1$-$C_6$ haloalkyl, heteroaryl, and optionally substituted phenyl, where said optionally substituted $C_1$-$C_6$ alkyl is optionally substituted by one or two substituents each independently selected from the following: hydroxy, $C_1$-$C_6$ alkoxy, —OCH$_2$CH$_2$N(CH$_3$)$_2$, methylthio, $C_3$-$C_6$ cycloalkyl, $C_3$-$C_6$ cycloalkyl substituted by one $C_1$-$C_3$ alkyl group; heterocycloalkyl, heterocycloalkyl substituted by one $C_1$-$C_3$ alkyl, one oxo group, or one 4-fluorobenzyl group; —NRkRk, heteroaryl, —NHC(O)CH$_3$, and —S(O)$_2$Ri;

where said phenyl is optionally substituted by one to three substituents each independently selected from the following: $C_1$-$C_3$ alkoxy, —NHC(O)CH$_3$, —C(O)NH$_2$, halo, CF$_3$, —S(O)$_2$Ri, —S(O)$_2$NHRi, hydroxy, —$C_1$-$C_3$-alkyl-NRkRk, —NRkRk, $C_1$-$C_3$ alkyl, heterocycloalkyl, and heterocycloalkyl substituted with one —C(O)CH$_3$ group; and each Rk is independently selected from H, $C_1$-$C_6$ alkyl, $C_1$-$C_6$ alkyl substituted by one or two hydroxyl groups; phenyl, and phenyl substituted with one $C_1$-$C_3$ alkyl group;

or a pharmaceutically-acceptable salt, solvate, or polymorph thereof.

In one embodiment of the present invention:

Z is optionally substituted aryl or optionally substituted heteroaryl, where said aryl and heteroaryl are optionally substituted with one to three substituents independently selected from the group consisting of: halo, —CN, —N(Rb)SO$_2$Re, —N(Rb)C(O)Ra, —C(O)NRaRb, —C(O)NRfRg, —C(O)H, —SO$_2$Ri, —NRaRb, —SO$_2$NRaRb, —SO$_2$NRfRg, —ORc, —N(Rb)C(O)NRaRb, —N(Rb)C(O)NRfRg, —N(Rb)C(O) ORd, $C_1$-$C_6$ alkyl, $C_1$-$C_6$ alkyl substituted with one to three substituents independently selected from the group consisting of: —NRaRb, $C_3$-$C_6$ cycloalkyl, phenyl, —ORc, heterocycloalkyl, and heterocycloalkyl substituted with one or one or two $C_1$-$C_6$ alkyl groups; $C_1$-$C_6$ haloalkyl, $C_1$-$C_6$ haloalkyl substituted with one to three substituents independently selected from the group consisting of —NRaRb, $C_3$-$C_6$ cycloalkyl, phenyl, heterocycloalkyl, and heterocycloalkyl substituted with one or two $C_1$-$C_6$ alkyl groups; heterocycloalkyl and heterocycloalkyl substituted with one or two $C_1$-$C_6$ alkyl groups;

each Ra is independently selected from the group consisting of: H, $C_2$-$C_6$ alkenyl, $C_2$-$C_6$ alkynyl, $C_1$-$C_6$ alkyl, $C_1$-$C_6$ alkyl substituted with one to three substituents independently selected from the group consisting of: halo, —CN, —C(O)NH$_2$, —NRkRk, —SO$_2$Ri, —N(Rb)SO$_2$Re, —C(O)ORb, —N(Rb)C(O)Rb, —ORc, —SRc, $C_3$-$C_7$ cycloalkyl, $C_1$-$C_6$ haloalkyl, heterocycloalkyl, phenyl, phenolyl, and heteroaryl; phenyl, phenyl substituted with one to three substituents independently selected from the group consisting of: halo, oxo, $C_1$-$C_6$ alkyl, $C_1$-$C_6$ haloalkyl, NH$_2$, heteroaryl, —ORc, and —NRfRg; heteroaryl, heteroaryl substituted with one to three substituents independently selected from the group consisting of: halo, oxo, $C_1$-$C_6$ alkyl, $C_1$-$C_6$ haloalkyl, NH$_2$, heteroaryl, —ORc, and —NRfRg; $C_3$-$C_7$ cycloalkyl, $C_3$-$C_7$ cycloalkyl substituted with one to three substituents independently selected from the group consisting of: halo, oxo, $C_1$-$C_6$ alkyl, $C_1$-$C_6$ haloalkyl, NH$_2$, heteroaryl, —ORc, and —NRfRg; heterocycloalkyl, and heterocycloalkyl substituted with one to three substituents independently selected from the group consisting of: halo, oxo, $C_1$-$C_6$ alkyl, —CH$_2$C(O)Rb, $C_1$-$C_6$ haloalkyl, —C(O)ORb, NH$_2$, heteroaryl, —ORc and NRfRg; and Rj is selected from the group consisting of H, optionally substituted $C_1$-$C_6$ alkyl, $C_1$-$C_6$ haloalkyl, heteroaryl, and optionally substituted phenyl, where said optionally substituted $C_1$-$C_6$ alkyl is optionally substituted by one or two substituents each independently selected from the following: hydroxy, methylthio, $C_3$-$C_6$ cycloalkyl, $C_3$-$C_6$ cycloalkyl substituted by one $C_1$-$C_3$ alkyl group; heterocycloalkyl, heterocycloalkyl substituted by one $C_1$-$C_3$ alkyl, one oxo group, or one 4-fluorobenzyl group; —NRkRk, heteroaryl, —NHC(O)CH$_3$, and —S(O)$_2$Ri;

where said phenyl is optionally substituted by one to three substituents each independently selected from the following: $C_1$-$C_3$ alkoxy, —NHC(O)CH$_3$, —C(O)NH$_2$, halo, CF$_3$, —S(O)$_2$Ri, —S(O)$_2$NHRi, hydroxy, —$C_1$-$C_3$-alkyl-NRkRk, —NRkRk, $C_1$-$C_3$ alkyl, heterocycloalkyl, and heterocycloalkyl substituted with one —C(O)CH$_3$ group;

or a pharmaceutically-acceptable salt, solvate, or polymorph thereof.

Another embodiment of the present invention is a compound according to formula I where:

R1 is a group —YZ;

Y is a bond;

Z is optionally substituted phenyl or optionally substituted heteroaryl where said phenyl and heteroaryl are optionally substituted with one or two substituents selected from the group consisting of: halo, cyano, —N(Rb)SO$_2$Re, —N(Rb)C(O)Ra, $C_1$-$C_6$ alkyl, and $C_1$-$C_6$ alkyl substituted with one substituent selected from the group consisting of: —NRaRb, —ORc, heterocycloalkyl, and heterocycloalkyl substituted with one $C_1$-$C_3$ alkyl group;

R2 is H;

R3 is H;

U is a bond;

V is phenyl, or a 5 or 6 membered heteroaryl each of which is substituted by —N(Rb)S(O)$_m$R4, —S(O)$_m$N(Rb)R4, or —S(O)$_m$R4;

m is 1 or 2;

R4 is the group X—R5;

X is a bond, $C_1$-$C_6$ alkylene, heteroaryl, or $C_1$-$C_6$ alkylene-heterocycloalkyl;

R5 is NRaRb, ORj, optionally substituted heterocycloalkyl, or optionally substituted heteroaryl, where said heterocycloalkyl and heteroaryl are optionally substituted with one to three substituents independently selected from the group consisting of: halo, —C(O)Ra, —NRaRb, heterocycloalkyl, heterocycloalkyl substituted with one $C_1$-$C_6$ alkyl group; phenyl, $C_1$-$C_6$ alkyl, $C_1$-$C_6$ alkyl substituted with one or two substitutents selected from the group consisting of: —ORc, —C(O)Rc, —C(O)NRaRb, and phenyl; heteroaryl, oxo, N(Rb)C(O)Ra, —ORc, —C(O)NRaRb, and —C(O)ORc;

each Ra is independently selected from the group consisting of: H, heterocycloalkyl, heterocycloalkyl substituted with one —C(O)ORb group; $C_2$-$C_6$ alkynyl, optionally substituted $C_1$-$C_6$ alkyl, $C_3$-$C_6$ cycloalkyl, $C_3$-$C_7$ cycloalkyl substituted with one —ORc group, and phenyl, where said optionally substituted $C_1$-$C_6$ alkyl is optionally substituted with one to three substituents selected from the group consisting of: halo, heteroaryl, heterocycloalkyl, —ORc, N(Rb)SO$_2$Re, —N(Rk)$_2$, $C_3$-$C_7$ cycloalkyl, phenyl, and phenolyl;

each Rb is independently selected from the group consisting of: H, $C_1$-$C_6$ alkyl, $C_1$-$C_6$ alkyl substituted with one —ORc group;

each Rc is independently selected from the group consisting of: H, $C_1$-$C_6$ alkyl, heterocycloalkyl, and aryl;

each Re is independently selected from the group consisting of: $C_1$-$C_6$ alkyl, phenyl, and phenyl substituted with one $C_1$-$C_6$ alkyl group;

each Ri is independently selected from the group consisting of: $C_1$-$C_3$ alkyl and phenyl;

Rj is selected from the group consisting of H, optionally substituted $C_1$-$C_6$ alkyl, $C_1$-$C_6$ haloalkyl, heteroaryl, and optionally substituted phenyl, where said optionally substituted $C_1$-$C_6$ alkyl is optionally substituted by one or two substituents each independently selected from the following: hydroxy, methylthio, $C_3$-$C_6$ cycloalkyl, $C_3$-$C_6$ cycloalkyl substituted by one $C_1$-$C_3$ alkyl group; heterocycloalkyl, heterocycloalkyl substituted by one $C_1$-$C_3$ alkyl, one oxo group, or one 4-fluorobenzyl group; —NRkRk, heteroaryl, —NHC(O)CH$_3$, and —S(O)$_2$Ri;

where said phenyl is optionally substituted by one to three substituents each independently selected from the following: $C_1$-$C_3$ alkoxy, —NHC(O)CH$_3$, —C(O)NH$_2$, halo, CF$_3$, —S(O)$_2$Ri, —S(O)$_2$NHRi, hydroxy, —$C_1$-$C_3$-alkyl-NRkRk, —NRkRk, $C_1$-$C_3$ alkyl, heterocycloalkyl, and heterocycloalkyl substituted with one —C(O)CH$_3$ group; and each Rk is independently selected from the group consisting of H, $C_1$-$C_6$ alkyl; or a pharmaceutically-acceptable salt, solvate, or polymorph thereof.

Another embodiment of the present invention is a compound according to formula I where:

R1 is a group —YZ;

Y is a bond;

Z is optionally substituted phenyl or optionally substituted heteroaryl where said phenyl and heteroaryl are optionally substituted with one or two substituents selected from the group consisting of: halo, cyano, —N(Rb)SO$_2$Re, —N(Rb)C(O)Ra, $C_1$-$C_6$ alkyl, and $C_1$-$C_6$ alkyl substituted with one substituent selected from the group consisting of: —NRaRb, —ORc, heterocycloalkyl, and heterocycloalkyl substituted with one OH, —C(O)NH$_2$, or $C_1$-$C_3$ alkyl group;

R2 is H;

R3 is H;

U is a bond;

V is;

U ← ⬡NS(O)$_m$R4;

m is 2;

R4 is the group —X—R5;

X is a bond or $C_1$-$C_6$ alkylene;

R5 is —NRaRb, optionally substituted heterocycloalkyl, or optionally substituted heteroaryl, where said heterocycloalkyl and heteroaryl are optionally substituted with one to three substituents independently selected from the group consisting of: halo, —C(O)Ra, —NRaRb, heterocycloalkyl, heterocycloalkyl substituted with one $C_1$-$C_6$ alkyl group; phenyl, $C_1$-$C_6$ alkyl, $C_1$-$C_6$ alkyl substituted with one or two substitutents selected from the group consisting of: —ORc, —C(O)Rc, —C(O)NRaRb, and phenyl; heteroaryl, oxo, N(Rb)C(O)Ra, —ORc, —C(O)NRaRb, and —C(O)ORc;

each Ra is independently selected from the group consisting of: H, —ORh, heterocycloalkyl, heterocycloalkyl substituted with one —C(O)ORb group; $C_2$-$C_6$ alkynyl, optionally substituted $C_1$-$C_6$ alkyl, $C_3$-$C_6$ cycloalkyl, $C_3$-$C_7$ cycloalkyl substituted with one —ORc group, and phenyl, where said optionally substituted $C_1$-$C_6$ alkyl is optionally substituted with one to three substituents selected from the group consisting of: halo, heteroaryl, heterocycloalkyl, —ORc, N(Rb)SO$_2$Re, —N(Rk)$_2$, $C_3$-$C_7$ cycloalkyl, phenyl, and phenolyl;

each Rb is independently selected from the group consisting of: H, $C_1$-$C_6$ alkyl, $C_1$-$C_6$ alkyl substituted with one —ORc group;

each Rc is independently selected from the group consisting of: H, $C_1$-$C_6$ alkyl, heterocycloalkyl, and aryl;

each Re is independently selected from the group consisting of: $C_1$-$C_6$ alkyl, phenyl, and phenyl substituted with one $C_1$-$C_6$ alkyl group;

each Rh is independently selected from the group consisting of: H, $C_1$-$C_6$ alkyl, and $C_1$-$C_6$ haloalkyl; and each Rk is independently selected from the group consisting of H, $C_1$-$C_6$ alkyl; or a pharmaceutically-acceptable salt, solvate, or polymorph thereof.

Another embodiment of the present invention is a compound according to formula I where:

R1 is a group —YZ;

Y is a bond;

Z is optionally substituted phenyl or optionally substituted heteroaryl
where said phenyl and heteroaryl are optionally substituted with one or two substituents selected from the group consisting of: halo, cyano, —N(Rb)SO$_2$Re, —N(Rb)C(O)Ra, C$_1$-C$_6$ alkyl, and C$_1$-C$_6$ alkyl substituted with one substituent selected from the group consisting of: —NRaRb, —ORc, heterocycloalkyl, and heterocycloalkyl substituted with one C$_1$-C$_3$ alkyl group;

R2 is H;

R3 is H;

U is a bond;

V is

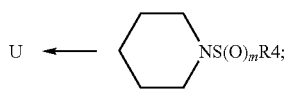

m is 2;

R4 is the group —X—R5;

X is a bond or C$_1$-C$_6$ alkylene;

R5 is —NRaRb, optionally substituted heterocycloalkyl, or optionally substituted heteroaryl,
where said heterocycloalkyl and heteroaryl are optionally substituted with one to three substituents independently selected from the group consisting of: halo, —C(O)Ra, —NRaRb, heterocycloalkyl, heterocycloalkyl substituted with one C$_1$-C$_6$ alkyl group; phenyl, C$_1$-C$_6$ alkyl, C$_1$-C$_6$ alkyl substituted with one or two substituents selected from the group consisting of: —ORc, —C(O)Rc, —C(O)NRaRb, and phenyl; heteroaryl, oxo, N(Rb)C(O)Ra, —ORc, —C(O)NRaRb, and —C(O)ORc;

each Ra is independently selected from the group consisting of: H, heterocycloalkyl, heterocycloalkyl substituted with one —C(O)ORb group; C$_2$-C$_6$ alkynyl, optionally substituted C$_1$-C$_6$ alkyl, C$_3$-C$_6$ cycloalkyl, C$_3$-C$_7$ cycloalkyl substituted with one —ORc group, and phenyl, where said optionally substituted C$_1$-C$_6$ alkyl is optionally substituted with one to three substituents selected from the group consisting of: halo, heteroaryl, heterocycloalkyl, —ORc, N(Rb)SO$_2$Re, —N(Rk)$_2$, C$_3$-C$_7$ cycloalkyl, phenyl, and phenolyl;

each Rb is independently selected from the group consisting of: H, C$_1$-C$_6$ alkyl, C$_1$-C$_6$ alkyl substituted with one —ORc group;

each Rc is independently selected from the group consisting of: H, C$_1$-C$_6$ alkyl, heterocycloalkyl, and aryl;

each Re is independently selected from the group consisting of: C$_1$-C$_6$ alkyl, phenyl, and phenyl substituted with one C$_1$-C$_6$ alkyl group;

each Rh is independently selected from the group consisting of: H, C$_1$-C$_6$ alkyl, and C$_1$-C$_6$ haloalkyl; and each Rk is independently selected from the group consisting of H, C$_1$-C$_6$ alkyl; or a pharmaceutically-acceptable salt, solvate, or polymorph thereof.

Another embodiment of the present invention is a compound according to formula I where:

R1 is a group —YZ;

Y is a bond;

Z is phenyl;

R2 is H;

R3 is H;

U is a bond;

V is

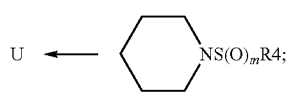

m is 2;

R4 is the group X—R5;

X is a bond or C$_1$-C$_6$ alkylene;

R5 is —ORj;

each Ri is independently selected from the group consisting of: C$_1$-C$_3$ alkyl and phenyl;

Rj is selected from the group consisting of H, optionally substituted C$_1$-C$_6$ alkyl, C$_1$-C$_6$ haloalkyl, heteroaryl, and optionally substituted phenyl,
where said optionally substituted C$_1$-C$_6$ alkyl is optionally substituted by one or two substituents each independently selected from the following: hydroxy, C$_1$-C$_6$ alkoxy, —OCH$_2$CH$_2$N(CH$_3$)$_2$, methylthio, C$_3$-C$_6$ cycloalkyl, C$_3$-C$_6$ cycloalkyl substituted by one C$_1$-C$_3$ alkyl group; heterocycloalkyl, heterocycloalkyl substituted by one C$_1$-C$_3$ alkyl, one oxo group, or one 4-fluorobenzyl group; —NRkRk, heteroaryl, —NHC(O)CH$_3$, and —S(O)$_2$Ri;
where said phenyl is optionally substituted by one to three substituents each independently selected from the following: C$_1$-C$_3$ alkoxy, —NHC(O)CH$_3$, —C(O)NH$_2$, halo, CF$_3$, —S(O)$_2$Ri, —S(O)$_2$NHRi, hydroxy, —C$_1$-C$_3$-alkyl-NRkRk, —NRkRk, C$_1$-C$_3$ alkyl, heterocycloalkyl, and heterocycloalkyl substituted with one —C(O)CH$_3$ group; and each Rk is independently selected from H, C$_1$-C$_6$ alkyl, C$_1$-C$_6$ alkyl substituted by one or two hydroxyl groups; phenyl, and phenyl substituted with one C$_1$-C$_3$ alkyl group;

or a pharmaceutically-acceptable salt, solvate, or polymorph thereof.

Another embodiment of the present invention is a compound according to formula I where:

R1 is a group —YZ;

Y is a bond;

Z is phenyl;

R2 is H;

R3 is H;

U is a bond;

V is

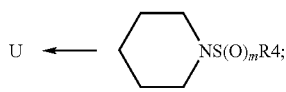

m is 2;

R4 is the group X—R5;

X is a bond or $C_1$-$C_6$ alkylene;

R5 is —ORj;

each Ri is independently selected from the group consisting of: $C_1$-$C_3$ alkyl and phenyl;

Rj is selected from the group consisting of H, optionally substituted $C_1$-$C_6$ alkyl, $C_1$-$C_6$ haloalkyl, heteroaryl, and optionally substituted phenyl,
where said optionally substituted $C_1$-$C_6$ alkyl is optionally substituted by one or two substituents each independently selected from the following: hydroxy, methylthio, $C_3$-$C_6$ cycloalkyl, $C_3$-$C_6$ cycloalkyl substituted by one $C_1$-$C_3$ alkyl group; heterocycloalkyl, heterocycloalkyl substituted by one $C_1$-$C_3$ alkyl, one oxo group, or one 4-fluorobenzyl group; —NRkRk, heteroaryl, —NHC(O)CH$_3$, and —S(O)$_2$Ri;
where said phenyl is optionally substituted by one to three substituents each independently selected from the following: $C_1$-$C_3$ alkoxy, —NHC(O)CH$_3$, —C(O)NH$_2$, halo, CF$_3$, —S(O)$_2$Ri, —S(O)$_2$NHRi, hydroxy, —$C_1$-$C_3$-alkyl-NRkRk, —NRkRk, $C_1$-$C_3$ alkyl, heterocycloalkyl, and heterocycloalkyl substituted with one —C(O)CH$_3$ group; and each Rk is independently selected from H, $C_1$-$C_6$ alkyl, $C_1$-$C_6$ alkyl substituted by one or two hydroxyl groups; phenyl, and phenyl substituted with one $C_1$-$C_3$ alkyl group; or a pharmaceutically-acceptable salt, solvate, or polymorph thereof.

Another embodiment of the present invention is a compound which is:

3-{1-[(2-aminoethyl)sulfonyl]-4-piperidinyl}-5-phenyl-1H-indole-7-carboxamide;

3-(1-{[2-(dimethylamino)ethyl]sulfonyl}-4-piperidinyl)-5-phenyl-1H-indole-7-carboxamide;

3-(1-{[3-(dimethylamino)propyl]sulfonyl}-4-piperidinyl)-5-phenyl-1H-indole-7-carboxamide;

3-(1-{[3-(4-methyl-1-piperazinyl)propyl]sulfonyl}-4-piperidinyl)-5-phenyl-1H-indole-7-carboxamide;

5-phenyl-3-(1-{[3-(1-piperidinyl)propyl]sulfonyl}-4-piperidinyl)-1H-indole-7-carboxamide;

3-(1-{[3-(4-morpholinyl)propyl]sulfonyl}-4-piperidinyl)-5-phenyl-1H-indole-7-carboxamide;

5-phenyl-3-(1-{[3-(1-pyrrolidinyl)propyl]sulfonyl}-4-piperidinyl)-1H-indole-7-carboxamide;

3-(1-{[3-(1-pyrrolidinyl)propyl]sulfonyl}-4-piperidinyl)-5-(3-thienyl)-1H-indole-7-carboxamide;

3-(1-{[3-(dimethylamino)propyl]sulfonyl}-4-piperidinyl)-5-(3-thienyl)-1H-indole-7-carboxamide;

3-(1-{[3-(dimethylamino)propyl]sulfonyl}-4-piperidinyl)-5-(2-thienyl)-1H-indole-7-carboxamide;

3-(1-{[3-(1-pyrrolidinyl)propyl]sulfonyl}-4-piperidinyl)-5-(2-thienyl)-1H-indole-7-carboxamide;

3-(1-{[3-(2-methyl-1-pyrrolidinyl)propyl]sulfonyl}-4-piperidinyl)-5-(2-thienyl)-1H-indole-7-carboxamide;

3-(1-{[3-(cyclopentylamino)propyl]sulfonyl}-4-piperidinyl)-5-(2-thienyl)-1H-indole-7-carboxamide;

3-(1-{[3-(4-hydroxy-1-piperidinyl)propyl]sulfonyl}-4-piperidinyl)-5-(2-thienyl)-1H-indole-7-carboxamide;

3-(1-{[2-(cyclopentylamino)ethyl]sulfonyl}-4-piperidinyl)-5-(2-thienyl)-1H-indole-7-carboxamide;

3-(1-{[2-(1-pyrrolidinyl)ethyl]sulfonyl}-4-piperidinyl)-5-(3-thienyl)-1H-indole-7-carboxamide;

3-(1-{[2-(dimethylamino)ethyl]sulfonyl}-4-piperidinyl)-5-(3-thienyl)-1H-indole-7-carboxamide;

3-(1-{[2-(cyclopentylamino)ethyl]sulfonyl}-4-piperidinyl)-5-(3-thienyl)-1H-indole-7-carboxamide;

3-(1-{[2-(4-hydroxy-1-piperidinyl)ethyl]sulfonyl}-4-piperidinyl)-5-(3-thienyl)-1H-indole-7-carboxamide;

3-{1-[(2-hydroxyethyl)sulfonyl]-4-piperidinyl}-5-phenyl-1H-indole-7-carboxamide;

5-(5-chloro-2-thienyl)-3-(1-{[3-(1-pyrrolidinyl)propyl]sulfonyl}-4-piperidinyl)-1H-indole-7-carboxamide;

3-(1-{[2-(methylamino)ethyl]sulfonyl}-4-piperidinyl)-5-phenyl-1H-indole-7-carboxamide;

5-phenyl-3-(1-{[2-(1-piperidinyl)ethyl]sulfonyl}-4-piperidinyl)-1H-indole-7-carboxamide;

3-(1-{[2-(4-methyl-1-piperazinyl)ethyl]sulfonyl}-4-piperidinyl)-5-phenyl-1H-indole-7-carboxamide;

3-[1-({2-[[2-(dimethylamino)ethyl](methyl)amino]ethyl}sulfonyl)-4-piperidinyl]-5-phenyl-1H-indole-7-carboxamide;

3-(1-{[2-(4-morpholinyl)ethyl]sulfonyl}-4-piperidinyl)-5-phenyl-1H-indole-7-carboxamide;

3-[1-({2-[3-(2-hydroxyethyl)-1-piperazinyl]ethyl}sulfonyl)-4-piperidinyl]-5-phenyl-1H-indole-7-carboxamide;

3-(1-{[2-(cyclopentylamino)ethyl]sulfonyl}-4-piperidinyl)-5-phenyl-1H-indole-7-carboxamide;

3-(1-{[2-(cyclobutylamino)ethyl]sulfonyl}-4-piperidinyl)-5-phenyl-1H-indole-7-carboxamide;

5-phenyl-3-[1-({2-[(phenylmethyl)amino]ethyl}sulfonyl)-4-piperidinyl]-1H-indole-7-carboxamide;

5-phenyl-3-(1-{[2-(1-pyrrolidinyl)ethyl]sulfonyl}-4-piperidinyl)-1H-indole-7-carboxamide;

3-(1-{[2-(4-hydroxy-1-piperidinyl)ethyl]sulfonyl}-4-piperidinyl)-5-phenyl-1H-indole-7-carboxamide;

3-[1-({2-[[3-(dimethylamino)propyl](methyl)amino]ethyl}sulfonyl)-4-piperidinyl]-5-phenyl-1H-indole-7-carboxamide;

3-(1-{[2-(1,4'-bipiperidin-1'-yl)ethyl]sulfonyl}-4-piperidinyl)-5-phenyl-1H-indole-7-carboxamide;

3-(1-{[2-(diethylamino)ethyl]sulfonyl}-4-piperidinyl)-5-phenyl-1H-indole-7-carboxamide;

5-phenyl-3-(1-{[2-(2-phenyl-1-pyrrolidinyl)ethyl]sulfonyl}-4-piperidinyl)-1H-indole-7-carboxamide;

3-(1-{[2-(hexahydro-1H-azepin-1-yl)ethyl]sulfonyl}-4-piperidinyl)-5-phenyl-1H-indole-7-carboxamide;

3-[1-({2-[(cyclohexylmethyl)amino]ethyl}sulfonyl)-4-piperidinyl]-5-phenyl-1H-indole-7-carboxamide;

3-{1-[(2-{[2-hydroxy-1-(hydroxymethyl)ethyl]amino}ethyl)sulfonyl]-4-piperidinyl}-5-phenyl-1H-indole-7-carboxamide;

3-(1-{[2-(ethylamino)ethyl]sulfonyl}-4-piperidinyl)-5-phenyl-1H-indole-7-carboxamide;

3-[1-({2-[ethyl(methyl)amino]ethyl}sulfonyl)-4-piperidinyl]-5-phenyl-1H-indole-7-carboxamide;

3-[1-({2-[(2-hydroxyethyl)amino]ethyl}sulfonyl)-4-piperidinyl]-5-phenyl-1H-indole-7-carboxamide;

3-{1-[(2-{[(2S)-2-hydroxypropyl]amino}ethyl)sulfonyl]-4-piperidinyl}-5-phenyl-1H-indole-7-carboxamide;

3-{1-[(2-{[(1S)-2-hydroxy-1-methylethyl]amino}ethyl)sulfonyl]-4-piperidinyl}-5-phenyl-1H-indole-7-carboxamide;

3-{1-[(2-{[(1R)-2-hydroxy-1-methylethyl]amino}ethyl)sulfonyl]-4-piperidinyl}-5-phenyl-1H-indole-7-carboxamide;
3-[1-({2-[4-(aminocarbonyl)-1-piperidinyl]ethyl}sulfonyl)-4-piperidinyl]-5-phenyl-1H-indole-7-carboxamide;
3-[1-({2-[4-(4-morpholinyl)-1-piperidinyl]ethyl}sulfonyl)-4-piperidinyl]-5-phenyl-1H-indole-7-carboxamide;
3-{1-[(2-{[2-(dimethylamino)ethyl]amino}ethyl)sulfonyl]-4-piperidinyl}-5-phenyl-1H-indole-7-carboxamide;
3-(1-{[2-(4-methyl-1,4'-bipiperidin-1'-yl)ethyl]sulfonyl}-4-piperidinyl)-5-phenyl-1H-indole-7-carboxamide;
3-[1-({2-[4-(4-methyl-1-piperazinyl)-1-piperidinyl]ethyl}sulfonyl)-4-piperidinyl]-5-phenyl-1H-indole-7-carboxamide;
3-{1-[(2-{[2-(methyloxy)ethyl]amino}ethyl)sulfonyl]-4-piperidinyl}-5-phenyl-1H-indole-7-carboxamide;
3-{1-[(2-{[3-(4-morpholinyl)propyl]amino}ethyl)sulfonyl]-4-piperidinyl}-phenyl-1H-indole-7-carboxamide;
3-(1-{[2-(4-acetyl-1-piperazinyl)ethyl]sulfonyl}-4-piperidinyl)-5-phenyl-1H-indole-7-carboxamide;
3-[1-({2-[4-(2-hydroxyethyl)-1-piperazinyl]ethyl}sulfonyl)-4-piperidinyl]-5-phenyl-1H-indole-7-carboxamide;
3-[1-({2-[3-(hydroxymethyl)-1-piperidinyl]ethyl}sulfonyl)-4-piperidinyl]-5-phenyl-1H-indole-7-carboxamide;
3-[1-({2-[(2-{[(4-methylphenyl)sulfonyl]amino}ethyl)amino]ethyl}sulfonyl)-4-piperidinyl]-5-phenyl-1H-indole-7-carboxamide;
3-{1-[(2-{[2-(4-morpholinyl)ethyl]amino}ethyl)sulfonyl]-4-piperidinyl}-5-phenyl-1H-indole-7-carboxamide;
3-{1-[(2-{methyl[2-(methylamino)ethyl]amino}ethyl)sulfonyl]-4-piperidinyl}-5-phenyl-1H-indole-7-carboxamide;
3-{1-[(2-{4-[2-oxo-2-(1-pyrrolidinyl)ethyl]-1-piperazinyl}ethyl)sulfonyl]-4-piperidinyl}-5-phenyl-1H-indole-7-carboxamide;
3-{1-[(2-{2-[(dimethylamino)carbonyl]-1-pyrrolidinyl}ethyl)sulfonyl]-4-piperidinyl}-5-phenyl-1H-indole-7-carboxamide;
3-[1-({2-[(2S)-2-(hydroxymethyl)-1-pyrrolidinyl]ethyl}sulfonyl)-4-piperidinyl]-5-phenyl-1H-indole-7-carboxamide;
3-[1-({2-[(2S)-2-(aminocarbonyl)-1-pyrrolidinyl]ethyl}sulfonyl)-4-piperidinyl]-5-phenyl-1H-indole-7-carboxamide;
5-[5-(hydroxymethyl)-2-thienyl]-3-(1-{[3-(1-pyrrolidinyl)propyl]sulfonyl}-4-piperidinyl)-1H-indole-7-carboxamide;
5-[5-(1-pyrrolidinylmethyl)-2-thienyl]-3-(1-{[3-(1-pyrrolidinyl)propyl]sulfonyl}-4-piperidinyl)-1H-indole-7-carboxamide;
5-{5-[(methylamino)methyl]-2-thienyl}-3-(1-{[3-(4-morpholinyl)propyl]sulfonyl}-4-piperidinyl)-1H-indole-7-carboxamide;
5-{5-[(ethylamino)methyl]-2-thienyl}-3-(1-{[3-(4-morpholinyl)propyl]sulfonyl}-4-piperidinyl)-1H-indole-7-carboxamide;
3-[1-({3-[bis(1-methylethyl)amino]propyl}sulfonyl)-4-piperidinyl]-5-phenyl-1H-indole-7-carboxamide;
3-(1-{[2-(methyloxy)ethyl]sulfonyl}-4-piperidinyl)-5-phenyl-1H-indole-7-carboxamide;
3-[1-({3-[(2S,5S)-2,5-dimethyl-1-pyrrolidinyl]propyl}sulfonyl)-4-piperidinyl]-5-phenyl-1H-indole-7-carboxamide;
3-(1-{[3-(4-methyl-1-piperazinyl)propyl]sulfonyl}-4-piperidinyl)-5-(2-thienyl)-1H-indole-7-carboxamide;
3-(1-{[3-(4-hydroxy-1-piperidinyl)propyl]sulfonyl}-4-piperidinyl)-5-(3-thienyl)-1H-indole-7-carboxamide;
3-(1-{[3-(4-methyl-1-piperazinyl)propyl]sulfonyl}-4-piperidinyl)-5-(3-thienyl)-1H-indole-7-carboxamide;
3-(1-{[3-(4-morpholinyl)propyl]sulfonyl}-4-piperidinyl)-5-(2-thienyl)-1H-indole-7-carboxamide;
3-(1-{[3-(4-morpholinyl)propyl]sulfonyl}-4-piperidinyl)-5-(3-thienyl)-1H-indole-7-carboxamide;
5-(4-fluorophenyl)-3-(1-{[3-(1-pyrrolidinyl)propyl]sulfonyl}-4-piperidinyl)-1H-indole-7-carboxamide;
3-(1-{[3-(dimethylamino)propyl]sulfonyl}-4-piperidinyl)-5-[3-(hydroxymethyl)phenyl]-1H-indole-7-carboxamide;
3-(1-{[3-(dimethylamino)propyl]sulfonyl}-4-piperidinyl)-5-[4-(hydroxymethyl)phenyl]-1H-indole-7-carboxamide;
3-(1-{[3-(dimethylamino)propyl]sulfonyl}-4-piperidinyl)-5-(4-methylphenyl)-1H-indole-7-carboxamide;
5-[4-(acetylamino)phenyl]-3-(1-{[3-(dimethylamino)propyl]sulfonyl}-4-piperidinyl)-1H-indole-7-carboxamide;
3-(1-{[3-(dimethylamino)propyl]sulfonyl}-4-piperidinyl)-5-{4-[(methylsulfonyl)amino]phenyl}-1H-indole-7-carboxamide;
3-(1-{[3-(dimethylamino)propyl]sulfonyl}-4-piperidinyl)-5-(1H-pyrazol-4-yl)-1H-indole-7-carboxamide;
3-(1-{[3-(dimethylamino)propyl]sulfonyl}-4-piperidinyl)-5-[3-(methylsulfonyl)phenyl]-1H-indole-7-carboxamide;
5-[3-(hydroxymethyl)phenyl]-3-(1-{[3-(1-pyrrolidinyl)propyl]sulfonyl}-4-piperidinyl)-1H-indole-7-carboxamide;
5-(4-methylphenyl)-3-(1-{[3-(1-pyrrolidinyl)propyl]sulfonyl}-4-piperidinyl)-1H-indole-7-carboxamide;
5-[4-(acetylamino)phenyl]-3-(1-{[3-(1-pyrrolidinyl)propyl]sulfonyl}-4-piperidinyl)-1H-indole-7-carboxamide;
5-{4-[(methylsulfonyl)amino]phenyl}-3-(1-{[3-(1-pyrrolidinyl)propyl]sulfonyl}-4-piperidinyl)-1H-indole-7-carboxamide;
5-(1H-pyrazol-4-yl)-3-(1-{[3-(1-pyrrolidinyl)propyl]sulfonyl}-4-piperidinyl)-1H-indole-7-carboxamide;
5-[3-(methylsulfonyl)phenyl]-3-(1-{[3-(1-pyrrolidinyl)propyl]sulfonyl}-4-piperidinyl)-1H-indole-7-carboxamide;
5-[4-(hydroxymethyl)phenyl]-3-(1-{[3-(1-pyrrolidinyl)propyl]sulfonyl}-4-piperidinyl)-1H-indole-7-carboxamide;
5-{3-[(ethylamino)methyl]phenyl}-3-(1-{[3-(1-pyrrolidinyl)propyl]sulfonyl}-4-piperidinyl)-1H-indole-7-carboxamide;
5-{3-[(methylamino)methyl]phenyl}-3-(1-{[3-(1-pyrrolidinyl)propyl]sulfonyl}-4-piperidinyl)-1H-indole-7-carboxamide;
5-(3-{[(1-methylethyl)amino]methyl}phenyl)-3-(1-{[3-(1-pyrrolidinyl)propyl]sulfonyl}-4-piperidinyl)-1H-indole-7-carboxamide;
5-[3-({[(2S)-2-hydroxypropyl]amino}methyl)phenyl]-3-(1-{[3-(1-pyrrolidinyl)propyl]sulfonyl}-4-piperidinyl)-1H-indole-7-carboxamide;
5-{3-[(cyclopentylamino)methyl]phenyl}-3-(1-{[3-(1-pyrrolidinyl)propyl]sulfonyl}-4-piperidinyl)-1H-indole-7-carboxamide;
5-[3-({[(1S)-2-hydroxy-1-methylethyl]amino}methyl)phenyl]-3-(1-{[3-(1-pyrrolidinyl)propyl]sulfonyl}-4-piperidinyl)-1H-indole-7-carboxamide;
3-(1-{[3-(dimethylamino)propyl]sulfonyl}-4-piperidinyl)-5-{3-[(ethylamino)methyl]phenyl}-1H-indole-7-carboxamide;
3-(1-{[3-(dimethylamino)propyl]sulfonyl}-4-piperidinyl)-5-[3-({[(1S)-2-hydroxy-1-methylethyl]amino}methyl)phenyl]-1H-indole-7-carboxamide;
3-(1-{[3-(dimethylamino)propyl]sulfonyl}-4-piperidinyl)-5-[3-({[(2S)-2-hydroxypropyl]amino}methyl)phenyl]-1H-indole-7-carboxamide;

3-(1-{[3-(dimethylamino)propyl]sulfonyl}-4-piperidinyl)-5-[4-(1-piperidinylmethyl)phenyl]-1H-indole-7-carboxamide;

3-(1-{[3-(dimethylamino)propyl]sulfonyl}-4-piperidinyl)-5-[4-(4-morpholinylmethyl)phenyl]-1H-indole-7-carboxamide;

3-(1-{[3-(dimethylamino)propyl]sulfonyl}-4-piperidinyl)-5-[4-(1-pyrrolidinylmethyl)phenyl]-1H-indole-7-carboxamide;

3-(1-{[3-(cyclopentylamino)propyl]sulfonyl}-4-piperidinyl)-5-[3-(hydroxymethyl)phenyl]-1H-indole-7-carboxamide;

3-(1-{[3-(cyclopentylamino)propyl]sulfonyl}-4-piperidinyl)-5-(4-methylphenyl)-1H-indole-7-carboxamide;

3-(1-{[3-(cyclopentylamino)propyl]sulfonyl}-4-piperidinyl)-5-(3,4-difluorophenyl)-1H-indole-7-carboxamide;

5-(3-chlorophenyl)-3-(1-{[3-(cyclopentylamino)propyl]sulfonyl}-4-piperidinyl)-1H-indole-7-carboxamide;

3-(1-{[3-(cyclopentylamino)propyl]sulfonyl}-4-piperidinyl)-5-(4-ethylphenyl)-1H-indole-7-carboxamide;

3-(1-{[3-(cyclopentylamino)propyl]sulfonyl}-4-piperidinyl)-5-[4-(dimethylamino)phenyl]-1H-indole-7-carboxamide;

1,1-dimethylethyl 4-{[3-({4-[7-(aminocarbonyl)-5-phenyl-1H-indol-3-yl]-1-piperidinyl}sulfonyl)propyl]amino}-1-piperidinecarboxylate;

5-phenyl-3-(1-{[3-(4-piperidinylamino)propyl]sulfonyl}-4-piperidinyl)-1H-indole-7-carboxamide;

5-phenyl-3-{1-[(3-{[(2R)-tetrahydro-2-furanylmethyl]amino}propyl)sulfonyl]-4-piperidinyl}-1H-indole-7-carboxamide;

3-(1-{[3-(cyclopentylamino)propyl]sulfonyl}-4-piperidinyl)-5-phenyl-1H-indole-7-carboxamide;

3-[1-({3-[[3-(dimethylamino)propyl](methyl)amino]propyl}sulfonyl)-4-piperidinyl]-5-phenyl-1H-indole-7-carboxamide;

3-[1-({3-[4-(aminocarbonyl)-1-piperidinyl]propyl}sulfonyl)-4-piperidinyl]-5-phenyl-1H-indole-7-carboxamide;

3-(1-{[3-(4-hydroxy-1-piperidinyl)propyl]sulfonyl}-4-piperidinyl)-5-phenyl-1H-indole-7-carboxamide;

3-(1-{[3-(1,4'-bipiperidin-1'-yl)propyl]sulfonyl}-4-piperidinyl)-5-phenyl-1H-indole-7-carboxamide;

5-phenyl-3-[(1-({3-[4-(phenylmethyl)-1-piperidinyl]propyl}sulfonyl)-4-piperidinyl]-1H-indole-7-carboxamide;

3-(1-{[3-(octahydro-1(2H)-quinolinyl)propyl]sulfonyl}-4-piperidinyl)-5-phenyl-1H-indole-7-carboxamide;

3-(1-{[3-(hexahydro-1H-azepin-1-yl)propyl]sulfonyl}-4-piperidinyl)-5-phenyl-1H-indole-7-carboxamide;

3-(1-{[3-(4-{2-[(1-methylethyl)amino]-2-oxoethyl}-1-piperazinyl)propyl]sulfonyl}-4-piperidinyl)-5-phenyl-1H-indole-7-carboxamide;

3-(1-{[3-(2-ethyl-1-piperidinyl)propyl]sulfonyl}-4-piperidinyl)-5-phenyl-1H-indole-7-carboxamide;

3-(1-{[3-(2-methyl-1-pyrrolidinyl)propyl]sulfonyl}-4-piperidinyl)-5-phenyl-1H-indole-7-carboxamide;

5-phenyl-3-[1-({3-[2-(2-thienyl)-1-pyrrolidinyl]propyl}sulfonyl)-4-piperidinyl]-1H-indole-7-carboxamide;

3-(1-{[3-(3-hydroxy-1-pyrrolidinyl)propyl]sulfonyl}-4-piperidinyl)-5-phenyl-1H-indole-7-carboxamide;

3-(1-{[3-(4-hydroxy-4-phenyl-1-piperidinyl)propyl]sulfonyl}-4-piperidinyl)-5-phenyl-1H-indole-7-carboxamide;

3-(1-{[3-(3-hydroxy-1-piperidinyl)propyl]sulfonyl}-4-piperidinyl)-5-phenyl-1H-indole-7-carboxamide;

3-[1-({3-[(2R)-2-(aminocarbonyl)-1-pyrrolidinyl]propyl}sulfonyl)-4-piperidinyl]-5-phenyl-1H-indole-7-carboxamide;

3-[1-({3-[(2S)-2-(hydroxymethyl)-1-pyrrolidinyl]propyl}sulfonyl)-4-piperidinyl]-5-phenyl-1H-indole-7-carboxamide;

3-[1-({3-[(2-hydroxyethyl)(1-methylethyl)amino]propyl}sulfonyl)-4-piperidinyl]-5-phenyl-1H-indole-7-carboxamide;

3-[1-({3-[methyl(2-propyn-1-yl)amino]propyl}sulfonyl)-4-piperidinyl]-5-phenyl-1H-indole-7-carboxamide;

5-phenyl-3-(1-{[3-(1,3-thiazolidin-3-yl)propyl]sulfonyl}-4-piperidinyl)-1H-indole-7-carboxamide;

5-phenyl-3-[1-({3-[2-(1,3-thiazol-2-yl)-1-pyrrolidinyl]propyl}sulfonyl)-4-piperidinyl]-1H-indole-7-carboxamide;

(3-[1-({3-[(2-furanylmethyl)(methyl)amino]propyl}sulfonyl)-4-piperidinyl]-5-phenyl-1H-indole-7-carboxamide;

3-(1-{[3-(2-methyl-1-aziridinyl)propyl]sulfonyl}-4-piperidinyl)-5-phenyl-1H-indole-7-carboxamide;

3-[1-({3-[ethyl(1-methylethyl)amino]propyl}sulfonyl)-4-piperidinyl]-5-phenyl-1H-indole-7-carboxamide;

3-{1-[(3-{ethyl[2-(methyloxy)ethyl]amino}propyl)sulfonyl]-4-piperidinyl}-5-phenyl-1H-indole-7-carboxamide;

3-(1-{[3-(diethylamino)propyl]sulfonyl}-4-piperidinyl)-5-phenyl-1H-indole-7-carboxamide;

3-[1-({3-[[2-hydroxy-2-(4-hydroxyphenyl)ethyl](methyl)amino]propyl}sulfonyl)-4-piperidinyl]-5-phenyl-1H-indole-7-carboxamide;

3-(1-{[3-(3-amino-1-pyrrolidinyl)propyl]sulfonyl}-4-piperidinyl)-5-phenyl-1H-indole-7-carboxamide;

3-[1-({3-[ethyl(methyl)amino]propyl}sulfonyl)-4-piperidinyl]-5-phenyl-1H-indole-7-carboxamide;

3-{1-[(3-{bis[2-(methyloxy)ethyl]amino}propyl)sulfonyl]-4-piperidinyl}-5-phenyl-1H-indole-7-carboxamide;

3-(1-{[3-(2,6-dimethyl-4-morpholinyl)propyl]sulfonyl}-4-piperidinyl)-5-phenyl-1H-indole-7-carboxamide;

3-[1-({3-[2-(hydroxymethyl)-1-piperidinyl]propyl}sulfonyl)-4-piperidinyl]-5-phenyl-1H-indole-7-carboxamide;

3-[1-({3-[3-(hydroxymethyl)-1-piperidinyl]propyl}sulfonyl)-4-piperidinyl]-5-phenyl-1H-indole-7-carboxamide;

3-{1-[(3-{(2S)-2-[(methyloxy)methyl]-1-pyrrolidinyl}propyl)sulfonyl]-4-piperidinyl}-5-phenyl-1H-indole-7-carboxamide;

3-[1-({3-[methyl(1-methylethyl)amino]propyl}sulfonyl)-4-piperidinyl]-5-phenyl-1H-indole-7-carboxamide;

3-{1-[(3-{[(1S)-1-(hydroxymethyl)-2-methylpropyl]amino}propyl)sulfonyl]-4-piperidinyl}-5-phenyl-1H-indole-7-carboxamide;

3-[1-({3-[(2-hydroxy-1-methylethyl)amino]propyl}sulfonyl)-4-piperidinyl]-5-phenyl-1H-indole-7-carboxamide;

3-{1-[(3-{[2-(dimethylamino)ethyl]amino}propyl)sulfonyl]-4-piperidinyl}-5-phenyl-1H-indole-7-carboxamide;

3-[1-({3-[(trans-4-hydroxycyclohexyl)amino]propyl}sulfonyl)-4-piperidinyl]-5-phenyl-1H-indole-7-carboxamide;

3-[1-({3-[(2-hydroxypropyl)amino]propyl}sulfonyl)-4-piperidinyl]-5-phenyl-1H-indole-7-carboxamide;

3-{1-[(3-{[1-methyl-2-(methyloxy)ethyl]amino}propyl)sulfonyl]-4-piperidinyl}-5-phenyl-1H-indole-7-carboxamide;

3-[1-({3-[(2-hydroxyethyl)amino]propyl}sulfonyl)-4-piperidinyl]-5-phenyl-1H-indole-7-carboxamide;

3-[1-({3-[(2-hydroxybutyl)amino]propyl}sulfonyl)-4-piperidinyl]-5-phenyl-1H-indole-7-carboxamide;
3-{1-[(3-{[2-(4-morpholinyl)ethyl]amino}propyl)sulfonyl]-4-piperidinyl}-5-phenyl-1H-indole-7-carboxamide;
3-{1-[(3-{[(2R)-2-hydroxypropyl]amino}propyl)sulfonyl]-4-piperidinyl}-5-phenyl-1H-indole-7-carboxamide;
3-{1-[(3-{[(1R)-1-(hydroxymethyl)-2-methylpropyl]amino}propyl)sulfonyl]-4-piperidinyl}-5-phenyl-1H-indole-7-carboxamide;
3-{1-[(3-{[(1S)-1-(hydroxymethyl)propyl]amino}propyl)sulfonyl]-4-piperidinyl}-5-phenyl-1H-indole-7-carboxamide;
3-(1-{[3-(cyclohexylamino)propyl]sulfonyl}-4-piperidinyl)-5-phenyl-1H-indole-7-carboxamide;
3-[1-({3-[(4-methylphenyl)oxy]propyl}sulfonyl)-4-piperidinyl]-5-phenyl-1H-indole-7-carboxamide;
3-(1-{[3-(methyloxy)propyl]sulfonyl}-4-piperidinyl)-5-phenyl-1H-indole-7-carboxamide;
5-phenyl-3-(1-{[3-(phenyloxy)propyl]sulfonyl}-4-piperidinyl)-1H-indole-7-carboxamide;
5-phenyl-3-{1-[(3-{[2-(trifluoromethyl)phenyl]oxy}propyl)sulfonyl]-4-piperidinyl}-1H-indole-7-carboxamide;
3-[1-({3-[(4-hydroxybutyl)oxy]propyl}sulfonyl)-4-piperidinyl]-5-phenyl-1H-indole-7-carboxamide;
3-[1-({3-[(cyclopropylmethyl)oxy]propyl}sulfonyl)-4-piperidinyl]-5-phenyl-1H-indole-7-carboxamide;
3-[1-({3-[(2-hydroxy-1-methylpropyl)oxy]propyl}sulfonyl)-4-piperidinyl]-5-phenyl-1H-indole-7-carboxamide;
3-[1-({3-[(cyclobutylmethyl)oxy]propyl}sulfonyl)-4-piperidinyl]-5-phenyl-1H-indole-7-carboxamide;
5-phenyl-3-[1-({3-[(tetrahydro-3-furanylmethyl)oxy]propyl}sulfonyl)-4-piperidinyl]-1H-indole-7-carboxamide;
3-{1-[(3-{[4-(acetylamino)phenyl]oxy}propyl)sulfonyl]-4-piperidinyl}-5-phenyl-1H-indole-7-carboxamide;
3-{1-[(3-{[4-(methyloxy)phenyl]oxy}propyl)sulfonyl]-4-piperidinyl}-5-phenyl-1H-indole-7-carboxamide;
3-{1-[(3-{[2-(methyloxy)phenyl]oxy}-propyl)sulfonyl]-4-piperidinyl}-5-phenyl-1H-indole-7-carboxamide;
3-[1-({3-[(4-fluorophenyl)oxy]propyl}sulfonyl)-4-piperidinyl]-5-phenyl-1H-indole-7-carboxamide;
5-phenyl-3-{1-[(3-{[3-(trifluoromethyl)phenyl]oxy}propyl)sulfonyl]-4-piperidinyl}-1H-indole-7-carboxamide;
3-{1-[(3-{[3-(methoxy)phenyl]oxy}propyl)sulfonyl]-4-piperidinyl}-5-phenyl-1H-indole-7-carboxamide;
3-{1-[(3-hydroxypropyl)sulfonyl]-4-piperidinyl}-5-phenyl-1H-indole-7-carboxamide;
3-(1-{[2-(ethyloxy)ethyl]sulfonyl}-4-piperidinyl)-5-phenyl-1H-indole-7-carboxamide;
3-(1-{[3-(ethyloxy)propyl]sulfonyl}-4-piperidinyl)-5-phenyl-1H-indole-7-carboxamide;
3-(1-{[3-(dimethylamino)propyl]sulfonyl}-4-piperidinyl)-5-{3-[(methylamino)methyl]phenyl}-1H-indole-7-carboxamide;
5-phenyl-3-{1-[(2-{[2-(1-piperidinyl)ethyl]oxy}ethyl)sulfonyl]-4-piperidinyl}-1H-indole-7-carboxamide;
3-(1-{[2-({[(2S)-1-methyl-2-pyrrolidinyl]methyl}oxy)ethyl]sulfonyl}-4-piperidinyl)-5-phenyl-1H-indole-7-carboxamide;
3-{1-[(2-{[2-(2-oxo-1-pyrrolidinyl)ethyl]oxy}ethyl)sulfonyl]-4-piperidinyl}-5-phenyl-1H-indole-7-carboxamide;
3-(1-{[2-({2-[bis(1-methylethyl)amino]ethyl}oxy)ethyl]sulfonyl}-4-piperidinyl)-5-phenyl-1H-indole-7-carboxamide;
3-{1-[(2-{[2-(4-morpholinyl)ethyl]oxy}ethyl)sulfonyl]-4-piperidinyl}-5-phenyl-1H-indole-7-carboxamide;
3-{1-[(2-{[2-(hexahydro-1H-azepin-1-yl)ethyl]oxy}ethyl)sulfonyl]-4-piperidinyl}-5-phenyl-1H-indole-7-carboxamide;
3-{1-[(2-{[2-(diethylamino)ethyl]oxy}ethyl)sulfonyl]-4-piperidinyl}-5-phenyl-1H-indole-7-carboxamide;
3-[1-({2-[(2-{4-[(4-fluorophenyl)methyl]-1-piperazinyl}ethyl)oxy]ethyl}sulfonyl)-4-piperidinyl]-5-phenyl-1H-indole-7-carboxamide;
3-(1-{[2-({2-[ethyl(3-methylphenyl)amino]ethyl}oxy)ethyl]sulfonyl}-4-piperidinyl)-5-phenyl-1H-indole-7-carboxamide;
3-(1-{[2-({2-[bis(2-hydroxypropyl)amino]ethyl}oxy)ethyl]sulfonyl}-4-piperidinyl)-5-phenyl-1H-indole-7-carboxamide;
3-{1-[(2-{[2-(acetylamino)ethyl]oxy}ethyl)sulfonyl]-4-piperidinyl}-5-phenyl-1H-indole-7-carboxamide;
3-(1-{[2-({2-[(1-methylethyl)oxy]ethyl}oxy)ethyl]sulfonyl}-4-piperidinyl)-5-phenyl-1H-indole-7-carboxamide;
3-[1-({2-[(2-furanylmethyl)oxy]ethyl}sulfonyl)-4-piperidinyl]-5-phenyl-1H-indole-7-carboxamide;
3-[1-({2-[(3-furanylmethyl)oxy]ethyl}sulfonyl)-4-piperidinyl]-5-phenyl-1H-indole-7-carboxamide;
3-{1-[(2-{[2-(methylthio)ethyl]oxy}ethyl)sulfonyl]-4-piperidinyl}-5-phenyl-1H-indole-7-carboxamide;
5-phenyl-3-{1-[(2-{[2-(3-thienyl)ethyl]oxy}ethyl)sulfonyl]-4-piperidinyl}-1H-indole-7-carboxamide;
3-{1-[(2-{[(2-methylcyclopropyl)methyl]oxy}ethyl)sulfonyl]-4-piperidinyl}-5-phenyl-1H-indole-7-carboxamide;
3-{1-[(2-{[2-(ethyloxy)ethyl]oxy}ethyl)sulfonyl]-4-piperidinyl}-5-phenyl-1H-indole-7-carboxamide;
3-[1-({2-[(2,2,3,3,3-pentafluoropropyl)oxy]ethyl}sulfonyl)-4-piperidinyl]-5-phenyl-1H-indole-7-carboxamide;
3-[1-({2-[(2-methylpropyl)oxy]ethyl}sulfonyl)-4-piperidinyl]-5-phenyl-1H-indole-7-carboxamide;
5-phenyl-3-(1-{[2-(propyloxy)ethyl]sulfonyl}-4-piperidinyl)-1H-indole-7-carboxamide;
5-phenyl-3-[1-({2-[(2,2,2-trifluoroethyl)oxy]ethyl}sulfonyl)-4-piperidinyl]-1H-indole-7-carboxamide;
5-phenyl-3-[1-({2-[(tetrahydro-3-furanylmethyl)oxy]ethyl}sulfonyl)-4-piperidinyl]-1H-indole-7-carboxamide;
3-{1-[(2-{[2-(methylsulfonyl)ethyl]oxy}ethyl)sulfonyl]-4-piperidinyl}-5-phenyl-1H-indole-7-carboxamide;
3-(1-{[2-({[(2S)-5-oxo-2-pyrrolidinyl]methyl}oxy)ethyl]sulfonyl}-4-piperidinyl)-5-phenyl-1H-indole-7-carboxamide;
3-{1-[(2-{[3-(dimethylamino)propyl]oxy}ethyl)sulfonyl]-4-piperidinyl}-5-phenyl-1H-indole-7-carboxamide;
3-[1-({2-[(cyclopropylmethyl)oxy]ethyl}sulfonyl)-4-piperidinyl]-5-phenyl-1H-indole-7-carboxamide;
3-[1-({2-[(cyclopentylmethyl)oxy]ethyl}sulfonyl)-4-piperidinyl]-5-phenyl-1H-indole-7-carboxamide;
3-[1-({2-[(1-methylethyl)oxy]ethyl}sulfonyl)-4-piperidinyl]-5-phenyl-1H-indole-7-carboxamide;
3-[1-({2-(2-{[2-(dimethylamino)ethyl]oxy}ethyl)oxy]ethyl}sulfonyl)-4-piperidinyl]-5-phenyl-1H-indole-7-carboxamide;
3-{1-[(2-{[(1S,3S)-3-hydroxy-1-methylbutyl]oxy}ethyl)sulfonyl]-4-piperidinyl}-5-phenyl-1H-indole-7-carboxamide;
3-[1-({2-[(4-hydroxybutyl)oxy]ethyl}sulfonyl)-4-piperidinyl]-5-phenyl-1H-indole-7-carboxamide;
3-{1-[(2-{[(1R,3R)-3-hydroxy-1-methylbutyl]oxy}ethyl)sulfonyl]-4-piperidinyl}-5-phenyl-1H-indole-7-carboxamide;
3-[1-({2-[(2-hydroxy-1-methylpropyl)oxy]ethyl}sulfonyl)-4-piperidinyl]-5-phenyl-1H-indole-7-carboxamide;

5-phenyl-3-{1-[(2-{[2-(2-thienyl)ethyl]oxy}ethyl)sulfonyl]-4-piperidinyl}-1H-indole-7-carboxamide;

5-phenyl-3-{1-[(2-{[2-(1-pyrrolidinyl)ethyl]oxy}ethyl)sulfonyl]-4-piperidinyl}-1H-indole-7-carboxamide;

3-(1-{[3-(dimethylamino)propyl]sulfonyl}-4-piperidinyl)-5-(3-{[(1-methylethyl)amino]methyl}phenyl)-1H-indole-7-carboxamide;

3-[1-({2-[(methyloxy)amino]ethyl}sulfonyl)-4-piperidinyl]-5-phenyl-1H-indole-7-carboxamide;

3-[1-({2-[hydroxy(methyl)amino]ethyl}sulfonyl)-4-piperidinyl]-5-phenyl-1H-indole-7-carboxamide;

3-[1-({2-[methyl(methyloxy)amino]ethyl}sulfonyl)-4-piperidinyl]-5-phenyl-1H-indole-7-carboxamide;

3-[1-({2-[(ethyloxy)amino]ethyl}sulfonyl)-4-piperidinyl]-5-phenyl-1H-indole-7-carboxamide;

3-[1-({3-[(methyloxy)amino]propyl}sulfonyl)-4-piperidinyl]-5-phenyl-1H-indole-7-carboxamide;

3-[1-({3-[hydroxy(methyl)amino]propyl}sulfonyl)-4-piperidinyl]-5-phenyl-1H-indole-7-carboxamide;

3-[1-({3-[methyl(methyloxy)amino]propyl}sulfonyl)-4-piperidinyl]-5-phenyl-1H-indole-7-carboxamide;

3-[1-({3-[(ethyloxy)amino]propyl}sulfonyl)-4-piperidinyl]-5-phenyl-1H-indole-7-carboxamide;

5-{3-[(methylamino)methyl]phenyl}-3-(1-{[3-(methyloxy)propyl]sulfonyl}-4-piperidinyl)-1H-indole-7-carboxamide;

5-{3-[(ethylamino)methyl]phenyl}-3-(1-{[3-(methyloxy)propyl]sulfonyl}-4-piperidinyl)-1H-indole-7-carboxamide;

5-(3-{[(1-methylethyl)amino]methyl}phenyl)-3-(1-{[3-(methyloxy)propyl]sulfonyl}-4-piperidinyl)-1H-indole-7-carboxamide;

3-(1-{[3-(methyloxy)propyl]sulfonyl}-4-piperidinyl)-5-{3-[(propylamino)methyl]phenyl}-1H-indole-7-carboxamide;

5-[3-({[(2R)-2-hydroxypropyl]amino}methyl)phenyl]-3-(1-{[3-(methyloxy)propyl]sulfonyl}-4-piperidinyl)-1H-indole-7-carboxamide;

5-[3-({[(2S)-2-hydroxypropyl]amino}methyl)phenyl]-3-(1-{[3-(methyloxy)propyl]sulfonyl}-4-piperidinyl)-1H-indole-7-carboxamide;

5-(3-{[(cyclopropylmethyl)amino]methyl}phenyl)-3-(1-{[3-(methyloxy)propyl]sulfonyl}-4-piperidinyl)-1H-indole-7-carboxamide;

5-[3-({[2-(methyloxy)ethyl]amino}methyl)phenyl]-3-(1-{[3-(methyloxy)propyl]sulfonyl}-4-piperidinyl)-1H-indole-7-carboxamide;

5-[3-({[(2R)-2-methylbutyl]amino}methyl)phenyl]-3-(1-{[3-(methyloxy)propyl]sulfonyl}-4-piperidinyl)-1H-indole-7-carboxamide;

5-(3-{[(2,2-dimethylpropyl)amino]methyl}phenyl)-3-(1-{[3-(methyloxy)propyl]sulfonyl}-4-piperidinyl)-1H-indole-7-carboxamide;

5-[3-({[3-(methyloxy)propyl]amino}methyl)phenyl]-3-(1-{[3-(methyloxy)propyl]sulfonyl}-4-piperidinyl)-1H-indole-7-carboxamide;

5-[3-({[2-(ethyloxy)ethyl]amino}methyl)phenyl]-3-(1-{[3-(methyloxy)propyl]sulfonyl}-4-piperidinyl)-1H-indole-7-carboxamide;

3-(1-{[3-(methyloxy)propyl]sulfonyl}-4-piperidinyl)-5-(3-{[(tetrahydro-2-furanylmethyl)amino]methyl}phenyl)-1H-indole-7-carboxamide;

3-(1-{[3-(methyloxy)propyl]sulfonyl}-4-piperidinyl)-5-[3-({[(2R)-tetrahydro-2-furanylmethyl]amino}methyl)phenyl]-1H-indole-7-carboxamide;

5-[3-({[(1S)-1,2-dimethylpropyl]amino}methyl)phenyl]-3-(1-{[3-(methyloxy)propyl]sulfonyl}-4-piperidinyl)-1H-indole-7-carboxamide;

5-[3-({[1-methyl-2-(methyloxy)ethyl]amino}methyl)phenyl]-3-(1-{[3-(methyloxy)propyl]sulfonyl}-4-piperidinyl)-1H-indole-7-carboxamide;

3-(1-{[3-(methyloxy)propyl]sulfonyl}-4-piperidinyl)-5-[3-({[(1S)-1,2,2-trimethylpropyl]amino}methyl)phenyl]-1H-indole-7-carboxamide;

5-{3-[({1-[(methyloxy)methyl]propyl}amino)methyl]phenyl}-3-(1-{[3-(methyloxy)propyl]sulfonyl}-4-piperidinyl)-1H-indole-7-carboxamide;

5-[3-({[(5-methyl-2-furanyl)methyl]amino}methyl)phenyl]-3-(1-{[3-(methyloxy)propyl]sulfonyl}-4-piperidinyl)-1H-indole-7-carboxamide;

5-(3-{[(2-hydroxy-1-methylethyl)amino]methyl}phenyl)-3-(1-{[3-(methyloxy)propyl]sulfonyl}-4-piperidinyl)-1H-indole-7-carboxamide;

5-(3-{[(1,1-dimethylpropyl)amino]methyl}phenyl)-3-(1-{[3-(methyloxy)propyl]sulfonyl}-4-piperidinyl)-1H-indole-7-carboxamide;

5-(3-{[(4-hydroxybutyl)amino]methyl}phenyl)-3-(1-{[3-(methyloxy)propyl]sulfonyl}-4-piperidinyl)-1H-indole-7-carboxamide;

3-(1-{[3-(methyloxy)propyl]sulfonyl}-4-piperidinyl)-5-(3-{[(4-pyridinylmethyl)amino]methyl}phenyl)-1H-indole-7-carboxamide;

3-(1-{[3-(methyloxy)propyl]sulfonyl}-4-piperidinyl)-5-(3-{[(2-pyridinylmethyl)amino]methyl}phenyl)-1H-indole-7-carboxamide;

5-[3-({[3-(1H-imidazol-1-yl)propyl]amino}methyl)phenyl]-3-(1-{[3-(methyloxy)propyl]sulfonyl}-4-piperidinyl)-1H-indole-7-carboxamide;

3-(1-{[3-(methyloxy)propyl]sulfonyl}-4-piperidinyl)-5-[3-({[3-(1-pyrrolidinyl)propyl]amino}methyl)phenyl]-1H-indole-7-carboxamide;

3-(1-{[3-(methyloxy)propyl]sulfonyl}-4-piperidinyl)-5-[3-({[2-(1-piperidinyl)ethyl]amino}methyl)phenyl]-1H-indole-7-carboxamide;

3-(1-{[3-(methyloxy)propyl]sulfonyl}-4-piperidinyl)-5-[3-({[3-(4-morpholinyl)propyl]amino}methyl)phenyl]-1H-indole-7-carboxamide;

5-[3-({[(1S)-1-cyclohexylethyl]amino}methyl)phenyl]-3-(1-{[3-(methyloxy)propyl]sulfonyl}-4-piperidinyl)-1H-indole-7-carboxamide;

3-(1-{[3-(methyloxy)propyl]sulfonyl}-4-piperidinyl)-5-(3-{[methyl(2-propen-1-yl)amino]methyl}phenyl)-1H-indole-7-carboxamide;

5-(3-{[(3R)-3-hydroxy-1-pyrrolidinyl]methyl}phenyl)-3-(1-{[3-(methyloxy)propyl]sulfonyl}-4-piperidinyl)-1H-indole-7-carboxamide;

5-(3-{[(2-hydroxyethyl)(propyl)amino]methyl}phenyl)-3-(1-{[3-(methyloxy)propyl]sulfonyl}-4-piperidinyl)-1H-indole-7-carboxamide;

3-(1-{[3-(methyloxy)propyl]sulfonyl}-4-piperidinyl)-5-{3-[(2-propyl-1-pyrrolidinyl)methyl]phenyl}-1H-indole-7-carboxamide;

5-(3-{[2-(1-methylethyl)-1-pyrrolidinyl]methyl}phenyl)-3-(1-{[3-(methyloxy)propyl]sulfonyl}-4-piperidinyl)-1H-indole-7-carboxamide;

5-{3-[(3,5-dimethyl-1-piperidinyl)methyl]phenyl}-3-(1-{[3-(methyloxy)propyl]sulfonyl}-4-piperidinyl)-1H-indole-7-carboxamide;

5-(3-{[(2S)-2-(aminocarbonyl)-1-pyrrolidinyl]methyl}phenyl)-3-(1-{[3-(methyloxy)propyl]sulfonyl}-4-piperidinyl)-1H-indole-7-carboxamide;

5-(3-{[(1-dimethylethyl)amino]methyl}phenyl)-3-(1-{[3-(methyloxy)propyl]sulfonyl}-4-piperidinyl)-1H-indole-7-carboxamide;

5-{3-[(methylamino)methyl]phenyl}-3-(1-{[2-(methyloxy)ethyl]sulfonyl}-4-piperidinyl)-1H-indole-7-carboxamide;

5-(3-{[(1-dimethylpropyl)amino]methyl}phenyl)-3-(1-{[2-(methyloxy)ethyl]sulfonyl}-4-piperidinyl)-1H-indole-7-carboxamide;

3-(1-{[3-(methyloxy)propyl]sulfonyl}-4-piperidinyl)-5-(2-thienyl)-1H-indole-7-carboxamide;

3-(1-{[3-(ethyloxy)propyl]sulfonyl}-4-piperidinyl)-5-(3-thienyl)-1H-indole-7-carboxamide;

3-(1-{[3-(ethyloxy)propyl]sulfonyl}-4-piperidinyl)-5-(2-thienyl)-1H-indole-7-carboxamide;

3-{1-[(3-hydroxypropyl)sulfonyl]-4-piperidinyl}-5-(2-thienyl)-1H-indole-7-carboxamide;

3-(1-{[3-(methyloxy)propyl]sulfonyl}-4-piperidinyl)-5-(3-thienyl)-1H-indole-7-carboxamide;

3-{1-[(1-methyl-1H-imidazol-4-yl)sulfonyl]-4-piperidinyl}-5-phenyl-1H-indole-7-carboxamide;

5-phenyl-3-[1-(2-thienylsulfonyl)-4-piperidinyl]-1H-indole-7-carboxamide;

3-{1-[(5-chloro-2-thienyl)sulfonyl]-4-piperidinyl}-5-phenyl-1H-indole-7-carboxamide;

3-(1-{[5-(3-isoxazolyl)-3-thienyl]sulfonyl}-4-piperidinyl)-5-phenyl-1H-indole-7-carboxamide;

5-phenyl-3-{1-[(5-{[(phenylmethyl)amino]methyl}-2-thienyl)sulfonyl]-4-piperidinyl}-1H-indole-7-carboxamide;

3-(1-{[2-(acetylamino)-4-methyl-1,3-thiazol-5-yl]sulfonyl}-4-piperidinyl)-5-phenyl-1H-indole-7-carboxamide;

3-{1-[(5-chloro-1,3-dimethyl-1H-pyrazol-4-yl)sulfonyl]-4-piperidinyl}-5-phenyl-1H-indole-7-carboxamide;

3-{1-[(4-chloro-2,1,3-benzoxadiazol-5-yl)sulfonyl]-4-piperidinyl}-5-phenyl-1H-indole-7-carboxamide;

3-{1-[(1,2-dimethyl-1H-imidazol-4-yl)sulfonyl]-4-piperidinyl}-5-phenyl-1H-indole-7-carboxamide;

5-phenyl-3-{1-[(1,3,5-trimethyl-1H-pyrazol-4-yl)sulfonyl]-4-piperidinyl}-1H-indole-7-carboxamide;

3-{1-[(3,5-dimethyl-4-isoxazolyl)sulfonyl]-4-piperidinyl}-5-phenyl-1H-indole-7-carboxamide;

3-{1-[(2,4-dimethyl-1,3-thiazol-5-yl)sulfonyl]-4-piperidinyl}-5-phenyl-1H-indole-7-carboxamide;

3-{1-[(1,2-dimethyl-1H-imidazol-5-yl)sulfonyl]-4-piperidinyl}-5-phenyl-1H-indole-7-carboxamide;

3-{1-[(1-methyl-1H-imidazol-4-yl)sulfonyl]-4-piperidinyl}-5-(3-thienyl)-1H-indole-7-carboxamide;

3-(1-{[3-(methyloxy)propyl]sulfonyl}-4-piperidinyl)-5-[5-(1-pyrrolidinylmethyl)-3-thienyl]-1H-indole-7-carboxamide;

5-(5-{[(2,2-dimethylpropyl)amino]methyl}-3-thienyl)-3-(1-{[3-(methyloxy)propyl]sulfonyl}-4-piperidinyl)-1H-indole-7-carboxamide;

3-[1-({3-[(3-ethylphenyl)oxy]propyl}sulfonyl)-4-piperidinyl]-5-phenyl-1H-indole-7-carboxamide;

3-[1-({3-[(3-methylphenyl)oxy]propyl}sulfonyl)-4-piperidinyl]-5-phenyl-1H-indole-7-carboxamide;

3-{1-[(3-{[4-(ethyloxy)phenyl]oxy}propyl)sulfonyl]-4-piperidinyl}-5-phenyl-1H-indole-7-carboxamide;

3-{1-[(3-{[4-(aminocarbonyl)phenyl]oxy}propyl)sulfonyl]-4-piperidinyl}-5-phenyl-1H-indole-7-carboxamide;

3-{1-[(3-{[2-(acetylamino)-5-methylphenyl]oxy}propyl)sulfonyl]-4-piperidinyl}-5-phenyl-1H-indole-7-carboxamide;

3-{1-[(3-{[2-fluoro-6-(methyloxy)phenyl]oxy}-propyl)sulfonyl]-4-piperidinyl}-5-phenyl-1H-indole-7-carboxamide;

3-{1-[(3-{[2-fluoro-3-(trifluoromethyl)phenyl]oxy}propyl)sulfonyl]-4-piperidinyl}-5-phenyl-1H-indole-7-carboxamide;

3-(1-{[3-({2-[(dimethylamino)methyl]phenyl}oxy)propyl]sulfonyl}-4-piperidinyl)-5-phenyl-1H-indole-7-carboxamide;

3-[1-({3-[(3-fluorophenyl)oxy]propyl}sulfonyl)-4-piperidinyl]-5-phenyl-1H-indole-7-carboxamide;

3-{1-[(3-{[3-(acetylamino)phenyl]oxy}propyl)sulfonyl]-4-piperidinyl}-5-phenyl-1H-indole-7-carboxamide;

3-[1-({3-[(2-fluorophenyl)oxy]propyl}sulfonyl)-4-piperidinyl]-5-phenyl-1H-indole-7-carboxamide;

3-{1-[(3-{[3-(dimethylamino)phenyl]oxy}propyl)sulfonyl]-4-piperidinyl}-5-phenyl-1H-indole-7-carboxamide;

3-[1-({3-[(2,6-difluorophenyl)oxy]propyl}sulfonyl)-4-piperidinyl]-5-phenyl-1H-indole-7-carboxamide;

3-{1-[(3-{[2-(acetylamino)phenyl]oxy}propyl)sulfonyl]-4-piperidinyl}-5-phenyl-1H-indole-7-carboxamide;

3-{1-[(3-{[3-(diethylamino)phenyl]oxy}propyl)sulfonyl]-4-piperidinyl}-5-phenyl-1H-indole-7-carboxamide;

3-(1-{[3-(1,3-benzodioxol-5-yloxy)propyl]sulfonyl}-4-piperidinyl)-5-phenyl-1H-indole-7-carboxamide;

5-phenyl-3-(1-{[3-({3-[(phenylamino)sulfonyl]phenyl}oxy)propyl]sulfonyl}-4-piperidinyl)-1H-indole-7-carboxamide;

3-{1-[(3-{[4-(4-acetyl-1-piperazinyl)phenyl]oxy}propyl)sulfonyl]-4-piperidinyl}-5-phenyl-1H-indole-7-carboxamide;

3-[1-({3-[(4-hydroxyphenyl)oxy]propyl}sulfonyl)-4-piperidinyl]-5-phenyl-1H-indole-7-carboxamide;

3-{1-[(3-{[2-(acetylamino)-4-methylphenyl]oxy}propyl)sulfonyl]-4-piperidinyl}-5-phenyl-1H-indole-7-carboxamide;

3-{1-[(3-{[2-(methylsulfonyl)phenyl]oxy}propyl)sulfonyl]-4-piperidinyl}-5-phenyl-1H-indole-7-carboxamide;

5-phenyl-3-{1-[(3-{[3-(1-piperidinyl)phenyl]oxy}propyl)sulfonyl]-4-piperidinyl}-1H-indole-7-carboxamide;

3-[1-({3-[(2-hydroxyphenyl)oxy]propyl}sulfonyl)-4-piperidinyl]-5-phenyl-1H-indole-7-carboxamide;

3-[1-({3-[(3-hydroxyphenyl)oxy]propyl}sulfonyl)-4-piperidinyl]-5-phenyl-1H-indole-7-carboxamide;

5-phenyl-3-{1-[(3-{[4-(trifluoromethyl)phenyl]oxy}propyl)sulfonyl]-4-piperidinyl}-1H-indole-7-carboxamide;

5-[3-(1-pyrrolidinylmethyl)phenyl]-3-(1-{[3-(1-pyrrolidinyl)propyl]sulfonyl}-4-piperidinyl)-1H-indole-7-carboxamide;

5-[3-(4-morpholinylmethyl)phenyl]-3-(1-{[3-(1-pyrrolidinyl)propyl]sulfonyl}-4-piperidinyl)-1H-indole-7-carboxamide;

5-[3-(1-piperidinylmethyl)phenyl]-3-(1-{[3-(1-pyrrolidinyl)propyl]sulfonyl}-4-piperidinyl)-1H-indole-7-carboxamide;

5-phenyl-3-[1-(3-thienylsulfonyl)-4-piperidinyl]-1H-indole-7-carboxamide;

3-{1-[(4-methyl-2-thienyl)sulfonyl]-4-piperidinyl}-5-phenyl-1H-indole-7-carboxamide;

3-{1-[(5-methyl-2-thienyl)sulfonyl]-4-piperidinyl}-5-phenyl-1H-indole-7-carboxamide;

3-[1-(1-benzothien-3-ylsulfonyl)-4-piperidinyl]-5-phenyl-1H-indole-7-carboxamide;

methyl 5-({4-[7-(aminocarbonyl)-5-phenyl-1H-indol-3-yl]-1-piperidinyl}sulfonyl)-1-methyl-1H-pyrrole-2-carboxylate; or methyl 5-({4-[7-(aminocarbonyl)-5-phenyl-1H-indol-3-yl]-1-piperidinyl}sulfonyl)-2-methyl-3-furancarboxylate; or a pharmaceutically acceptable salt thereof.

Another embodiment of the present invention is a compound which is:

3-{1-[(2-aminoethyl)sulfonyl]-4-piperidinyl}-5-phenyl-1H-indole-7-carboxamide;
3-(1-{[2-(dimethylamino)ethyl]sulfonyl}-4-piperidinyl)-5-phenyl-1H-indole-7-carboxamide;
3-(1-{[3-(dimethylamino)propyl]sulfonyl}-4-piperidinyl)-5-phenyl-1H-indole-7-carboxamide;
3-(1-{[3-(4-morpholinyl)propyl]sulfonyl}-4-piperidinyl)-5-phenyl-1H-indole-7-carboxamide;
5-phenyl-3-(1-{[3-(1-pyrrolidinyl)propyl]sulfonyl}-4-piperidinyl)-1H-indole-7-carboxamide;
3-(1-{[3-(dimethylamino)propyl]sulfonyl}-4-piperidinyl)-5-(3-thienyl)-1H-indole-7-carboxamide;
3-(1-{[3-(dimethylamino)propyl]sulfonyl}-4-piperidinyl)-5-(2-thienyl)-1H-indole-7-carboxamide;
3-(1-{[3-(1-pyrrolidinyl)propyl]sulfonyl}-4-piperidinyl)-5-(2-thienyl)-1H-indole-7-carboxamide;
3-(1-{[3-(2-methyl-1-pyrrolidinyl)propyl]sulfonyl}-4-piperidinyl)-5-(2-thienyl)-1H-indole-7-carboxamide;
3-(1-{[3-(cyclopentylamino)propyl]sulfonyl}-4-piperidinyl)-5-(2-thienyl)-1H-indole-7-carboxamide;
3-(1-{[3-(4-hydroxy-1-piperidinyl)propyl]sulfonyl}-4-piperidinyl)-5-(2-thienyl)-1H-indole-7-carboxamide;
3-(1-{[2-(cyclopentylamino)ethyl]sulfonyl}-4-piperidinyl)-5-(2-thienyl)-1H-indole-7-carboxamide;
3-(1-{[2-(1-pyrrolidinyl)ethyl]sulfonyl}-4-piperidinyl)-5-(3-thienyl)-1H-indole-7-carboxamide;
3-(1-{[2-(dimethylamino)ethyl]sulfonyl}-4-piperidinyl)-5-(3-thienyl)-1H-indole-7-carboxamide;
3-(1-{[2-(cyclopentylamino)ethyl]sulfonyl}-4-piperidinyl)-5-(3-thienyl)-1H-indole-7-carboxamide;
3-(1-{[2-(4-hydroxy-1-piperidinyl)ethyl]sulfonyl}-4-piperidinyl)-5-(3-thienyl)-1H-indole-7-carboxamide;
3-{1-[(2-hydroxyethyl)sulfonyl]-4-piperidinyl}-5-phenyl-1H-indole-7-carboxamide;
5-(5-chloro-2-thienyl)-3-(1-{[3-(1-pyrrolidinyl)propyl]sulfonyl}-4-piperidinyl)-1H-indole-7-carboxamide;
3-(1-{[2-(methylamino)ethyl]sulfonyl}-4-piperidinyl)-5-phenyl-1H-indole-7-carboxamide;
5-phenyl-3-(1-{[2-(1-piperidinyl)ethyl]sulfonyl}-4-piperidinyl)-1H-indole-7-carboxamide;
3-(1-{[2-(4-methyl-1-piperazinyl)ethyl]sulfonyl}-4-piperidinyl)-5-phenyl-1H-indole-7-carboxamide;
3-(1-{[2-(4-morpholinyl)ethyl]sulfonyl}-4-piperidinyl)-5-phenyl-1H-indole-7-carboxamide;
5-phenyl-3-(1-{[2-(1-pyrrolidinyl)ethyl]sulfonyl}-4-piperidinyl)-1H-indole-7-Carboxamide;
3-(1-{[2-(4-hydroxy-1-piperidinyl)ethyl]sulfonyl}-4-piperidinyl)-5-phenyl-1H-indole-7-carboxamide;
3-[1-({2-[[3-(dimethylamino)propyl](methyl)amino]ethyl}sulfonyl)-4-piperidinyl]-5-phenyl-1H-indole-7-carboxamide;
3-(1-{[2-(1,4'-bipiperidin-1'-yl)ethyl]sulfonyl}-4-piperidinyl)-5-phenyl-1H-indole-7-carboxamide;
3-(1-{[2-(diethylamino)ethyl]sulfonyl}-4-piperidinyl)-5-phenyl-1H-indole-7-carboxamide;
3-(1-{[2-(hexahydro-1H-azepin-1-yl)ethyl]sulfonyl}-4-piperidinyl)-5-phenyl-1H-indole-7-carboxamide;
3-(1-{[2-(ethylamino)ethyl]sulfonyl}-4-piperidinyl)-5-phenyl-1H-indole-7-carboxamide;
3-[1-({2-[ethyl(methyl)amino]ethyl}sulfonyl)-4-piperidinyl]-5-phenyl-1H-indole-7-carboxamide;
3-[1-({2-[(2-hydroxyethyl)amino]ethyl}sulfonyl)-4-piperidinyl]-5-phenyl-1H-indole-7-carboxamide;
3-{1-[(2-{[(2S)-2-hydroxypropyl]amino}ethyl)sulfonyl]-4-piperidinyl}-5-phenyl-1H-indole-7-carboxamide;
3-{1-[(2-{[(1S)-2-hydroxy-1-methylethyl]amino}ethyl)sulfonyl]-4-piperidinyl}-5-phenyl-1H-indole-7-carboxamide;
3-(1-{[2-(4-acetyl-1-piperazinyl)ethyl]sulfonyl}-4-piperidinyl)-5-phenyl-1H-indole-7-carboxamide;
3-[1-({2-[4-(2-hydroxyethyl)-1-piperazinyl]ethyl}sulfonyl)-4-piperidinyl]-5-phenyl-1H-indole-7-carboxamide;
3-{1-[(2-{methyl[2-(methylamino)ethyl]amino}ethyl)sulfonyl]-4-piperidinyl}-5-phenyl-1H-indole-7-carboxamide;
3-{1-[(2-{4-[2-oxo-2-(1-pyrrolidinyl)ethyl]-1-piperazinyl}ethyl)sulfonyl]-4-piperidinyl}-5-phenyl-1H-indole-7-carboxamide;
3-{1-[(2-{2-[(dimethylamino)carbonyl]-1-pyrrolidinyl}ethyl)sulfonyl]-4-piperidinyl}-5-phenyl-1H-indole-7-carboxamide;
3-[1-({2-[(2S)-2-(hydroxymethyl)-1-pyrrolidinyl]ethyl}sulfonyl)-4-piperidinyl]-5-phenyl-1H-indole-7-carboxamide;
3-[1-({2-[(2S)-2-(aminocarbonyl)-1-pyrrolidinyl]ethyl}sulfonyl)-4-piperidinyl]-5-phenyl-1H-indole-7-carboxamide;
5-[5-(hydroxymethyl)-2-thienyl]-3-(1-{[3-(1-pyrrolidinyl)propyl]sulfonyl}-4-piperidinyl)-1H-indole-7-carboxamide;
5-[5-(1-pyrrolidinylmethyl)-2-thienyl]-3-(1-{[3-(1-pyrrolidinyl)propyl]sulfonyl}-4-piperidinyl)-1H-indole-7-carboxamide;
3-[1-({3-[bis(1-methylethyl)amino]propyl}sulfonyl)-4-piperidinyl]-5-phenyl-1H-indole-7-carboxamide;
3-(1-{[2-(methyloxy)ethyl]sulfonyl}-4-piperidinyl)-5-phenyl-1H-indole-7-carboxamide;
3-[1-({3-[(2S,5S)-2,5-dimethyl-1-pyrrolidinyl]propyl}sulfonyl)-4-piperidinyl]-5-phenyl-1H-indole-7-carboxamide;
3-(1-{[3-(4-methyl-1-piperazinyl)propyl]sulfonyl}-4-piperidinyl)-5-(2-thienyl)-1H-indole-7-carboxamide;
3-(1-{[3-(4-hydroxy-1-piperidinyl)propyl]sulfonyl}-4-piperidinyl)-5-(3-thienyl)-1H-indole-7-carboxamide;
3-(1-{[3-(4-methyl-1-piperazinyl)propyl]sulfonyl}-4-piperidinyl)-5-(3-thienyl)-1H-indole-7-carboxamide;
3-(1-{[3-(4-morpholinyl)propyl]sulfonyl}-4-piperidinyl)-5-(2-thienyl)-1H-indole-7-carboxamide;
3-(1-{[3-(4-morpholinyl)propyl]sulfonyl}-4-piperidinyl)-5-(3-thienyl)-1H-indole-7-carboxamide;
5-(4-fluorophenyl)-3-(1-{[3-(1-pyrrolidinyl)propyl]sulfonyl}-4-piperidinyl)-1H-indole-7-carboxamide;
3-(1-{[3-(dimethylamino)propyl]sulfonyl}-4-piperidinyl)-5-(1H-pyrazol-4-yl)-1H-indole-7-carboxamide;
5-[3-(hydroxymethyl)phenyl]-3-(1-{[3-(1-pyrrolidinyl)propyl]sulfonyl}-4-piperidinyl)-1H-indole-7-carboxamide;
5-(4-methylphenyl)-3-(1-{[3-(1-pyrrolidinyl)propyl]sulfonyl}-4-piperidinyl)-1H-indole-7-carboxamide;
3-[1-({3-[[3-(dimethylamino)propyl](methyl)amino]propyl}sulfonyl)-4-piperidinyl]-5-phenyl-1H-indole-7-carboxamide;
3-(1-{[3-(1,4'-bipiperidin-1'-yl)propyl]sulfonyl}-4-piperidinyl)-5-phenyl-1H-indole-7-carboxamide;
3-(1-{[3-(hexahydro-1H-azepin-1-yl)propyl]sulfonyl}-4-piperidinyl)-5-phenyl-1H-indole-7-carboxamide;
3-(1-{[3-(4-{2-[(1-methylethyl)amino]-2-oxoethyl}-1-piperazinyl)propyl]sulfonyl}-4-piperidinyl)-5-phenyl-1H-indole-7-carboxamide;
3-(1-{[3-(3-hydroxy-1-pyrrolidinyl)propyl]sulfonyl}-4-piperidinyl)-5-phenyl-1H-indole-7-carboxamide;

3-[1-({3-[(2S)-2-(hydroxymethyl)-1-pyrrolidinyl]propyl}sulfonyl)-4-piperidinyl]-5-phenyl-1H-indole-7-carboxamide;

3-(1-{[3-(diethylamino)propyl]sulfonyl}-4-piperidinyl)-5-phenyl-1H-indole-7-carboxamide;

3-[1-({3-[[2-hydroxy-2-(4-hydroxyphenyl)ethyl](methyl)amino]propyl}sulfonyl)-4-piperidinyl]-5-phenyl-1H-indole-7-carboxamide;

3-[1-({3-[2-(hydroxymethyl)-1-piperidinyl]propyl}sulfonyl)-4-piperidinyl]-5-phenyl-1H-indole-7-carboxamide;

3-{1-[(3-{[(1S)-1-(hydroxymethyl)-2-methylpropyl]amino}propyl)sulfonyl]-4-piperidinyl}-5-phenyl-1H-indole-7-carboxamide;

3-[1-({3-[(2-hydroxy-1-methylethyl)amino]propyl}sulfonyl)-4-piperidinyl]-5-phenyl-1H-indole-7-carboxamide;

3-{1-[(3-{[2-(dimethylamino)ethyl]amino}propyl)sulfonyl]-4-piperidinyl}-5-phenyl-1H-indole-7-carboxamide;

3-[1-({3-[(trans-4-hydroxycyclohexyl)amino]propyl}sulfonyl)-4-piperidinyl]-5-phenyl-1H-indole-7-carboxamide;

3-[1-({3-[(2-hydroxypropyl)amino]propyl}sulfonyl]-4-piperidinyl]-5-phenyl-1H-indole-7-carboxamide;

3-{1-[(3-{[1-methyl-2-(methyloxy)ethyl]amino}propyl)sulfonyl]-4-piperidinyl}-5-phenyl-1H-indole-7-carboxamide;

3-[1-({3-[(2-hydroxybutyl)amino]propyl}sulfonyl)-4-piperidinyl]-5-phenyl-1H-indole-7-carboxamide;

3-{1-[(3-{[(2R)-2-hydroxypropyl]amino}propyl)sulfonyl]-4-piperidinyl}-5-phenyl-1H-indole-7-carboxamide;

3-{1-[(3-{[(1R)-1-(hydroxymethyl)-2-methylpropyl]amino}propyl)sulfonyl]-4-piperidinyl}-5-phenyl-1H-indole-7-carboxamide;

3-{1-[(3-{[(1S)-1-(hydroxymethyl)propyl]amino}propyl)sulfonyl]-4-piperidinyl}-5-phenyl-1H-indole-7-carboxamide;

3-(1-{[3-(cyclohexylamino)propyl]sulfonyl}-4-piperidinyl)-5-phenyl-1H-indole-7-carboxamide;

3-(1-{[3-(methyloxy)propyl]sulfonyl}-4-piperidinyl)-5-phenyl-1H-indole-7-carboxamide;

3-{1-[(3-hydroxypropyl)sulfonyl]-4-piperidinyl}-5-phenyl-1H-indole-7-carboxamide;

3-(1-{[2-(ethyloxy)ethyl]sulfonyl}-4-piperidinyl)-5-phenyl-1H-indole-7-carboxamide;

3-(1-{[3-(ethyloxy)propyl]sulfonyl}-4-piperidinyl)-5-phenyl-1H-indole-7-carboxamide;

3-[1-({2-[(4-hydroxybutyl)oxy]ethyl}sulfonyl)-4-piperidinyl]-5-phenyl-1H-indole-7-carboxamide;

5-phenyl-3-{1-[(2-{[2-(1-pyrrolidinyl)ethyl]oxy}ethyl)sulfonyl]-4-piperidinyl}-1H-indole-7-carboxamide;

5-{3-[(methylamino)methyl]phenyl}-3-(1-{[3-(methyloxy)propyl]sulfonyl}-4-piperidinyl)-1H-indole-7-carboxamide;

5-{3-[(ethylamino)methyl]phenyl}-3-(1-{[3-(methyloxy)propyl]sulfonyl}-4-piperidinyl)-1H-indole-7-carboxamide;

5-(3-{[(1-methylethyl)amino]methyl}phenyl)-3-(1-{[3-(methyloxy)propyl]sulfonyl}-4-piperidinyl)-1H-indole-7-carboxamide;

3-(1-{[3-(methyloxy)propyl]sulfonyl}-4-piperidinyl)-5-{3-[(propylamino)methyl]phenyl}-1H-indole-7-carboxamide;

5-[3-({[(2S)-2-hydroxypropyl]amino}methyl)phenyl]-3-(1-{[3-(methyloxy)propyl]sulfonyl}-4-piperidinyl)-1H-indole-7-carboxamide;

5-(3-{[(cyclopropylmethyl)amino]methyl}phenyl)-3-(1-{[3-(methyloxy)propyl]sulfonyl}-4-piperidinyl)-1H-indole-7-carboxamide;

5-[3-({[2-(methyloxy)ethyl]amino}methyl)phenyl]-3-(1-{[3-(methyloxy)propyl]sulfonyl}-4-piperidinyl)-1H-indole-7-carboxamide;

5-(3-{[(2,2-dimethylpropyl)amino]methyl}phenyl)-3-(1-{[3-(methyloxy)propyl]sulfonyl}-4-piperidinyl)-1H-indole-7-carboxamide;

5-[3-({[3-(methyloxy)propyl]amino}methyl)phenyl]-3-(1-{[3-(methyloxy)propyl]sulfonyl}-4-piperidinyl)-1H-indole-7-carboxamide;

5-[3-({[2-(ethyloxy)ethyl]amino}methyl)phenyl]-3-(1-{[3-(methyloxy)propyl]sulfonyl}-4-piperidinyl)-1H-indole-7-carboxamide;

3-(1-{[3-(methyloxy)propyl]sulfonyl}-4-piperidinyl)-5-(3-{[(tetrahydro-2-furanylmethyl)amino]methyl}phenyl)-1H-indole-7-carboxamide;

3-(1-{[3-(methyloxy)propyl]sulfonyl}-4-piperidinyl)-5-[3-({[(2R)-tetrahydro-2-furanylmethyl]amino}methyl)phenyl]-1H-indole-7-carboxamide;

5-[3-({[(1S)-1,2-dimethylpropyl]amino}methyl)phenyl]-3-(1-{[3-(methyloxy)propyl]sulfonyl}-4-piperidinyl)-1H-indole-7-carboxamide;

5-[3-({[1-methyl-2-(methyloxy)ethyl]amino}methyl)phenyl]-3-(1-{[3-(methyloxy)propyl]sulfonyl}-4-piperidinyl)-1H-indole-7-carboxamide;

3-(1-{[3-(methyloxy)propyl]sulfonyl}-4-piperidinyl)-5-[3-({[(1S)-1,2,2-trimethylpropyl]amino}methyl)phenyl]-1H-indole-7-carboxamide;

5-[3-({[(5-methyl-2-furanyl)methyl]amino}methyl)phenyl]-3-(1-{[3-(methyloxy)propyl]sulfonyl}-4-piperidinyl)-1H-indole-7-carboxamide;

5-(3-{[(4-hydroxybutyl)amino]methyl}phenyl)-3-(1-{[3-(methyloxy)propyl]sulfonyl}-4-piperidinyl)-1H-indole-7-carboxamide;

3-(1-{[3-(methyloxy)propyl]sulfonyl}-4-piperidinyl)-5-(3-{[(4-pyridinylmethyl)amino]methyl}phenyl)-1H-indole-7-carboxamide;

3-(1-{[3-(methyloxy)propyl]sulfonyl}-4-piperidinyl)-5-(3-{[(2-pyridinylmethyl)amino]methyl}phenyl)-1H-indole-7-carboxamide;

3-(1-{[3-(methyloxy)propyl]sulfonyl}-4-piperidinyl)-5-(3-{[methyl(2-propen-1-yl)amino]methyl}phenyl)-1H-indole-7-carboxamide;

5-(3-{[(3R)-3-hydroxy-1-pyrrolidinyl]methyl}phenyl)-3-(1-{[3-(methyloxy)propyl]sulfonyl}-4-piperidinyl)-1H-indole-7-carboxamide;

3-(1-{[3-(methyloxy)propyl]sulfonyl}-4-piperidinyl)-5-(2-thienyl)-1H-indole-7-carboxamide;

3-(1-{[3-(ethyloxy)propyl]sulfonyl}-4-piperidinyl)-5-(2-thienyl)-1H-indole-7-carboxamide; or 3-(1-{[3-(methyloxy)propyl]sulfonyl}-4-piperidinyl)-5-(3-thienyl)-1H-indole-7-carboxamide;

or a pharmaceutically acceptable salt thereof.

Another embodiment of the present invention is a compound which is:

3-{1-[(2-aminoethyl)sulfonyl]-4-piperidinyl}-5-phenyl-1H-indole-7-carboxamide;

3-(1-{[2-(dimethylamino)ethyl]sulfonyl}-4-piperidinyl)-5-phenyl-1H-indole-7-carboxamide;

3-(1-{[3-(dimethylamino)propyl]sulfonyl}-4-piperidinyl)-5-phenyl-1H-indole-7-carboxamide;

3-(1-{[3-(4-morpholinyl)propyl]sulfonyl}-4-piperidinyl)-5-phenyl-1H-indole-7-carboxamide;

5-phenyl-3-(1-{[3-(1-pyrrolidinyl)propyl]sulfonyl}-4-piperidinyl)-1H-indole-7-carboxamide;
3-(1-{[3-(dimethylamino)propyl]sulfonyl}-4-piperidinyl)-5-(3-thienyl)-1H-indole-7-carboxamide;
5-phenyl-3-(1-{[2-(1-pyrrolidinyl)ethyl]sulfonyl}-4-piperidinyl)-1H-indole-7-carboxamide;
3-(1-{[2-(methyloxy)ethyl]sulfonyl}-4-piperidinyl)-5-phenyl-1H-indole-7-carboxamide;
3-[1-({3-[(2S,5S)-2,5-dimethyl-1-pyrrolidinyl]propyl}sulfonyl)-4-piperidinyl]-5-phenyl-1H-indole-7-carboxamide;
3-(1-{[3-(4-morpholinyl)propyl]sulfonyl}-4-piperidinyl)-5-(2-thienyl)-1H-indole-7-carboxamide;
3-(1-{[3-(4-morpholinyl)propyl]sulfonyl}-4-piperidinyl)-5-(3-thienyl)-1H-indole-7-carboxamide;
3-(1-{[3-(diethylamino)propyl]sulfonyl}-4-piperidinyl)-5-phenyl-1H-indole-7-carboxamide;
3-(1-{[3-(methyloxy)propyl]sulfonyl}-4-piperidinyl)-5-phenyl-1H-indole-7-carboxamide;
5-(3-{[(2,2-dimethylpropyl)amino]methyl}phenyl)-3-(1-{[3-(methyloxy)propyl]sulfonyl}-4-piperidinyl)-1H-indole-7-carboxamide; or
3-(1-{[3-(methyloxy)propyl]sulfonyl}-4-piperidinyl)-5-(3-thienyl)-1H-indole-7-carboxamide;

or a pharmaceutically acceptable salt thereof.

Another embodiment of the present invention is a compound according to formula Ia wherein:

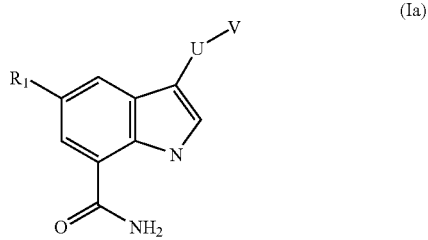

(Ia)

where $R_1$ is H, halogen, or a group —YZ;

Y is a bond, $C_1$-$C_6$ alkylene, $C_2$-$C_6$ alkenylene, or $C_2$-$C_6$ alkynylene;

Z is optionally substituted aryl or optionally substituted heteroaryl, where said aryl and heteroaryl are optionally substituted with one to three substituents independently selected from the group consisting of: halo, CN, N(Rb)SO$_2$Re, N(Rb)C(O)Ra, C(O)NRaRb, C(O)NRfRg, SO$_2$NRaRb, SO$_2$NRfRg, ORc, N(Rb)C(O)NRaRb, N(Rb)C(O)NRfRg, N(Rb)C(O)ORd, $C_1$-$C_6$ alkyl, $C_1$-$C_6$ alkyl substituted with one to three substituents independently selected from the group consisting of: NRaRb, $C_3$-$C_6$ cycloalkyl, phenyl, heterocycloalkyl, and heterocycloalkyl substituted with one or two $C_1$-$C_6$ alkyl groups; $C_1$-$C_6$ haloalkyl, $C_1$-$C_6$ haloalkyl substituted with one to three substituents independently selected from the group consisting of NRaRb, $C_3$-$C_6$ cycloalkyl, phenyl, heterocycloalkyl, and heterocycloalkyl substituted with one or two $C_1$-$C_6$ alkyl groups; heterocycloalkyl and heterocycloalkyl substituted with one or two $C_1$-$C_6$ alkyl groups;

U is a bond, $C_1$-$C_6$ alkylene or $C_2$-$C_6$ alkenylene;

V is phenyl, 5 or 6 membered heteroaryl, 5-7 membered heterocycloalkyl, $C_5$-$C_7$cycloalkyl, or $C_5$-$C_7$cycloalkenyl, each of which is substituted by N(Rb)S(O)$_m$R$_2$; or V is N(Rb)S(O)$_m$R$_2$,

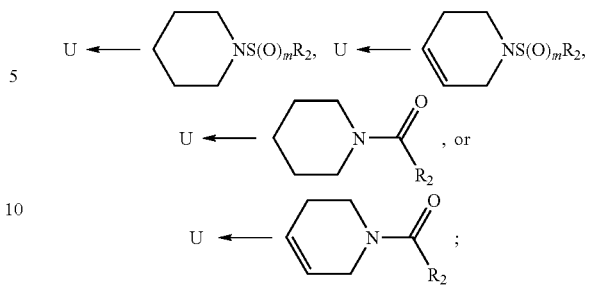

m is 1 or 2;

$R_2$ is the group X—$R_3$;

X is a bond, $C_1$-$C_6$ alkylene, $C_2$-$C_6$ alkenylene, $C_2$-$C_6$ alkynylene, aryl, $C_1$-$C_6$ alkylene-aryl, heteroaryl, $C_1$-$C_6$ alkylene-heteroaryl, heterocycloalkyl, $C_1$-$C_6$ alkylene-heterocycloalkyl, $C_4$-$C_7$cycloalkyl, $C_1$-$C_6$ alkylene-$C_4$-$C_7$cycloalkyl, $C_5$-$C_7$cycloalkenyl, or $C_1$-$C_6$ alkylene-$C_5$-$C_7$cycloalkenyl;

$R_3$ is NRaRb, optionally substituted heterocycloalkyl, or optionally substituted heteroaryl;

where said heterocycloalkyl and heteroaryl are optionally substituted with one to three substituents independently selected from the group consisting of: halo, heterocycloalkyl, oxo, CN, C(O)Ra, N(Rb)SO$_2$Re, N(Rb)C(O)Ra, NRaRb, C(O)NRaRb, C(O)NRfRg, SO$_2$NRaRb, SO$_2$NRfRg, ORc, C(O)ORc, N(Rb)C(O)NRaRb, N(Rb)C(O)NRfRg, N(Rb)C(O)ORd, $C_1$-$C_6$ alkyl, $C_1$-$C_6$ alkyl substituted with one to three substituents independently selected from the group consisting of: NRaRb, ORc, C(O)NRaRb, $C_3$-$C_6$ cycloalkyl, heterocycloalkyl, and phenyl; $C_1$-$C_6$ haloalkyl, $C_1$-$C_6$ haloalkyl substituted with one to three substituents independently selected from the group consisting of: NRaRb, ORc, C(O)NRaRb, $C_3$-$C_6$ cycloalkyl, heterocycloalkyl, and phenyl; heterocycloalkyl, heterocycloalkyl substituted with one to three substituents independently selected from the group consisting of: halo, ORc, haloalkyl, CN, and SO$_2$Ri; phenyl, and phenyl substituted with one to three substituents independently selected from the group consisting of: halo, ORc, haloalkyl, CN, and SO$_2$Ri;

each Ra is independently selected from the group consisting of: H, $C_2$-$C_6$ alkenyl, $C_1$-$C_6$ alkyl, $C_1$-$C_6$ alkyl substituted with one to three substituents independently selected from the group consisting of: halo, CN, C(O)NH$_2$, N(CH$_3$)$_2$, SO$_2$Ri, C(O)ORb, N(Rb)C(O)Rb, ORe, SRc, $C_3$-$C_7$ cycloalkyl, $C_1$-$C_6$ haloalkyl, heterocycloalkyl, phenyl, and heteroaryl; phenyl, phenyl substituted with one to three substituents independently selected from the group consisting of: halo, oxo, $C_1$-$C_6$ alkyl, $C_1$-$C_6$ haloalkyl, NH$_2$, heteroaryl, ORc, and NRfRg; heteroaryl, heteroaryl substituted with one to three substituents independently selected from the group consisting of: halo, oxo, $C_1$-$C_6$ alkyl, $C_1$-$C_6$ haloalkyl, NH$_2$, heteroaryl, ORc, and NRfRg; $C_3$-$C_7$ cycloalkyl, $C_3$-$C_7$ cycloalkyl substituted with one to three substituents independently selected from the group consisting of: halo, oxo, $C_1$-$C_6$ alkyl, $C_1$-$C_6$ haloalkyl, NH$_2$, heteroaryl, ORc, and NRfRg; heterocycloalkyl, and heterocycloalkyl substituted with one to three substituents independently selected from the group consisting of: halo, oxo, $C_1$-$C_6$ alkyl, $C_1$-$C_6$ haloalkyl, NH$_2$, heteroaryl, ORc and NRfRg;

each Rb is independently selected from the group consisting of: H, $C_1$-$C_3$ alkyl, and $C_3$-$C_7$ cycloalkyl;

each Rc is independently selected from the group consisting of: H, $C_1$-$C_6$ alkyl, $C_1$-$C_6$ alkyl substituted with one to three substituents independently selected from the group consisting of: OH, $C_3$-$C_6$ cycloalkyl, phenyl, heterocycloalkyl, and heteroaryl; $C_1$-$C_6$ haloalkyl, $C_1$-$C_6$ haloalkyl substituted with one to three substituents independently selected from the group consisting of: OH, $C_3$-$C_6$ cycloalkyl, phenyl, heterocycloalkyl, and heteroaryl; $C_3$-$C_7$ cycloalkyl, $C_3$-$C_7$ cycloalkyl substituted with one to three $C_1$-$C_3$ alkyl groups; heterocycloalkyl, heterocycloalkyl substituted with one to three $C_1$-$C_3$ alkyl groups; aryl, aryl substituted with one to three substituents independently selected from the group consisting of: halo, $C_1$-$C_3$ alkyl, $C_1$-$C_3$ haloalkyl, and OH; heteroaryl, and heteroaryl substituted with one to three substituents independently selected from the group consisting of: halo, $C_1$-$C_3$ alkyl, $C_1$-$C_3$ haloalkyl, and OH;

each Rd is independently an optionally substituted $C_1$-$C_3$ alkyl, where said $C_1$-$C_3$ alkyl is optionally substituted with one to three substituents selected from the group consisting of: $C_3$-$C_6$ cycloalkyl, optionally substituted phenyl, and optionally substituted heteroaryl; where said phenyl and heteroaryl are optionally substituted with one to three substituents selected from the group consisting of: halo, $C_1$-$C_6$ alkyl and $C_3$-$C_6$ cycloalkyl;

each Re is independently selected from the group consisting of: $C_1$-$C_6$ alkyl, $C_1$-$C_6$ alkyl substituted with one substituent selected from the group consisting of: phenyl, heteroaryl, heterocycloalkyl, and NRaRb; phenyl, phenyl substituted with one to three substituents selected from the group consisting of: halo, CN, $C_1$-$C_6$ alkyl, $C_1$-$C_6$ haloalkyl, and ORh; heteroaryl, heteroaryl substituted with one to three substituents selected from the group consisting of: halo, CN, $C_1$-$C_6$ alkyl, $C_1$-$C_6$ haloalkyl, and, ORh; $C_5$-$C_7$ cycloalkyl, $C_5$-$C_7$ cycloalkyl substituted with one to three substituents selected from the group consisting of: halo, $C_1$-$C_6$ alkyl, and $C_3$-$C_6$ cycloalkyl; heterocycloalkyl, and heterocycloalkyl substituted with one to three substituents selected from the group consisting of: halo, $C_1$-$C_6$ alkyl, and $C_3$-$C_6$ cycloalkyl;

Rf and Rg taken together with the nitrogen atom to which they are attached form a ring having from 5 to 7 member atoms wherein said ring optionally contains one additional heteroatom as a member atom, said ring is saturated or unsaturated but not aromatic, and said ring is optionally substituted with one or two $C_1$-$C_3$ alkyl substituents;

each Rh is independently selected from the group consisting of: H, $C_1$-$C_6$ alkyl, and $C_1$-$C_6$ haloalkyl; and each Ri is independently selected from the group consisting of: $C_1$-$C_3$ alkyl and OH; or a pharmaceutically-acceptable salt, solvate, or polymorph thereof.

Another embodiment of the present invention is a compound according to formula Ia wherein:

$R_1$ is a group —YZ;

Y is a bond;

Z is heteroaryl, phenyl, or phenyl substituted with one substituent selected from the group consisting of: halo, N(Rb)SO$_2$Re, SO$_2$NRaRb, $C_1$-$C_6$ alkyl, and $C_1$-$C_6$ alkyl substituted with one substituent selected from the group consisting of: NRaRb, heterocycloalkyl, and heterocycloalkyl substituted with one $C_1$-$C_3$ alkyl group;

U is a bond;

V is m is 2;

$R_2$ is the group X—$R_3$;

X is a bond or $C_1$-$C_6$ alkylene;

$R_3$ is NRaRb, optionally substituted heterocycloalkyl, or optionally substituted heteroaryl;

where said heterocycloalkyl and heteroaryl are optionally substituted with one to three substituents independently selected from the group consisting of: halo, optionally substituted $C_1$-$C_6$ alkyl, heteroaryl, oxo, N(Rb)C(O)Ra, ORc, and C(O)ORc; where said $C_1$-$C_6$ alkyl is optionally substituted with one NRaRb group;

each Ra is independently selected from the group consisting of: H, optionally substituted $C_1$-$C_3$ alkyl, and phenyl, where said $C_1$-$C_3$ alkyl is optionally substituted with one to three substituents selected from the group consisting of: halo and phenyl;

each Rb is independently selected from the group consisting of: H and $C_1$-$C_3$ alkyl;

each Rc is independently selected from the group consisting of: H, $C_1$-$C_6$ alkyl, and aryl; and each Re is independently selected from the group consisting of: $C_1$-$C_6$ alkyl and phenyl; or a pharmaceutically-acceptable salt, solvate, or polymorph thereof.

Another embodiment of the present invention is a compound which is:

3-(1-{[2-(1,3-dioxo-1,3-dihydro-2H-isoindol-2-yl)ethyl]sulfonyl}-4-piperidinyl)-5-phenyl-1H-indole-7-carboxamide;

3-{1-[(2-aminoethyl)sulfonyl]-4-piperidinyl}-5-phenyl-1H-indole-7-carboxamide;

3-(1-{[2-(dimethylamino)ethyl]sulfonyl}-4-piperidinyl)-5-phenyl-1H-indole-7-carboxamide;

3-(1-{[3-(dimethylamino)propyl]sulfonyl}-4-piperidinyl)-5-phenyl-1H-indole-7-carboxamide;

3-(1-{[3-(4-methyl-1-piperazinyl)propyl]sulfonyl}-4-piperidinyl)-5-phenyl-1H-indole-7-carboxamide;

5-phenyl-3-(1-{[3-(1-piperidinyl)propyl]sulfonyl}-4-piperidinyl)-1H-indole-7-carboxamide;

3-(1-{[3-(4-morpholinyl)propyl]sulfonyl}-4-piperidinyl)-5-phenyl-1H-indole-7-carboxamide; or 5-phenyl-3-(1-{[3-(1-pyrrolidinyl)propyl]sulfonyl}-4-piperidinyl)-1H-indole-7-carboxamide;

or a pharmaceutically acceptable salt thereof.

TERMS AND DEFINITIONS

"Alkyl" refers to a saturated hydrocarbon chain having the specified number of member atoms. For example, $C_1$-$C_6$ alkyl refers to an alkyl group having from 1 to 6 member atoms. Alkyl groups may be optionally substituted with one or more substituents as defined herein. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Alkylene" when used alone or in forming other groups (such as the $C_1$-$C_6$ alkylene-heteroaryl, $C_1$-$C_6$ alkylene-heterocycloalkyl, $C_1$-$C_6$ alkylene-$C_4$-$C_7$cycloalkyl, and $C_1$-$C_6$ alkylene-$C_5$-$C_7$cycloalkenyl groups) refers to a saturated divalent hydrocarbon chain having the specified number of member atoms. For example, $C_1$-$C_6$ alkylene refers to an alkylene group having from 1 to 6 member atoms. Alkylene groups may be optionally substituted with one or more substituents as defined herein. Alkylene groups may be straight or branched. Representative branched alkylene groups have one, two, or three branches. Alkylene includes methylene, ethylene, propylene (n-propylene and isopropylene), butylene (n-butylene, isobutylene, and t-butylene), pentylene (n-pentylene, isopentylene, and neopentylene), and hexylene.

"Alkenyl" refers to an unsaturated hydrocarbon chain having the specified number of member atoms and having one or more carbon-carbon double bond within the chain. For example, $C_2$-$C_6$ alkenyl refers to an alkenyl group having from 2 to 6 member atoms. In certain embodiments alkenyl groups have one carbon-carbon double bond within the chain. In other embodiments, alkenyl groups have more than one carbon-carbon double bond within the chain. Alkenyl groups may be optionally substituted with one or more substituents as defined herein. Alkenyl groups may be straight or branched. Representative branched alkenyl groups have one, two, or three branches. Alkenyl includes ethylenyl, propenyl, butenyl, pentenyl, and hexenyl.

"Alkenylene" refers to an unsaturated divalent hydrocarbon chain having the specified number of member atoms and having one or more carbon-carbon double bond within the chain. For example, $C_2$-$C_6$ alkenylene refers to an alkenylene group having from 2 to 6 member atoms. In certain embodiments alkenylene groups have one carbon-carbon double bond within the chain. In other embodiments, alkenylene groups have more than one carbon-carbon double bond within the chain. Alkenylene groups may be optionally substituted with one or more substituents as defined herein. Alkenylene groups may be straight or branched. Representative branched alkenylene groups have one, two, or three branches. Alkenyl includes ethylenylene, propenylene, butenylene, pentenylene, and hexenylene.

"Alkynylene" refers to an unsaturated divalent hydrocarbon chain having the specified number of member atoms and having one or more carbon-carbon triple bond within the chain. For example, $C_2$-$C_6$ alkynylene refers to an alkynylene group having from 2 to 6 member atoms. In certain embodiments alkynylene groups have one carbon-carbon triple bond within the chain. In other embodiments, alkynylene groups have more than one carbon-carbon triple bond within the chain. For the sake of clarity, unsaturated divalent hydrocarbon chains having one or more carbon-carbon triple bond within the chain and one or more carbon-carbon double bond within the chain are alkynylene groups. Alkynylene groups may be optionally substituted with one or more substituents as defined herein. Alkynylene groups may be straight or branched. Representative branched alkynylene groups have one, two, or three branches. Alkynyl includes ethylynylene, propynylene, butynylene, pentynylene, and hexynylene.

"Aryl" refers to an aromatic hydrocarbon ring. Aryl groups are monocyclic ring systems or bicyclic ring systems. Monocyclic aryl ring refers to phenyl. Bicyclic aryl rings refer to napthyl and rings wherein phenyl is fused to a cycloalkyl or cycloalkenyl ring having 5, 6, or 7 member atoms. Aryl groups may be optionally substituted with one or more substituents as defined herein.

"Cycloalkyl" refers to a saturated hydrocarbon ring having the specified number of member atoms. Cycloalkyl groups are monocyclic ring systems. For example, $C_3$-$C_6$ cycloalkyl refers to a cycloalkyl group having from 3 to 6 member atoms. Cycloalkyl groups may be optionally substituted with one or more substituents as defined herein. Cycloalkyl includes cyclopropyl, cyclobutyl, cyclopentyl, and cyclohexyl.

"Cycloalkenyl" refers to an unsaturated hydrocarbon ring having the specified number of member atoms and having a carbon-carbon double bond within the ring. For example, $C_3$-$C_6$ cycloalkenyl refers to a cycloalkenyl group having from 3 to 6 member atoms. In certain embodiments cycloalkenyl groups have one carbon-carbon double bond within the ring. In other embodiments, cycloalkenyl groups have more than one carbon-carbon double bond within the ring. However, cycloalkenyl rings are not aromatic. Cycloalkenyl groups are monocyclic ring systems. Cycloalkenyl groups may be optionally substituted with one or more substituents as defined herein. Cycloalkenyl includes cyclopropenyl, cyclobutenyl, cyclopentenyl, and cyclohexenyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" (or "half-lives") refers to the time required for half of a quantity of a substance to be converted to another chemically distinct specie in vitro or in vivo.

"Halo" refers to the halogen radical fluoro, chloro, bromo, or iodo.

"Haloalkyl" refers to an alkyl group wherein at least one hydrogen atom attached to a member atom within the alkyl group is replaced with halo. Haloalkyl includes trifluoromethyl.

"Heteroaryl" refers to an aromatic ring containing from 1 to 4 heteroatoms as member atoms in the ring. Heteroaryl groups containing more than one heteroatom may contain different heteroatoms. Heteroaryl groups may be optionally substituted with one or more substituents as defined herein. Heteroaryl groups are monocyclic ring systems or are fused, spiro, or bridged bicyclic ring systems. Monocyclic heteroaryl rings have 5 or 6 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Heteroaryl includes pyrrolyl, pyrazolyl, imidazolyl, oxazolyl, isoxazolyl, thiazolyl, isothiazolyl, furanyl, furazanyl, thienyl, triazolyl, pyridinyl, pyrimidinyl, pyridazinyl, pyrazinyl, triazinyl, tetrazinyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benopyranyl, benzoxazolyl, benzofuranyl, isobenzofuranyl, benzothiazolyl, benzothienyl, furopyridinyl, and napthyridinyl.

"Heteroatom" refers to a nitrogen, sulphur, or oxygen atom.

"Heterocycloalkyl" refers to a saturated or unsaturated ring containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituents as defined herein. Heterocycloalkyl groups are monocyclic ring systems having from 4 to 7 member atoms or a heterocycloalkyl group can be the bicyclic ring system decahydroisoquinoline. In certain embodiments, heterocycloalkyl is saturated. In other embodiments, heterocycloalkyl is unsaturated but not aromatic. Heterocycloalkyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, 1,3-dioxolanyl, 1,3-dioxanyl, 1,4-dioxanyl, 1,3-oxathiolanyl, 1,3-oxathianyl, 1,3-dithianyl, and azetidinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted or substituted with one or more substituents as defined herein. "Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
i.v. (intravenous); Hz (Hertz);
MHz (megahertz); mol (moles);
mmol (millimoles); rt (room temperature);
min (minutes); h (hours);
mp (melting point); TLC (thin layer chromatography);
$T_r$ (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); AcOEt (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1-carbonyldiimidazole);
IBCF (isobutyl chloroformate); HOAc (acetic acid);
HOSu (N-hydroxysuccinimide); HOBT (1-hydroxybenzotriazole);
mCPBA (meta-chloroperbenzoic acid;
EDC (1-[3-dimethylamino)propyl]-3-ethylcarbodiimide hydrochloride);
BOC (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); BSA (bovine serum albumin);
ATP (adenosine triphosphate); HRP (horseradish peroxidase);
DMEM (Dulbecco's modified Eagle medium);
HPLC (high pressure liquid chromatography);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluroniumhexafluoro phosphate);
HEPES (4-(2-hydroxyethyl)-1-piperazine ethane sulfonic acid);
DPPA (diphenylphosphoryl azide);
fHNO$_3$ (fuming HNO$_3$);
EDTA (ethylenediaminetetraacetic acid);
TMEDA (N,N,N',N'-tetramethyl-1,2-ethanediamine);
NBS (N-bromosuccinimide);
HATU (O-(7azabenzobenzotriazol-1-yl)-N,N,N',N'-tetramethyluronium hexafluorophosphate);
DIPEA (diisopropylethylamine);
Imes (1,3-Bis(2,4,6-trimethylphenyl)imidazolium chloride);
dppf (1,1'-bis(diphenylphosphino)ferrocene);
CLR (Controlled Laboratory Reactor); and
NIS (N-iodsuccinimide).

All references to ether are to diethyl ether and brine refers to a saturated aqueous solution of NaCl.

The compounds according to formulae I and Ia may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in formulae I and Ia, or in any chemical structure illustrated herein, is not specified the structure is intended to encompass any stereoisomer and all mixtures thereof. Thus, compounds according to formula I and Ia containing one or more chiral center may be used as racemic mixtures, enantiomerically enriched mixtures, or as enantiomerically pure individual stereoisomers.

Individual stereoisomers of a compound according to formulae I and Ia which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzamatic oxidation or reduction; or (3) by gas-liquid or liquid chromatography in a chiral enviornment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to formulae I and Ia may also contain double bonds or other centers of geometric asymmetry. Where the stereochemistry of a center of geometric asymmetry present in formulae I and Ia, or in any chemical structure illustrated herein, is not specified, the structure is intended to encompass the trans (E) geometric isomer, the cis (Z) geometric isomer, and all mixtures thereof. Likewise, all tautomeric forms are also included in formulae I and Ia whether such tautomers exist in equilibrium or predominately in one form.

The skilled artisan will appreciate that pharmaceutically-acceptable salts of the compounds according to formulae I and Ia may be prepared. Indeed, in certain embodiments of the invention, pharmaceutically-acceptable salts of the compounds according to formulae I and Ia may be preferred over the respective free base or free acid because such salts impart greater stability or solubility to the molecule thereby facilitating formulation into a dosage form. Accordingly, the invention is further directed to pharmaceutically-acceptable salts of the compounds according to formulae I and Ia.

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

In certain embodiments, compounds according to formulae I and Ia may contain an acidic functional group. Suitable pharmaceutically-acceptable salts include salts of such acidic functional groups. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to formulae I and Ia may contain a basic functional group and are therefore capable of forming pharmaceutically-acceptable acid addition salts by treatment with a suitable acid. Suitable acids include pharmaceutically-acceptable inorganic acids and pharmaceutically-acceptable organic acids. Representative pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

As used herein, the term "compounds of the invention" means both the compounds according to formulae I and Ia and the pharmaceutically-acceptable salts thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Compound Preparation

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Examples section.

Compounds of formulae I and Ia can be prepared, for example, according to Schemes 1, 2, and 3 depicted below:

Scheme 1

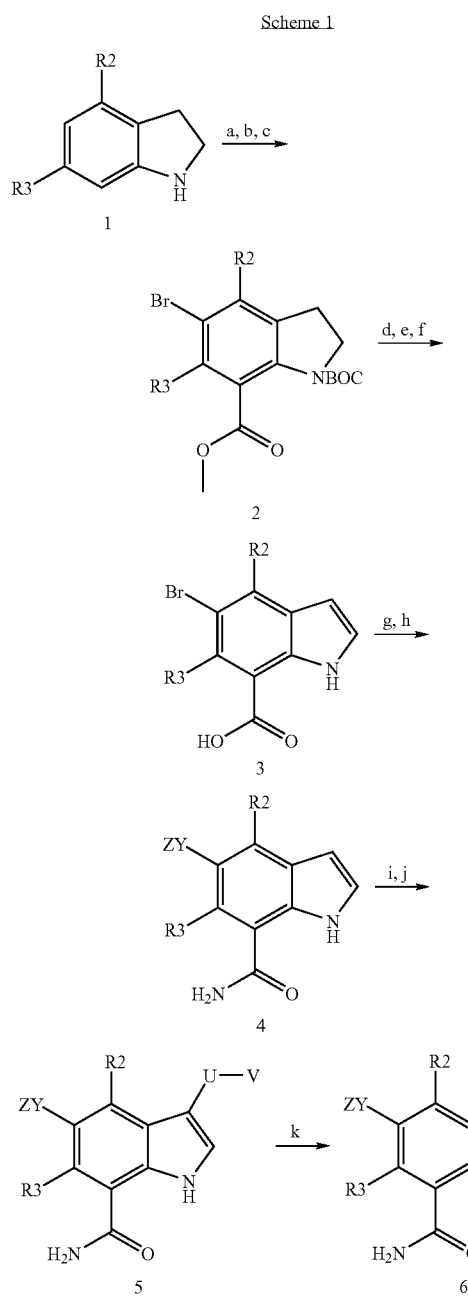

Conditions: a) (BOC)₂O, THF; b) s-BuLi, ClCO₂Me, TMEDA, Et₂O; c) N-bromosuccinimide, Methylene chloride; d) TFA; e) MnO₂, THF; f) LiOH, MeOH, water; g) ZYB(OR)₂, Imes-HCl, Pd(OAc)₂, Dioxane/water; h) HATU, NH₃, DMF; i) RCHO (or) RC(O)R', NaOMe, MeOH; j) Pd(OH)₂, H₂, HOAc, EtOH; k) R4Cl, TEA, Methylene chloride (or) (R4)₂O, DMAP, Methylene chloride Scheme 1 represents a general scheme for the preparation of compounds according to formula I wherein R2 and R3 are H, F, or Cl, U is a bond or $C_1$-$C_6$ alkylene or $C_2$-$C_6$ alkenylene and V is C5-C7 cycloalkyl or C5-C7 cycloalkenyl or heterocycloalkyl or heterocycloalkenyl. Scheme 1 also represents a general scheme for the preparation of compounds according to formula I wherein U is $C_1$-$C_6$ alkylene or $C_2$-$C_6$ alkenylene and V is NH, aryl, or heteroaryl. In Scheme 1, Y and Z are defined above unless defined otherwise. The indoline 1 depicted as starting material is commercially available. Reaction conditions are as described above in the scheme; however, the skilled artisan will appreciate that certain modifications in the reaction conditions and/or reagents used are possible.

Treatment of indoline 1 with di-tertbutyl dicarbonate in a suitable solvent such as THF or methylene chloride produces the desired BOG protected product. Further transformation to the desired bromide 2 can be accomplished via lithiation using sec-butyllithium in the presence of TMEDA and quenching with methyl chloroformate followed by bromination with N-bromosuccinimide. Treatment of bromide 2 with trifluoroacetic acid followed by oxidation of the resulting indoline to the indole with manganese dioxide and subsequent hydrolysis of the methyl ester to the acid yields the desired carboxylic acid 3. Installation of the substituent YZ can be accomplished via a transition metal mediated coupling using an appropriate catalyst and coupling partner. As an example of such a transformation, for the case in Scheme 1 condition "g", a Suzuki cross-coupling reaction can be completed using a boronic ester or acid in the presence of Pd(OAc)₂, Imes-HCl, and Cs₂CO₃ in 1,4-dioxane and water. Preparation of the primary carboxamide 4 can be completed via reaction of the carboxylic acid with ammonia in the presence of HATU. Conversion of 4 to 5 incorporating the group U-V is performed via reaction with the appropriate aldehyde or ketone precursor to U-V. This transformation can be completed Linder either basic or acidic conditions. For the case where the group U-V is fully saturated, a subsequent reduction of the intermediate product will produce the desired product 5. As an example of such a reduction, for the case in Scheme 1 condition "j", a hydrogenation reaction in the presence of Pd(OH)₂ completes the transformation to 5. In the case where U-V and/or YZ contains a suitable protecting group, removal of the protecting group under the appropriate conditions and further transformation to other products may be accomplished. Subsequent transformation of the amine function of the group U-V to either the sulfonamide or amide of R4 can be performed with the appropriate sulfonyl or acid chloride or acid anhydride of R4. It will be appreciated by the skilled artisan that upon conversion to either the sulfonamide or amide of R4 the resulting product may require further elaboration to R4. This can include but is not limited to suitable protecting and functional group manipulations and reactions with amines/alcohols R5.

Scheme 2

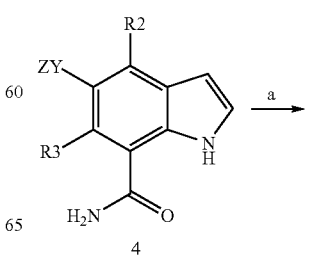

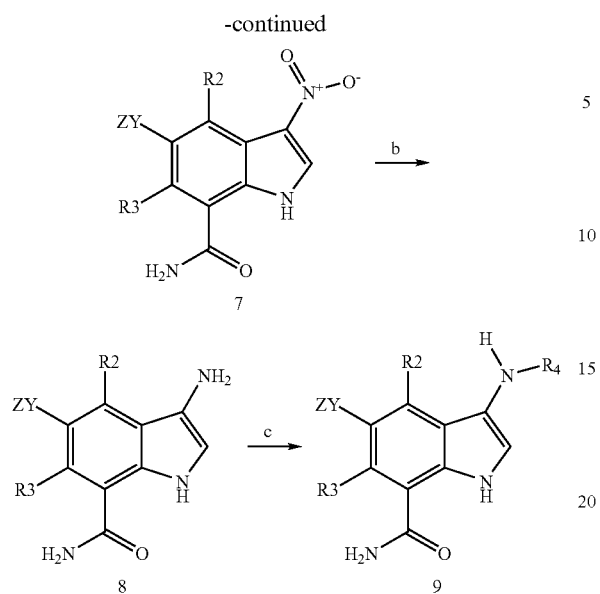

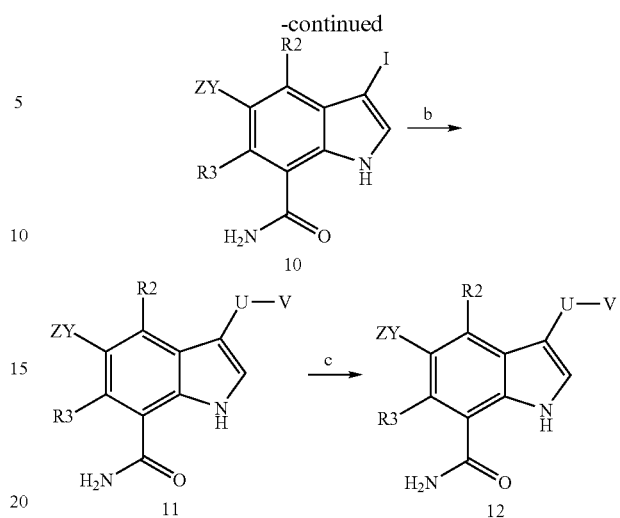

Conditions: a) Sodium nitrite, HOAc; b) Sodium dithionite; c) R4Cl, TEA, Methylene chloride (or) (R4)$_2$O, DMAP, Methylene chloride Scheme 2 represents a general scheme for the preparation of compounds according to formula I wherein U is a bond and V is NH. In Scheme 2, Y and Z are defined above unless defined otherwise. The indolecarboxamide 4 depicted as starting material is obtained as described in Scheme 1. Reaction conditions are as described above in the scheme; however, the skilled artisan will appreciate that certain modifications in the reaction conditions and/or reagents used are possible.

The preparation of C3 amino indoles can be accomplished via nitration and subsequent reduction. The conversion of 4 to 7 is performed via treatment with sodium nitrite in the presence of acetic acid. Reduction of the C3 nitro group to the amino can be accomplished using sodium dithionite. Subsequent transformation of the amine function to either the sulfonamide or amide of R4 can be performed with the appropriate sulfonyl or acid chloride or acid anhydride of R4. It will be appreciated by the skilled artisan that upon conversion to either the sulfonamide or amide of R4 the resulting product may require further elaboration to R4. This can include but is not limited to suitable protecting and functional group manipulations and reactions with amines/alcohols R5.

Scheme 3

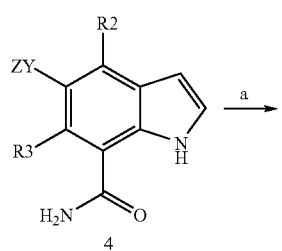

Conditions: a) N-iodosuccinimide, CH$_2$Cl$_2$; b) VUB(OR)$_2$, Pd(PPh$_3$)$_4$, Cs$_2$CO$_3$, 1,4-dioxane, water; c) R4Cl, TEA, Methylene chloride (or) (R4)$_2$O, DMAP, Methylene chloride Scheme 3 represents a general scheme for the preparation of compounds according to formula I wherein U is a bond and V is aryl or heteroaryl. In Scheme 2, Y and Z are defined above unless defined otherwise. The indolecarboxamide 4 depicted as starting material is obtained as described in Scheme 1. Reaction conditions are as described above in the scheme; however, the skilled artisan will appreciate that certain modifications in the reaction conditions and/or reagents used are possible.

The preparation of compounds of structure 12 can be completed by first converting the starting indolecarboxamide 4 to the C3 halide 10. As an example of a halide and for purposes of illustration, a C3 iodide is shown in Scheme 3. Installation of the substituent U-V can be accomplished via a transition metal mediated coupling using an appropriate catalyst and coupling partner. As an example of such a transformation, for the case in Scheme 3 condition "b", a Suzuki cross-coupling reaction can be completed using a boronic ester or acid in the presence of Pd(PPh$_3$)$_4$, and Cs$_2$CO$_3$ in 1,4-dioxane and water. Subsequent transformation of the amine function to either the sulfonamide or amide of R4 can be performed with the appropriate sulfonyl or acid chloride or acid anhydride of R4. It will be appreciated by the skilled artisan that upon conversion to either the sulfonamide or amide of R4 the resulting product may require further elaboration to R4. This can include but is not limited to suitable protecting and functional group manipulations and reactions with amines/alcohols R5.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

Methods of Use

The compounds of the invention are inhibitors of IKK2. These compounds can be useful in the treatment of disorders wherein the underlying pathology is (at least in part) attributable to inappropriate IKK2 (also known as IKKβ) activity such as rheumatoid arthritis, inflammatory bowel disease, asthma, and COPD (chronic obstructive pulmonary disease). "Inappropriate IKK2 activity" refers to any IKK2 activity that deviates from the normal IKK2 activity expected in a particular patient. Inappropriate IKK2 activity may take the form of, for instance, an abnormal increase in activity, or an aberration in the timing and or control of IKK2 activity. Such inappropriate activity may result then, for example, from overexpression or mutation of the protein kinase leading to inappropriate or uncontrolled activation. Accordingly, in another aspect the invention is directed to methods of treating such disorders.

Such disorders include inflammatory and tissue repair disorders, particularly rheumatoid arthritis, inflammatory bowel disease, asthma and COPD (chronic obstructive pulmonary disease); osteoarthritis, osteoporosis and fibrotic diseases; dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restonosis, diabetes, glomerulonephritis, cancer, including Hodgkins disease, cachexia, inflammation associated with infection and certain viral infections, including acquired immune deficiency syndrome (AIDS), adult respiratory distress syndrome, and Ataxia Telangiestasia.

The methods of treatment of the invention comprise administering a safe and effective amount of a compound according to formulae I and Ia or a pharmaceutically-acceptable salt thereof to a patient in need thereof. Individual embodiments of the invention include methods of treating any one of the above-mentioned disorders by administering a safe and effective amount of a compound according to formula I and Ia or a pharmaceutically-acceptable salt thereof to a patient in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

As indicated above, "treatment" of a disorder includes prevention of the disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.001 mg to 50 mg per kg of total body weight.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

The invention also provides a compound of the invention for use in medical therapy, and particularly in the treatment of disorders mediated by IKK2 activity. Thus, in a further aspect, the invention is directed to the use of a compound according to formulae I and Ia or a pharmaceutically-acceptable salt thereof in the preparation of a medicament for the treatment of a disorder characterized by inappropriate IKK2 activity.

Particular disorders characterised by inappropriate IKK2 activity include inflammatory and tissue repair disorders, particularly rheumatoid arthritis, inflammatory bowel disease, asthma and COPD (chronic obstructive pulmonary disease); osteoarthritis, osteoporosis and fibrotic diseases; dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including acquired immune deficiency syndrome (AIDS), adult respiratory distress syndrome, and Ataxia Telangiestasia as a result of inhibition of the protein kinase IKK2.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically may contain, for example, from 0.5 mg to 1 g, or from 1 mg to 700 mg, or from 5 mg to 100 mg of a compound of the invention.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when comingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company). In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of the invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of the invention. Syrups can be prepared by dissolving the compound of the invention in a suitably flavored aqueous solution, while elixirs are prepared through the use of a non-toxic alcoholic vehicle. Suspensions can be formulated by dispersing the compound of the invention in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides.

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 µg-10 mg of the compound of the invention.

Aerosols may be formed by suspending or dissolving a compound of the invention in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of the invention may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions may be applied as a topical ointment or cream. When formulated in an ointment, the compound of the invention may be employed with either a paraffinic or a water-miscible ointment base. Alternatively, the compound of the invention may be formulated in a cream with an oil-in-water cream base or a water-in-oil base.

Pharmaceutical compositions adapted for nasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of the invention.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Examples

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Unless otherwise noted, all starting materials were obtained from commercial suppliers and used without further purification. Unless otherwise indicated, all temperatures are expressed in ° C. (degrees Centigrade). Unless otherwise indicated, all reactions are conducted under an inert atmosphere at room temperature. For reverse phase HPLC purification (unless otherwise stated), a 50×20 mm I. D. Luna C18 5µ column using acetonitrile containing 0.1% TFA and water containing 0.1% TFA and UV detection at 215 nM and 254 nM was used.

Nuclear magnetic resonance spectra were recorded at 400 MHz using a Bruker AC 400 spectrometer. CDCl$_3$ is deuteriochloroform, DMSO-d$_6$ is hexadeuteriodimethylsulfoxide, and CD$_3$OD is tetradeuteriomethanol. Chemical shifts are reported in parts per million (δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Mass spectra were taken on a PE Sciex Single Quadrupole LC/MS API-150 using electrospray (ES) ionization techniques. Elemental analyses were obtained using a Perkin-Elmer 240C elemental analyzer.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel.

Intermediates (1) 1,1-dimethylethyl-2,3-dihydro-1H-indole-1-carboxylate

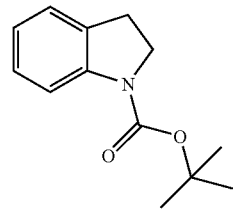

Indoline (10 g, 84 mmol) was dissolved in tetrahydrofuran (100 mL) and di-tert-butylcarbonate (22 g, 0.1 mol) was added. The mixture was left stirring for 16 hours at room temperature under an inert nitrogen atmosphere. The tetrahydrofuran was removed in vacuo and the crude product purified by vacuum distillation to give the title compound (15.1 g) as a clear pale pink oil that crystallised upon standing (temperature: 160-162° C., pressure 1-0.1 mm Hg).

$^1$H NMR (400 MHz, DMSO-D6) δ ppm 1.50 (s, 9H) 3.04 (t, J=8.7 Hz, 2H) 3.89 (t, J=8.8 Hz, 2H) 6.91 (td, J=7.3, 0.8 Hz, 1H) 7.13 (t, J=7.5 Hz, 1H) 7.18 (d, J=7.3 Hz, 1H) 7.5-7.8 (bs, 1H).

Alternative Synthesis:

To a stirred solution of indoline (250 g, 2.1 mol) and triethylamine (28.9 mL, 0.21 mol) in dichloromethane (2.5 L) at 0° C. was added portionwise di-tert-butyl dicarbonate (458 g, 2.1 mol). The mixture was stirred at 0° C. for 5 h then allowed to warm to room temperature and left to stir overnight. The mixture washed with 1N citric acid (1 L), saturated sodium bicarbonate (1 L), and brine (1 L). The organic phase was dried (MgSO$_4$), filtered, and the solvent was removed under reduced pressure to afford an oil which crystallised upon standing. The crude compound was purified by distillation (bp 110° C./0.3 mmHg) to afford 392 g (85%) of tert-butyl indoline-1-carboxylate.

(2) 1-(1,1-dimethylethyl) 7-methyl-2,3-dihydro-1H-indole-1,7-dicarboxylate

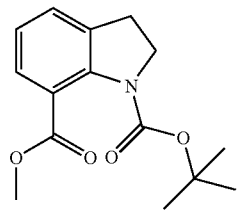

1,1-dimethylethyl 2,3-dihydro-1H-indole-1-carboxylate (5 g, 22.8 mmol) and N,N,N',N'-tetramethyl-1,2-ethanediamine (4.6 mL, 30.5 mmol) was dissolved in dry diethyl ether (300 mL) and cooled to −78° C. in an acetone/dry ice bath. Sec-butyl lithium (1.4 M solution in cyclohexane, 17.6 mL, 24.6 mmol) was added dropwise over 10 minutes and the reaction left stirring for 90 minutes at this temperature. Methyl chloroformate (8.8 mL, 10.8 g, 0.1 mmol) was added to the mixture and the reaction was allowed to warm up to room temperature over 1 hour. Water was added carefully to the mixture and the organic layer separated and washed 3 times with more water. The organic layer was dried over magnesium sulfate, filtered and concentrated in vacuo to give the title compound (4.91 g) as a gummy yellow solid.

LCMS m/z 278 (M+H).

(3) 1-(1,1-dimethylethyl)7-methyl-5-bromo-2,3-dihydro-1H-indole-1,7-dicarboxylate

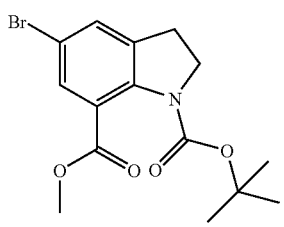

1-(1,1-dimethylethyl) 7-methyl 2,3-dihydro-1H-indole-1,7-dicarboxylate (3.1 g, 11.2 mmol) and N-bromosuccinimide (2.0 g, 11.2 mmol) were dissolved in dry dichloromethane (100 mL) and stirred under a nitrogen atmosphere at room temperature for 16 hours. The reaction was partitioned with sodium hydroxide solution (2 M), separated and washed with more sodium hydroxide solution. The organic layer was dried over magnesium sulfate and concentrated in vacuo to give the title compound as a gummy red solid (3.55 g).

LCMS m/z 356/358 (M+H).

(4) Methyl 5-bromo-2,3-dihydro-1H-indole-7-carboxylate

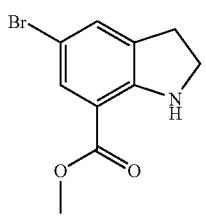

1-(1,1-dimethylethyl) 7-methyl 5-bromo-2,3-dihydro-1H-indole-1,7-dicarboxylate (9 g, 25 mmol) was dissolved in trifluoroacetic acid (6 mL) and stirred at room temperature for 16 hours. Dichloromethane and sodium hydroxide solution (2 M) were added and the organic layer washed twice with sodium hydroxide solution until the aqueous layer pH>7. The organic layer was then concentrated in vacuo to give the title compound as a brown solid (6.5 g).

LCMS m/z 256/258 (M+H)

(5) Methyl 5-bromo-1H-indole-7-carboxylate

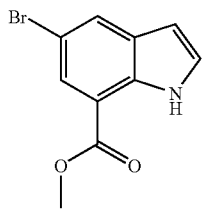

Methyl 5-bromo-2,3-dihydro-1H-indole-7-carboxylate (6.5 g, 25 mmol) was dissolved in tetrahydrofuran (100 mL). Activated manganese dioxide (5 μm particle size, 22 g, 0.25 mol) was added and the mixture stirred at room temperature for 16 hours. A further 22 g of activated manganese dioxide was added and the reaction stirred for 96 hours. The reaction was then filtered through celite and concentrated in vacuo to give the title compound (5.1 g) as a beige solid.

LCMS m/z 252/254 (M+H).

(6) 5-bromo-1H-indole-7-carboxylic acid

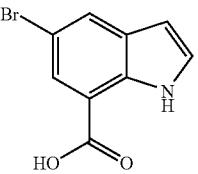

Methyl 5-bromo-1H-indole-7-carboxylate (5 g, 19.7 mmol) was dissolved in methanol (200 mL) and a solution of lithium hydroxide (0.99 g, 41 mmol) in water (10 mL) was added. The mixture was heated at reflux for 50 hours. The methanol was removed in vacuo and the residue diluted with aqueous hydrochloric acid (2 M). The resulting precipitate was filtered off and dried in a heated vacuum pistol to give the title compound as a beige solid (4.7 g).

LCMS m/z 238/240 (M+H).

(7) 5-phenyl-1H-indole-7-carboxylic acid

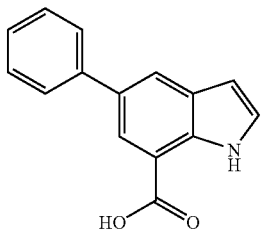

To a solution of 5-bromo-1H-indole-7-carboxylic acid (10 g, 41.8 mmol) in dioxane (150 mL) and water (50 mL) was added phenylboronic acid (19.5 g, 159.9 mmol), cesium carbonate (26.0 g, 79.8 mmol), 1,3-Bis(2,4,6-trimethylphenyl) imidazolium chloride (2.8 g, 8.2 mmol), and palladiumacetate (0.9 g, 4.01 mmol). The reaction mixture was stirred at ambient temperature for 15 min, and then was refluxed at 80° C. for 15 hr. The organic solvent was removed under reduced pressure and the water layer was adjusted to pH=1-2 with 6 M hydrochloric acid before ethyl acetate (350 mL) was added into it. The organic layer washed with water (100 mL×3), dried and concentrated at 45° C. to a thick oil (approximately 40 mL solvent left), cooled to −20° C., and filtered. The solid was washed with cold ethyl acetate (10 mL×3), and collected. The filtrate was concentrated to a thick oil at 45° C., then was cooled to −20° C., and off-white solid was obtained. The suspension was filtered and washed with cold ethyl acetate (5 mL×3). The filtrate was discard after 3 iterations of the above procedure.

LCMS m/z 238 (M+H).

(8) 5-phenyl-1H-indole-7-carboxamide

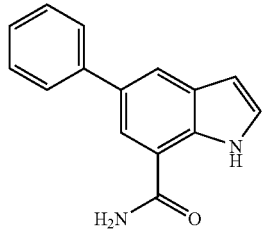

To a solution of 5-phenyl-1H-indole-7-carboxylic acid (1.25 g, 5.25 mmol) and O-(7-Azabenzotriazol-1-yl)-N,N,N',N'-tetramethyluronium hexafluorophosphate (HATU) (3.25 g, 8.55 mmol) in DMF (15 mL) was added a solution of ammonia in methanol (8.5 mL of a 2.0 M solution) at ambient temperature. After 3 hours, the solution was diluted with ethyl acetate and extracted with 4% HCl (1×50 mL), water (1×50 mL), brine (1×50 mL), dried over magnesium sulfate and filtered. The solvent was removed under reduced pressure to give a yellow solid (1.33 g).

LCMS m/z 237 (M+H).

Alternative Synthesis I:

To a solution of 5-phenyl-1H-indole-7-carboxylic acid (10.0 g, 42.0 mmol) in a mixture of $CH_2Cl_2$ (100 mL) and THF (100 mL) at room temperature, N-(3-Dimethylaminopropy)-N'-ethylcarbodiimide hydrochloride (9.66 g, 50.4 mmol), 1-Hydroxybenzotriazole hydrate (6.81 g, 50.4 mmol) and ammonia (2 M in methanol, 168 mmol, 84 mL) were added. The reaction mixture was stirred at room temperature for 24 hours. All solvent were evaporated and the reaction mixture was partitioned between ethyl acetate (200 mL) and water (200 mL). The organic layer was separated and the aqueous layer was extracted with ethyl acetate (×2). The combined organic phase washed with brine, dried over $Mg_2SO_4$ and concentration to give the product which is pure enough for next reaction (10 g, 100%).

LC-MS m/z 237.2 (M+H), 1.94 min.

Alternative Synthesis II:

To a 5 L three necked flask was charged 5-bromo-1H-indole-7-carboxamide (60 g, 0.251 mole, 1 eq). This was followed by the addition of phenyl boronic acid (91.88 g, 0.753 mole, 3 eq) and potassium phosphate tribasic (106 g, 0.502 mole, 2 eq). Nitrogen purged 1,4-dioxane (1.2 L, 20 vol wrt 12) was then charged to the flask followed by water (1.2 L, 20 vol wrt 12). 2'-(dimethylamino)-2-biphenylyl-palladium(II) chloride dinorbornylphosphine complex (7.03 g, 0.0126 mole, 0.05 eq) was then added and the reaction mixture was heated to reflux for 3 hrs. The reaction mixture was cooled to room temperature and then was filtered through celite. The filtrate was then partitioned between ethyl acetate and brine. The layers were separated and the organic was concentrated in vacuo. The residue was then dissolved in acetonitrile/water (550 mL/50 mL, 10 vol wrt 12) with heating. The solution was then treated with water (1.5 L, 30 vol wrt 12) with stirring. The solid was formed collected by filtration and washed with 3:1 water/acetonitrile followed by hot water it was then dried in vacuo at 40° C. to yield the desired product (57.69 g).

MS: (M+H): 237

(9) 5-Phenyl-3-[1-(phenylmethyl)-1,2,3,6-tetrahydro-4-pyridinyl]-1H-indole-7-carboxamide

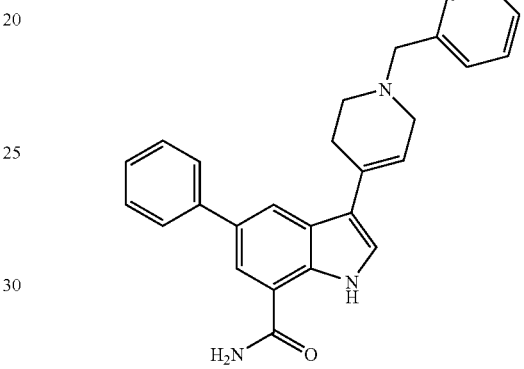

To the solution of 5-phenyl-1H-indole-7-carboxamide (3.11 g, 12 mmol) in methanol (100 mL) was added benzyl piperidone (7.4 g, 36 mmol), followed by 156 mL of NaOMe (0.5 M in MeOH). The reaction mixture was then heated at 80° C. overnight. The solution was cooled to ambient temperature and the solvent removed under reduced pressure, and the resulting residue redisolved in a bilayer of ethyl acetate and 5% sodium hydroxide solution. The organic phase washed with brine, dried over potassium carbonate, and the solvent removed under reduced pressure. The residue was purified by silica gel chromatography ($CH_2Cl_2$:MeOH:$NH_4OH$=96:3:1) to provide the desired product (2.66 g, 51%).

LCMS m/z 408 (M+H).

Alternative Synthesis:

To a 5 L three necked flask was charged 85% wt Phosphoric acid (423 mL, 6.16 moles, 25 eq), benzyl piperidone (142 mL, 0.733 mole, 3 eq) and glacial acetic acid (400 mL). The resulting mixture was heated to 90° C. A solution of 5-phenyl-1H-indole-7-carboxamide (57.69 g, 0.244 mole, 1 eq) in glacial acetic acid (755 mL) was then added portionwise. The reaction was then maintained at 90° C. overnight. The reaction mixture was cooled to room temperature. It was then divided into two equal portions and each was added slowly to separate stirring mixtures of ice/0.88 ammonia (1 L/1 L). A dry ice/acetone bath was also used to control the exotherm. Ethyl acetate (600 mL) was then added to the mixture with stirring. It was then filtered and the solid washed well with ethyl acetate. The filtrate was then separated and the aq was re-extracted with ethyl acetate. The organics were then dried over magnesium sulfate and filtered before the two batches were combined and evaporated under reduced pressure. The residue was then dissolved in 3% (3.5M ammonia in methanol) in DCM (300 mL). The solid precipitate was then collected by filtration and was then dried in vacuo to yield the desired product. (42.25 g) MS: (M+H): 408.

(10) 5-Phenyl-3-(4-piperidinyl)-1H-indole-7-carboxamide

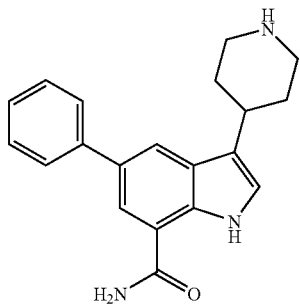

To the solution of 5-Phenyl-3-[1-(phenylmethyl)-1,2,3,6-tetrahydro-4-pyridinyl]-1H-indole-7-carboxamide (2.66 g, 6.5 mmol) in ethanol (150 mL) and acetic acid (3 mL) was added Pd(OH)$_2$ (20% by weight on carbon) (0.8 g,) at ambient temperature. The solution was stirred under 1 atm of hydrogen for 2 days. The reaction mixture was then filtered through Celite, neutralized with 5% sodium hydroxide solution, and extracted with ethyl acetate. The solvent was removed under reduced pressure to yield the desired product (1.45 g, 70%).
LCMS m/z 320 (M+H)

(11) 3-{1-[(3-chloropropyl)sulfonyl]-4-piperidinyl}-5-phenyl-1H-indole-7-carboxamide

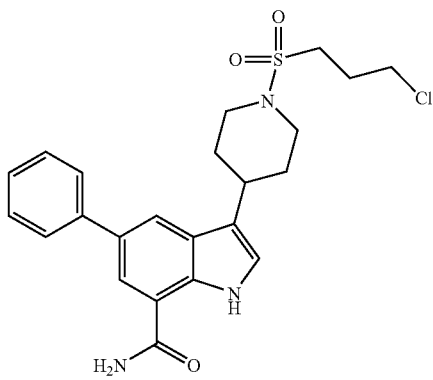

To a solution of 5-phenyl-3-(4-piperidinyl)-1H-indole-7-carboxamide (404 mg, 1.26 mmol) in CH$_2$Cl$_2$ at 0° C., triethylamine (0.7 mL, 5.04 mmol) and 3-chloropropanesulfonyl chloride (0.23 mL, 1.89 mmol) were added. The reaction mixture was stirred at 0° C. for 30 min. The reaction mixture was partitioned between CH$_2$Cl$_2$ (100 mL) and water (50 mL). The organic layer was separated and the aqueous layer was extracted with CH$_2$Cl$_2$ (2×100 mL). The combined organic phase washed with brine (50 mL), dried over magnesium sulfate and filtered. The solvent was removed under reduced pressure and purified via filtration through an SPE Cartridge (Aminopropyl NH$_2$, 500 mg/6 mL) to give the title compound (370 mg, 64%).
LCMS m/z 460.0 (M+H).

(12) 5-bromo-1H-indole-7-carboxamide

To a solution of 5-bromo-1H-indole-7-carboxylic acid (10.0 g, 42 mmol) in CH$_2$Cl$_2$ (100 mL) at room temperature, EDC (9.66 g, 50.4 mmol), HOBt (6.81 g, 50.4 mmol) and NH$_3$ (2.0 M in MeOH, 84 mL, 168 mmol) were added. The reaction mixture was stirred at room temperature for 16 hours. The solvent was evaporated and the residue partitioned between ethyl acetate (100 mL) and water (100 mL). The water layer was extracted with ethyl acetate (100 mL×2) and the combined organic phase was dried over MgSO$_4$ and concentrated to give the crude product (10 g, 98%). This crude product was used directly in the next step without further purification.
LC/MS: m/z 240.0 (M+H), 1.95 min.

(13) 1,1-dimethylethyl-4-[7-(aminocarbonyl)-5-bromo-1 indol-3-yl]-3,6-dihydro-1(2H)-pyridinecarboxylate

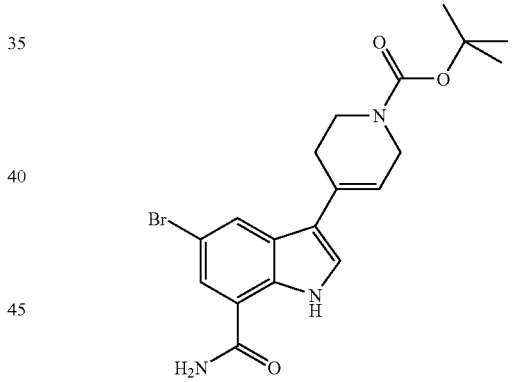

To a solution of 5-bromo-1H-indole-7-carboxamide (10 g, 41.84 mmol) in methanol (5 mL), 1,1-dimethylethyl-4-oxo-1-piperidinecarboxylate (684 mg, 3.42 mmol) and sodium methoxide (0.5 M in THF, 13.7 mL, 6.84 mmol) were added. The reaction mixture was stirred at reflux temperature for 16 hours. All solvent was evaporated under reduced pressure. The residue was partitioned between ethyl acetate (100 mL) and water (100 mL). The combined organic phase was dried over MgSO$_4$ and concentrated under reduced pressure, and purified by flash column chromatography (ethyl acetate/hexane, 1/1) to yield the desired product (7.4 g, 43%).
LC/MS: m/z 420.0 (M+H), Rt 2.35 min.

Alternative Synthesis:

To a 10 L CLR was charged Boc-piperidone (270 g, 1.356 moles, 3 eq). This was followed by 85% wt phosphoric acid (782 mL, 11.42 moles, 25 eq) and glacial acetic acid (2160 mL, 20 vol wrt 12). The resulting mixture was heated to 90°

C. followed by the addition of 5-bromo-1H-indole-7-carboxamide (108 g, 0.452 mole, 1 eq) was then charged to the CLR. The mixture was then maintained at 90° C. overnight. The reaction mixture was then cooled to room temperature and drained from the reactor. 0.88 ammonia (3.5 L) was then charged to the reactor and it was cooled to 0° C. The reaction mixture was then slowly charged back into the reactor. Ice was added over the course of the addition to maintain the temperature below 50° C. The precipitate was then drained from the reactor and filtered. The solid residue was then charged back to the reactor and stirred vigorously with water (7 L). The solid was then re-filtered then dried at the pump. The crude product was then triturated in methanol (216 ml, 2 vol. wrt 12). The solid was collected by filtration and washed well with methanol. The solid was then dried in vacuo at 40° C. to yield the 95 g condensation compound without Boc protection. The compound was used toward the next step without further purification.

To a 10 L CLR was charged the condensation compound (100 g, 0.3125 moles, 1 eq). This was followed by anhydrous DMF (1000 mL, 10 vol.). The resulting mixture was then treated with triethylamine (87 mL, 0.627 mole, 2 eq) followed by boc-anhydride (81.84 g, 0.375 mole, 1.2 eq). The resulting mixture was then stirred under a nitrogen atmosphere for 2 hrs. The mixture was then drained slowly from the reactor onto water (7.5 L). The mixture was then transferred to a 20 L separator and was partitioned between ethyl acetate and 10% LiCl. The layers were separated and the aqueous was re-extracted with ethyl acetate. The combined organics were then washed with 10% LiCl solution, brine then dried over magnesium sulfate then filtered and evaporated. The orange residue was then suspended in water, filtered then dried in vacuo at 40° C. to yield the desired product. (113 g).

MS: (M+H): 420.422.

(14) 1,1-dimethylethyl-4-[7-(aminocarbonyl)-5-bromo-1H-indol-3-yl]-1-piperidine carboxylate

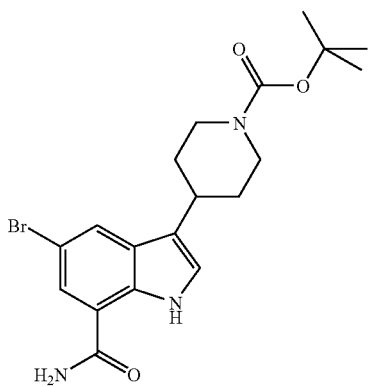

To a solution of 1,1-dimethylethyl 4-[7-(aminocarbonyl)-5-bromo-1H-indol-3-yl]-3,6-dihydro-1(2H)-pyridinecarboxylate (7.41 g, 17.64 mmol) in ethanol (600 mL), platinum oxide (200 mg, 5%) was added. The reaction mixture was hydrogenated under an atmosphere of $H_2$ balloon for 16 hours. The resulting mixture was filtered through celite and the filtrate was concentrated. The resulting residue was purified by flash column chromatography (Ethyl acetate/Hexane, 1:4 to 2:1 v/v) to give the desired product (3.6 g, 48%).

LC/MS: m/z 422.0 (M+H), Rt 2.25 min.

(15) 5-bromo-3-(4-piperidinyl)-1H-indole-7-carboxamide

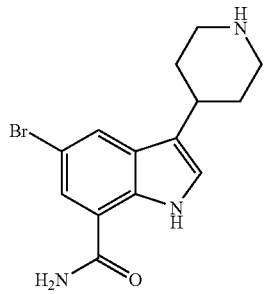

To a solution of 1,1-dimethylethyl 4-[7-(aminocarbonyl)-5-bromo-1H-indol-3-yl]-1-piperidinecarboxylate (1.56 g, 3.7 mmol) in methanol (10 mL), HCl in dioxane (4M, 35.5 mL) was added. The reaction mixture was stirred at room temperature for 2 hours. The solvent was evaporated under reduced pressure and the resulting residue was partitioned between ethyl acetate (50 mL) and 5% of aqueous NaOH (50 mL). The aqueous layer washed with ethyl acetate (2×50 mL) and the combined organic phases were dried and concentrated under reduced pressure to give desired product (685 mg, 58%), which was used in the next step without further purification.

LC/MS: m/z 322.0 (M+H), Rt 1.45 min.

(16) 1,1-dimethylethyl-4-[7-(aminocarbonyl)-5-(2-thienyl)-1H-indol-3-yl]-1-piperidinecarboxylate

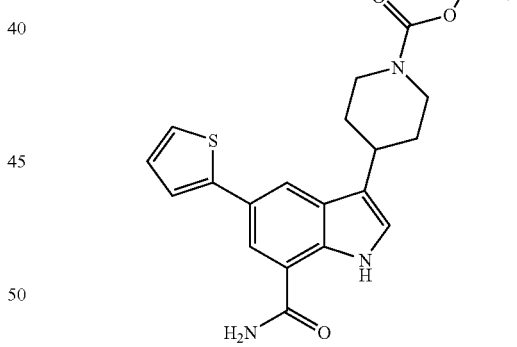

To a solution of 1,1-dimethylethyl 4-[7-(aminocarbonyl)-5-bromo-1H-indol-3-yl]-1-piperidinecarboxylate/(95 mg, 0.23 mmol) in dioxane (1.5 mL) and water (0.5 ml), 2-thienylboronic acid (115.2 mg, 0.92 mmol), Pd(PPh$_3$)$_4$ (26.6 mg, 10%) and potassium carbonate (254 mg, 1.84 mmol) were added. The reaction mixture was heated in a Smith synthesizer microwave at 150° C. for 20 min. All solvent was evaporated under reduced pressure. The residue was partitioned between ethyl acetate (10 mL) and water (10 mL). The organic phase was dried over MgSO$_4$ and concentrated under reduced pressure, and purified by flash column chromatography (ethyl acetate/hexane, 1/1) to yield the desired product (90 mg, 95%).

LC/MS: m/z 426.0 (M+H), Rt 2.47 min.

(17) 3-(4-piperidinyl)-5-(2-thienyl)-1H-indole-7-carboxamide

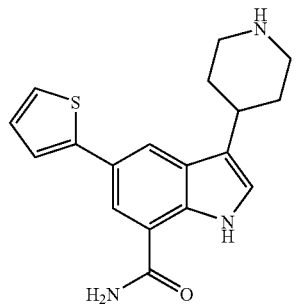

To a solution of 1,1-dimethylethyl 4-[7-(aminocarbonyl)-5-(2-thienyl)-1H-indol-3-yl]-1-piperidinecarboxylate (90 mg, 0.22 mmol) in MeOH (3 mL), HCl (4.0M in dioxane, 2.06 mL) was added. The reaction mixture was stirred at ambient temperature for 2 hours, after which time the solvent was removed under reduced pressure and the resulting residue was partitioned between ethyl acetate (10 mL) and 10% sodium hydroxide (10 mL). The aqueous layer was extracted with ethyl acetate (10 mL×2) and the combined organic phase was dried over MgSO$_4$ and concentrated to give a crude product (53 mg, 77%). This was used directly in the next step without further purification.

LC/MS: m/z 326.0 (M+H), Rt 1.49 min.

(18) 1,1-dimethylethyl-4-[7-(aminocarbonyl)-5-(3-thienyl)-1H-indol-3-yl]-1-piperidinecarboxylate

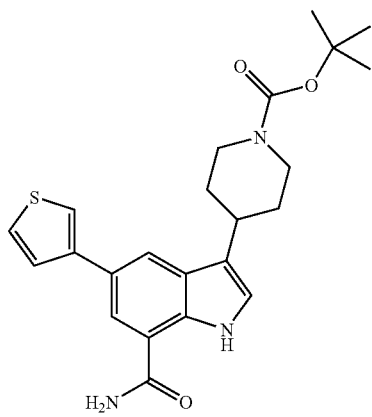

The title compound was prepared according to the general procedure for intermediate 16. Thus, 1,1-dimethylethyl-4-[7-(aminocarbonyl)-5-bromo-1H-indol-3-yl]-1-piperidinecarboxylate (500 mg, 1.18 mmol) in dioxane (1.5 mL) and water (0.5 mL), 3-thienylboronic acid (606 mg, 4.72 mmol), Pd(PPh$_3$)$_4$ (136 mg, 10%) and potassium carbonate (651 mg, 4.72 mmol) in dioxane (3.0 mL) and water (1.0 mL) were reacted to form the desired product which was purified by flash column chromatography (ethyl acetate/hexane, 1/1) to yield the desired product (460 mg, 92%).

LC/MS: m/z 426.0 (M+H), Rt 2.45 min.

(19) 3-(4-piperidinyl)-5-(3-thienyl)-1H-indole-7-carboxamide

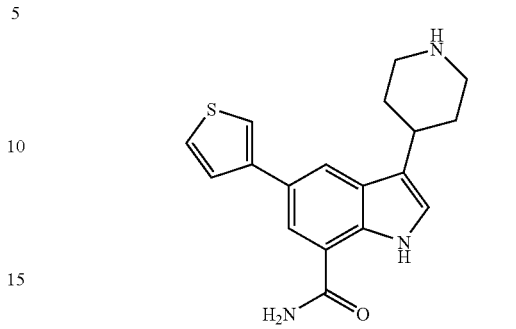

The title compound was prepared according to the general procedure for intermediate 17. Thus, 1,1-dimethylethyl 4-[7-(aminocarbonyl)-5-(3-thienyl)-1H-indol-3-yl]-1-piperidinecarboxylate (460 mg, 1.08 mmol) and HCl (4.0M in dioxane, 10 mL) in MeOH (5 mL) was reacted to form the desired product without further purification (260 mg, 74%).

LC/MS: m/z 326.0 (M+H), Rt 1.60 min.

(20) 3-(1-{[2-(1,3-dioxo-1,3-dihydro-2H-isoindol-2-yl)ethyl]sulfonyl}-4-piperidinyl)-5-phenyl-1H-indole-7-carboxamide

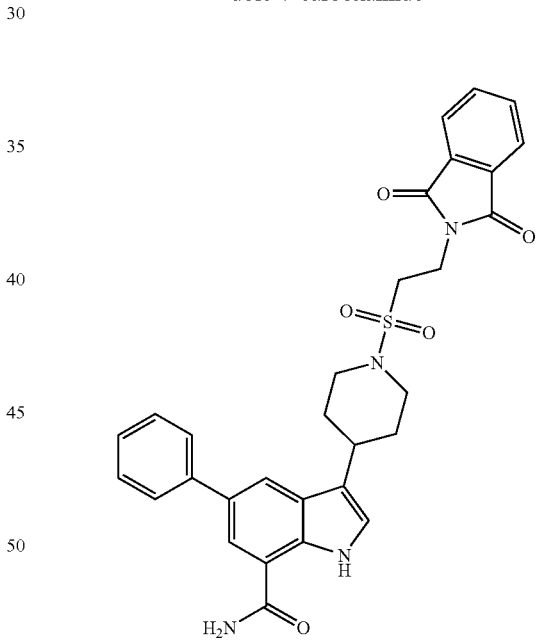

To a solution of 5-phenyl-3-(4-piperidinyl)-1H-indole-7-carboxamide (84.8 mg, 0.265 mmol) in CH$_2$Cl$_2$ at 0° C., triethylamine (0.15 mL, 1.06 mmol) and 2-(1,3-dioxo-1,3-dihydro-2H-isoindol-2-yl)ethanesulfonyl chloride (87.03 mg, 0.32 mmol) were added. The reaction mixture was stirred at 0° C. for 30 min. The reaction mixture was partitioned between CH$_2$Cl$_2$ and water. The organic layer was separated and the aqueous layer was extracted with CH$_2$Cl$_2$ (2×). The combined organic phase washed with brine, dried over magnesium sulfate and filtered. The solvent was removed under reduced pressure to give the crude product (90 mg, 61%).

LC/MS m/z 557.2 (M+H).

(21) 3-{1-[(2-chloroethyl)sulfonyl]-4-piperidinyl}-5-phenyl-1H-indole-7-carboxamide

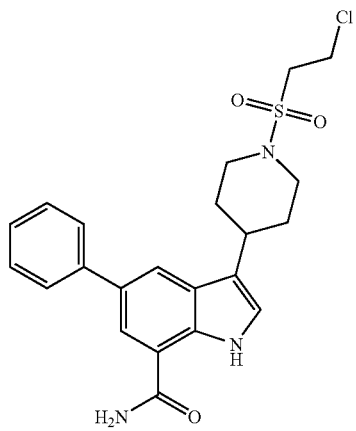

To a solution of 5-phenyl-3-(4-piperidinyl)-1H-indole-7-carboxamide (65 mg, 0.2 mmol) in CH$_2$Cl$_2$ (5 mL) at 0° C., triethylamine (0.11 mL, 0.8 mmol) and 2-chloroethanesulfonyl chloride (0.042 mL, 0.4 mmol) were added. After stirring at 0° C. for 30 min. the reaction mixture was partitioned between CH$_2$Cl$_2$ and water. The organic layer was separated and the aqueous layer was extracted with CH$_2$Cl$_2$ (2×). The combined organic phase was dried over magnesium sulfate and the solvent removed under reduced pressure. The resulting residue was purified by filtration through an SPE Cartridge (Aminopropyl NH$_2$, 500 mg/6 mL) to give the desired product (26 mg, 32%).

LC/MS m/z 445.0 (M+H).

(22) 3-{1-[(3-chloropropyl)sulfonyl]-4-piperidinyl}-5-(3-thienyl)-1H-indole-7-carboxamide

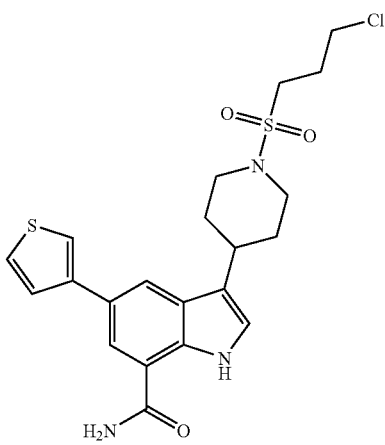

The title compound was prepared according to the general procedure for intermediate 11. 3-(4-piperidinyl)-5-(3-thienyl)-1H-indole-7-carboxamide (220 mg, 0.67 mmol) was reacted with triethyl amine (0.4 mL, 2.68 mmol) and 3-chloropropylsulfonyl chloride (0.12 mL, 1.01 mmol) to give the title compound (117 mg, 37%)

LC/MS: m/z 466.0 (M+H), Rt 2.18 min.

(23) 3-{1-[(3-chloropropyl)sulfonyl]-4-piperidinyl}-5-(2-thienyl)-1H-indole-7-carboxamide

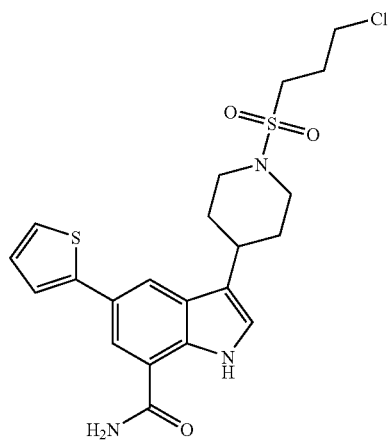

The title compound was prepared according to the general procedure for intermediate 11. 3-(4-piperidinyl)-5-(3-thienyl)-1H-indole-7-carboxamide (275 mg, 0.84 mmol) was reacted with triethyl amine (0.35 mL, 2.52 mmol) and 3-chloropropylsulfonyl chloride (0.4 mL, 1.68 mmol) to give the title compound (250 mg, 64%)

LC/MS: m/z 466.2 (M+H), Rt 2.22 min.

(24) 5-bromo-3-{1-[(3-chloropropyl)sulfonyl]-4-piperidinyl}-1H-indole-7-carboxamide

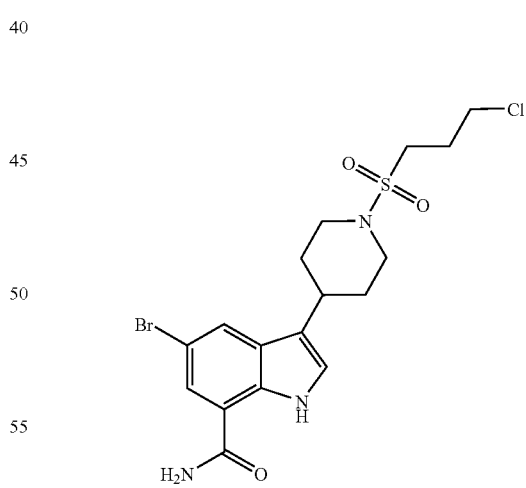

The title compound was prepared according to the general procedure for intermediate 11. 5-bromo-3-(4-piperidinyl)-1H-indole-7-carboxamide (875 mg, 2.72 mmol) was reacted with triethyl amine (2.27 mL, 16.32 mmol) and 3-chloropropylsulfonyl chloride (0.64 mL, 5.44 mmol) to give the title compound (656 mg, 52%)

LC/MS: m/z 462.0 (M+H), Rt 2.15 min.

(25) 5-bromo-3-(1-{[3-(1-pyrrolidinyl)propyl]sulfonyl}-4-piperidinyl)-1H-indole-7-carboxamide

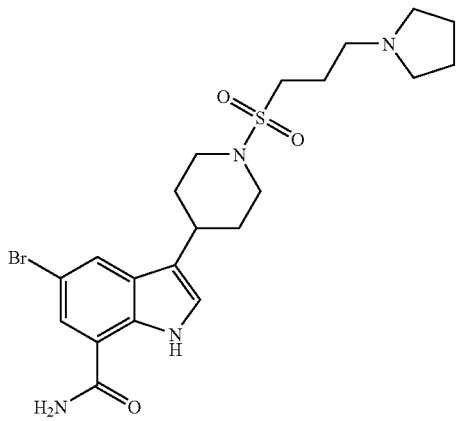

Following the general procedure for aminosulfonamide formation outlined in example 2, 5-bromo-3-{1-[(3-chloropropyl)sulfonyl]-4-piperidinyl}-1H-indole-carboxamide (656 mg, 1.41 mmol) and pyrrolidine (505 mg, 7.05 mmol) were allowed to react in the presence of $K_2CO_3$ (389.16 mg, 2.82 mmol). The resulting residue was purified by reverse phase HPLC eluting with 10% B to 80% B, where A=$H_2O$ (0.1% trifluoroacetic acid) and B=$CH_3CN$ (0.1% trifluoroacetic acid) to give the title compound (600 mg, 87%).

LC/MS: m/z 497.4 (M+H), Rt 1.57 min.

(26) 3-[1-(ethenylsulfonyl)-4-piperidinyl]-5-phenyl-1H-indole-7-carboxamide

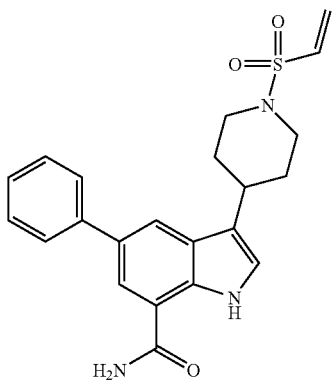

To a solution of 5-phenyl-3-(4-piperidinyl)-1H-indole-7-carboxamide (260 mg, 0.8 mmol) in $CH_2Cl_2$ at 0° C., triethylamine (0.44 mL, 3.2 mmol) and 2-chloroethylsulfonyl chloride (0.168 mL, 1.6 mmol) were added. The reaction mixture was stirred at 0° C. for 30 min. The reaction mixture was partitioned between $CH_2Cl_2$ (100 mL) and water (50 mL). The organic layer was separated and the aqueous layer was extracted with $CH_2Cl_2$ (2×100 mL). The combined organic phase washed with brine (50 mL), dried over magnesium sulfate and filtered. The solvent was removed under reduced pressure and purified via filtration through an SPE Cartridge (Aminopropyl $NH_2$, 500 mg/6 mL) to give the title compound (245 mg, 75%).

LCMS m/z 410 (M+H).

(27) 5-(5-formyl-2-thienyl)-3-(1-{[3-(1-pyrrolidinyl)propyl]sulfonyl}-4-piperidinyl)-1H-indole-7-carboxamide

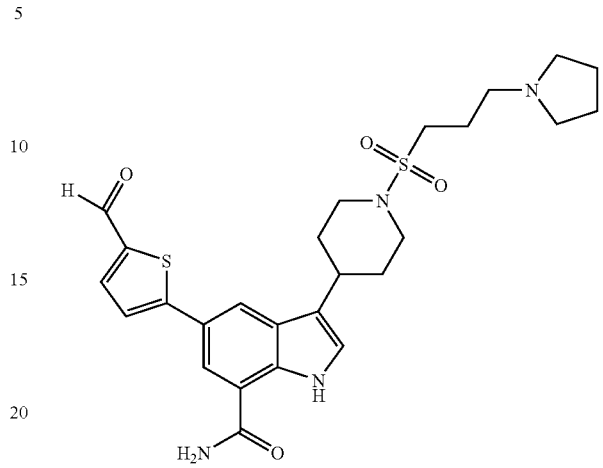

To a solution of 5-[5-(hydroxymethyl)-2-thienyl]-3-(1-{[3-(1-pyrrolidinyl)propyl]sulfonyl}-4-piperidinyl)-1H-indole-7-carboxamide (14.4 mg, 0.027 mmol) in THF (5 mL) was added $MnO_2$ (71.7 mg, 0.81 mmol). The reaction mixture was stirred at room temperature overnight and filtered through a pad of celite after that. The filtrate was collected and concentrated at reduced pressure to give the crude product (8.3 mg, 58%), which was used in the next step without further purification.

LC/MS: m/z 529.4 (M+H), Rt 1.67 min.

(28) 5-bromo-3-(1-{[3-(4-morpholinyl)propyl]sulfonyl}-4-piperidinyl)-1 indole-7-carboxamide

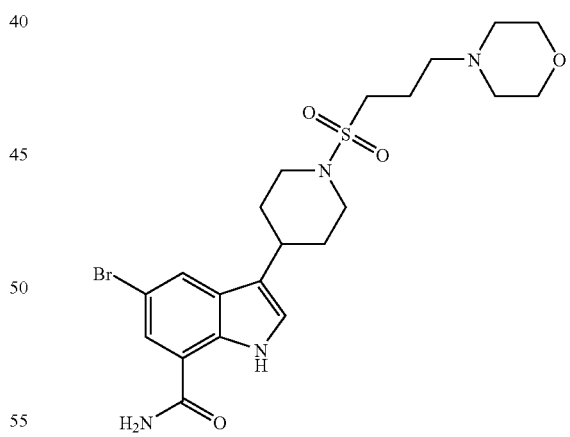

Following the general procedure for aminosulfonamide formation outlined in example 2, 5-bromo-3-{1-[(3-chloropropyl)sulfonyl]-4-piperidinyl}-1H-indole-carboxamide (1.81 mmol) and morpholine (0.8 mL, 9.05 mmol) were allowed to react in the presence of $K_2CO_3$ (500 mg, 3.62 mmol). The resulting residue was purified by reverse phase HPLC eluting with 10% B to 80% B, where A=$H_2O$ (0.1% trifluoroacetic acid) and B=$CH_3CN$ (0.1% trifluoroacetic acid) to give the title compound (426 mg, 51%).

LC/MS: m/z 462.2 (M+H), Rt 2.14 min

(29) 5-[5-(hydroxymethyl)-2-thienyl]-3-(1-{[3-(4-morpholinyl)propyl]sulfonyl}-4-piperidinyl)-1H-indole-7-carboxamide

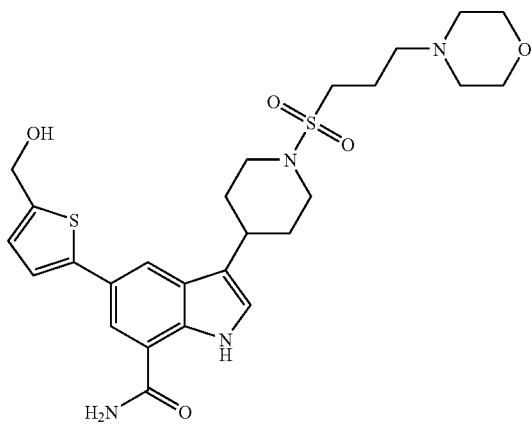

The title compound was prepared according to the general procedure for intermediate 16. Thus, 5-bromo-3-(1-{[3-(4-morpholinyl)propyl]sulfonyl}-4-piperidinyl)-1H-indole-7-carboxamide (400 mg, 0.78 mmol) in dioxane (3 mL) and water (1 mL), [5-(hydroxymethyl)-2-thienyl]boronic acid (493 mg, 3.12 mmol), Pd(PPh$_3$)$_4$ (90 mg, 10%) and potassium carbonate (861 mg, 6.24 mmol) were reacted to form the desired product which was purified by flash column chromatography (ethyl acetate/hexane, 1/1) to yield the desired product (83 mg, 20%).

LC/MS: m/z 547.4 (M+H), Rt 1.38 min.

(30) 5-(5-formyl-2-thienyl)-3-(1-{[3-(4-morpholinyl)propyl]sulfonyl}-4-piperidinyl)-1H-indole-7-carboxamide

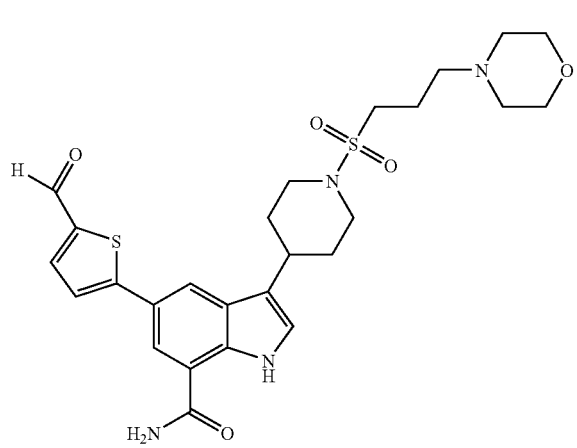

To a solution of 5-[5-(hydroxymethyl)-2-thienyl]-3-(1-{[3-(4-morpholinyl)propyl]sulfonyl}-4-piperidinyl)-1H-indole-7-carboxamide (82.5 mg, 0.015 mmol) in THF (10 mL) was added MnO$_2$ (391 mg, 4.5 mmol). The reaction mixture was stirred at room temperature overnight and filtered through a pad of celite after that. The filtrate was collected and concentrated at reduced pressure to give the crude product (60 mg, 73%), which was used in the next step without further purification.

LC/MS: m/z 545.0 (M+H), Rt 1.62 min.

(31) 1,1-dimethylethyl 4-[7-(aminocarbonyl)-5-(4-fluorophenyl)-1H-indol-3-yl]-1-piperidinecarboxylate

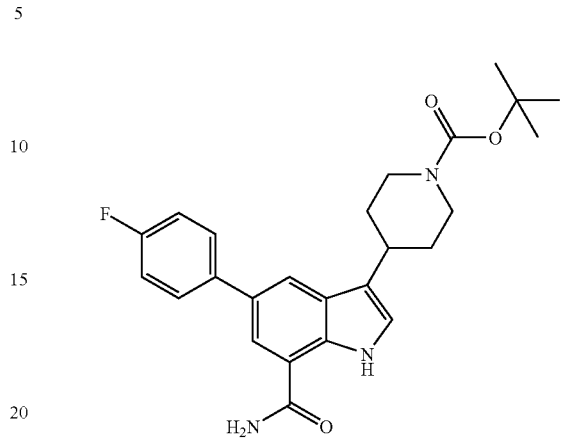

The title compound was prepared according to the general procedure for intermediate 16. Thus, 1,1-dimethylethyl-4-[7-(aminocarbonyl)-5-bromo-1H-indol-3-yl]-1-piperidine carboxylate (100 mg, 0.24 mmol) in dioxane (3 mL) and water (1 mL), (4-fluorophenyl)boronic acid (134 mg, 0.98 mmol), Pd(PPh$_3$)$_4$ (28 mg, 10%) and potassium carbonate (265 mg, 1.92 mmol) were reacted to form the desired product which was purified by flash column chromatography (ethyl acetate/hexane, 1/1) to yield the desired product (92.8 mg, 90%).

LC/MS: m/z 339.4 (M+H), Rt 2.92 min.

(32) 5-(4-fluorophenyl)-3-(4-piperidinyl)-1H-indole-7-carboxamide

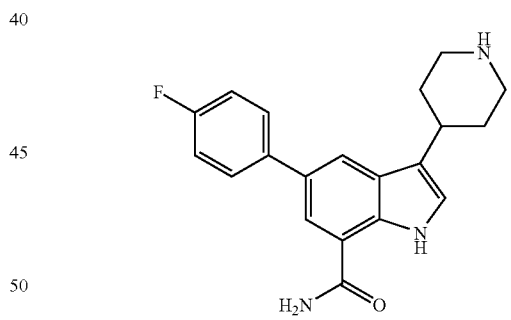

To a solution of 1,1-dimethylethyl 4-[7-(aminocarbonyl)-5-(4-fluorophenyl)-1H-indol-3-yl]-1-piperidinecarboxylate (92.9 g, 0.205 mmol) in methanol (10 mL), HCl in dioxane (4M, 2.01 mL) was added. The reaction mixture was stirred at room temperature for 2 hours. The solvent was evaporated under reduced pressure and the resulting residue was partitioned between ethyl acetate (50 mL) and 5% of aqueous NaOH (50 mL). The aqueous layer washed with ethyl acetate (2×50 mL) and the combined organic phases were dried and concentrated under reduced pressure to give desired product (55.9 mg, 78%), which was used in the next step without further purification.

LC/MS: m/z 338.6 (M+H), Rt 1.53 min.

(33) 5-bromo-3-(1-{[3-(dimethylamino)propyl]sulfonyl}-4-piperidinyl)-1H-indole-7-carboxamide

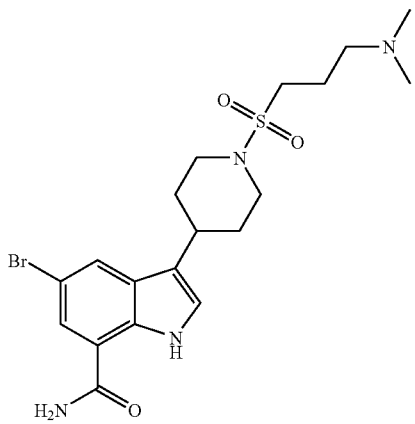

Following the general procedure for aminosulfonamide formation outlined in example 2, 5-bromo-3-{1-[(3-chloropropyl)sulfonyl]-4-piperidinyl}-1H-indole-carboxamide (434 mg, 0.93 mmol) and 2 M in THF dimethyl amine (7 mL, 14 mmol) were allowed to react in the presence of $K_2CO_3$ (650 mg, 4.7 mmol) and NaI (10 mg). The reaction mixture was concentrated under reduce pressure. The resulting residue was purified by reverse phase HPLC eluting with 10% B to 80% B, where A=$H_2O$ (0.1% trifluoroacetic acid) and B=$CH_3CN$ (0.1% trifluoroacetic acid) to give the title compound (220 mg, 50%).

LC/MS: m/z 471.4 (M+H), Rt 1.39 min.

(34) 5-(3-formylphenyl)-3-(1-{[3-(1-pyrrolidinyl)propyl]sulfonyl}-4-piperidinyl)-1H-indole-7-carboxamide

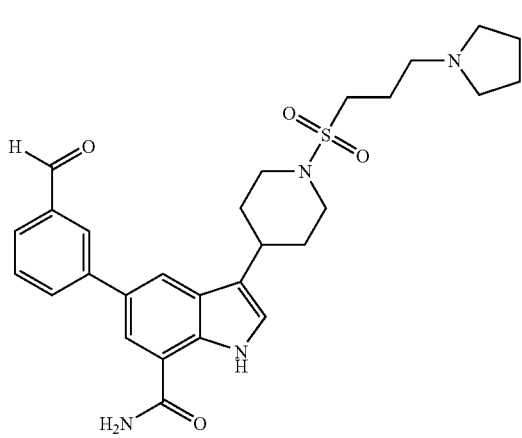

To a solution of 5-[3-(hydroxymethyl)phenyl]-3-(1-{[3-(1-pyrrolidinyl)propyl]sulfonyl}-4-piperidinyl)-1H-indole-7-carboxamide (250 mg, 0.477 mmol) in THF (60 mL) was added $MnO_2$ (1.3 g, 14.30 mmol). The reaction mixture was stirred at room temperature overnight and filtered through a pad of celite after that. The filtrate was collected and concentrated at reduced pressure to give the crude product (150 mg, 60%), which was used in the next step without further purification.

LC/MS: m/z 525.6 (M+H), Rt 1.50 min.

(35) 3-(1-{[3-(dimethylamino)propyl]sulfonyl}-4-piperidinyl)-5-(3-formylphenyl)-1H-indole-7-carboxamide

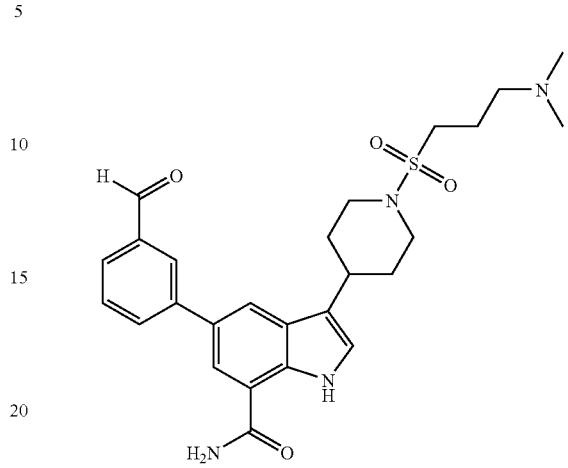

To a solution of 3-(1-{[3-(dimethylamino)propyl]sulfonyl}-4-piperidinyl)-5-[3-(hydroxymethyl)phenyl]-1H-indole-7-carboxamide (230 mg, 0.47 mmol) in THF (60 mL) was added $MnO_2$ (1.3 g, 14.05 mmol). The reaction mixture was stirred at room temperature overnight and filtered through a pad of celite after that. The filtrate was collected and concentrated at reduced pressure to give the crude product (150 mg, 65%), which was used in the next step without further purification.

LC/MS: m/z 499.6 (M+H), Rt 1.55 min.

(36) 5-bromo-3-(1-{[3-(cyclopentylamino)propyl]sulfonyl}-4-piperidinyl)-1H-indole-7-carboxamide

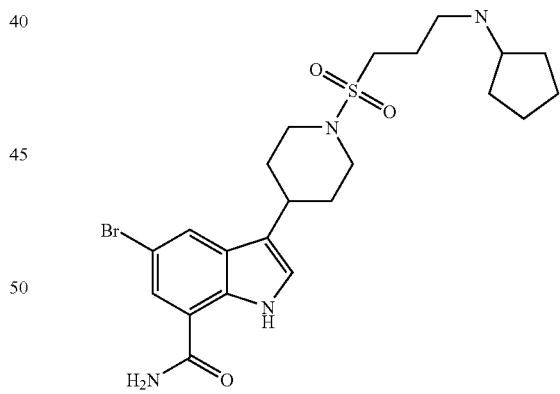

Following the general procedure for aminosulfonamide formation outlined in example 2, 5-bromo-3-{1-[(3-chloropropyl)sulfonyl]-4-piperidinyl}-1H-indole-carboxamide (2.00 g, 4.320 mmol) and cyclolpentyl amine (2.73 mL, 21.6 mmol) were allowed to react in the presence of $K_2CO_3$ (2.4 g, 17.3 mmol) and NaI (80 mg, 0.433 mmol). The reaction mixture was concentrated under reduce pressure. The resulting residue was purified by reverse phase HPLC eluting with 10% B to 80% B, where A=$H_2O$ (0.1% trifluoroacetic acid) and B=$CH_3CN$ (0.1% trifluoroacetic acid) to give the title compound (176 mg, 8%).

LC/MS: m/z 513.2 (M+H), Rt 1.54 min.

(37) 5-bromo-3-(1-{[3-(methyloxy)propyl]sulfonyl}-4-piperidinyl)-1H-indole-7-carboxamide

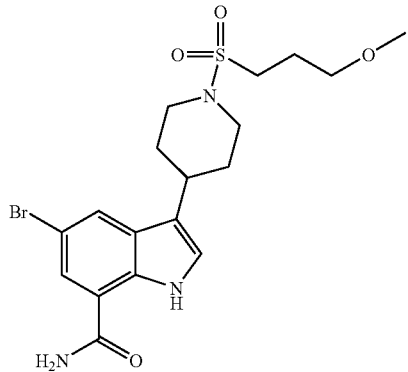

The mixture of 5-bromo-3-{1-[(3-chloropropyl)sulfonyl]-4-piperidinyl}-1H-indole-7-carboxamide (23 mg, 0.050 mmol), 0.1 M NaOMe (1 ml) in methanol (1 mL) was refluxed overnight. The reaction mixture was concentrated and purified by reverse phase HPLC (water/CH$_3$CN, 0.1% TFA 10-90%) to give the title compound (18.0 mg, 78%).

LC/MS: 458.2 r.t: 2.13 min.

(38) 5-(3-formylphenyl)-3-(1-{[3-(methyloxy)propyl]sulfonyl}-4-piperidinyl)-1H-indole-7-carboxamide

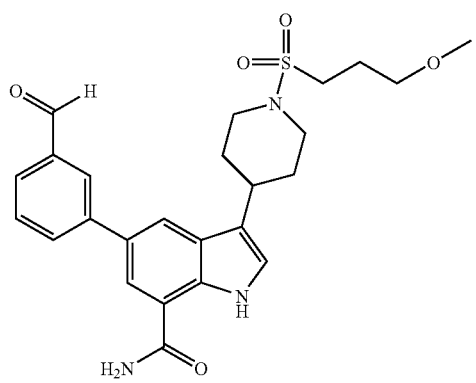

To a solution of 5-bromo-3-(1-{[3-(methyloxy)propyl]sulfonyl}-4-piperidinyl)-1H-indole-7-carboxamide (420 mg, 0.9 mmol) in dioxane (6.0 mL) and water (2.0 ml), (3-formylphenyl)boronic acid (750.0 mg, 5.0 mmol), Pd(PPh$_3$)$_4$ (100.0 mg, 10%) and cessium carbonate (800 mg, 1.8 mmol) were added. The reaction mixture was heated in a Smith synthesizer microwave at 160° C. for 20 min. All solvent was evaporated under reduced pressure. The residue was purified by flash column chromatography (ethyl acetate/hexane, 1/1) to yield the desired product (300.0 mg, 70%).

LC/MS: m/z 484.2 (M+H), Rt 2.06 min.

(39) 5-bromo-3-[1-(ethenylsulfonyl)-4-piperidinyl]-1H-indole-7-carboxamide

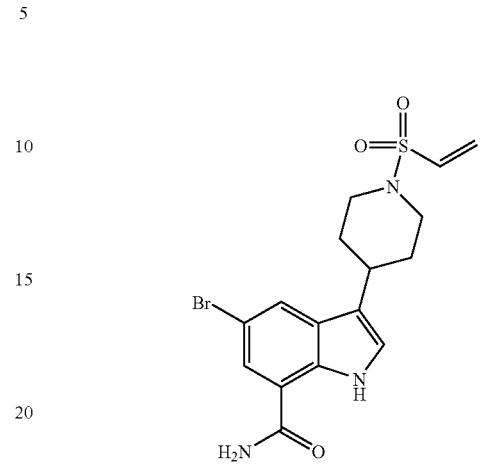

To a solution of 5-bromo-3-(4-piperidinyl)-1H-indole-7-carboxamide (500 mg, 1.3 mmol) in methylene chloride at room temperature, triethylamine (0.44 mL, 3.2 mmol) and 2-chloroethylsulfonyl chloride (0.168 mL, 1.6 mmol) were added. The reaction mixture was stirred for 30 min. Removed the solvent, the residue was purified by combiflash to give the title compound (150 mg, 75%).

LCMS m/z 413.8 (M+H), 1.96 min.

(40) 5-bromo-3-(1-{[2-(methyloxy)ethyl]sulfonyl}-4-piperidinyl)-1H-indole-7-carboxamide

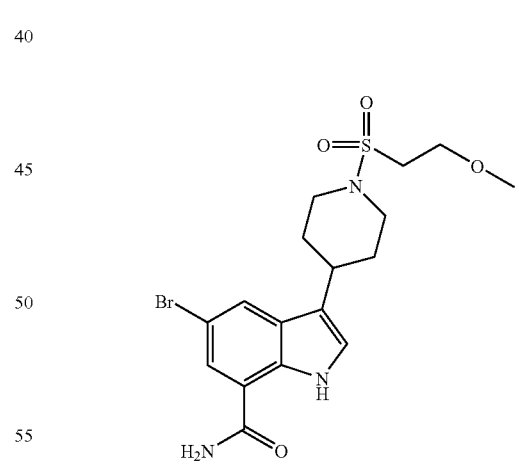

The mixture of 5-bromo-3-[1-(ethenylsulfonyl)-4-piperidinyl]-1H-indole-7-carboxamide (150 mg, 0.36 mmol), sodium methoxide in methanol (25%, 1.0 mL) and methanol (2.0 mL) was stirred at 80° C. for 1 hr. After which time the reaction mixture was concentrated under reduced pressure. The residue was purified by combiflash to give the title compound (100.0 mg, 63%).

LC/MS: 444.4 r.t: 1.90 min.

(41) 5-(3-formylphenyl)-3-(1-{[2-(methyloxy)ethyl]sulfonyl}-4-piperidinyl)-1H-indole-7-carboxamide

(43) 5-(5-formyl-3-thienyl)-3-(1-{[3-(methyloxy)propyl]sulfonyl}-4-piperidinyl)-1H-indole-7-carboxamide

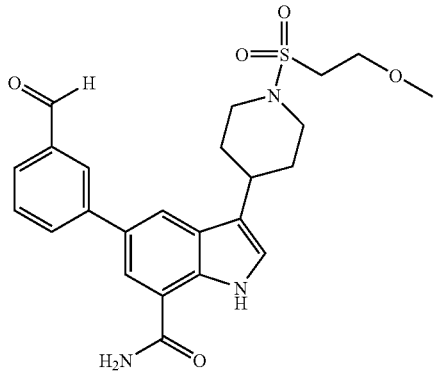

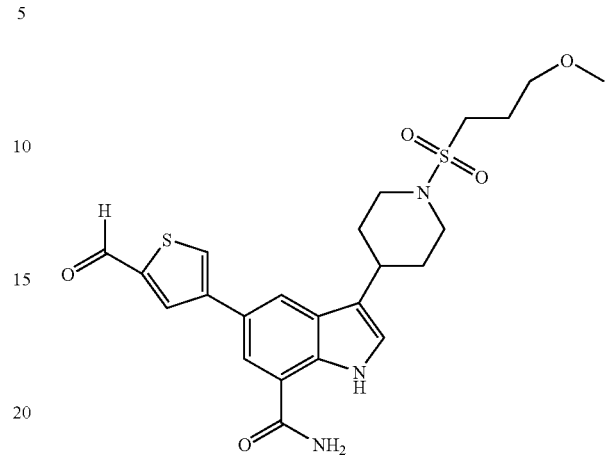

To a solution of 5-bromo-3-(1-{[2-(methyloxy)ethyl]sulfonyl}-4-piperidinyl)-1H-indole-7-carboxamide (100 mg, 0.22 mmol) in dioxane (3.0 mL) and water (1.0 ml), (3-formylphenyl)boronic acid (186 mg, 1.25 mmol), Pd(PPh$_3$)$_4$ (25.0 mg, 10%) and cessium carbonate (200 mg, 0.45 mmol) were added. The reaction mixture was heated in a Smith synthesizer microwave at 160° C. for 20 min. All solvent was evaporated under reduced pressure. The residue was purified by flash column chromatography (ethyl acetate/hexane, 1/1) to yield the desired product (50.0 mg, 48%).

LC/MS: m/z 470.4 (M+H), Rt 1.95 min.

(42) 4-(4,4,5,5-tetramethyl-1,3,2-dioxaborolan-2-yl)-2-thiophenecarbaldehyde

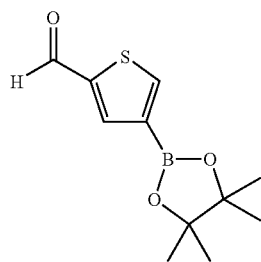

To 4-bromo-2-thiophenecarbaldehyde (500 mg, 2.61 mmol) in DME (18 mL), bis(pinacolato)diboron (865 mg, 3.403 mmol), potassium acetate (667 mg, 6.81 mmol) and PdCl$_2$(dppf) (96 mg, 0.131 mmol) were added. The reaction mixture was heated by microwave at 150° C. for 20 minutes. Then all the solvent was evaporated. The residue was partitioned between ethyl acetate (100 mL) and water (100 mL). The water layer was extracted with ethyl acetate (2×100 mL). The combined organic phase washed with brine (100 mL) and dried with Mg$_2$SO$_4$ and concentrated. The crude product was purified by Combiflash (Hexane/ethyl acetate, 1%-30% ethyl acetate, 20 min.) to give title compound (550 mg, 88%).

LC/MS: m/z, 238.2 (M+H), 1.88 min.

To 5-bromo-3-(1-{[3-(methyloxy)propyl]sulfonyl}-4-piperidinyl)-1H-indole-7-carboxamide (170 mg, 0.37 mmol) in mixture of dioxane (4.5 mL) and water (1.5 mL), 4-(4,4,5,5-tetramethyl-1,3,2-dioxaborolan-2-yl)-2-thiophenecarbaldehyde (265.2 mg, 1.11 mmol), potassium carbonate (309 mg, 2.22 mmol) and Pd(PPh$_3$)$_4$ (44.2 mg, 0.04 mmol) were added. The reaction mixture was heated by microwave at 150° C. for 20 minutes. Then all the solvent was evaporated. The residue was partitioned between ethyl acetate (50 mL) and water (50 mL). The water layer was extracted with ethyl acetate (2×50 mL). The combined organic phase washed with brine (50 mL) and dried with Mg$_2$SO$_4$ and concentrated. The crude product was purified by Combiflash (dichloromethane/methanol, 1%-40% methanol, 25 min.) to give title compound (110 mg, 61%).

LC/MS: m/z, 490.2 (M+H), 2.00 min.

EXAMPLES

(1) 3-{1-[(2-aminoethyl)sulfonyl]-4-piperidinyl}-5-phenyl-1H-indole-7-carboxamide

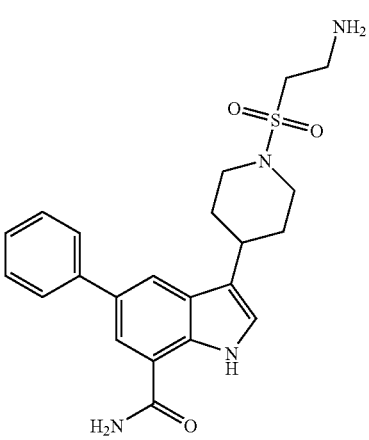

To a solution of 3-(1-{[2-(1,3-dioxo-1,3-dihydro-2H-isoindol-2-yl)ethyl]sulfonyl}-4-piperidinyl)-5-phenyl-1H-indole-7-carboxamide (70 mg, 0.13 mmol) in EtOH (2 mL) at room temperature, hydrazine (0.3 mL) was added. The reaction mixture was stirred at room temperature for 2 hours. The solvent was removed under reduced pressure and the resulting residue purified by reverse phase HPLC eluting with 10% B to 80% B, where A=H$_2$O (0.1% trifluoroacetic acid) and B=CH$_3$CN (0.1% trifluoroacetic acid) to give the title compound (26.9 mg, 50%).

LC/MS m/z 427.0 (M+H).

(2) 3-(1-{[2-(dimethylamino)ethyl]sulfonyl}-4-piperidinyl)-5-phenyl-1H-indole-7-carboxamide

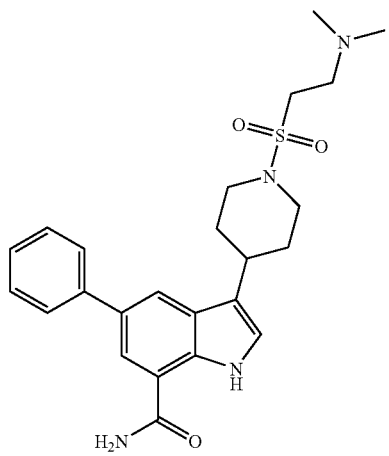

To a solution of 3-{1-[(2-chloroethyl)sulfonyl]-4-piperidinyl}-5-phenyl-1H-indole-7-carboxamide (26 mg, 0.063 mmol) in CH$_3$CN (5 mL), dimethylamine (0.16 mL, 0.315 mmol), K$_2$CO$_3$ (35 mg, 0.252 mmol) and NaI (cat. 0.5 mg) were added. The reaction mixture was stirred at 80° C. for 16 hours. The solvent was removed under reduced pressure. The residue was partitioned between ethyl acetate and water. The organic phase was dried over magnesium sulfate, filtered and the solvent removed under reduced pressure. The resulting residue was purified by reverse phase HPLC (CH$_3$CN/water, 0.1% TFA) to give title compound (14 mg, 48%).

LC/MS m/z 455.2 (M+H).

(3) 3-(1-{[3-(dimethylamino)propyl]sulfonyl}-4-piperidinyl)-5-phenyl-1H-indole-7-carboxamide

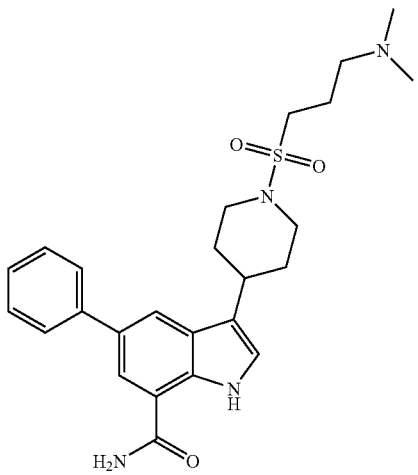

Following the general procedure for aminosulfonamide formation outlined in example 2, 3-{1-[(3-chloropropyl)sulfonyl]-4-piperidinyl}-5-phenyl-1H-indole-7-carboxamide (47 mg, 0.1 mmol) and dimethylamine (2.0M in THF, 0.5 mL, 0.5 mmol), were allowed to react in the presence of K$_2$CO$_3$ (55.2 mg, 0.4 mmol) and NaI (Cat. 1.51 mg). The resulting residue was purified by reverse phase HPLC eluting with 10% B to 80% B, where A=H$_2$O (0.1% trifluoroacetic acid) and B=CH$_3$CN (0.1% trifluoroacetic acid) to give the title compound (8.7 mg, 19%).

LC/MS m/z 469.0 (M+H).

(4) 3-(1-{[3-(4-methyl-1-piperazinyl)propyl]sulfonyl}-4-piperidinyl)-5-phenyl-1H-indole-7-carboxamide

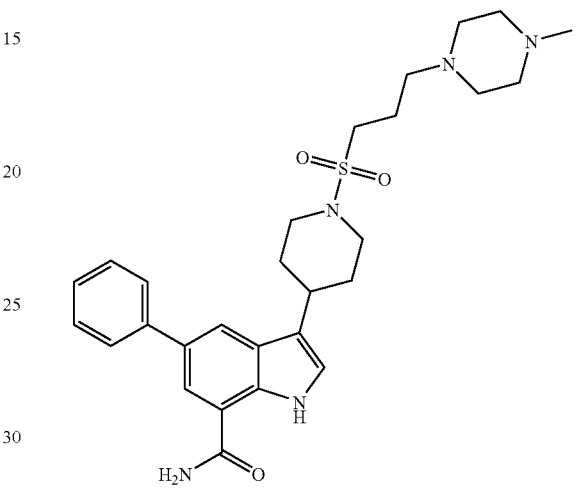

Following the general procedure for aminosulfonamide formation outlined in example 2, 3-{1-[(3-chloropropyl)sulfonyl]-4-piperidinyl}-5-phenyl-1H-indole-7-carboxamide (65 mg, 0.14 mmol) and 1-methylpiperazine (70.5 mg, 0.7 mmol) were allowed to react in the presence of K$_2$CO$_3$ (77.3 mg, 0.56 mmol) and NaI (Cat. 2.13 mg). The resulting residue was purified by reverse phase HPLC eluting with 10% B to 80% B, where A=H$_2$O (0.1% trifluoroacetic acid) and B=CH$_3$CN (0.1% trifluoroacetic acid) to give the title compound (52.7 mg, 71%).

LC/MS m/z 524.2 (M+H).

(5) 5-phenyl-3-(1-{[3-(1-piperidinyl)propyl]sulfonyl}-4-piperidinyl)-1H-indole-7-carboxamide

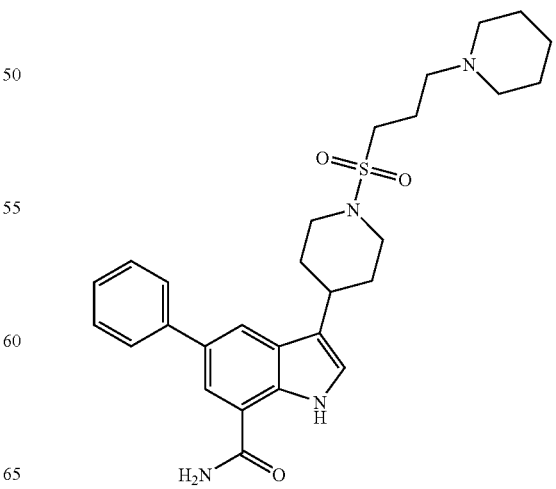

Following the general procedure for aminosulfonamide formation outlined in example 2, 3-{1-[(3-chloropropyl)sulfonyl]-4-piperidinyl}-5-phenyl-1H-indole-7-carboxamide (62 mg, 0.13 mmol) and piperidine (55.25 mg, 0.65 mmol) were allowed to react in the presence of $K_2CO_3$ (72 mg, 0.56 mmol) and NaI (Cat. 2.0 mg). The resulting residue purified by reverse phase HPLC eluting with 10% B to 80% B, where $A=H_2O$ (0.1% trifluoroacetic acid) and $B=CH_3CN$ (0.1% trifluoroacetic acid) to give the title compound (31.5 mg, 46%).

LC/MS m/z 509.2 (M+H).

(6) 3-(1-{[3-(4-morpholinyl)propyl]sulfonyl}-4-piperidinyl)-5-phenyl-1H-indole-7-carboxamide

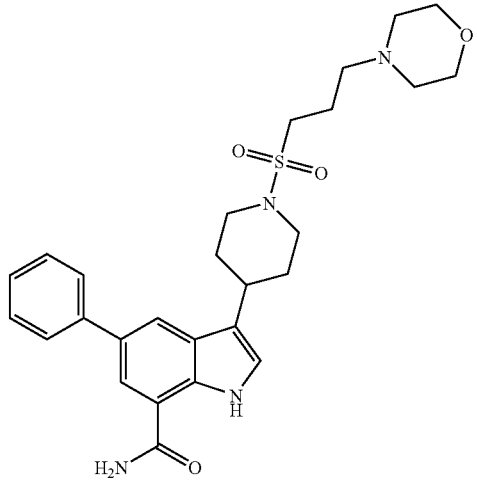

Following the general procedure for aminosulfonamide formation outlined in example 2, 3-{1-[(3-chloropropyl)sulfonyl]-4-piperidinyl}-5-phenyl-1H-indole-7-carboxamide (60 mg, 0.13 mmol) and morpholine (56.63 mg, 0.65 mmol) were allowed to react in the presence of $K_2CO_3$ (77 mg, 0.56 mmol) and NaI (Cat. 2.13 mg). The resulting residue was purified by reverse phase HPLC eluting with 10% B to 80% B, where $A=H_2O$ (0.1% trifluoroacetic acid) and $B=CH_3CN$ (0.1% trifluoroacetic acid) to give the title compound (20 mg, 30%).

LC/MS m/z 511.0 (M+H).

(7) 5-phenyl-3-(1-{[3-(1-pyrrolidinyl)propyl]sulfonyl}-4-piperidinyl)-1H-indole-7-carboxamide

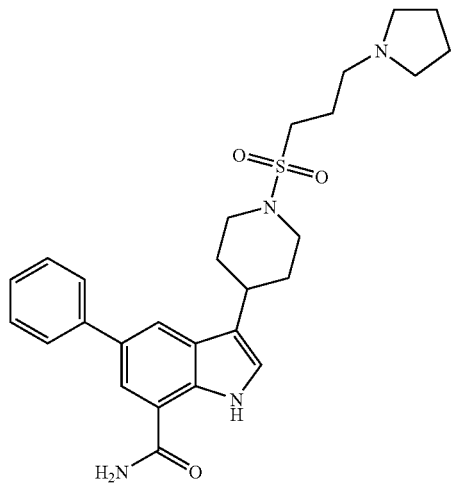

Following the general procedure for aminosulfonamide formation outlined in example 2, 3-{1-[(3-chloropropyl)sulfonyl]-4-piperidinyl}-5-phenyl-1H-indole-7-carboxamide (60 mg, 0.13 mmol) and pyrrolidine (46.2 mg, 0.65 mmol) were allowed to react in the presence of $K_2CO_3$ (77 mg, 0.56 mmol) and NaI (Cat. 2.13 mg). The resulting residue was purified by reverse phase HPLC eluting with 10% B to 80% B, where $A=H_2O$ (0.1% trifluoroacetic acid) and $B=CH_3CN$ (0.1% trifluoroacetic acid) to give the title compound (27 mg, 42%).

LC/MS m/z 495.4 (M+H).

(8) 3-(1-{[3-(1-pyrrolidinyl)propyl]sulfonyl}-4-piperidinyl)-5-(3-thienyl)-1H-indole-7-carboxamide

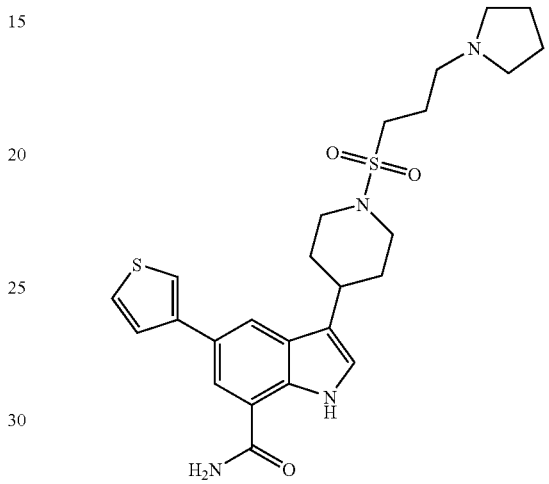

Following the general procedure for aminosulfonamide formation outlined in example 2, 3-{1-[(3-chloropropyl)sulfonyl]-4-piperidinyl}-5-(3-thienyl)-1H-indole-7-carboxamide (55 mg, 0.12 mmol) and pyrrolidine (42.6 mg, 0.60 mmol) were allowed to react in the presence of $K_2CO_3$ (84.6 mg, 0.24 mmol) and NaI (Cat. 5 mg). The resulting residue was purified by reverse phase HPLC eluting with 10% B to 80% B, where $A=H_2O$ (0.1% trifluoroacetic acid) and $B=CH_3CN$ (0.1% trifluoroacetic acid) to give the title compound (23.2 mg, 39%).

LC/MS: m/z 501.4 (M+H) Rt 1.66 min.

(9) 3-(1-{[3-(dimethylamino)propyl]sulfonyl}-4-piperidinyl)-5-(3-thienyl)-1H-indole-7-carboxamide

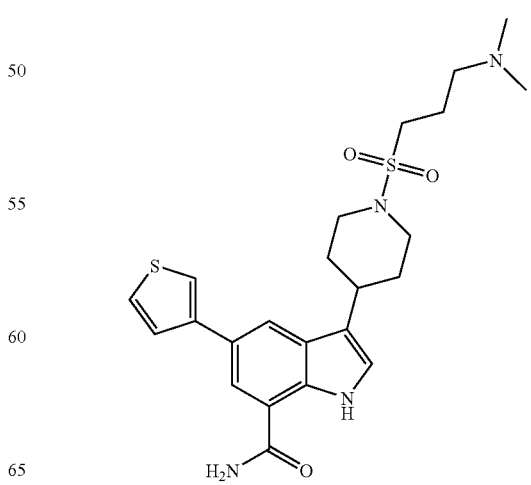

Following the general procedure for aminosulfonamide formation outlined in example 2, 3-{1-[(3-chloropropyl)sulfonyl]-4-piperidinyl}-5-(3-thienyl)-1H-indole-7-carboxamide (50 mg, 0.12 mmol) and 2M dimethyl amine in THF (0.3 mL, 0.60 mmol) were allowed to react in the presence of $K_2CO_3$ (84.6 mg, 0.24 mmol) and NaI (Cat. 5 mg). The resulting residue was purified by reverse phase HPLC eluting with 10% B to 80% B, where A=$H_2O$ (0.1% trifluoroacetic acid) and B=$CH_3CN$ (0.1% trifluoroacetic acid) to give the title compound (17.1 mg, 30%).

LC/MS: m/z 475.4 (M+H) Rt 1.64 min.

(10) 3-(1-{[3-(dimethylamino)propyl]sulfonyl}-4-piperidinyl)-5-(2-thienyl)-1 indole-7-carboxamide

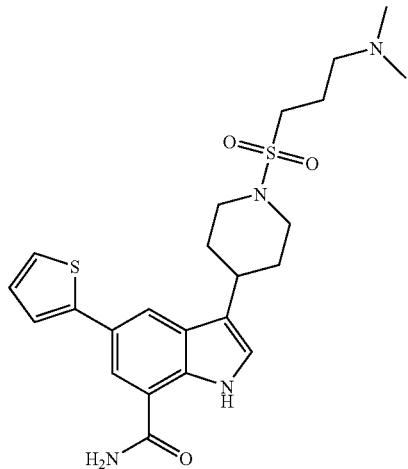

Following the general procedure for aminosulfonamide formation outlined in example 2, 3-{1-[(3-chloropropyl)sulfonyl]-4-piperidinyl}-5-(2-thienyl)-1H-indole-7-carboxamide (50 mg, 0.12 mmol) and 2M dimethyl amine in THF (0.3 mL, 0.60 mmol) were allowed to react in the presence of $K_2CO_3$ (74 mg, 0.55 mmol) and NaI (Cat. 5 mg) at 80° C. The resulting residue was purified by reverse phase HPLC eluting with 10% B to 80% B, where A=$H_2O$ (0.1% trifluoroacetic acid) and B=$CH_3CN$ (0.1% trifluoroacetic acid) to give the title compound (35 mg, 61%).

LC/MS: m/z 475.4 (M+H) Rt 1.55 min.

(11) 3-(1-{[3-(1-pyrrolidinyl)propyl]sulfonyl}-4-piperidinyl)-5-(2-thienyl)-1 indole-7-carboxamide

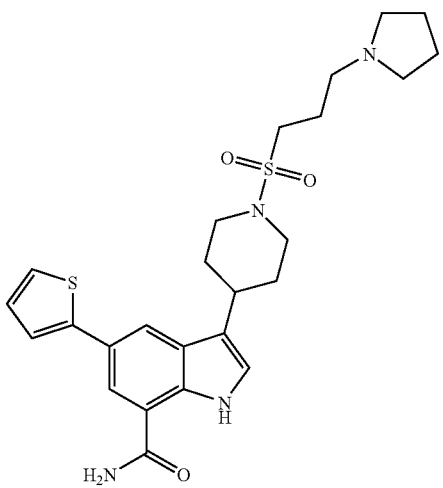

Following the general procedure for aminosulfonamide formation outlined in example 2, 3-{1-[(3-chloropropyl)sulfonyl]-4-piperidinyl}-5-(2-thienyl)-1H-indole-7-carboxamide (50 mg, 0.12 mmol) and pyrrolidine (45 uL, 0.60 mmol) were allowed to react in the presence of $K_2CO_3$ (74 mg, 0.55 mmol) and NaI (Cat. 5 mg) at 80° C. The resulting residue was purified by reverse phase HPLC eluting with 10% B to 80% B, where A=$H_2O$ (0.1% trifluoroacetic acid) and B=$CH_3CN$ (0.1% trifluoroacetic acid) to give the title compound (41.2 mg, 68%).

LC/MS: m/z 501.4 (M+H) Rt 1.57 min.

(12) 3-(1-{[3-(2-methyl-1-pyrrolidinyl)propyl]sulfonyl}-4-piperidinyl)-5-(2-thienyl)-11 indole-7-carboxamide

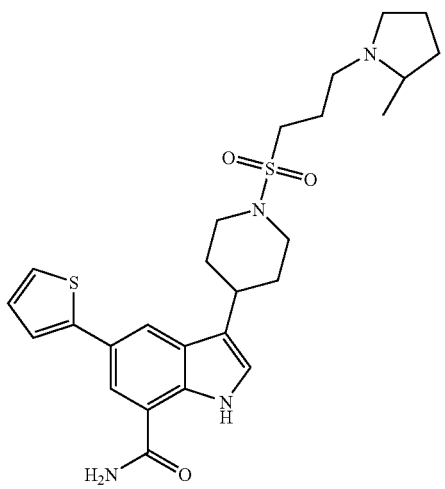

Following the general procedure for aminosulfonamide formation outlined in example 2, 3-{1-[(3-chloropropyl)sulfonyl]-4-piperidinyl}-5-(2-thienyl)-1H-indole-7-carboxamide (50 mg, 0.12 mmol) and 2-methylpyrrolidine (56 uL, 0.60 mmol) were allowed to react in the presence of $K_2CO_3$ (74 mg, 0.55 mmol) and NaI (Cat. 5 mg) at 80° C. The resulting residue was purified by reverse phase HPLC eluting with 10% B to 80% B, where A=$H_2O$ (0.1% trifluoroacetic acid) and B=$CH_3CN$ (0.1% trifluoroacetic acid) to give the title compound (36.5 mg, 59%).

LC/MS: m/z 515.4 (M+H) Rt 1.60 min.

(13) 3-(1-{[3-(cyclopentylamino)propyl]sulfonyl}-4-piperidinyl)-5-(2-thienyl)-1H-indole-7-carboxamide

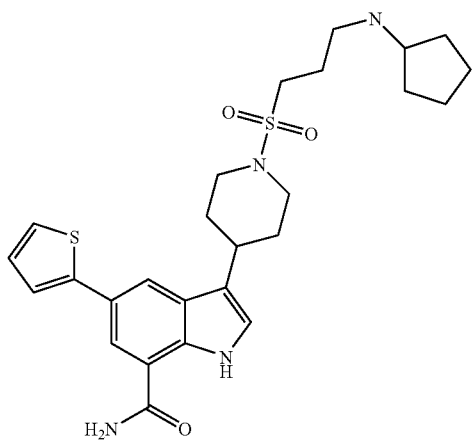

Following the general procedure for aminosulfonamide formation outlined in example 2, 3-{1-[(3-chloropropyl)sulfonyl]-4-piperidinyl}-5-(2-thienyl)-1H-indole-7-carboxamide (50 mg, 0.12 mmol) and cyclopentyl amine (54 uL, 0.60 mmol) were allowed to react in the presence of $K_2CO_3$ (74 mg, 0.55 mmol) and NaI (Cat. 5 mg) in DMF at 120° C. The resulting residue was purified by reverse phase HPLC eluting with 10% B to 80% B, where A=$H_2O$ (0.1% trifluoroacetic acid) and B=$CH_3CN$ (0.1% trifluoroacetic acid) to give the title compound (27.2 mg, 44%).

LC/MS: m/z 515.4 (M+H) Rt 1.60 min.

(14) 3-(1-{[3-(4-hydroxy-1-piperidinyl)propyl]sulfonyl}-4-piperidinyl)-5-(2-thienyl)-1-indole-7-carboxamide

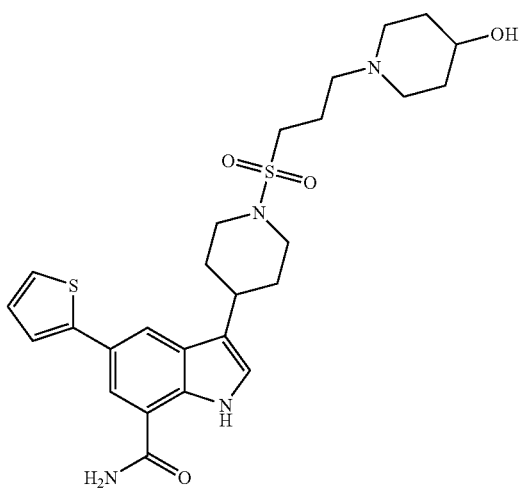

Following the general procedure for aminosulfonamide formation outlined in example 2, 3-{1-[(3-chloropropyl)sulfonyl]-4-piperidinyl}-5-(2-thienyl)-1H-indole-7-carboxamide (50 mg, 0.12 mmol) and 4-piperidinol (55.6 mg, 0.60 mmol) were allowed to react in the presence of $K_2CO_3$ (74 mg, 0.55 mmol) and NaI (Cat. 5 mg) in DMF at 120° C. The resulting residue was purified by reverse phase HPLC eluting with 10% B to 80% B, where A=$H_2O$ (0.1% trifluoroacetic acid) and B=$CH_3CN$ (0.1% trifluoroacetic acid) to give the title compound (32.3 mg, 51%).

LC/MS: m/z 531.4 (M+H) Rt 1.43 min.

(15) 3-(1-{[2-(cyclopentylamino)ethyl]sulfonyl}-4-piperidinyl)-5-(2-thienyl)-1H-indole-7-carboxamide

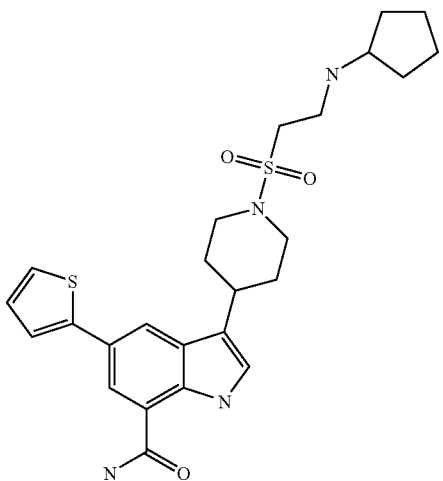

3-{1-[(2-chloroethyl)sulfonyl]-4-piperidinyl}-5-(2-thienyl)-1H-indole-7-carboxamide was prepared according to the procedure for intermediate 11. 3-(4-piperidinyl)-5-(2-thienyl)-1H-indole-7-carboxamide (30 mg, 0.09 mmol) was reacted with triethyl amine (0.04 mL, 0.27 mmol) and 2-chloroethylsulfonyl chloride (0.02 mL, 0.18 mmol) to give 3-{1-[(2-chloroethyl)sulfonyl]-4-piperidinyl}-5-(2-thienyl)-1H-indole-7-carboxamide, which was used in the next step without further purification.

Following the general procedure for aminosulfonamide formation outlined in example 2, 3-{1-[(2-chloroethyl)sulfonyl]-4-piperidinyl}-5-(2-thienyl)-1H-indole-7-carboxamide (0.09 mmol) and cyclopentanamine (0.04 mL, 0.45 mmol) were allowed to react in the presence of $K_2CO_3$ (44 mg, 0.45 mmol) and NaI (Cat. 5 mg). The resulting residue was purified by reverse phase HPLC eluting with 10% B to 80% B, where A=$H_2O$ (0.1% trifluoroacetic acid) and B=$CH_3CN$ (0.1% trifluoroacetic acid) to give the title compound (14 mg, 39%).

LC/MS: m/z 501.4 (M+H) Rt 1.73 min.

(16) 3-(1-{[2-(1-pyrrolidinyl)ethyl]sulfonyl}-4-piperidinyl)-5-(3-thienyl)-1H-indole-7-carboxamide

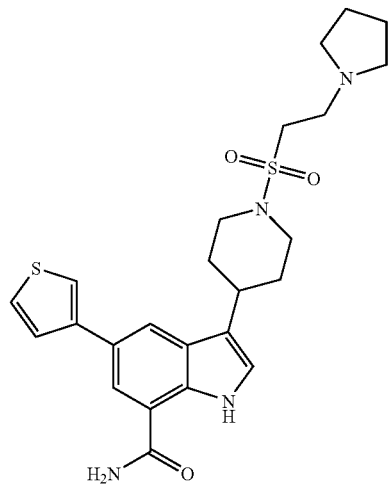

3-{1-[(2-chloroethyl)sulfonyl]-4-piperidinyl}-5-(3-thienyl)-1H-indole-7-carboxamide was prepared according to the procedure for intermediate 11. 3-(4-piperidinyl)-5-(3-thienyl)-1H-indole-7-carboxamide (30 mg, 0.09 mmol) was reacted with triethyl amine (0.025 mL, 0.18 mmol) and 2-chloroethylsulfonyl chloride (0.012 mL, 1.08 mmol) to give 3-{1-[(2-chloroethyl)sulfonyl]-4-piperidinyl}-5-(3-thienyl)-1H-indole-7-carboxamide, which was used in the next step without further purification.

Following the general procedure for aminosulfonamide formation outlined in example 2, 3-{1-[(2-chloroethyl)sulfonyl]-4-piperidinyl}-5-(3-thienyl)-1H-indole-7-carboxamide (0.09 mmol) and pyrrolidine (0.03 mL, 0.45 mmol) were allowed to react in the presence of $K_2CO_3$ (44 mg, 0.45 mmol) and NaI (Cat. 5 mg). The resulting residue was purified by reverse phase HPLC eluting with 10% B to 80% B, where A=$H_2O$ (0.1% trifluoroacetic acid) and B=$CH_3CN$ (0.1% trifluoroacetic acid) to give the title compound (12.4 mg, 28%).

LC/MS: m/z 487.2 (M+H) Rt 1.63 min.

(17) 3-(1-{[2-(dimethylamino)ethyl]sulfonyl}-4-piperidinyl)-5-(3-thienyl)-1H-indole-7-carboxamide

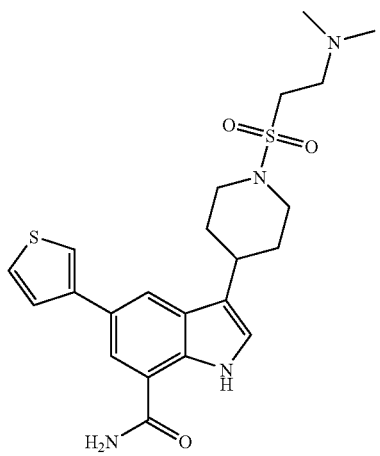

3-{1-[(2-chloroethyl)sulfonyl]-4-piperidinyl}-5-(3-thienyl)-1H-indole-7-carboxamide was prepared according to the procedure for intermediate 11. 3-(4-piperidinyl)-5-(3-thienyl)-1H-indole-7-carboxamide (30 mg, 0.09 mmol) was reacted with triethyl amine (0.025 mL, 0.18 mmol) and 2-chloroethylsulfonyl chloride (0.012 mL, 1.08 mmol) to give 3-{1-[(2-chloroethyl)sulfonyl]-4-piperidinyl}-5-(3-thienyl)-1H-indole-7-carboxamide, which was used in the next step without further purification.

Following the general procedure for aminosulfonamide formation outlined in example 2, 3-{1-[(2-chloroethyl)sulfonyl]-4-piperidinyl}-5-(3-thienyl)-1H-indole-7-carboxamide (0.09 mmol) and 2M dimethyl amine in THF (0.225 mL, 0.45 mmol) were allowed to react in the presence of $K_2CO_3$ (44 mg, 0.45 mmol) and NaI (Cat. 5 mg). The resulting residue was purified by reverse phase HPLC eluting with 10% B to 80% B, where $A=H_2O$ (0.1% trifluoroacetic acid) and $B=CH_3CN$ (0.1% trifluoroacetic acid) to give the title compound (5.5 mg, 13%).

LC/MS: m/z 461.2 (M+H) Rt 1.42 min.

(18) 3-(1-{[2-(cyclopentylamino)ethyl]sulfonyl}-4-piperidinyl)-5-(3-thienyl)-11 indole-7-carboxamide

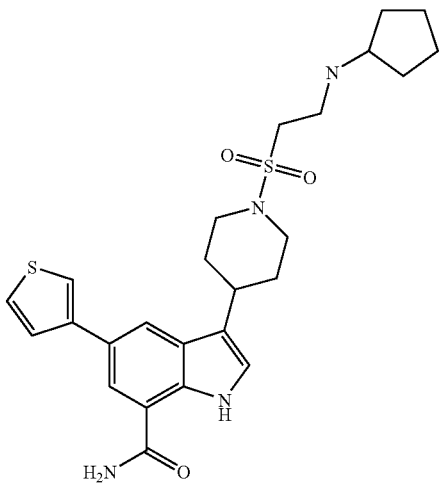

3-{1-[(2-chloroethyl)sulfonyl]-4-piperidinyl}-5-(3-thienyl)-1H-indole-7-carboxamide was prepared according to the procedure for intermediate 11. 3-(4-piperidinyl)-5-(3-thienyl)-1H-indole-7-carboxamide (30 mg, 0.09 mmol) was reacted with triethyl amine (0.025 mL, 0.18 mmol) and 2-chloroethylsulfonyl chloride (0.012 mL, 1.08 mmol) to give 3-{1-[(2-chloroethyl)sulfonyl]-4-piperidinyl}-5-(3-thienyl)-1H-indole-7-carboxamide, which was used in the next step without further purification.

Following the general procedure for aminosulfonamide formation outlined in example 2, 3-{1-[(2-chloroethyl)sulfonyl]-4-piperidinyl}-5-(3-thienyl)-1H-indole-7-carboxamide (0.09 mmol) and cyclopentyl amine (0.04 mL, 0.45 mmol) were allowed to react in the presence of $K_2CO_3$ (44 mg, 0.45 mmol) and NaI (Cat. 5 mg). The resulting residue was purified by reverse phase HPLC eluting with 10% B to 80% B, where $A=H_2O$ (0.1% trifluoroacetic acid) and $B=CH_3CN$ (0.1% trifluoroacetic acid) to give the title compound (7.1 mg, 16%).

LC/MS: m/z 501.2 (M+H) Rt 1.60 min.

(19) 3-[1-({2-[(4-hydroxycyclohexyl)amino]ethyl}sulfonyl)-4-piperidinyl]-5-(3-thienyl)-1H-indole-7-carboxamide

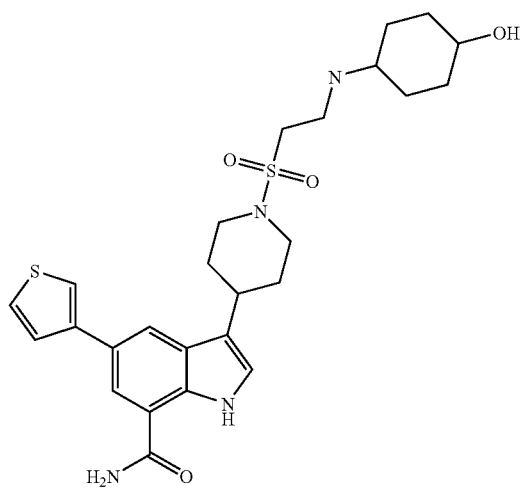

3-{1-[(2-chloroethyl)sulfonyl]-4-piperidinyl}-5-(3-thienyl)-1H-indole-7-carboxamide was prepared according to the procedure for intermediate 11. 3-(4-piperidinyl)-5-(3-thienyl)-1H-indole-7-carboxamide (30 mg, 0.09 mmol) was reacted with triethyl amine (0.025 mL, 0.18 mmol) and 2-chloroethylsulfonyl chloride (0.012 mL, 1.08 mmol) to give 3-{1-[(2-chloroethyl)sulfonyl]-4-piperidinyl}-5-(3-thienyl)-1H-indole-7-carboxamide, which was used in the next step without further purification.

Following the general procedure for aminosulfonamide formation outlined in example 2, 3-{1-[(2-chloroethyl)sulfonyl]-4-piperidinyl}-5-(3-thienyl)-1H-indole-7-carboxamide (0.09 mmol) and 4-aminocyclohexanol (33.4 mg, 0.45 mmol) were allowed to react in the presence of $K_2CO_3$ (44 mg, 0.45 mmol) and NaI (Cat. 5 mg). The resulting residue was purified by reverse phase HPLC eluting with 10% B to 80% B, where $A=H_2O$ (0.1% trifluoroacetic acid) and $B=CH_3CN$ (0.1% trifluoroacetic acid) to give the title compound (3.6 mg, 7.7%).

LC/MS: m/z 517.2 (M+H) Rt 1.40 min.

(20) 3-{1-[(2-hydroxyethyl)sulfonyl]-4-piperidinyl}-5-phenyl-1H-indole-7-carboxamide

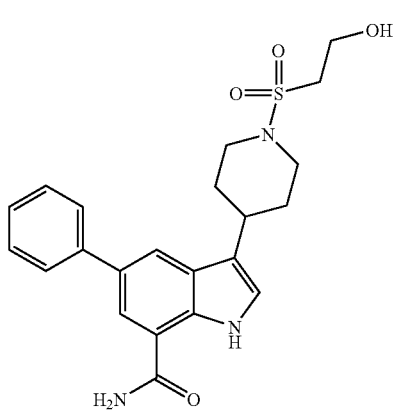

The mixture of 3-[1-(ethenylsulfonyl)-4-piperidinyl]-5-phenyl-1H-indole-7-carboxamide (26 mg, 0.063 mmol) and aqueous 6M NaOH (0.2 mL) in DMSO was heated to 80° C. overnight. After which time the reaction mixture was filtered and purified by reverse phase HPLC (water/CH$_3$CN, 0.1% TFA 3-70%) to give the title compound (16 mg, 59%).

LC/MS: 428.2 r.t: 1.79 min.

(21) 5-(5-chloro-2-thienyl)-3-(1-{[3-(1-pyrrolidinyl)propyl]sulfonyl}-4-piperidinyl)-1H-indole-7-carboxamide

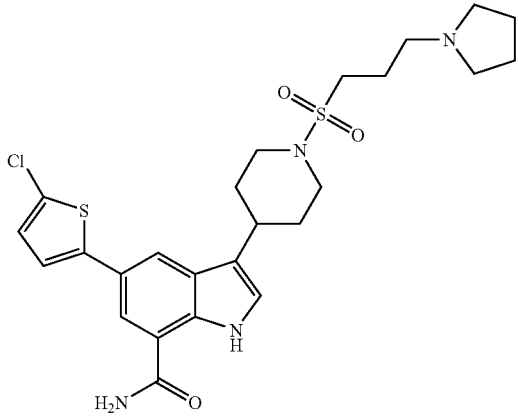

The title compound was prepared following the general procedure described in intermediate 16. Thus, 15-bromo-3-(1-{[3-(1-pyrrolidinyl)propyl]sulfonyl}-4-piperidinyl)-1H-indole-7-carboxamide (95 mg, 0.19 mmol) in dioxane (3 mL) and water (1 mL), 5-chloro-2-thienylboronic acid (123 mg, 0.76 mmol), Pd(PPh$_3$)$_4$ (22.2 mg, 10%) and potassium carbonate (211 mg, 1.52 mmol) in dioxane (3.0 mL) and water (1.0 mL) were reacted to form the desired product which was purified by reverse phase HPLC eluting with 10% B to 80% B, where A=H$_2$O (0.1% trifluoroacetic acid) and B=CH$_3$CN (0.1% trifluoroacetic acid) to give the title compound (11 mg, 11%).

LC/MS: m/z 535.0 (M+H), Rt 1.84 min.

(22) 3-(1-{[2-(methylamino)ethyl]sulfonyl}-4-piperidinyl)-5-phenyl-1H-indole-7-carboxamide

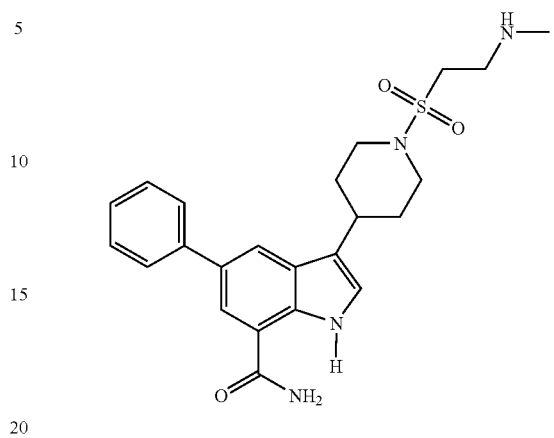

To a solution of 3-[1-(ethenylsulfonyl)-4-piperidinyl]-5-phenyl-1H-indole-7-carboxamide (26 mg, 0.063 mmol) in CH$_3$CN (1.0 mL), were added methylamine (19.5 mg, 0.63 mmol). The reaction solution was heated to 80° C. overnight. After which time the reaction mixture was purified by reverse phase HPLC (water/CH$_3$CN, 0.1% TFA 10-90%) to give the title compound (15 mg, 54%).

LC/MS: m/z 414.4.0 (M+H), Rt 1.61 min.

Following the general procedure described in example 22, but replacing methylamine with the appropriate amines, compounds listed in Table 1 were prepared.

TABLE 1

| Example | T1 | MS [M]$^+$ | Rt (min) |
|---|---|---|---|
| 23 | piperidinyl | 495.4 | 1.79 |
| 24 | 4-methylpiperazinyl | 510.4 | 1.69 |
| 25 | N,N,N'-trimethylethylenediamine | 512.6 | 1.87 |

TABLE 1-continued

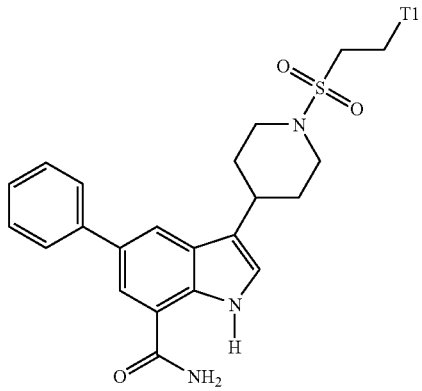

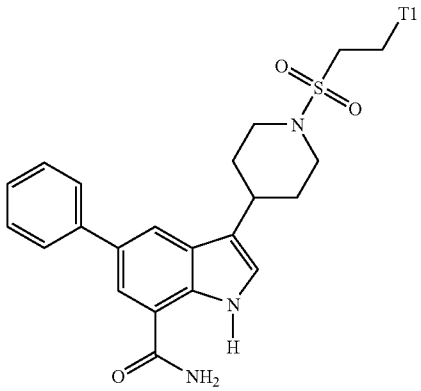

| Example | T1 | MS [M]+ | Rt (min) |
|---|---|---|---|
| 26 | 4-methylmorpholine | 497.6 | 1.64 |
| 27 | 1-methyl-3-(2-hydroxyethyl)piperazine | 540.2 | 1.59 |
| 28 | N-methylcyclopentylamine | 495.4 | 1.78 |
| 29 | N-methylcyclobutylamine | 481.2 | 1.68 |
| 30 | N-methylbenzylamine | 517.4 | 1.86 |
| 31 | 1-methylpyrrolidine | 481.2 | 1.70 |
| 32 | 1-methyl-4-hydroxypiperidine | 511.2 | 1.62 |
| 33 | N,N,N',N'-tetramethyl-1,3-propanediamine | 526.6 | 1.52 |
| 34 | 1-methyl-4-(piperidin-1-yl)piperidine | 578.6 | 1.52 |

| Example | T1 | MS [M]+ | Rt (min) |
|---|---|---|---|
| 35 | N,N-diethylmethylamine | 483.4 | 1.76 |
| 36 | 1-methyl-2-phenylpyrrolidine | 557.4 | 1.98 |
| 37 | 1-methylazepane | 509.4 | 1.80 |
| 38 | N-methyl-cyclohexylmethylamine | 523.6 | 1.93 |
| 39 | 2-(methylamino)-1,3-propanediol | 501.5 | 1.49 |
| 40 | N-methyl-N-ethylamine | 455.2 | 1.63 |
| 41 | N,N-dimethylethylamine | 469.4 | 1.55 |
| 42 | N-methyl-ethanolamine | 471.6 | 1.55 |

TABLE 1-continued

| Example | T1 | MS [M]+ | Rt (min) |
|---|---|---|---|
| 43 | (S)-2-hydroxypropyl-N-methyl | 485.4 | 1.51 |
| 44 | (R)-2-hydroxy-1-methylethyl-N-methyl | 485.4 | 1.52 |
| 45 | (S)-2-hydroxy-1-methylethyl-N-methyl | 485.4 | 1.52 |
| 46 | 1-methylpiperidine-4-carboxamide | 538.4 | 1.60 |
| 47 | 4-(1-methylpiperidin-4-yl)morpholine | 580.8 | 1.52 |
| 48 | N,N-dimethyl-N'-methylethylenediamine | 498.7 | 1.53 |
| 49 | 1'-methyl-4-methyl-[1,4'-bipiperidine] | 592.4 | 1.61 |
| 50 | 1-methyl-4-(4-methylpiperazin-1-yl)piperidine | 593.4 | 1.44 |

TABLE 1-continued

| Example | T1 | MS [M]+ | Rt (min) |
|---|---|---|---|
| 51 | N-(2-methoxyethyl)-N-methyl | 485.7 | 1.85 |
| 52 | 3-morpholinopropyl-N-methyl | 554.6 | 1.67 |
| 53 | 1-acetyl-4-methylpiperazine | 538.7 | 1.71 |
| 54 | 2-(4-methylpiperazin-1-yl)ethanol | 540.7 | 1.69 |
| 55 | (1-methylpiperidin-3-yl)methanol | 525.6 | 1.70 |
| 56 | N-methyl-N-(2-tosylamidoethyl) | 624.4 | 1.96 |
| 57 | N-methyl-2-morpholinoethyl | 540.4 | 1.56 |

TABLE 1-continued

| Example | T1 | MS [M]+ | Rt (min) |
|---|---|---|---|
| 58 | (N,N,N',N'-tetramethylethylenediamine group) | 498.8 | 1.65 |
| 59 | (methylpiperazinyl-acetyl-pyrrolidine group) | 607.8 | 1.83 |
| 60 | (N,N-dimethyl-1-methylpyrrolidine-2-carboxamide group) | 552.6 | 1.87 |
| 61 | ((1-methylpyrrolidin-2-yl)methanol group) | 511.4 | 1.78 |
| 62 | (1-methylpyrrolidine-2-carboxamide group) | 524.4 | 1.77 |

(63) 5-[5-(hydroxymethyl)-2-thienyl]-3-(1-{[3-(1-pyrrolidinyl)propyl]sulfonyl}-4-piperidinyl)-1H-indole-7-carboxamide The title compound was prepared following the general procedure described in intermediate 16. Thus, 5-bromo-3-(1-{[3-(1-pyrrolidinyl)propyl]sulfonyl}-4-piperidinyl)-1H-indole-7-carboxamide (95 mg, 0.19 mmol) in dioxane (3 mL) and water (1 mL), [5-(hydroxymethyl)-2-thienyl]boronic acid (120 mg, 0.76 mmol), Pd(PPh$_3$)$_4$ (22.2 mg, 10%) and potassium carbonate (211 mg, 1.52 mmol) were reacted to form the desired product which was purified by flash column chromatography (ethyl acetate/hexane, 1/1) to yield the desired product (25 mg, 25%).

LC/MS: m/z 531.4 (M+H), Rt 1.44 min.

(64) 5-[5-(1-pyrrolidinylmethyl)-2-thienyl]-3-(1-{[3-(1-pyrrolidinyl)propyl]sulfonyl}-4-piperidinyl)-1H-indole-7-carboxamide To a solution of 5-(5-formyl-2-thienyl)-3-(1-{[3-(1-pyrrolidinyl)propyl]sulfonyl}-4-piperidinyl)-1H-indole-7-carboxamide (8.3 mg, 0.016 mmol) in methylene chloride (5 mL) was added pyrrolidine (0.001 mL, 0.016 mmol). The reaction mixture was stirred at room temperature for 1 hour before NaBH(OAc)$_3$ (10.2 mg, 0.048 mmol) was added. The reaction mixture was stirred at room temperature overnight and evaporated all the solvent. The residue was purified by using a Gilson semi-preparative HPLC system, eluting with 10% B to 80% B, where A=H₂O (0.1% trifluoroacetic acid) and B=CH₃CN (0.1% trifluoroacetic acid) pumped at 25 mL/min to give the title compound (7 mg, 92%).
LC/MS: m/z 484.4 (M+H), Rt 1.40 min.

(65) 5-{5-[(methylamino)methyl]-2-thienyl}-3-(1-{[3-(4-morpholinyl)propyl]sulfonyl}-4-piperidinyl)-1H-indole-7-carboxamide

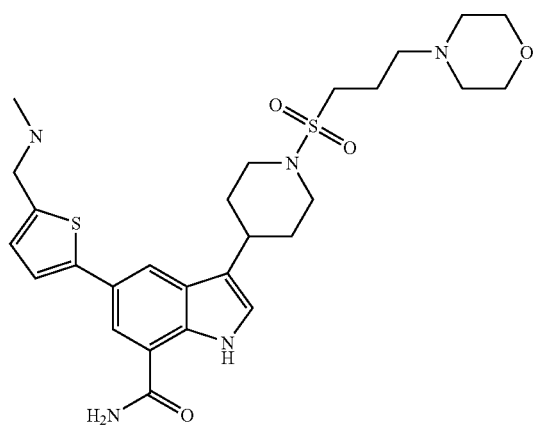

To a solution of 5-(5-formyl-2-thienyl)-3-(1-{[3-(4-morpholinyl)propyl]sulfonyl}-4-piperidinyl)-1H-indole-7-carboxamide (20 mg, 0.04 mmol) in MeOH/CH₂Cl₂ (1 mL/1 mL) was added methyl amine (0.11 mL, 0.24 mmol). The reaction mixture was stirred at room temperature for 2 hours before NaBH₄ (10.5 mg, 0.24 mmol) was added. The reaction mixture was stirred at room temperature overnight and evaporated all the solvent. The residue was purified by using a Gilson semi-preparative HPLC system, eluting with 10% B to 80% B, where A=H₂O (0.1% trifluoroacetic acid) and B=CH₃CN (0.1% trifluoroacetic acid) pumped at 25 mL/min to give the title compound (13.4 mg, 65%).
LC/MS: m/z 560.4 (M+H), Rt 1.46 min.

(66) 5-{5-[(ethylamino)methyl]-2-thienyl}-3-(1-{[3-(4-morpholinyl)propyl]sulfonyl}-4-piperidinyl)-1H-indole-7-carboxamide

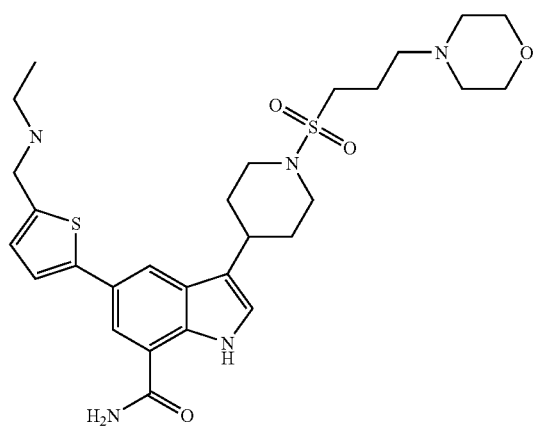

To a solution of 5-(5-formyl-2-thienyl)-3-(1-{[3-(4-morpholinyl)propyl]sulfonyl}-4-piperidinyl)-1H-indole-7-carboxamide (20 mg, 0.04 mmol) in MeOH/CH₂Cl₂ (1 mL/1 mL) was added ethyl amine (0.13 mL, 0.24 mmol). The reaction mixture was stirred at room temperature for 2 hours before NaBH₄ (10.5 mg, 0.24 mmol) was added. The reaction mixture was stirred at room temperature overnight and evaporated all the solvent. The residue was purified by using a Gilson semi-preparative HPLC system, eluting with 10% B to 80% B, where A=H₂O (0.1% trifluoroacetic acid) and B=CH₃CN (0.1% trifluoroacetic acid) pumped at 25 mL/min to give the title compound (11 mg, 52%)
LC/MS: m/z 574.2, Rt 1.33 min.

(67) 3-[1-({3-[bis(1-methylethyl)amino]propyl}sulfonyl)-4-piperidinyl]-5-phenyl-1H-indole-7-carboxamide

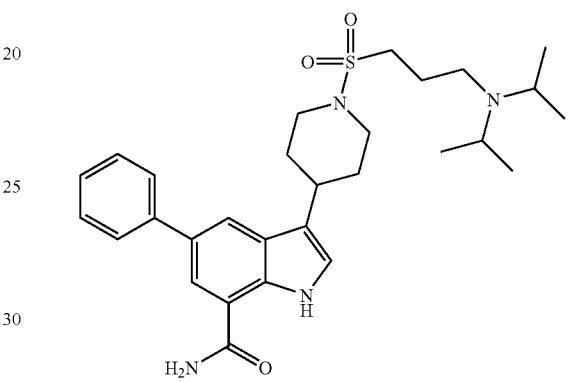

Following the general procedure for aminosulfonamide formation outlined in example 2, 3-{1-[(3-chloropropyl)sulfonyl]-4-piperidinyl}-5-phenyl-1H-indole-7-carboxamide (100 mg, 0.313 mmol) and N-(1-methylethyl)-2-propanamine (0.22 mL, 1.55 mmol) were allowed to react in the presence of K₂CO₃ (172.5 mg, 1.28 mmol). The resulting residue was purified by reverse phase HPLC eluting with 10% B to 80% B, where A=H₂O (0.1% trifluoroacetic acid) and B=CH₃CN (0.1% triflucaroacetic acid) to give the title compound (20.5 mg, 13%).
LC/MS: m/z 525.4 (M+H) Rt 1.63 min.

(68) 3-(1-{[2-(methyloxy)ethyl]sulfonyl}-4-piperidinyl)-5-phenyl-1 indole-7-carboxamide

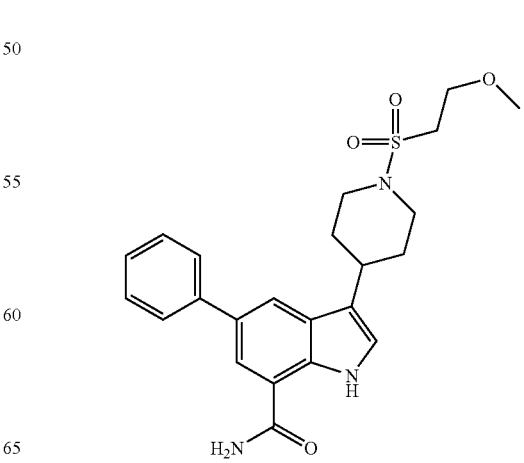

The mixture of 3-[1-(ethenylsulfonyl)-4-piperidinyl]-5-phenyl-1H-indole-7-carboxamide (26 mg, 0.063 mmol), 0.5 M sodium methoxide in methanol (0.1 mL) and methanol (1.0 mL) was stirred at 60 C for 1 hr. After which time the reaction mixture vvas concentrated under reduced pressure. The residue was purified by reverse phase HPLC (water/CH₃CN, 0.1% TFA 10-90%) to give the title compound (11.0 mg, 40%).

LC/MS: 442.4 r.t: 2.05 min.

(69) 3-[1-({3-[(2R,5R)-2,5-dimethyl-1-pyrrolidinyl]propyl}sulfonyl)-4-piperidinyl]-5-phenyl-1H-indole-7-carboxamide

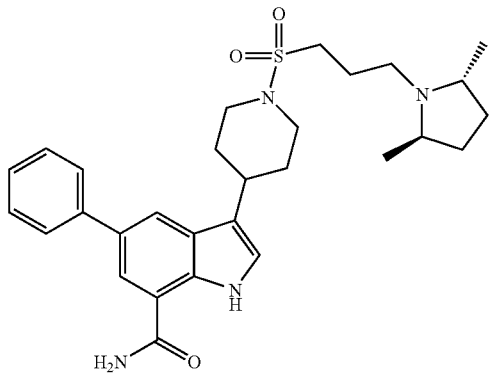

Following the general procedure for aminosulfonamide formation outlined in example 2, 3-{1-[(3-chloropropyl)sulfonyl]-4-piperidinyl}-5-phenyl-1H-indole-7-carboxamide (100 mg, 0.313 mmol) and (2R,5R)-2,5-dimethylpyrrolidine (449 mg, 1.56 mmol) were allowed to react in the presence of K₂CO₃ (886 mg, 0.63 mmol) and NaI (251 mg, 1.56 mmol). The resulting residue was purified by reverse phase HPLC eluting with 10% B to 80% B, where A=H₂O (0.1% trifluoroacetic acid) and B=CH₃CN (0.1% trifluoroacetic acid) to give the title compound (60 mg, 37%).

LC/MS: m/z 523.6 (M+H) Rt 1.73 min.

(70) 3-(1-{[3-(4-methyl-1-piperazinyl)propyl]sulfonyl}-4-piperidinyl)-5-(2-thienyl)-1H-indole-7-carboxamide

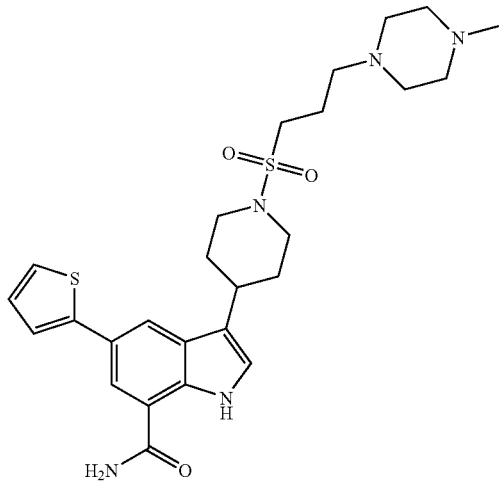

Following the general procedure for aminosulfonamide formation outlined in example 2, 3-{1-[(3-chloropropyl)sulfonyl]-4-piperidinyl}-5-(2-thienyl)-1H-indole-7-carboxamide (40 mg, 0.13 mmol) and 1-methylpiperazine (0.068 mL, 0.65 mmol) were allowed to react in the presence of K₂CO₃ (74 mg, 0.65 mmol). The resulting residue was purified by reverse phase HPLC eluting with 10% B to 80% B, where A=H₂O (0.1% trifluoroacetic acid) and B=CH₃CN (0.1% trifluoroacetic acid) to give the title compound (7.0 mg, 11%).

LC/MS: m/z 530.0 (M+H) Rt 1.52 min.

(71) 3-(1-{[3-(4-hydroxy-1-piperidinyl)propyl]sulfonyl}-4-piperidinyl)-5-(3-thienyl)-1H-indole-7-carboxamide

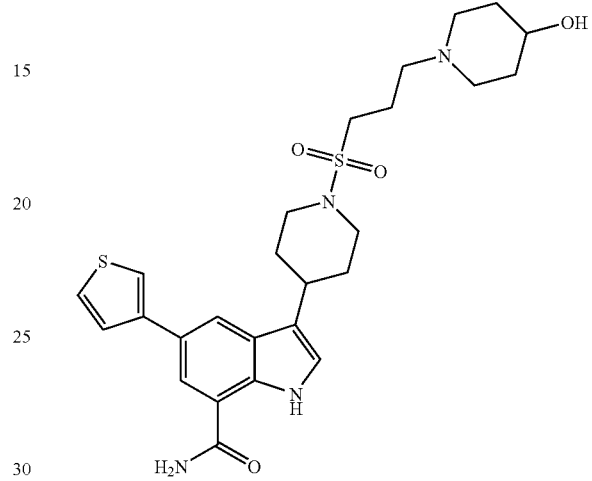

Following the general procedure for aminosulfonamide formation outlined in example 2, 3-{1-[(3-chloropropyl)sulfonyl]-4-piperidinyl}-5-(3-thienyl)-1H-indole-7-carboxamide (40 mg, 0.13 mmol) and 4-piperidinol (0.068 mL, 0.65 mmol) were allowed to react in the presence of K₂CO₃ (74 mg, 0.65 mmol). The resulting residue was purified by reverse phase HPLC eluting with 10% B to 80% B, where A=H₂O (0.1% trifluoroacetic acid) and B=CH₃CN (0.1% trifluoroacetic acid) to give the title compound (8.2 mg, 13%).

LC/MS: m/z 531.0 (M+H) Rt 1.54 min.

(72) 3-(1-{[3-(4-methyl-1-piperazinyl)propyl]sulfonyl}-4-piperidinyl)-5-(3-thienyl)-1H-indole-7-carboxamide

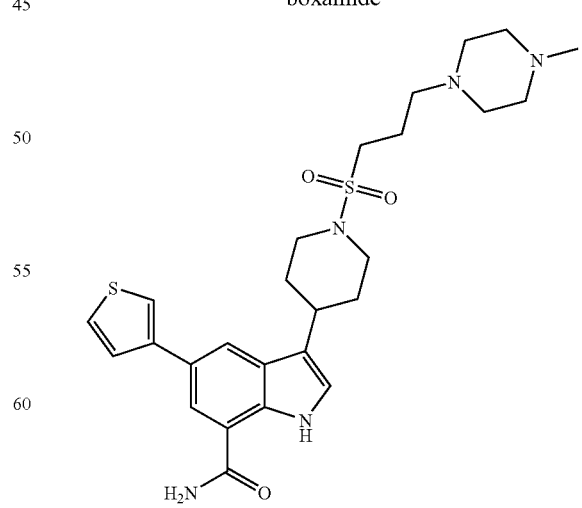

Following the general procedure for aminosulfonamide formation outlined in example 2, 3-{1-[(3-chloropropyl)sulfonyl]-4-piperidinyl}-5-(3-thienyl)-1H-indole-7-carboxamide (40 mg, 0.13 mmol) and 1-methylpiperazine (0.068 mL, 0.65 mmol) were allowed to react in the presence of $K_2CO_3$ (74 mg, 0.65 mmol). The resulting residue was purified by reverse phase HPLC eluting with 10% B to 80% B, where $A=H_2O$ (0.1% trifluoroacetic acid) and $B=CH_3CN$ (0.1% trifluoroacetic acid) to give the title compound (11.2 mg, 17.2%).

LC/MS: m/z 530.2 (M+H) Rt 1.45 min.

(73) 3-(1-{[3-(4-morpholinyl)propyl]sulfonyl}-4-piperidinyl)-5-(2-thienyl)-1H-indole-7-carboxamide

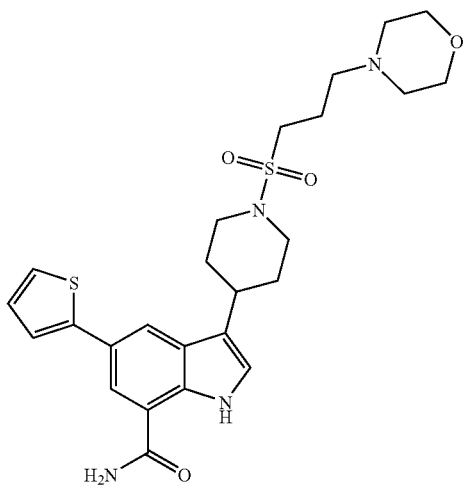

Following the general procedure for aminosulfonamide formation outlined in example 2, 3-{1-[(3-chloropropyl)sulfonyl]-4-piperidinyl}-5-(2-thienyl)-1H-indole-7-carboxamide (40 mg, 0.13 mmol) and morpholine (0.069 mL, 0.65 mmol) were allowed to react in the presence of $K_2CO_3$ (74 mg, 0.65 mmol). The resulting residue was purified by reverse phase HPLC eluting with 10% B to 80% B, where $A=H_2O$ (0.1% trifluoroacetic acid) and $B=CH_3CN$ (0.1% trifluoroacetic acid) to give the title compound (37.3 mg, 57%).

LC/MS: m/z 517.2 (M+H) Rt 1.57 min.

(74) 3-(1-{[3-(4-morpholinyl)propyl]sulfonyl}-4-piperidinyl)-5-(3-thienyl)-1H-indole-7-carboxamide

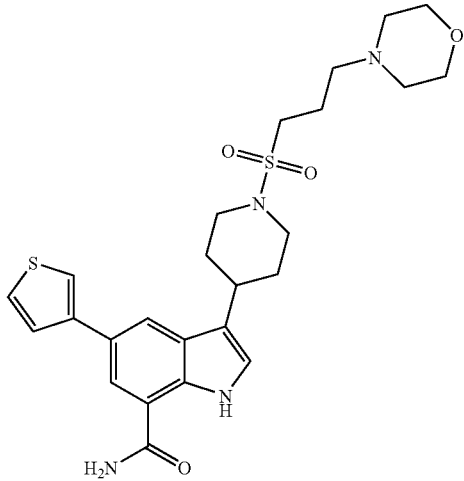

Following the general procedure for aminosulfonamide formation outlined in example 2, 3-{1-[(3-chloropropyl)sulfonyl]-4-piperidinyl}-5-(3-thienyl)-1H-indole-7-carboxamide (40 mg, 0.13 mmol) and morpholine (0.069 mL, 0.65 mmol) were allowed to react in the presence of $K_2CO_3$ (74 mg, 0.65 mmol). The resulting residue was purified by reverse phase HPLC eluting with 10% B to 80% B, where $A=H_2O$ (0.1% trifluoroacetic acid) and $B=CH_3CN$ (0.1% trifluoroacetic acid) to give the title compound (33 mg, 51%).

LC/MS: m/z 517.2 (M+H) Rt 1.50 min.

(75) 5-(4-fluorophenyl)-3-(1-{[3-(1-pyrrolidinyl)propyl]sulfonyl}-4-piperidinyl)-1H-indole-7-carboxamide

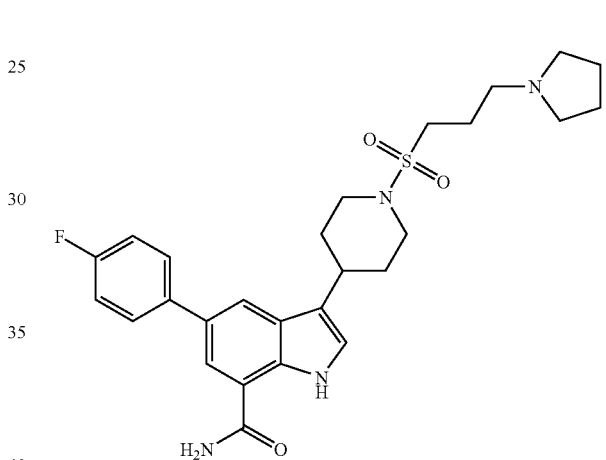

3-{1-[(3-chloropropyl)sulfonyl]-4-piperidinyl}-5-(4-fluorophenyl)-1H-indole-7-carboxamide was prepared according to the procedure for intermediate 11. 5-(4-fluorophenyl)-3-(4-piperidinyl)-1H-indole-7-carboxamide (20 mg, 0.059 mmol) was reacted with triethyl amine (0.03 mL, 0.236 mmol) and 3-chloropropylsulfonyl chloride (0.03 mL, 0.118 mmol) to give 3-{1-[(3-chloropropyl)sulfonyl]-4-piperidinyl}-5-(4-fluorophenyl)-1H-indole-7-carboxamide, which was used in the next step without further purification.

Following the general procedure for aminosulfonamide formation outlined in example 2, 3-{1-[(3-chloropropyl)sulfonyl]-4-piperidinyl}-5-(4-fluorophenyl)-1H-indole-7-carboxamide (0.059 mmol) and pyrrolidine (0.025 mL, 0.295 mmol) were allowed to react in the presence of $K_2CO_3$ (37 mg, 0.118 mmol) and NaI (Cat. 2 mg). The resulting residue was purified by reverse phase HPLC eluting with 10% B to 80% B, where $A=H_2O$ (0.1% trifluoroacetic acid) and $B=CH_3CN$ (0.1% trifluoroacetic acid) to give the title compound (6.9 mg, 23%).

LC/MS: m/z 513.4 (M+H) Rt 1.72 min.

(76) 3-(1-{[3-(dimethylamino)propyl]sulfonyl}-4-piperidinyl)-5-[3-(hydroxymethyl)phenyl]-1H-indole-7-carboxamide

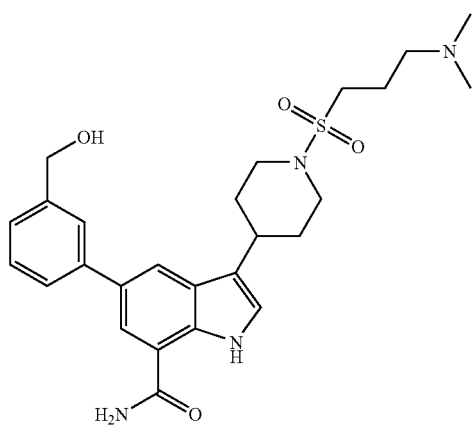

The title compound was prepared following the general procedure described in intermediate 16. Thus, 5-bromo-3-(1-{[3-(dimethylamino)propyl]sulfonyl}-4-piperidinyl)-1H-indole-7-carboxamide (150 mg, 0.32 mmol), [3-(hydroxymethyl)phenyl]boronic acid (195 mg, 1.27 mmol), Pd(PPh$_3$)$_4$ (31 mg, 10%) and cesium carbonate (220 mg, 0.64 mmol) were reacted to form the desired product which was purified by reverse phase HPLC eluting with 10% B to 80% B, where A=H$_2$O (0.1% trifluoroacetic acid) and B=CH$_3$CN (0.1% trifluoroacetic acid) to yield the desired product (230.0 mg, 36%).

LC/MS: m/z 499.6 (M+H), Rt 1.45 min.

Following the general procedure described in example 76, but replacing [3-(hydroxymethyl)phenyl]boronic acid with the appropriate boronic acid, compounds listed in Table 2 were prepared.

TABLE 2

| Example | T2 | MS [M]$^+$ | Rt (min) |
|---------|----|----|----|
| 77 | OH-CH$_2$-C$_6$H$_4$- | 499.6 | 1.46 |
| 78 | 4-methylphenyl | 483.2 | 1.74 |
| 79 | 4-acetamidophenyl | 526.6 | 1.40 |
| 80 | 4-(methylsulfonyl)aminophenyl | 562.2 | 1.42 |
| 81 | 1H-pyrazol-4-yl | 459.4 | 1.35 |
| 82 | 3-(methylsulfonyl)phenyl | 547.4 | 1.38 |

(83) 5-[3-(hydroxymethyl)phenyl]-3-(1-{[3-(1-pyrrolidinyl)propyl]sulfonyl}-4-piperidinyl)-1H-indole-7-carboxamide

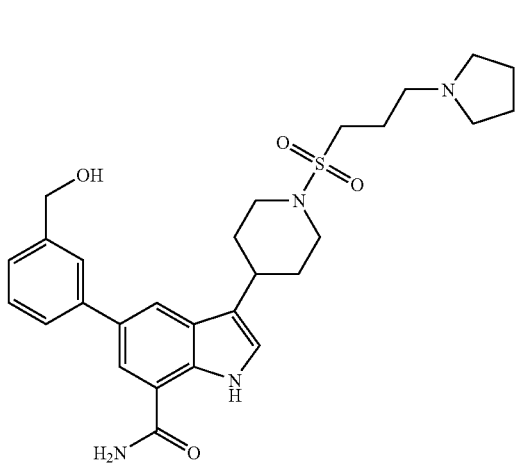

The title compound was prepared following the general procedure for intermediate 16. Thus, 5-bromo-3-(1-{[3-(1-pyrrolidinyl)propyl]sulfonyl}-4-piperidinyl)-1H-indole-7-carboxamide (150 mg, 0.30 mmol), [3-(hydroxymethyl)phenyl]boronic acid (188 mg, 1.20 mmol), Pd(PPh$_3$)$_4$ (30 mg, 10%) and cesium carbonate (200 mg, 0.60 mmol) were reacted to form the desired product which was purified by reverse phase HPLC eluting with 10% B to 80% B, where A=H$_2$O (0.1% trifluoroacetic acid) and B=CH$_3$CN (0.1% trifluoroacetic acid) to yield the desired product (280 mg, 44%).

LC/MS: m/z 525.6 (M+H), Rt 1.47 min.

Following the general procedure as described in example 83, but replacing [3-(hydroxymethyl)phenyl]boronic acid with the appropriate boronic acid, compounds listed in Table 3 were prepared.

TABLE 3

| Example | T3 | MS [M]+ | Rt (min) |
|---|---|---|---|
| 84 | 4-methylphenyl | 509.4 | 1.79 |
| 85 | 4-(acetamido)phenyl-methyl | 552.6 | 1.48 |
| 86 | 4-(methylsulfonamido)phenyl-methyl | 588.2 | 1.52 |
| 87 | 1H-pyrazol-4-yl | 485.4 | 1.29 |
| 88 | 3-(methylsulfonyl)phenyl-methyl | 573.2 | 1.53 |
| 89 | 4-(hydroxymethyl)phenyl | 525.0 | 1.47 |

(90) 5-{3-[(ethylamino)methyl]phenyl}-3-(1-{[3-(1-pyrrolidinyl)propyl]sulfonyl}-4-piperidinyl)-1H-indole-7-carboxamide

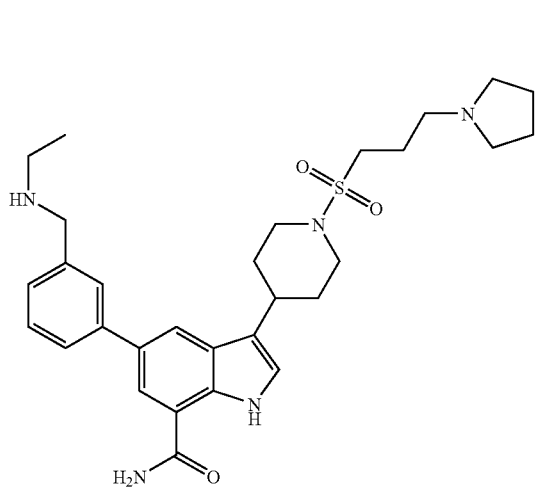

To a solution of 5-(3-formylphenyl)-3-(1-{[3-(1-pyrrolidinyl)propyl]sulfonyl}-4-piperidinyl)-1H-indole-7-carboxamide (25 mg, 0.048 mmol) in MeOH/CH$_2$Cl$_2$ (1 mL/1 mL) was added 2M ethyl amine in THF (0.144 mL, 0.288 mmol). The reaction mixture was stirred at room temperature for 2 hours before NaBH$_4$ (12 mg, 0.3 mmol) was added. The reaction mixture was stirred at room temperature overnight and evaporated all the solvent. The residue was purified by using a Gilson semi-preparative HPLC system, eluting with 10% B to 80% B, where A=H$_2$O (0.1% trifluoroacetic acid) and B=CH$_3$CN (0.1% trifluoroacetic acid) pumped at 25 mL/min to give the title compound (11 mg, 52%).

LC/MS: m/z 552.8 Rt 1.30 min.

Following the general procedure as described in example 90, but replacing ethyl amine with the appropriate amine, compounds listed in Table 4 were prepared.

TABLE 4

| Example | T4 | MS [M]$^+$ | Rt (min) |
|---|---|---|---|
| 91 | HN–CH₃ | 538.4 | 1.36 |
| 92 | HN–iPr | 566.4 | 1.42 |
| 93 | HN–CH₂CH(OH)CH₃ | 582.6 | 1.41 |
| 94 | HN–cyclopentyl | 592.4 | 1.39 |
| 95 | H₃C–CH(NHCH₃)–CH₂OH | 582.6 | 1.44 |

(96) 3-(1-{[3-(dimethylamino)propyl]sulfonyl}-4-piperidinyl)-5-{3-[(ethylamino) methyl]phenyl}-1H-indole-7-carboxamide To a solution of 3-(1-{[3-(dimethylamino)propyl]sulfonyl}-4-piperidinyl)-5-(3-formylphenyl)-1H-indole-7-carboxamide (25 mg, 0.05 mmol) in MeOH/CH$_2$Cl$_2$ (1 mL/1 mL) was added 2M ethyl amine in THF (0.15 mL, 0.30 mmol). The reaction mixture was stirred at room temperature for 2 hours before NaBH$_4$ (12 mg, 0.3 mmol) was added. The reaction mixture was stirred at room temperature overnight and evaporated all the solvent. The residue was purified by using a Gilson semi-preparative HPLC system, eluting with 10% B to 80% B, where A=H$_2$O (0.1% trifluoroacetic acid) and B=CH$_3$CN (0.1% trifluoroacetic acid) pumped at 25 mL/min to give the title compound (11 mg, 52%)

LC/MS: m/z 526.8, Rt 1.38 min.

Following the general procedure as described in example 96, but replacing ethyl amine with the appropriate amine, compounds listed in Table 5 were prepared.

TABLE 5

| Example | T5 | MS [M]$^+$ | Rt (min) |
|---------|----|-----------|----------|
| 97 | H$_3$C—CH(OH)—CH$_2$—HN—CH$_3$ | 556.4 | 1.31 |
| 98 | HN(CH$_3$)—CH$_2$—CH(OH)—CH$_3$ | 566.6 | 1.30 |

(99) 3-(1-{[3-(dimethylamino)propyl]sulfonyl}-4-piperidinyl)-5-[4-(1-piperidinylmethyl)phenyl]-1H-indole-7-carboxamide

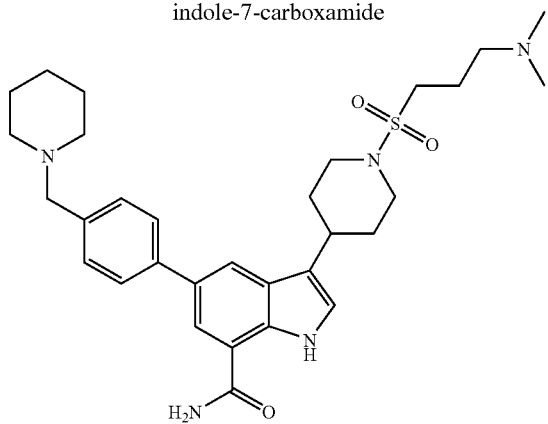

To a solution of 3-(1-{[3-(dimethylamino)propyl]sulfonyl}-4-piperidinyl)-5-[4-(hydroxymethyl)phenyl]-1H-indole-7-carboxamide (230 mg, 0.47 mmol) in THF (60 mL) was added MnO$_2$ (1.3 g, 14.05 mmol). The reaction mixture was stirred at room temperature overnight and filtered through a pad of celite after that. The filtrate was collected and concentrated at reduced pressure to give the aldehyde (150 mg, 65%), which was used in the next step without further purification.

To a solution of 3-(1-{[3-(dimethylamino)propyl]sulfonyl})-4-piperidinyl)-5-(4-formylphenyl)-1H-indole-7-carboxamide (50 mg, 0.1 mmol) in DCM (3 mL) were added piperidine (8 mg, 0.1 mmol) and NaBH(OAc)$_3$ (64 mg, 0.3 mmol). The reaction mixture was stirred at room temperature overnight. The solvent was evaporated and the residue was purified by solid phase extraction on a 1 g scx column (International Sorbent Technologies) eluting with dichloromethane (6 mL), dichloromethane/methanol 1:1 (6 mL), methanol (6 mL) and ammonia (6 mL×3). Then the combined tube was evaporated and the residue was purified by HPLC (water/CH$_3$CN, 0.1% TFA 10-90%) to give the title compound (8 mg, 15%).

LC/MS: m/z 566.2 (M+H), 1.34 min.

(100) 3-(1-{[3-(dimethylamino)propyl]sulfonyl}-4-piperidinyl)-5-[4-(4-morpholinylmethyl)phenyl]-1H-indole-7-carboxamide

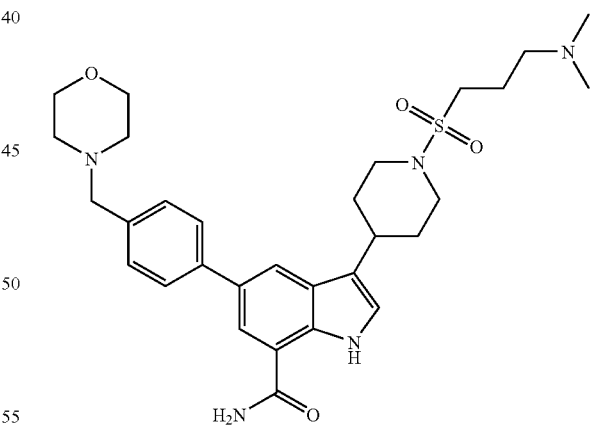

Following the general procedure of example (99), 3-(1-{[3-(dimethylamino)propyl]sulfonyl}-4-piperidinyl)-5-(4-formylphenyl)-1H-indole-7-carboxamide (50 mg, 0.1 mmol), morpholine (9 mg, 0.1 mmol) and NaBH(OAc)$_3$ (64 mg, 0.3 mmol) were reacted to give the title compound (15 mg, 30%).

LC/MS: m/z 568.4 (M+H), 1.22 min.

(101) 3-(1-{[3-(dimethylamino)propyl]sulfonyl}-4-piperidinyl)-5-[4-(1-pyrrolidinylmethyl)phenyl]-1H-indole-7-carboxamide

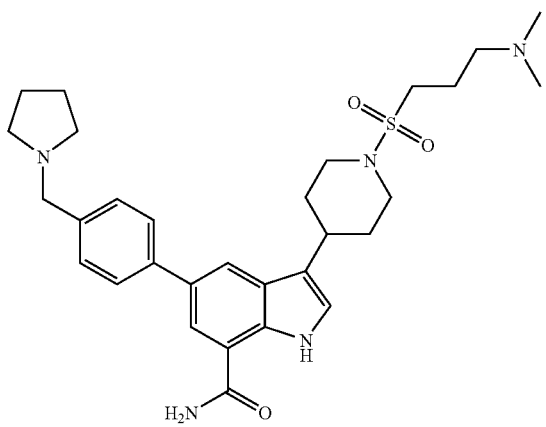

Following the general procedure of example (99), 3-(1-{[3-(dimethylamino)propyl]sulfonyl}-4-piperidinyl)-5-(4-formylphenyl)-1H-indole-7-carboxamide (50 mg, 0.1 mmol), pyrrolidine (9 mg, 0.1 mmol) and NaBH(OAc)$_3$ (64 mg, 0.3 mmol) were reacted to give the title compound (20 mg, 20%).

LC/MS: m/z 552.6 (M+H), 1.29 min.

(102) 3-(1-{[3-(cyclopentylamino)propyl]sulfonyl}-4-piperidinyl)-5-[3-(hydroxymethyl)phenyl]-1H-indole-7-carboxamide

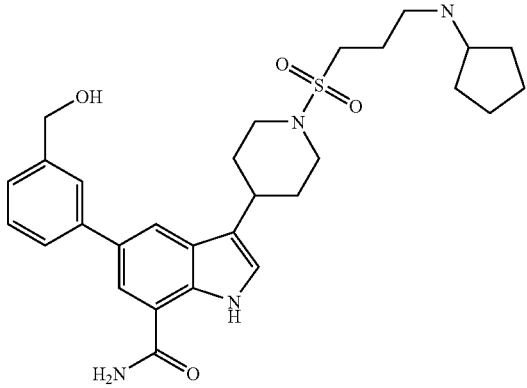

The title compound was prepared according to the general procedure for intermediate 16. Thus, 5-bromo-3-(1-{[3-(cyclopentylamino)propyl]sulfonyl}-4-piperidinyl)-1H-indole-7-carboxamide (46 mg, 0.09 mmol), [3-(hydroxymethyl)phenyl]boronic acid (55 mg, 0.36 mmol), Pd(PPh$_3$)$_4$ (10 mg, 10%) and cesium carbonate (117 mg, 0.36 mmol) were heated in microwave at 160° C. for 40 min to yield the desired product (16.5 mg, 34%), which was purified by reverse phase HPLC eluting with 10% B to 80% B, where A=H$_2$O (0.1% trifluoroacetic acid) and B=CH$_3$CN (0.1% trifluoroacetic acid)

LC/MS: m/z 539.4 (M+H), Rt 1.61 min.

Following the general procedure as described in example 102, but replacing [3-(hydroxymethyl)phenyl]boronic acid with the appropriate boronic acid, compounds listed in Table 6 were prepared.

TABLE 6

| Example | T6 | MS [M]$^+$ | Rt (min) |
|---|---|---|---|
| 103 | 4-methylphenyl | 523.4 | 1.90 |
| 104 | 3,4-difluorophenyl | 545.4 | 1.88 |
| 105 | 3-chlorophenyl | 543.4 | 1.95 |
| 106 | 4-ethylphenyl | 537.2 | 1.97 |
| 107 | 4-(dimethylamino)phenyl | 551.6 | 1.46 |

(108) 1,1-dimethylethyl 4-{[3-({4-[7-(aminocarbonyl)-5-phenyl-1H-indol-3-yl]-1-piperidinyl}sulfonyl)propyl]amino}-1-piperidinecarboxylate

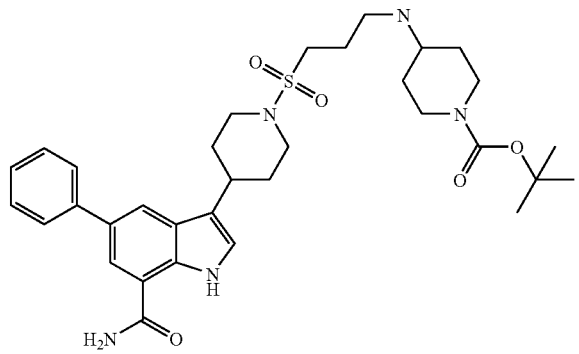

Following the general procedure for aminosulfonamide formation outlined in example 2, 3-{1-[(3-chloropropyl)sulfonyl]-4-piperidinyl}-5-phenyl-1H-indole-7-carboxamide (50 mg, 0.0.109 mmol) and 1,1-dimethylethyl 4-amino-1-piperidinecarboxylate (108.8 mg, 0.543 mmol) were allowed to react in the presence of $K_2CO_3$ (60 mg, 0.435 mmol) and sodium iodide (2 mg). The reaction mixture was concentrated under reduced pressure. The resulting residue was purified by reverse phase HPLC eluting with 10% B to 80% B, where $A=H_2O$ (0.1% trifluoroacetic acid) and $B=CH_3CN$ (0.1% trifluoroacetic acid) to give the title compound (17.3 mg, 26%).

LC/MS: m/z 624.4 (M+H) Rt 1.86 min.

(109) 5-phenyl-3-(1-{[3-(4-piperidinylamino)propyl]sulfonyl}-4-piperidinyl)-11 indole-7-carboxamide

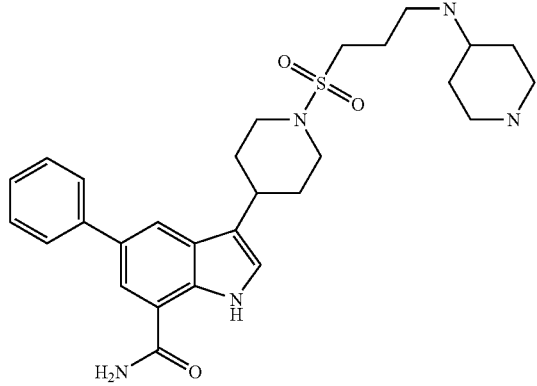

To a solution of 1,1-dimethylethyl 4-{[3-({4-[7-(aminocarbonyl)-5-phenyl-1H-indol-3-yl]-1-piperidinyl}sulfonyl)propyl]amino}-1-piperidinecarboxylate (15.4 mg, 0.025 mmol) in MeOH (3 mL), 36% HCl in water (0.1 mL) was added. The reaction mixture was stirred at 60° C. for 1 hour, after which time the solvent was removed under reduced pressure and the resulting residue was The reaction mixture was concentrated under reduced pressure. The resulting residue was purified by reverse phase HPLC eluting with 10% B to 80% B, where $A=H_2O$ (0.1% trifluoroacetic acid) and $B=CH_3CN$ (0.1% trifluoroacetic acid) to give the title compound (3.2 mg, 24%).

LC/MS: m/z 524.4 (M+H) Rt 1.27 min.

Following the general procedure as described in example 108, but replacing 1,1-dimethylethyl 4-amino-1-piperidinecarboxylate with the appropriate amine, compounds listed in Table 7 were prepared.

TABLE 7

| Example | T7 | MS [M]+ | Rt (min) |
|---|---|---|---|
| 110 | (tetrahydrofuran-2-ylmethyl)amine | 525.6 | 1.68 |
| 111 | cyclopentylamine | 509.4 | 1.80 |
| 112 | N,N,N'-trimethylethylenediamine | 540.4 | 1.52 |
| 113 | 1-methylpiperidine-4-carboxamide | 552.4 | 1.68 |
| 114 | 1-methylpiperidin-4-ol | 525.4 | 1.56 |
| 115 | 1'-methyl-1,4'-bipiperidine | 592.4 | 1.42 |
| 116 | 1-methyl-4-benzylpiperidine | 596.8 | 2.04 |

TABLE 7-continued

| Example | T7 | MS [M]+ | Rt (min) |
|---|---|---|---|
| 117 | (decahydroquinoline) | 563.4 | 1.85 |
| 118 | (azepane) | 523.6 | 1.75 |
| 119 | (piperazinyl-CH2-C(O)NH-iPr) | 609.6 | 1.63 |
| 120 | (2-ethylpiperidine) | 537.4 | 1.71 |
| 121 | (2-methylpyrrolidine) | 509.0 | 1.66 |
| 122 | (2-(thiophen-2-yl)pyrrolidine) | 577.4 | 1.77 |
| 123 | (3-hydroxypyrrolidine) | 511.6 | 1.55 |
| 124 | (4-hydroxy-4-phenylpiperidine) | 600.7 | 1.75 |
| 125 | (3-hydroxypiperidine) | 525.8 | 1.62 |
| 126 | (prolinamide) | 538.2 | 1.61 |
| 127 | (2-(hydroxymethyl)pyrrolidine) | 525.2 | 1.60 |
| 128 | (N-isopropyl-N-(2-hydroxyethyl)amine) | 527.8 | 1.65 |
| 129 | (N-methyl-N-propargylamine) | 493.0 | 1.69 |
| 130 | (thiazolidine) | 513.4 | 1.72 |
| 131 | (2-(thiazol-2-yl)pyrrolidine) | 578.8 | 1.76 |

TABLE 7-continued

[Core structure: 5-phenyl-3-(1-(propylsulfonyl with T7)-piperidin-4-yl)-1H-indole-7-carboxamide]

| Example | T7 | MS [M]+ | Rt (min) |
|---|---|---|---|
| 132 | N-methyl-N-(furan-2-ylmethyl) | 535.2 | 1.74 |
| 133 | 2-methylaziridin-1-yl | 481.6 | 1.70 |
| 134 | N-ethyl-N-isopropyl | 511.6 | 1.74 |
| 135 | N-ethyl-N-(2-methoxyethyl) | 527.8 | 1.70 |
| 136 | N,N-diethyl | 497.6 | 1.74 |
| 137 | N,N-dimethyl-2-(4-hydroxyphenyl)-2-hydroxyethylamino | 591.6 | 1.75 |
| 138 | 3-amino-1-methylpyrrolidin-1-yl | 510.2 | 1.38 |
| 139 | N-methyl-N-ethyl | 483.4 | 1.65 |

| Example | T7 | MS [M]+ | Rt (min) |
|---|---|---|---|
| 140 | N,N-bis(2-methoxyethyl) | 557.6 | 1.74 |
| 141 | 2,6-dimethylmorpholin-4-yl | 539.6 | 1.79 |
| 142 | 2-(hydroxymethyl)piperidin-1-yl | 539.7 | 1.64 |
| 143 | 3-(hydroxymethyl)piperidin-1-yl | 539.4 | 1.60 |
| 144 | 2-(methoxymethyl)pyrrolidin-1-yl | 539.6 | 1.75 |
| 145 | N-methyl-N-isopropyl | 497.4 | 1.73 |

TABLE 7-continued

| Example | T7 | MS [M]+ | Rt (min) |
|---|---|---|---|
| 146 | (N-methyl, 2-methyl-3-hydroxy-butyl-amine group) | 527.6 | 1.68 |
| 147 | (N-methyl, 1-hydroxy-propan-2-yl-amine group) | 499.6 | 1.67 |
| 148 | (N-methyl-N'-dimethyl-ethylenediamine group) | | |

148: 1H NMR(400 MHz, CD₃OD) δ ppm 1.77(q, 2H) 2.14(d, 2H) 2.25(m, 2H) 2.97(s, 6H) 3.03(m, 3H) 3.17(t, 2H) 3.53(m, 6H) 3.85(d, 2H) 7.18(s, 1H) 7.30(t, 1H) 7.43(t, 2H) 7.69(d, 2H) 7.94(s, 1H) 7.98(s, 1H)

| 149 | (N-methyl, trans-4-hydroxycyclohexyl-amine group) | | |

149: 1H NMR(400 MHz, DMSO) δ ppm 1.33(m, 3H) 1.37(m, 2H) 1.70(m, 2H) 1.88(d, 3H) 2.05(m, 6H) 2.55(s, 1H) 3.06(m, 6H) 3.24(m, 2H) 3.73(d, 2H) 4.70(br, 1H) 7.17(s, 1H) 7.33(t, 1H) 7.70(s, 1H) 7.48(t, 2H) 7.80(d, 2H) 8.02(s, 2H) 8.25(s, 1H) 8.64(br, 2H)

| 150 | (N-methyl, 2-hydroxy-propan-1-yl-amine group) | | |

150: 1H NMR(400 MHz, CD₃OD) δ ppm 1.26(d, 3H) 1.83(q, 2H) 2.22(m, 4H) 2.87(m, 1H) 3.10(m, 4H) 3.22(m, 4H) 3.88(d, 2H) 4.02(m, 1H) 7.22(s, 1H) 7.32(t, 1H) 7.46(t, 2H) 7.71(d, 2H) 7.95(s, 1H) 8.01(s, 1H)

| 151 | (N-methyl, 1-methoxy-propan-2-yl-amine group) | | |

151: 1H NMR(400 MHz, CD₃OD) δ ppm 1.30(d, 3H) 1.81(q, 2H) 2.21(m, 4H) 3.06(m, 4H) 3.22(m, 4H) 3.41(t, 3H) 3.62(m, 1H) 3.86(d, 2H) 7.09(s, 1H) 7.30(t, 1H) 7.43(t, 2H) 7.70(d, 2H) 7.93(s, 1H) 7.99(s, 1H)

| Example | T7 | MS [M]+ | Rt (min) |
|---|---|---|---|
| 152 | (N-methyl, 2-hydroxy-ethyl-amine group) | | |

152: 1H NMR(400 MHz, CD₃OD) δ ppm 1.30(t, 1H) 1.81(q, 2H) 2.20(m, 4H) 3.05(m, 3H) 3.25(m, 6H) 3.82(t, 2H) 3.88(d, 2H) 7.14(s, 1H) 7.35(t, 1H) 7.46(t, 2H) 7.72(d, 2H) 7.84(s, 1H) 7.88(s, 1H)

| 153 | (N-methyl, 2-hydroxy-butyl-amine group) | | |

153: 1H NMR(400 MHz, CD₃OD) δ ppm 1.01(t, 3H) 1.55(m, 2H) 1.86(m, 2H) 2.22(m, 4H) 2.95(m, 1H) 3.06(m, 4H) 3.12(m, 4H) 3.75(m, 1H) 3.93(d, 2H) 7.23(s, 1H) 7.33(t, 1H) 7.46(t, 2H) 7.72(d, 2H) 7.96(s, 1H) 3.03(s, 1H)

| 154 | (N-methyl, 2-morpholino-ethyl-amine group) | | |

154: 1H NMR(400 MHz, CD₃OD) δ ppm 1.88(m, 2H) 2.26(m, 4H) 3.09(m, 6H) 3.23(m, 4H) 3.32(m, 2H) 3.47(t, 2H) 4.93(m, 7H) 7.22(s, 1H) 7.32(t, 1H) 7.43(t, 2H) 7.72(d, 2H) 7.97(s, 1H) 8.02(s, 1H)

| 155 | (N-methyl, (S)-2-hydroxy-propan-1-yl-amine group) | | |

155: 1H NMR(400 MHz, CD₃OD) δ ppm 1.21(d, 3H) 1.82(m, 2H) 2.22(m, 4H) 3.01(m, 1H) 3.08(m, 4H) 3.23(m, 4H) 3.85(d, 2H) 4.02(m, 1H) 7.17(s, 1H) 7.29(t, 1H) 7.44(t, 2H) 7.69(d, 2H) 7.94(s, 1H) 7.98(s, 1H)

| 156 | (N-methyl, 2-methyl-3-hydroxy-butyl-amine group) | | |

156: 1H NMR(400 MHz, CD₃OD) δ ppm 1.02(d, 3H) 1.60(d, 3H) 1.82(m, 2H) 2.18(m, 5H) 3.05(m, 4H) 3.07(t, 2H) 3.75(m, 1H) 3.89(d, 4H) 7.20(s, 1H) 7.30(t, 1H) 7.44(t, 2H) 7.71(d, 2H) 7.95(s, 1H) 8.00(s, 1H)

TABLE 7-continued

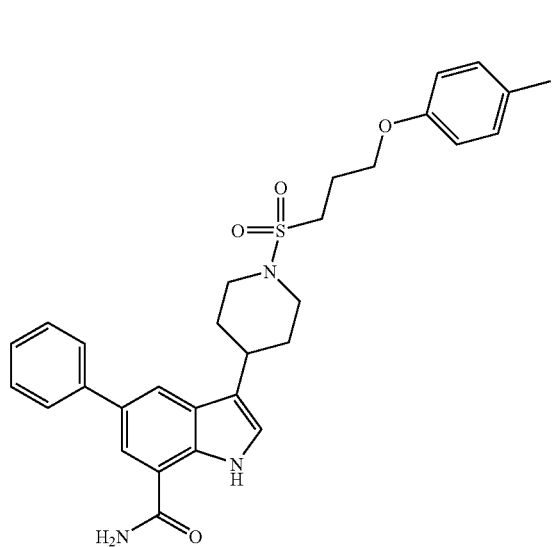

| Example | T7 | MS [M]+ | Rt (min) |
|---|---|---|---|
| 157 | -CH2CH3) 1H NMR(400 MHz, CD3OD) δ ppm 1.04(d, 3H) 1.73(m, 2H) 1.84(m, 2H) 2.23(m, 4H) 3.12(m, 4H) 3.24(m, 4H) 3.72(d, 1H) 3.87(m, 3H) 7.22(s, 1H) 7.32(t, 1H) 7.45(t, 2H) 7.72(d, 2H) 7.95(s, 1H) 8.01(s, 1H) | | |
| 158 | cyclohexyl-NH-Me 1H NMR(400 MHz, CD3OD) δ ppm 1.35(m. 6H) 1.92(m, 6H) 2.20(m, 4H) 3.10(m, 4H) 3.25(m, 4H) 3.91(d, 2H) 7.23(s, 1H) 7.32(t, 1H) 7.46(t, 2H) 7.73(d, 2H) 7.97(s, 1H) 8.02(s, 1H) | | |

(159) 3-[1-({3-[(4-methylphenyl)oxy]propyl}sulfonyl)-4-piperidiriyl]-5-phenyl-1H-indole-7-carboxamide

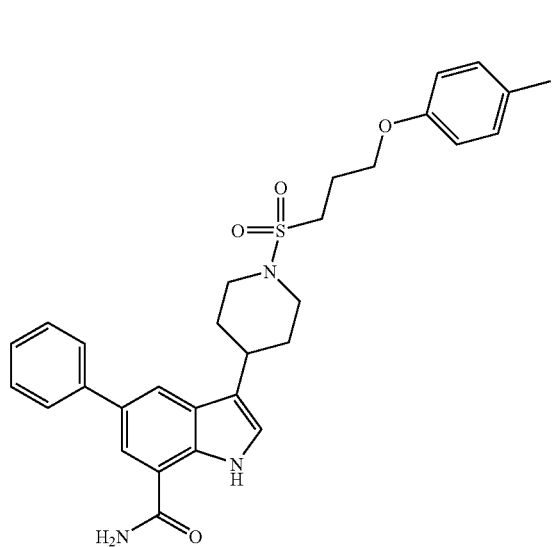

To a solution of 3-{1-[(3-chloropropyl)sulfonyl]-4-piperidinyl}-5-phenyl-1H-indole-7-carboxamide (40 mg, 0.087 mmol) in DMSO (1.0 mL), were added 4-methylphenol (108 mg, 0.87 mmol), K₂CO₃ (35.0 mg, 0.35 mmol) and sodium iodide (0.5 mg). The reaction solution was heated to 80° C. overnight. After which time the reaction mixture was filtered and purified by reverse phase HPLC (water/CH₃CN, 0.1% TFA 10-90%) to give the title compound (6.3 mg, 14%).

LC/MS: 532.2 r.t.: 2.54 min.

(160) 3-(1-{[3-(methyloxy)propyl]sulfonyl}-4-piperidinyl)-5-phenyl-1H-indole-7-carboxamide

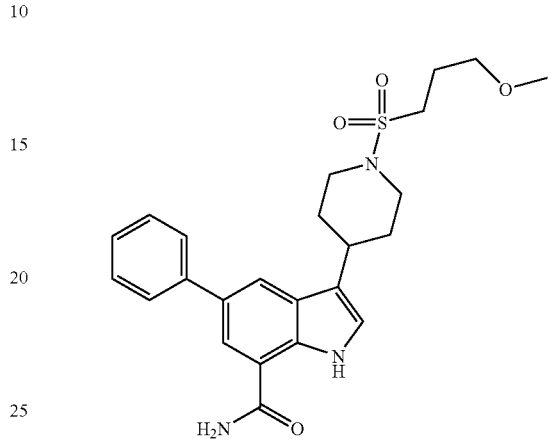

The mixture of 3-{1-[(3-chloropropyl)sulfonyl]-4-piperidinyl}-5-phenyl-1H-indole-7-carboxamide (46.0 mg, 0.1 mmol), 0.1 M NaOMe (4 ml) in methanol (2 mL) was refluxed overnight. The reaction mixture was concentrated and purified by reverse phase HPLC (water/CH₃CN, 0.1% TFA 10-90%) to give the title compound (20.0 mg, 44%).

LC/MS: 456.2 r.t: 2.04 min.

(161) 5-phenyl-3-(1-{[3-(phenyloxy)propyl]sulfonyl}-4-piperidinyl)-1H-indole-7-carboxamide

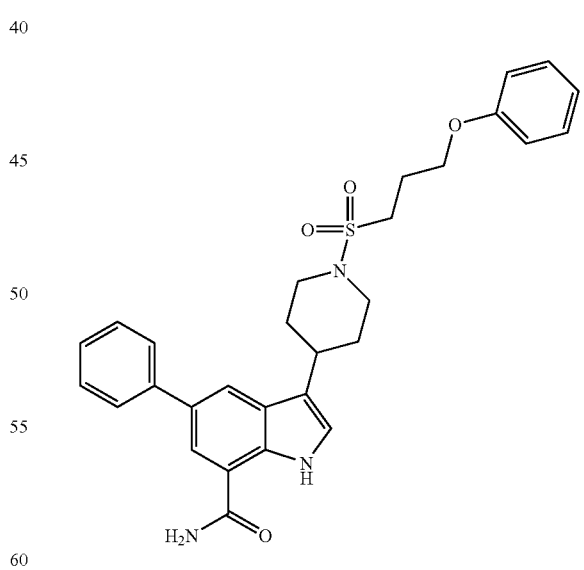

Following the general procedure of example 159, 3-{1-[(3-chloropropyl)sulfonyl]-4-piperidinyl}-5-phenyl-1H-indole-7-carboxamide (40.0 mg, 0.087 mmol), phenol (94 mg, 0.87 mmol), K₂CO₃ (35.0 mg, 0.35 mmol) and sodium iodide (0.5 mg) were reacted to give the title compound (4.2 mg, 9.3%).

LC/MS: 518.4 r.t: 2.45 min.

(162) 5-phenyl-3-{1-[(3-{[2-(trifluoromethyl)phenyl]oxy}propyl)sulfonyl]-4-piperidinyl}-1H-indole-7-carboxamide

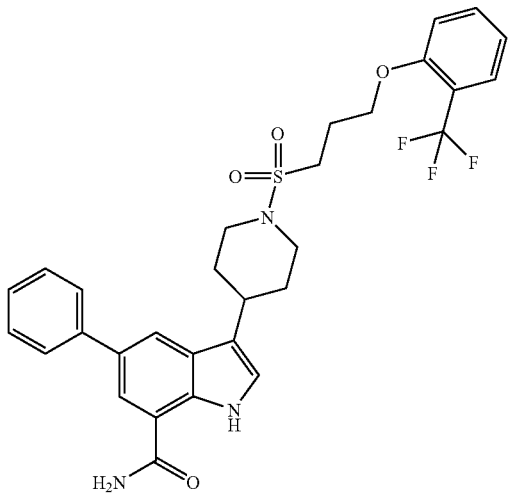

Following the general procedure of example 159, 3-{1-[(3-chloropropyl)sulfonyl]-4-piperidinyl}-5-phenyl-1H-indole-7-carboxamide (40.0 mg, 0.087 mmol), 2-(trifluoromethyl)phenol (162 mg, 0.87 mmol), $K_2CO_3$ (35.0 mg, 0.35 mmol) and sodium iodide (0.5 mg) were reacted to give the title compound (22.9 mg, 50%).

LC/MS: 586.2 r.t: 2.59 min.

(163) 3-[1-({3-[(4-hydroxybutyl)oxy]propyl}sulfonyl)-4-piperidinyl]-5-phenyl-1H-indole-7-carboxamide

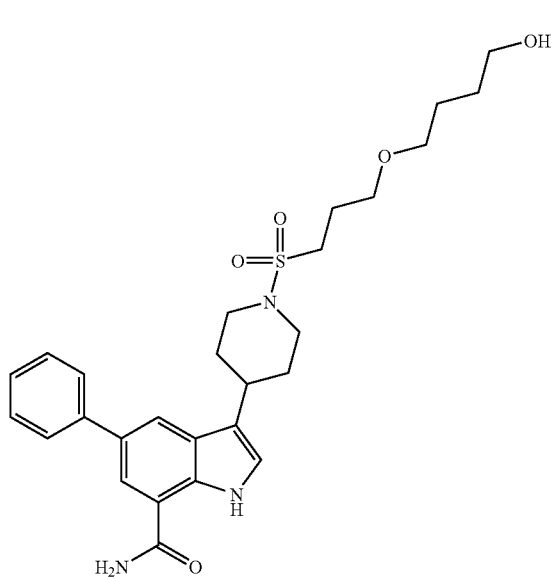

Following the general procedure of example 159, 3-{1-[(3-chloropropyl)sulfonyl]-4-piperidinyl}-5-phenyl-1H-indole-7-carboxamide (40.0 mg, 0.087 mmol), 1,4-butanediol (90 mg, 0.87 mmol), $K_2CO_3$ (35.0 mg, 0.35 mmol) and sodium iodide (0.5 mg) were reacted to give the title compound (9.1 mg, 20.4%).

LC/MS: 514.1 r.t: 1.93 min.

(164) 3-[1-({3-[(cyclopropylmethyl)oxy]propyl}sulfonyl)-4-piperidinyl]-5-phenyl-1H-indole-7-carboxamide

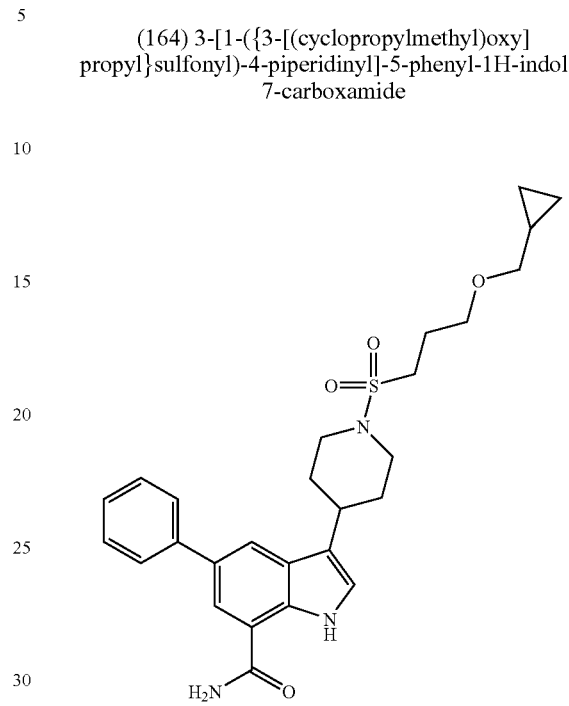

Following the general procedure of example 159, 3-{1-[(3-chloropropyl)sulfonyl]-4-piperidinyl}-5-phenyl-1H-indole-7-carboxamide (40.0 mg, 0.087 mmol), cyclopropylmethanol (72 mg, 0.87 mmol), $K_2CO_3$ (35.0 mg, 0.35 mmol) and sodium iodide (0.5 mg) were reacted to give the title compound (5.2 mg, 12%).

LC/MS: 496.1 r.t: 2.25 min.

(165) 3-[1-({3-[(2-hydroxy-1-methylpropyl)oxy]propyl}sulfonyl)-4-piperidinyl]-5-phenyl-1H-indole-7-carboxamide

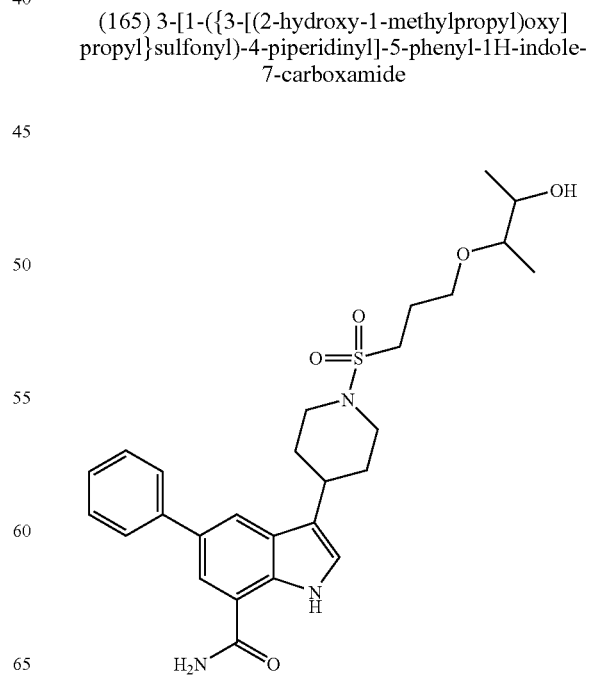

Following the general procedure of example 159, 3-{1-[(3-chloropropyl)sulfonyl]-4-piperidinyl}-5-phenyl-1H-indole-7-carboxamide (40.0 mg, 0.087 mmol), 2,3-butanediol (72 mg, 0.87 mmol), K$_2$CO$_3$ (35.0 mg, 0.35 mmol) and sodium iodide (0.5 mg) were reacted to give the title compound (4.0 mg, 8.9%).

LC/MS: 514.1 r.t: 2.00 min.

(166) 3-[1-({3-[(cyclobutylmethyl)oxy]propyl}sulfonyl)-4-piperidinyl]-5-phenyl-1H-indole-7-carboxamide

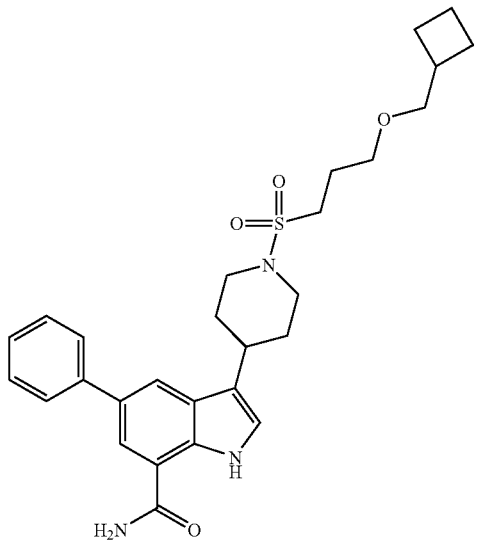

Following the general procedure of example 159, 3-{1-[(3-chloropropyl)sulfonyl]-4-piperidinyl}-5-phenyl-1H-indole-7-carboxamide (40.0 mg, 0.087 mmol), cyclobutylmethanol (86 mg, 0.87 mmol), K$_2$CO$_3$ (35.0 mg, 0.35 mmol) and sodium iodide (0.5 mg) were reacted to give the title compound (5.6 mg, 12.6%).

LC/MS: 510.4 r.t: 2.46 min.

(167) 5-phenyl-3-[1-({3-[(tetrahydro-3-furanylmethyl)oxy]propyl}sulfonyl)-4-piperidinyl]-1H-indole-7-carboxamide

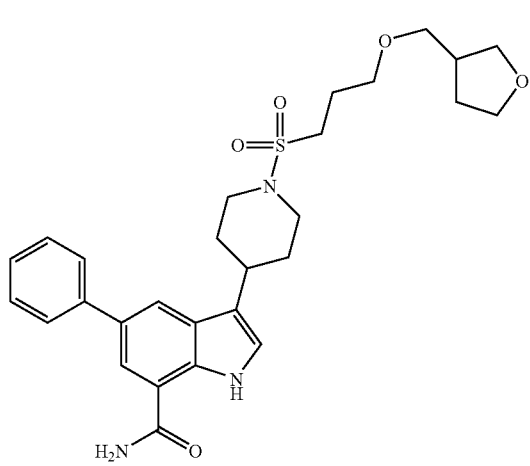

Following the general procedure of example 159, 3-{1-[(3-chloropropyl)sulfonyl]-4-piperidinyl}-5-phenyl-1H-indole-7-carboxamide (40.0 mg, 0.087 mmol), tetrahydro-3-furanylmethanol (102 mg, 0.87 mmol), K$_2$CO$_3$ (35.0 mg, 0.35 mmol) and sodium iodide (0.5 mg) were reacted to give the title compound (7.0 mg, 15.3%).

LC/MS: 526.6 r.t: 2.14 min.

(168) 3-{1-[(3-{[4-(acetylamino)phenyl]oxy}propyl)sulfonyl]-4-piperidinyl}-5-phenyl-1H-indole-7-carboxamide

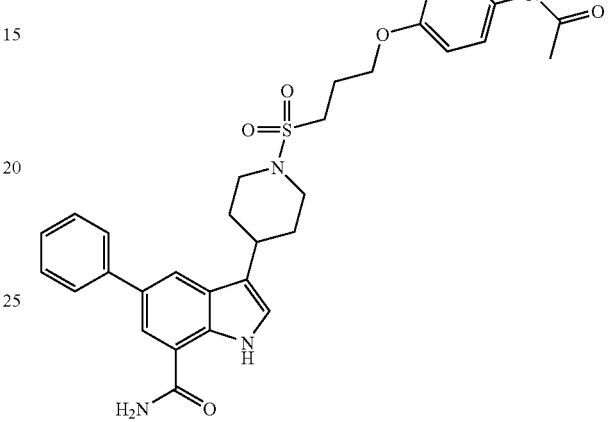

Following the general procedure of example 159, 3-{1-[(3-chloropropyl)sulfonyl]-4-piperidinyl}-5-phenyl-1H-indole-7-carboxamide (40.0 mg, 0.087 mmol), N-(4-hydroxyphenyl)acetamide (151 mg, 0.87 mmol), K$_2$CO$_3$ (35.0 mg, 0.35 mmol) and sodium iodide (0.5 mg) were reacted to give the title compound (21.0 mg, 42%).

LC/MS: 575.4 r.t: 2.12 min.

(169) 3-{1-[(3-{[4-(methyloxy)phenyl]oxy}propyl)sulfonyl]-4-piperidinyl}-5-phenyl-1H-indole-7-carboxamide

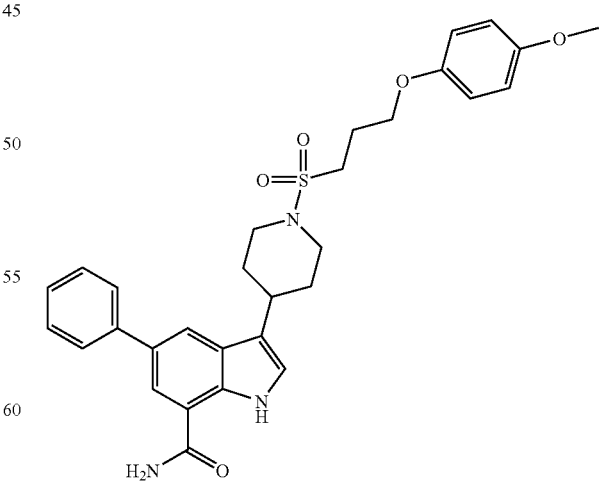

Following the general procedure of example 159, 3-{1-[(3-chloropropyl)sulfonyl]-4-piperidinyl}-5-phenyl-1H-indole-7-carboxamide (40.0 mg, 0.087 mmol), 4-(methyloxy)phenol (124 mg, 0.87 mmol), K₂CO₃ (35.0 mg, 0.35 mmol) and sodium iodide (0.5 mg) were reacted to give the title compound (21.0 mg, 44%).

LC/MS: 548.4 r.t: 2.42 min.

(170) 3-{1-[(3-{[2-(methyloxy)phenyl]oxy}propyl)sulfonyl]-4-piperidinyl}-5-phenyl-1H-indole-7-carboxamide

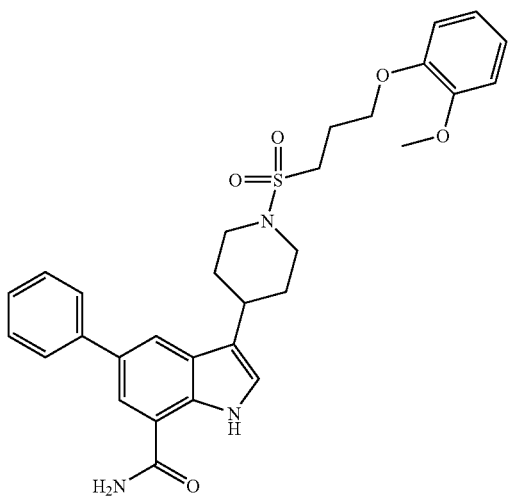

Following the general procedure of example 159, 3-{1-[(3-chloropropyl)sulfonyl]-4-piperidinyl}-5-phenyl-1H-indole-7-carboxamide (40.0 mg, 0.087 mmol), 2-(methyloxy)phenol (124 mg, 0.87 mmol), K₂CO₃ (35.0 mg, 0.35 mmol) and sodium iodide (0.5 mg) were reacted to give the title compound (23.0 mg, 48%).

LC/MS: 548.4 r.t: 2.35 min.

(171) 3-[1-({3-[(4-fluorophenyl)oxy]propyl}sulfonyl)-4-piperidinyl]-5-phenyl-1H-indole-7-carboxamide

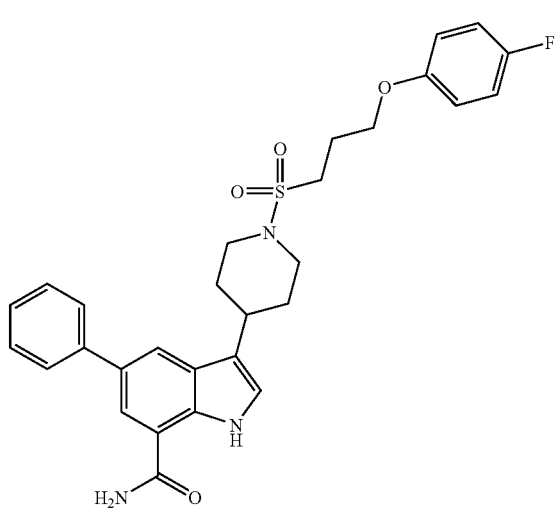

Following the general procedure of example 159, 3-{1-[(3-chloropropyl)sulfonyl]-4-piperidinyl}-5-phenyl-1H-indole- 7-carboxamide (40.0 mg, 0.087 mmol), 4-fluorophenol (112 mg, 0.87 mmol), K₂CO₃ (35.0 mg, 0.35 mmol) and sodium iodide (0.5 mg) were reacted to give the title compound (18.0 mg, 39%).

LC/MS: 536.2 r.t: 2.45 min.

(172) 5-phenyl-3-{1-[(3-{[3-(trifluoromethyl)phenyl]oxy}propyl)sulfonyl]-4-piperidinyl}-1H-indole-7-carboxamide

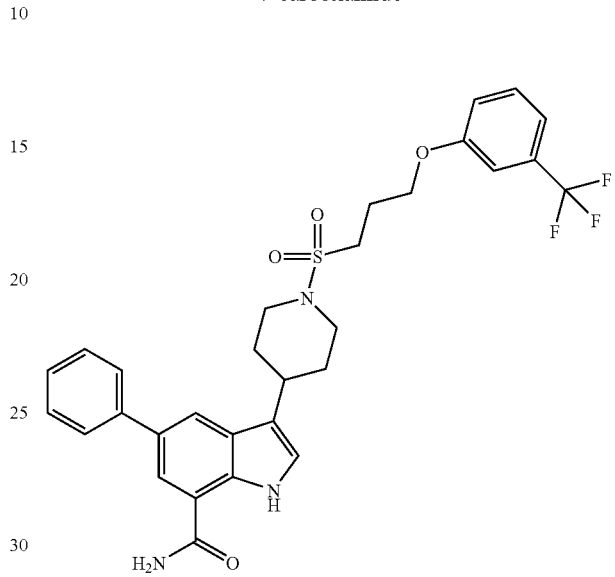

Following the general procedure of example 159, 3-{1-[(3-chloropropyl)sulfonyl]-4-piperidinyl}-5-phenyl-1H-indole-7-carboxamide (40.0 mg, 0.087 mmol), 3-trifluoromethylphenol (162 mg, 0.87 mmol), K₂CO₃ (35.0 mg, 0.35 mmol) and sodium iodide (0.5 mg) were reacted to give the title compound (25.0 mg, 49%).

LC/MS: 586.4 r.t: 2.63 min.

(173) 3-{1-[(3-{[3-(methyloxy)phenyl]oxy}propyl)sulfonyl]-4-piperidinyl}-5-phenyl-1H-indole-7-carboxamide

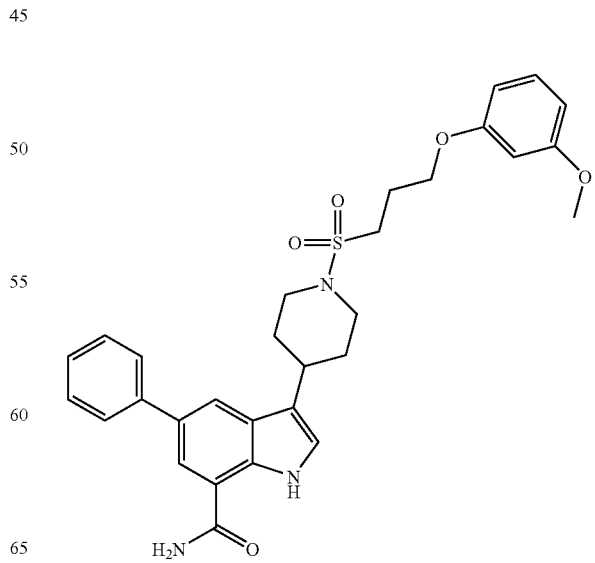

Following the general procedure of example 159, 3-{1-[(3-chloropropyl)sulfonyl]-4-piperidinyl}-5-phenyl-1H-indole-7-carboxamide (40.0 mg, 0.087 mmol), 3-methyloxyphenol (124 mg, 0.87 mmol), $K_2CO_3$ (35.0 mg, 0.35 mmol) and sodium iodide (0.5 mg) were reacted to give the title compound (20.0 mg, 42%).

LC/MS: 548.4 r.t: 2.45 min.

(174) 3-{1-[(3-hydroxypropyl)sulfonyl]-4-piperidinyl}-5-phenyl-1H-indole-7-carboxamide

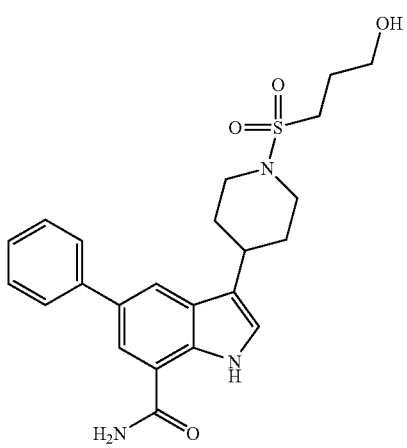

Following the general procedure of example 159, 3-{1-[(3-chloropropyl)sulfonyl]-4-piperidinyl}-5-phenyl-1H-indole-7-carboxamide (23.0 mg, 0.050 mmol), 50% NaOH in water (1 mL), and sodium iodide (5.0 mg) were reacted to give the title compound (15.0 mg, 68%).

LC/MS: 442.4 r.t: 1.90 min.

(175) 3-(1-{[2-(ethyloxy)ethyl]sulfonyl}-4-piperidinyl)-5-phenyl-1H-indole-7-carboxamide

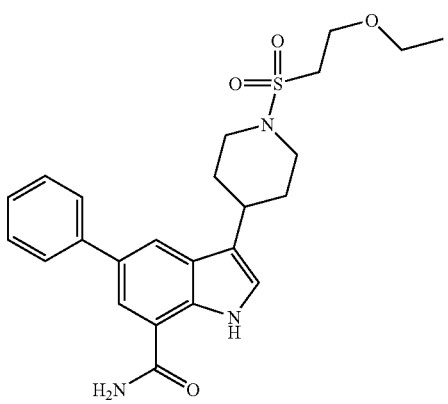

The mixture of 3-[1-(ethenylsulfonyl)-4-piperidinyl]-5-phenyl-1H-indole-7-carboxamide (23 mg, 0.056 mmol), NaOEt (10 mg) in ethanol (1 mL) was refluxed at 80° C. overnight. The reaction mixture was concentrated and purified by reverse phase HPLC (water/$CH_3CN$, 0.1% TFA 10-90%) to give the title compound (15.0 mg, 59%).

LC/MS: 456.2 r.t: 2.12 min.

(176) 3-(1-{[3-(ethyloxy)propyl]sulfonyl}-4-piperidinyl)-5-phenyl-1H-indole-7-carboxamide

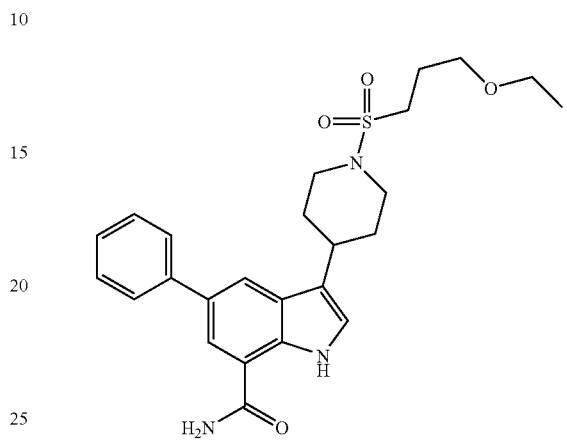

The mixture of 3-{1-[(3-chloropropyl)sulfonyl]-4-piperidinyl}-5-phenyl-1H-indole-7-carboxamide (23 mg, 0.050 mmol), NaOEt (10 mg) in ethanol (1 mL) was refluxed at 80° C. overnight. The reaction mixture was concentrated and purified by reverse phase HPLC (water/$CH_3CN$, 0.1% TFA 10-90%) to give the title compound (15.0 mg, 64%).

LC/MS: 469.8 r.t: 2.14 min.

(177) 3-(1-{[3-(dimethylamino)propyl]sulfonyl}-4-piperidinyl)-5-{3-[(methylamino)methyl]phenyl}-1H-indole-7-carboxamide

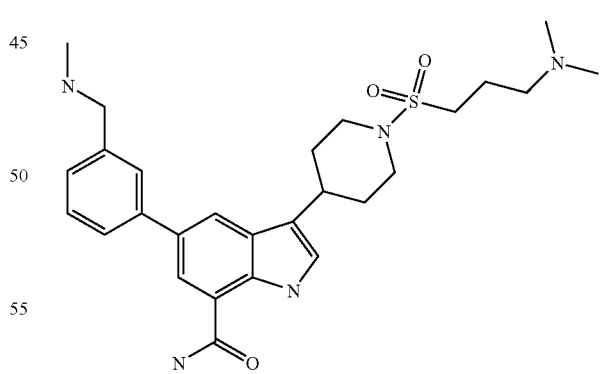

Following the general procedure as described in example 96, but replacing ethyl amine with methyl amine (0.026 mL, 0.3 mmol) produced the desired product 3-(1-{[3-(dimethylamino)propyl]sulfonyl}-4-piperidinyl)-5-{3-[(methylamino)methyl]phenyl}-1H-indole-7-carboxamide (10.8 mg, 40%).

LC/MS: m/z 512.4, Rt 1.36 min.

125

(178) 5-phenyl-3-{1-[(2-{[2-(1-piperidinyl)ethyl]oxy}ethyl)sulfonyl]-4-piperidinyl}-1H-indole-7-carboxamide

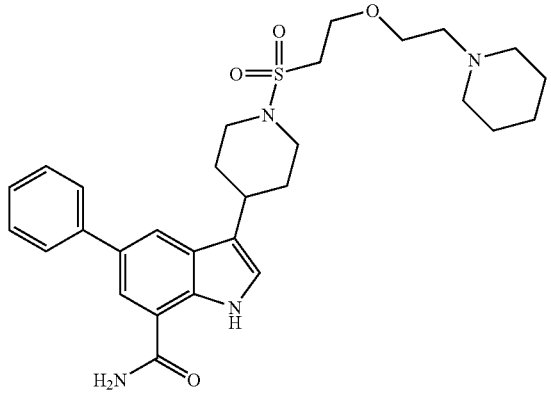

126

The mixture of 3-[1-(ethenylsulfonyl)-4-piperidinyl]-5-phenyl-1H-indole-7-carboxamide (21 mg, 0.05 mmol) in DMSO (1.0 mL), were added 2-(1-piperidinyl)ethanol (64.6 mg, 0.5 mmol), $K_2CO_3$ (35.0 mg, 0.35 mmol) and sodium iodide (0.5 mg). The reaction solution was heated to 80° C. overnight. The reaction mixture was concentrated and purified by reverse phase HPLC (water/$CH_3CN$, 0.1% TFA 10-90%) to give the title compound (12.0 mg, 50%).

LC/MS: 539.4 r.t: 1.80 min.

Following the general procedure as described in example 178, but replacing 2-(1-piperidinyl)ethanol with the appropriate alcohols, compounds listed in Table 8 were prepared.

TABLE 8

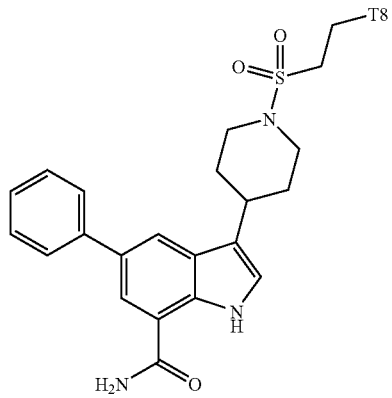

| Example | T8 | MS [M]⁺ | Rt (min) |
|---|---|---|---|
| 179 | (S)-2-(methoxymethyl)pyrrolidinyl | 525.6 | 1.74 |
| 180 | 1-(2-methoxyethyl)pyrrolidin-2-one via ether | 539.4 | 1.92 |
| 181 | N,N-diisopropyl-2-methoxyethylamine | 555.4 | 2.01 |
| 182 | 2-morpholinoethoxy | 541.4 | 1.69 |

TABLE 8-continued

| Example | T8 | MS [M]+ | Rt (min) |
|---|---|---|---|
| 183 | (methoxyethyl-azepane) | 553.4 | 1.83 |
| 184 | (diethylamino ethyl methyl ether) | 527.4 | 1.75 |
| 185 | (4-fluorobenzyl piperazine methoxyethyl) | 648.4 | 1.82 |
| 186 | (N-methoxyethyl-N-ethyl-m-toluidine) | 589.2 | 2.01 |
| 187 | (bis(2-hydroxypropyl) methoxyethyl amine) | 587.2 | 1.68 |
| 188 | (N-(2-methoxyethyl)acetamide) | 513.4 | 1.8 |
| 189 | (isopropoxy ethoxy methyl) | 514.4 | 2.19 |
| 190 | (2-(methoxymethyl)furan) | 508.2 | 2.21 |
| 191 | (3-(methoxymethyl)furan) | 508.0 | 2.25 |
| 192 | (methoxyethyl methyl sulfide) | 502.4 | 2.23 |

TABLE 8-continued
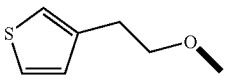
| Example | T8 | MS [M]+ | Rt (min) |
|---|---|---|---|
| 193 | 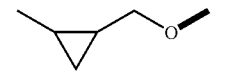 | 538.2 | 2.43 |
| 194 | 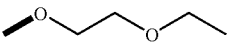 | 496.4 | 2.41 |
| 195 | 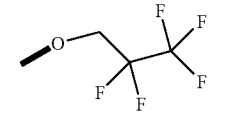 | 500.6 | 2.12 |
| 196 | 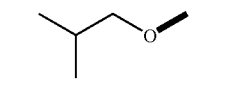 | 560.4 | 2.43 |
| 197 | 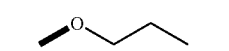 | 484.4 | 2.43 |
| 198 | 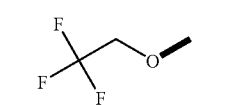 | 470.2 | 2.31 |
| 199 | 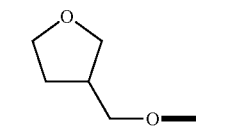 | 510.2 | 2.26 |
| 200 | 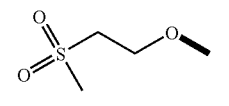 | 512.4 | 2.11 |
| 201 | 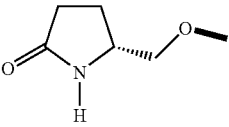 | 517.0 | 1.89 |
| 202 | 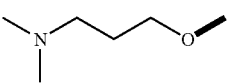 | 525.6 | 1.83 |
| 203 |  | 513.4 | 1.71 |

TABLE 8-continued
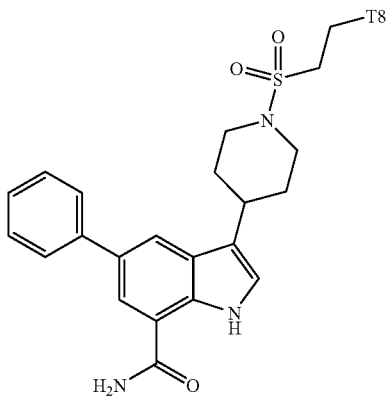
| Example | T8 | MS [M]+ | Rt (min) |
|---|---|---|---|
| 204 | | 482.2 | 2.24 |
| 205 | | 511.1 | 2.12 |
| 206 | | 470.1 | 2.16 |
| 207 | | 543.4 | 2.1 |
| 208 | | 514.4 | 2.0 |
| 209 | | 500.6 | 1.88 |
| 210 | | 514.4 | 2.01 |
| 211 | | 500.06 | 1.97 |
| 212 | | 538.2 | 2.43 |
| 213 | | 525.6 | 1.71 |

(214) 3-(1-{[3-(dimethylamino)propyl]sulfonyl}-4-piperidinyl)-5-(3-{[(1-methylethyl)amino]methyl}phenyl)-1H-indole-7-carboxamide

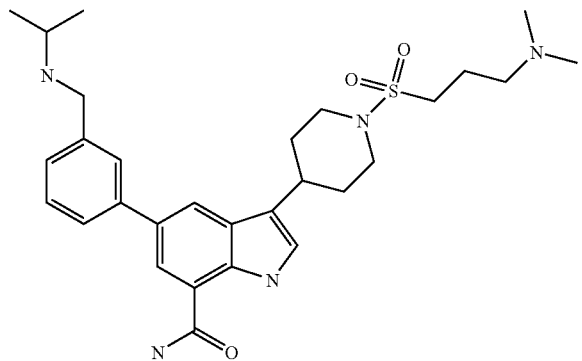

Following the general procedure as described in example 96, but replacing ethyl amine with isopropyl amine (0.15 mL, 0.3 mmol) produced the desired product 3-(1-{[3-(dimethylamino)propyl]sulfonyl}-4-piperidinyl)-5-(3-{[(1-methylethyl)amino]methyl}phenyl)-1H-indole-7-carboxamide. (11 mg, 43%)

LC/MS: m/z 540.2, Rt 1.34 min.

(215) 3-[1-({2-[(methyloxy)amino]ethyl}sulfonyl)-4-piperidinyl]-5-phenyl-1H-indole-7-carboxamide

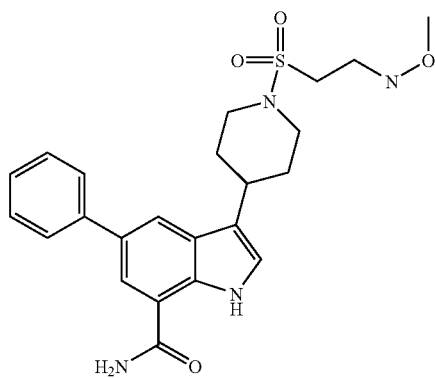

The mixture of 3-[1-(ethenylsulfonyl)-4-piperidinyl]-5-phenyl-1H-indole-7-carboxamide (41 mg, 0.1 mmol) in DMSO (2.0 mL), were added O-methylhydroxylamine hydrochloride (83.5 mg, 1.0 mmol), K₂CO₃ (70.0 mg, 0.70 mmol) and sodium iodide (0.5 mg). The reaction solution was heated to 80° C. overnight. The reaction mixture was concentrated and purified by reverse phase HPLC (water/CH₃CN, 0.1% TFA 10-90%) to give the title compound (20.7 mg, 43%).

LC/MS: 457.2 r.t: 2.11 min.

Following the general procedure as described in example above, but replacing O-methylhydroxylamine hydrochloride with the hydroxyamines, compounds listed in Table 9 were prepared.

TABLE 9

![Structure with T9 group]

| Example | T9 | MS [M]⁺ | Rt (min) |
|---------|----|---------|----------|
| 216 | N—OH | 457.2 | 1.92 |
| 217 | N—O— | 471.2 | 2.19 |
| 218 | H N—O— | 471.2 | 2.27 |

(219) 3-[1-({3-[(methyloxy)amino]propyl}sulfonyl)-4-piperidinyl]-5-phenyl-1H-indole-7-carboxamide The mixture of 3-{1-[(3-chloropropyl)sulfonyl]-4-piperidinyl}-5-phenyl-1H-indole-7-carboxamide (40.0 mg, 0.087 mmol) in DMSO (2.0 mL), were added O-methylhydroxylamine hydrochloride (83.5 mg, 1.0 mmol), K₂CO₃ (35.0 mg, 0.35 mmol) and sodium iodide (0.5 mg). The reaction solution was heated to 80° C. overnight. The reaction mixture was concentrated and purified by reverse phase HPLC (water/CH₃CN, 0.1°/o TFA 10-90%) to give the title compound (20.7 mg, 43%).

LC/MS: 471.0 r.t: 1.91 min.

Following the general procedure as described in example above, but replacing O-methylhydroxylamine hydrochloride with the hydroxyamines, compounds listed in Table 10 were prepared.

TABLE 10

| Example | T10 | MS [M]+ | Rt (min) |
|---------|-----|---------|----------|
| 220 | N—OH (N-methyl) | 471.4 | 1.95 |
| 221 | N—O— (N-methyl, O-methyl) | 485.2 | 2.36 |
| 222 | HN—O-ethyl | 485.2 | 1.94 |

(223) 5-{3-[(methylamino)methyl]phenyl}-3-(1-{[3-(methyloxy)propyl]sulfonyl}-4-piperidinyl)-1H-indole-7-carboxamide

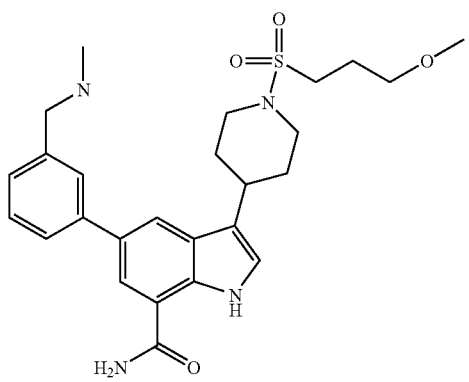

To a solution of 5-(3-formylphenyl)-3-(1-{[3-(methyloxy)propyl]sulfonyl}-4-piperidinyl)-1H-indole-7-carboxamide (25 mg, 0.055 mmol) in MeOH/CH$_2$Cl$_2$ (1 mL/1 mL) was added methyl amine (0.15 mL, 0.33 mmol). The reaction mixture was stirred at room temperature for 2 hours before NaBH$_4$ (13.2 mg, 0.33 mmol) was added. The reaction mixture was stirred at room temperature overnight and evaporated all the solvent. The residue was purified by using a Gilson semi-preparative HPLC system, eluting with 10% B to 80% B, where A=H$_2$O (0.1%/o trifluoroacetic acid) and B=CH$_3$CN (0.1% trifluoroacetic acid) pumped at 25 mL/min to give the title compound (9.0 mg, 36%).

LC/MS: m/z 499.8 (M+H), Rt 1.66 min.

Following the general procedure as described in example above, but replacing methylamine with the appropriate aminess, compounds listed in Table 11 were prepared.

TABLE 11

| Example | T11 | MS [M]+ | Rt (min) |
|---------|-----|---------|----------|
| 224 | ethylaminomethyl | 513.6 | 1.55 |
| 225 | isopropylaminomethyl | 527.6 | 1.61 |
| 226 | n-propylaminomethyl | 527.6 | 1.60 |
| 227 | (R)-2-hydroxypropylaminomethyl | 543.4 | 1.62 |
| 228 | (S)-2-hydroxypropylaminomethyl | 543.4 | 1.55 |
| 229 | cyclopropylmethylaminomethyl | 539.4 | 1.80 |
| 230 | 2-methoxyethylaminomethyl | 544.3 | 1.53 |
| 231 | (S)-sec-butylaminomethyl | 556.4 | 1.75 |
| 232 | neopentylaminomethyl | 556.4 | 1.73 |

TABLE 11-continued

| Example | T11 | MS [M]+ | Rt (min) |
|---|---|---|---|
| 233 | CH3-NH-CH2CH2CH2-O-CH3 | 558.3 | 1.55 |
| 234 | CH3-NH-CH2CH2-O-CH2CH3 | 558.4 | 1.64 |
| 235 | CH3-NH-CH2-(tetrahydrofuran-2-yl) | 570.5 | 1.55 |
| 236 | CH3-NH-CH2-((S)-tetrahydrofuran-2-yl) | 570.4 | 1.54 |
| 237 | CH3-NH-CH(CH3)-CH(CH3)2 | 556.4 | 1.67 |
| 238 | CH3-NH-CH(CH3)-CH2-OCH3 | 557.4 | 1.69 |
| 239 | CH3-NH-CH(CH3)-C(CH3)3 | 569.4 | 1.8 |
| 240 | CH3O-CH2-CH(CH2CH3)-NH-CH3 | 571.2 | 1.79 |
| 241 | CH3-NH-CH2-(5-methylfuran-2-yl) | 579.6 | 1.82 |
| 242 | CH3-NH-CH(CH3)-CH2OH | 543.4 | 1.67 |
| 243 | CH3-NH-C(CH3)2-CH2CH3 | 555.4 | 1.74 |
| 244 | CH3-NH-CH2CH2CH2CH2-OH | 557.4 | 1.56 |
| 245 | CH3-NH-CH2-(pyridin-4-yl) | 576.4 | 1.76 |
| 246 | CH3-NH-CH2-(pyridin-2-yl) | 576.4 | 1.77 |
| 247 | CH3-NH-CH2CH2CH2-(imidazol-1-yl) | 593.4 | 1.28 |
| 248 | CH3-NH-CH2CH2CH2-(pyrrolidin-1-yl) | 596.4 | 1.41 |
| 249 | CH3-NH-CH2CH2-(piperidin-1-yl) | 596.4 | 1.29 |

TABLE 11-continued

[Structure: 5-(3-T11-methylphenyl)-3-(1-{[3-(methyloxy)propyl]sulfonyl}-4-piperidinyl)-1H-indole-7-carboxamide]

| Example | T11 | MS [M]+ | Rt (min) |
|---------|-----|---------|----------|
| 250 | H-N-CH2CH2CH2-N(morpholine), N-methyl | 612.4 | 1.62 |
| 251 | N-methyl-N-(1-cyclohexylethyl)amine | 595.4 | 2.04 |
| 252 | N-methyl-N-allylamine | 539.4 | 1.64 |
| 253 | 3-hydroxy-1-methylpyrrolidine | 555.4 | 1.50 |
| 254 | N-methyl-N-(2-hydroxyethyl)-N-propyl | 571.4 | 1.60 |
| 255 | 1-methyl-2-propylpyrrolidine | 581.8 | 1.77 |
| 256 | 1-methyl-2-isopropylpyrrolidine | 581.8 | 1.76 |

TABLE 11-continued

[Structure: 5-(3-T11-methylphenyl)-3-(1-{[3-(methyloxy)propyl]sulfonyl}-4-piperidinyl)-1H-indole-7-carboxamide]

| Example | T11 | MS [M]+ | Rt (min) |
|---------|-----|---------|----------|
| 257 | 1,3,5-trimethylpiperidine | 581.6 | 1.75 |
| 258 | 1-methylprolinamide | 580.6 | 1.53 |
| 259 | N-tert-butyl-N-methylamine | 541.2 | 1.49 |

(260) 5-{3-[(methylamino)methyl]phenyl}-3-(1-{[2-(methyloxy)ethyl]sulfonyl}-4-piperidinyl)-1H-indole-7-carboxamide

[Structure of compound 260]

To a solution of 5-(3-formylphenyl)-3-(1-{[2-(methyloxy)ethyl]sulfonyl}-4-piperidinyl)-1H-indole-7-carboxamide (25 mg, 0.053 mmol) in MeOH/CH₂Cl₂ (1 mL/1 mL) was added methyl amine (0.15 mL, 0.33 mmol). The reaction mixture was stirred at room temperature for 2 hours before NaBH₄ (13.2 mg, 0.33 mmol) was added. The reaction mixture was stirred at room temperature overnight and evaporated all the solvent. The residue was purified by using a Gilson semi-preparative HPLC system, eluting with 10% B to 80% B, where A=H₂O (0.1% trifluoroacetic acid) and B=CH₃CN (0.1% trifluoroacetic acid) pumped at 25 mL/min to give the title compound (10.0 mg, 39%).

LC/MS: m/z 485.2 (M+H), Rt 1.42 min.

(261) 5-(3-{[(1,1-dimethylpropyl)amino]methyl}phenyl)-3-(1-{[2-(methyloxy)ethyl]sulfonyl}-4-piperidinyl)-1H-indole-7-carboxamide

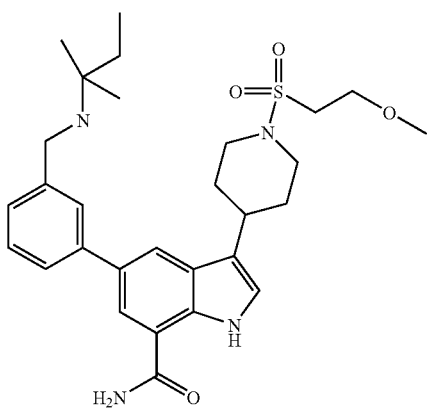

Following the general procedure as described in example 260, but replacing methyl amine with (1,1-dimethylpropyl) amine, the title compound was prepared (12.0 mg, 42%).

LC/MS: m/z 514.4 (M+H), Rt 1.61 min.

(262) 3-(1-{[3-(methyloxy)propyl]sulfonyl}-4-piperidinyl)-5-(2-thienyl)-1H-indole-7-carboxamide

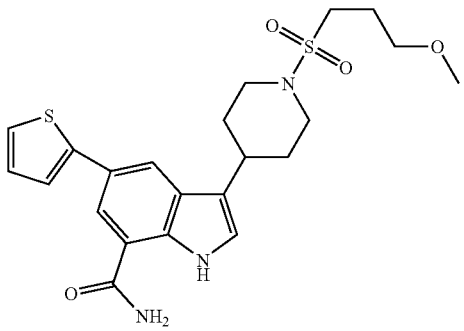

3-{1-[(3-chloropropyl)sulfonyl]-4-piperidinyl}-5-(2-thienyl)-1H-indole-7-carboxamide (35 mg, 0.075 mmol) was reacted with sodium methoxide (0.5 M in methanol, 1.0 mL, 0.488 mmol) in a mixture of methanol (4 ml) and DMSO (0.5 mL) at reflux for 16 h to form the desired product which was purified by reverse phase HPLC eluting with 10% B to 70% B, where A=H₂O (0.1% trifluoroacetic acid) and B=CH₃CN (0.1% trifluoroacetic acid) to give the title compound (15 mg, 43%).

LCMS: 462.2 (M+H), Rt 2.04 min.

(263) 3-(1-{[3-(ethyloxy)propyl]sulfonyl}-4-piperidinyl)-5-(3-thienyl)-1H-indole-7-carboxamide

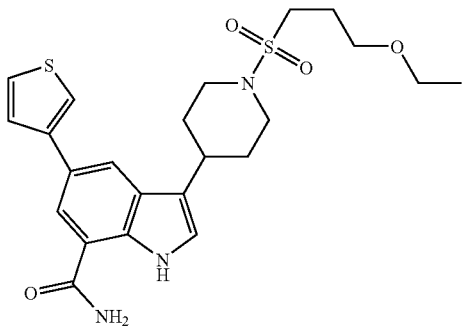

3-{1-[(3-chloropropyl)sulfonyl]-4-piperidinyl}-5-(3-thienyl)-1H-indole-7-carboxamide (60 mg, 0.129 mmol) was reacted with sodium ethoxide (0.5 M in ethanol, 0.5 mL, 0.25 mmol) in a mixture of ethanol (5 ml) and DMSO (0.2 mL) at reflux for 16 h to form the desired product which was purified by reverse phase HPLC eluting with 10% B to 70% B, where A=H₂O (0.1% trifluoroacetic acid) and B=CH₃CN (0.1% trifluoroacetic acid) to give the title compound (10 mg, 17%).

LCMS: 476.6 (M+H), Rt 2.10 min.

(264) 3-(1-{[3-(ethyloxy)propyl]sulfonyl}-4-piperidinyl)-5-(2-thienyl)-1H-indole-7-carboxamide

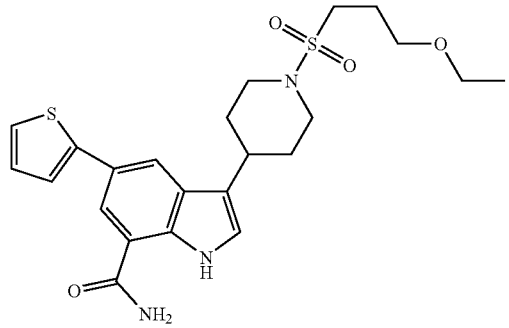

3-{1-[(3-chloropropyl)sulfonyl]-4-piperidinyl}-5-(3-thienyl)-1H-indole-7-carboxamide (80 mg, 0.172 mmol) was reacted with sodium ethoxide (0.5 M in ethanol, 0.7 mL, 0.344 mmol) in a mixture of ethanol (6 ml) and DMSO (0.2 mL) at reflux for 16 h to form the desired product which was purified by reverse phase HPLC eluting with 10% B to 70% B, where A=H₂O (0.1% trifluoroacetic acid) and B=CH₃CN (0.1% trifluoroacetic acid) to give the title compound (20 mg, 25%).

LCMS: 476.6 (M+H), Rt 2.10 min.

(265) 3-{1-[(3-hydroxypropyl)sulfonyl]-4-piperidinyl}-5-(2-thienyl)-1H-indole-7-carboxamide

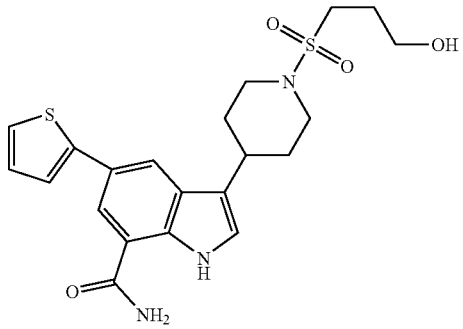

3-{1-[(3-chloropropyl)sulfonyl]-4-piperidinyl}-5-(3-thienyl)-1H-indole-7-carboxamide (50 mg, 0.107 mmol) was reacted in a mixture of 6N sodium hydroxide (1.3 mL) and DMSO (0.7 ml) with a catalytic amount of sodium iodide (1.6 mg, 0.107 mmol) at reflux for 16 h to form the desired product which was purified by reverse phase HPLC eluting with 10% B to 70% B, where A=$H_2O$ (0.1% trifluoroacetic acid) and B=$CH_3CN$ (0.1% trifluoroacetic acid) to give the title compound (12 mg, 25%).

LCMS: 448.6 (M+H), Rt 1.90 min.

(266) 3-(1-{[3-(methyloxy)propyl]sulfonyl}-4-piperidinyl)-5-(3-thienyl)-1H-indole-7-carboxamide

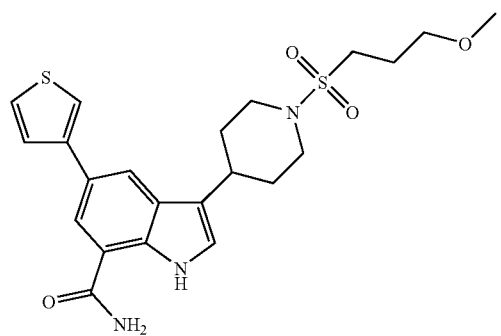

3-{1-[(3-chloropropyl)sulfonyl]-4-piperidinyl}-5-(2-thienyl)-1H-indole-7-carboxamide (165 mg, 0.355 mmol) was reacted with sodium methoxide (0.5 M in methanol, 1.5 mL, 0.710 mmol) in a mixture of methanol (5 ml) and DMSO (0.4 mL) at reflux for 16 h to form the desired product which was purified by reverse phase HPLC eluting with 10% B to 70% B, where A=$H_2O$ (0.1% trifluoroacetic acid) and B=$CH_3CN$ (0.1% trifluoroacetic acid) to give the title compound (25 mg, 15%).

LCMS: 462.2 (M+H), Rt 2.03 min.

(267) 3-{1-[(1-methyl-1H-imidazol-4-yl)sulfonyl]-4-piperidinyl}-5-phenyl-1H-indole-7-carboxamide

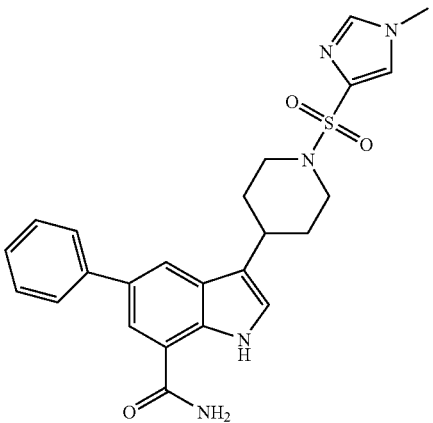

To 5-phenyl-3-(4-piperidinyl)-1H-indole-7-carboxamide (40 mg, 0.12 mmol) in methylene chloride (5 mL) at 0° C., 1-methyl-1H-imidazole-4-sulfonyl chloride (27.1 mg, 0.14 mmol) and triethylamine (0.07 mL, 0.50 mmol) were added. The reaction mixture was stirred at 0° C. for 30 min. Then the reaction mixture was partitioned between methylene chloride and water, the aqueous layer was extracted with methylene chloride (25 mL×2) and combined organic phase was dried with $Mg_2SO_4$ and concentrated by reduce pressure, and purified by Gilson HPLC (reverse phase, eluting with $CH_3CN$/Water, 0.1% TFA, 10/90, v/v, over 15 min) to give the title compound (22.5 mg, 39%).

LC/MS: m/z, 463.4 (M+H), 1.72 min.

(268) 5-phenyl-3-[1-(2-thienylsulfonyl)-4-piperidinyl]-1H-indole-7-carboxamide

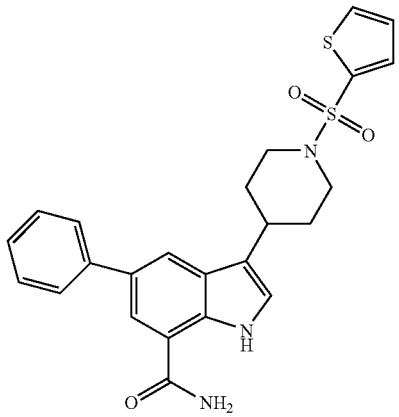

Following the general procedure in example 267, 5-(phenyl)-3-(4-piperidinyl)-1H-indole-7-carboxamide (40 mg, 0.12 mmol), 2-thiophenesulfonyl chloride (23 mg, 0.13 mmol) and triethylamine (0.07 mL, 0.5 mmol) were reacted to form the desired product which was purified by Gilson HPLC ($CH_3CN$/Water, 0.1% TFA) (30 mg, 52%).

LC/MS: m/z 466.2 (M+H), 2.23 min.

(269) 3-{1-[(5-chloro-2-thienyl)sulfonyl]-4-piperidinyl}-5-phenyl-1H-indole-7-carboxamide

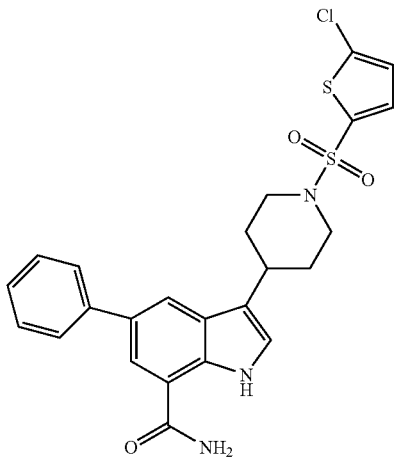

Following the general procedure in example 267, 5-(phenyl)-3-(4-piperidinyl)-1H-indole-7-carboxamide (13 mg, 0.04 mmol), 5-methyl-2-thiophenesulfonyl chloride (13.2 mg, 0.048 mmol) and triethylamine (0.02 mL, 0.16 mmol) were reacted to form the desired product which was purified by Gilson HPLC (CH$_3$CN/Water, 0.1% TFA) (6.1 mg, 30%).

LC/MS: m/z 500.4 (M+H), 2.62 min.

(270) 3-(1-{[5-(3-isoxazolyl)-3-thienyl]sulfonyl}-4-piperidinyl)-5-phenyl-1H-indole-7-carboxamide

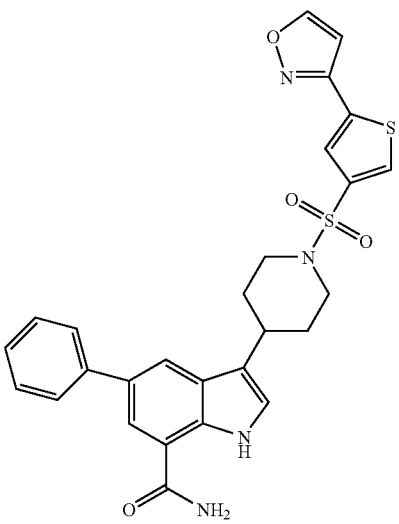

Following the general procedure in example 267, 5-(phenyl)-3-(4-piperidinyl)-1H-indole-7-carboxamide (32 mg, 0.1 mmol), 5-(3-isoxazolyl)-3-thiophenesulfonyl chloride (37.5 mg, 0.15 mmol) and triethylamine (0.06 mL, 0.3 mmol) were reacted to form the desired product which was purified by Gilson HPLC (CH$_3$CN/Water, 0.1% TFA) (11.7 mg, 22%).

LC/MS: m/z 533.4 (M+H), 2.59 min.

(271) 5-phenyl-3-{1-[(5-{[(phenylmethyl)amino]methyl}-2-thienyl)sulfonyl]-4-piperidinyl}-1H-indole-7-carboxamide

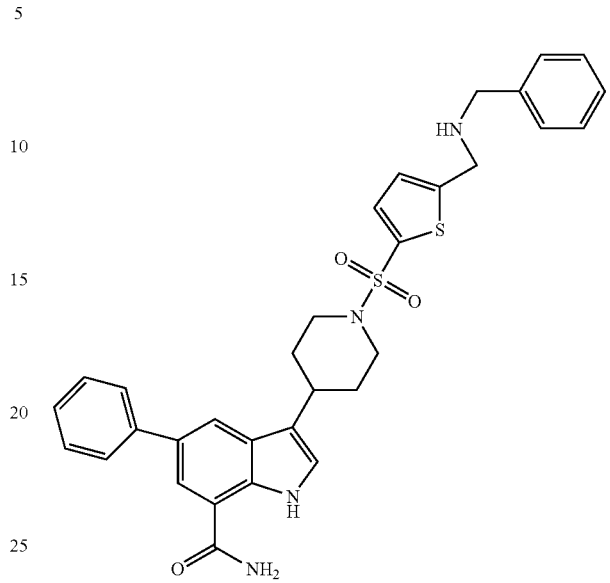

Following the general procedure in example 267, 5-(phenyl)-3-(4-piperidinyl)-1H-indole-7-carboxamide (32 mg, 0.1 mmol), 5-{[(phenylmethyl)amino]methyl}-2-thiophenesulfonyl chloride (45.3 mg, 0.15 mmol) and triethylamine (0.06 mL, 0.3 mmol) were reacted to form the desired product which was purified by Gilson HPLC (CH$_3$CN/Water, 0.1% TFA) (20 mg, 34%).

LC/MS: m/z 599.2 (M+H), 2.48 min.

(272) 3-(1-{[2-(acetylamino)-4-methyl-1,3-thiazol-5-yl]sulfonyl}-4-piperidinyl)-5-phenyl-1H-indole-7-carboxamide

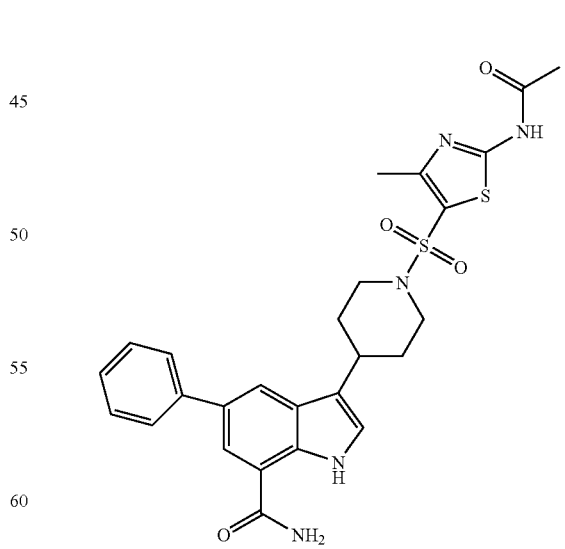

Following the general procedure in example 267, 5-(phenyl)-3-(4-piperidinyl)-1H-indole-7-carboxamide (32 mg, 0.1 mmol), 2-(acetylamino)-4-methyl-1,3-thiazole-5-sulfonyl chloride (38.2 mg, 0.15 mmol) and triethylamine (0.06 mL, 0.3 mmol) were reacted to form the desired product which was purified by Gilson HPLC (CH₃CN/Water, 0.1% TFA) (4.0 mg, 7.5%).

LC/MS: m/z 538.2 (M+H), 1.96 min.

(273) 3-{1-[(5-chloro-1,3-dimethyl-1H-pyrazol-4-yl)sulfonyl]-4-piperidinyl}-5-phenyl-1H-indole-7-carboxamide

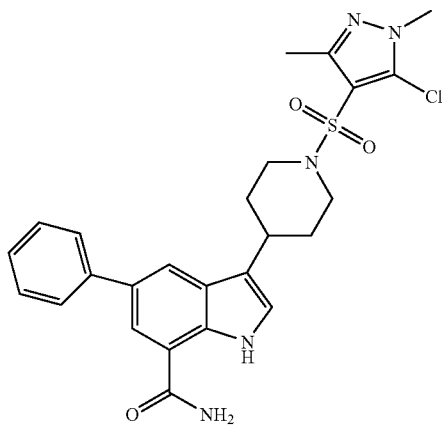

Following the general procedure in example 267, 5-(phenyl)-3-(4-piperidinyl)-1H-indole-7-carboxamide (32 mg, 0.1 mmol), 5-chloro-1,3-dimethyl-1H-pyrazole-4-sulfonyl chloride (34.5 mg, 0.15 mmol) and triethylamine (0.06 mL, 0.3 mmol) were reacted to form the desired product which was purified by Gilson HPLC (CH₃CN/Water, 0.1% TFA) (22 mg, 43%).

LC/MS: m/z 511.6, 2.12 min.

(274) 3-{1-[(4-chloro-2,1,3-benzoxadiazol-5-yl)sulfonyl]-4-piperidinyl}-5-phenyl-1H-indole-7-carboxamide

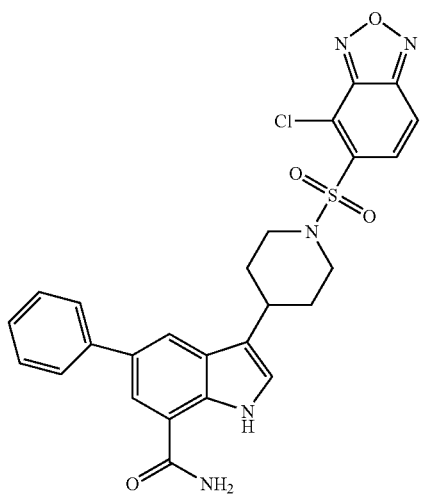

Following the general procedure in example 267, 5-phenyl-3-(1,2,3,6-tetrahydro-4-pyridinyl)-1H-indole-7 carboxamide (32 mg, 0.1 mmol), 4-chloro-2,1,3-benzoxadiazole-5-sulfonyl chloride (38 mg, 0.15 mmol) and triethylamine (0.06 mL, 0.3 mmol) were reacted to form the desired product which was purified by Gilson HPLC (CH₃CN/Water, 0.1% TFA) (8.0 mg, 15%).

LC/MS: m/z 536.0 (M+H), 2.44 min.

(275) 3-{1-[(1,2-dimethyl-1H-imidazol-4-yl)sulfonyl]-4-piperidinyl}-5-phenyl-1H-indole-7-carboxamide

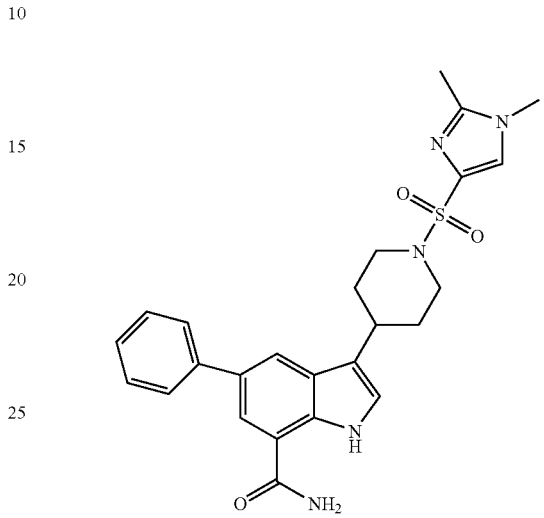

Following the general procedure in example 267, 5-phenyl-3-(1,2,3,6-tetrahydro-4-pyridinyl)-1H-indole-7-carboxamide (32 mg, 0.1 mmol), 1,2-dimethyl-1H-imidazole-4-sulfonyl chloride (22.8 mg, 0.15 mmol) and triethylamine (0.06 mL, 0.3 mmol) were reacted to form the desired product which was purified by Gilson HPLC (CH₃CN/Water, 0.1% TFA) (11 mg, 23%).

LC/MS: m/z 478.2 (M+H), 1.99 min.

(276) 5-phenyl-3-{1-[(1,3,5-trimethyl-1H-pyrazol-4-yl)sulfonyl]-4-piperidinyl}-1H-indole-7-carboxamide

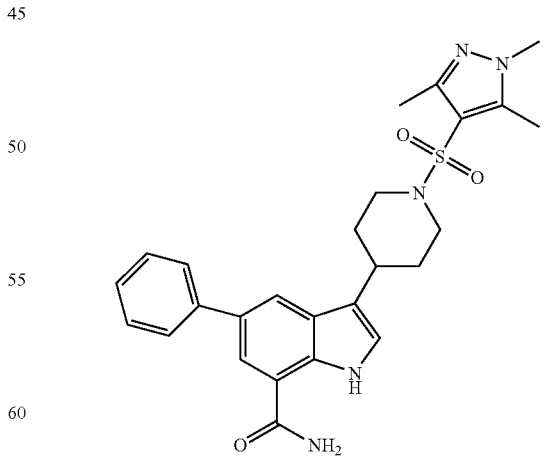

Following the general procedure in example 267, 5-phenyl-3-(1,2,3,6-tetrahydro-4-pyridinyl)-1H-indole-7-carboxamide (32 mg, 0.1 mmol), 1,3,5-trimethyl-1H-pyrazole-4-sulfonyl chloride (24.4 mg, 0.15 mmol) and triethylamine (0.06 mL, 0.3 mmol) were reacted to form the desired product which was purified by Gilson HPLC (CH₃CN/Water, 0.1% TFA) (9 mg, 18%).

LC/MS: m/z 492.0 (M+H), 2.26 min.

(277) 3-{1-[(3,5-dimethyl-4-isoxazolyl)sulfonyl]-4-piperidinyl}-5-phenyl-1H-indole-7-carboxamide

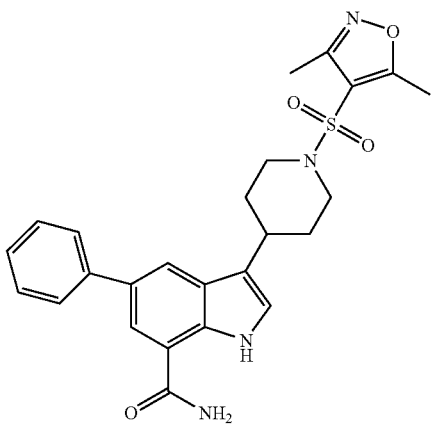

Following the general procedure in example 267, 5-phenyl-3-(1,2,3,6-tetrahydro-4-pyridinyl)-1H-indole-7-carboxamide (32 mg, 0.1 mmol), 3,5-dimethyl-4-isoxazolesulfonyl chloride (22.9 mg, 0.15 mmol) and triethylamine (0.06 mL, 0.3 mmol) were reacted to form the desired product which was purified by Gilson HPLC (CH₃CN/Water, 0.1% TFA) (11 mg, 23%).

LC/MS: m/z 479.4 (M+H), 2.32 min.

(278) 3-{1-[(2,4-dimethyl-1,3-thiazol-5-yl)sulfonyl]-4-piperidinyl}-5-phenyl-1H-indole-7-carboxamide

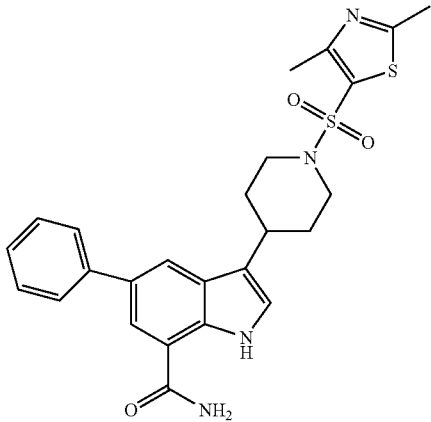

Following the general procedure in example 267, 5-phenyl-3-(4-piperidinyl)-1H-indole-7-carboxamide (32 mg, 0.1 mmol), 2,4-dimethyl-1,3-thiazole-5-sulfonyl chloride (24.8 mg, 0.15 mmol) and triethylamine (0.06 mL, 0.3 mmol) were reacted to form the desired product which was purified by Gilson HPLC (CH₃CN/Water, 0.1% TFA) (12.7 mg, 26%).

LC/MS: m/z 495.4 (M+H), 2.31 min.

(279) 3-{1-[(1,2-dimethyl-1H-imidazol-5-yl)sulfonyl]-4-piperidinyl}-5-phenyl-1H-indole-7-carboxamide

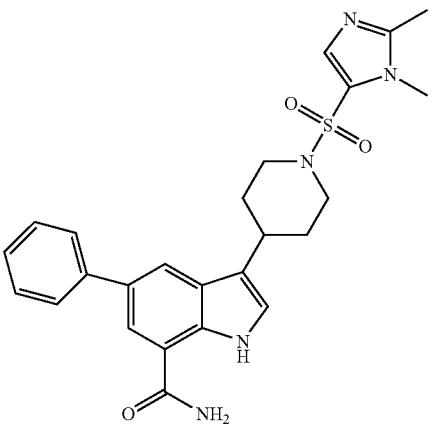

Following the general procedure in example 267, 5-(phenyl)-3-(4-piperidinyl)-1H-indole-7-carboxamide (72 mg, 0.22 mmol), 1,2-dimethyl-1H-imidazole-5-sulfonyl chloride (64.2 mg, 0.33 mmol) and triethylamine (0.13 mL, 0.66 mmol) were reacted to form the desired product which was purified by Gilson HPLC (CH₃CN/Water, 0.1% TFA) (48.3 mg, 45%).

LC/MS: m/z 478.0 (M+H), 1.65 min.

(280) 3-{1-[(1-methyl-1H-imidazol-4-yl)sulfonyl]-4-piperidinyl}-5-(3-thienyl)-1H-indole-7-carboxamide

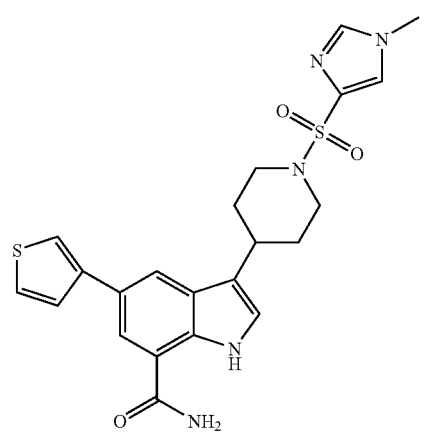

Following the general procedure in example 267, 3-(4-piperidinyl)-5-(3-thienyl)-1H-indole-7-carboxamide (40 mg, 0.12 mmol), 1-methyl-1H-imidazole-4-sulfonyl chloride (29.7 mg, 0.18 mmol) and triethylamine (0.05 mL, 0.36 mmol) were reacted to form the desired product which was purified by Gilson HPLC (CH₃CN/Water, 0.1% TFA) (20 mg, 34%).

LC/MS: m/z 470.4 (M+H), 1.76 min.

(281) 3-(1-{[3-(methyloxy)propyl]sulfonyl}-4-piperidinyl)-5-[5-(1-pyrrolidinylmethyl)-3-thienyl]-1H-indole-7-carboxamide

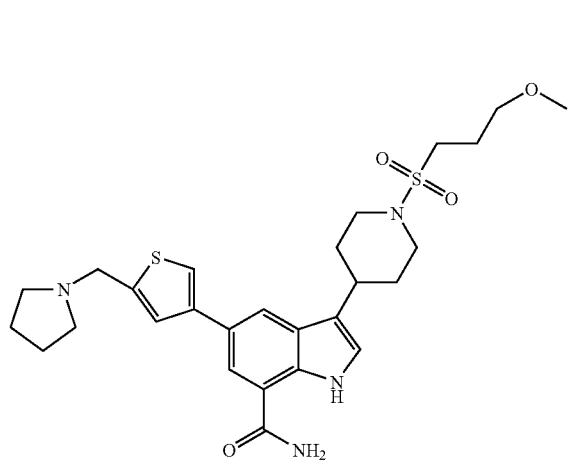

To 5-(5-formyl-3-thienyl)-3-(1-{[3-(methyloxy)propyl]sulfonyl}-4-piperidinyl)-1H-indole-7-carboxamide (40 mg, 0.08 mmol) in a mixture of dichloromethane (1.25 mL) and methanol (0.5 mL), pyrrolidine (0.07 mL, 0.8 mmol) and 2 drops of acetic acid were added. After the reaction mixture was stirred at room temperature for 6 hours, NaBH$_4$ (30.26 mg, 0.8 mmol) was added. Then the reaction mixture was stirred at room temperature for 30 minutes. All the solvent was evaporated and purified by Gilson HPLC (CH$_3$CN/Water, 0.1% TFA) to give title compound (6.5 mg, 15%).

LC/MS: m/z 545.2 (M+H), 1.65 min.

(282) 5-(5-{[(1,1-dimethylethyl)amino]methyl}-3-thienyl)-3-(1-{[3-(methyloxy)propyl]sulfonyl}-4-piperidinyl)-1H-indole-7-carboxamide

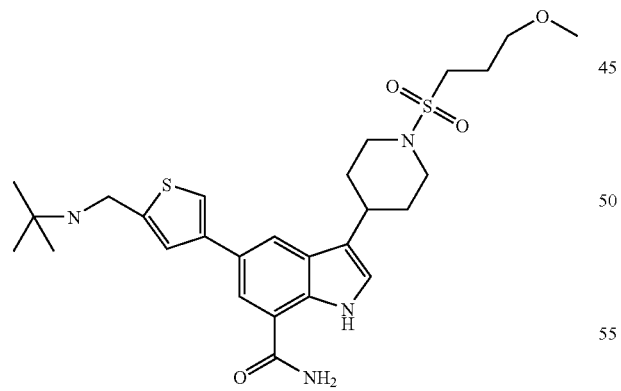

Following the general procedure in example 281, 5-(5-formyl-3-thienyl)-3-(1-{[3-(methyloxy)propyl]sulfonyl}-4-piperidinyl)-1H-indole-7-carboxamide (40 mg, 0.08 mmol), (1,1-dimethylethyl)amine (70 mg, 0.8 mmol) and NaBH$_4$ (30.26 mg, 0.8 mmol) were reacted to form the desired product which was purified by Gilson HPLC (CH$_3$CN/Water, 0.1% TFA) (8.4 mg, 19%).

LC/MS: m/z 561.2 (M+H), 1.65 min.

(283) 3-[1-({3-[(3-ethylphenyl)oxy]propyl}sulfonyl)-4-piperidinyl]-5-phenyl-1H-indole-7-carboxamide

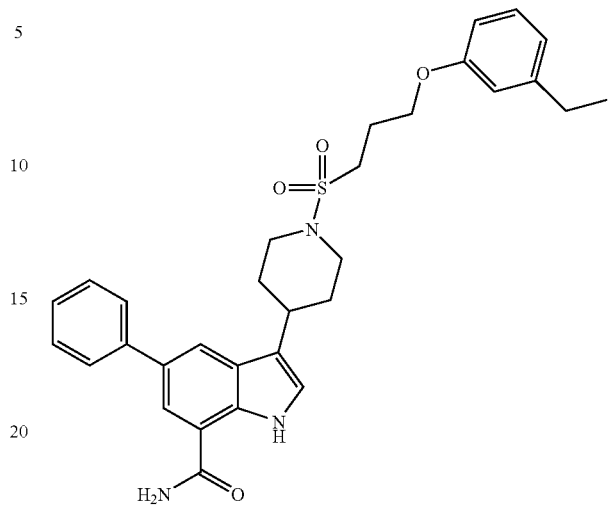

To a solution of 3-{1-[(3-chloropropyl)sulfonyl]-4-piperidinyl}-5-phenyl-1H-indole-7-carboxamide (23.0 mg, 0.05 mmol) in DMSO (1.0 mL), were added 3-ethylphenol (122.0 mg, 0.5 mmol), K$_2$CO$_3$ (35.0 mg, 0.25 mmol) and sodium iodide (1.0 mg). The reaction solution was heated to 80° C. overnight. After which time the reaction mixture was filtered and purified by reverse phase HPLC (water/CH$_3$CN, 0.1% TFA 10-90%) to give the title compound (5 mg, 18%).

LC/MS: 546.1 r.t: 2.76 min.

Following the general procedure as described in example above, but replacing 3-ethylphenol with the appropriate alcohols, compounds listed in Table 12 were prepared.

TABLE 12

| Example | T12 | MS [M]$^+$ | Rt (min) |
|---|---|---|---|
| 284 | (3-methylphenoxy) | 532.3 | 2.54 |

TABLE 12-continued

Structure: 5-phenyl-3-(1-(propylsulfonyl-T12)piperidin-4-yl)-1H-indole-7-carboxamide scaffold with T12 substituent on sulfonyl propyl chain.

| Example | T12 | MS [M]+ | Rt (min) |
|---------|-----|---------|----------|
| 285 | 4-ethoxy-methoxyphenyl | 562.1 | 2.49 |
| 286 | 4-methoxy-N-methylbenzamide | 561.3 | 2.02 |
| 287 | N-(2-methoxy-4-methylphenyl)acetamide | 589.1 | 2.34 |
| 288 | 1-fluoro-2,3-dimethoxybenzene | 566.3 | 2.42 |
| 289 | 1,2-difluoro-3-methoxy-4-(trifluoromethyl)benzene | 604.1 | 2.56 |
| 290 | N,N-dimethyl-(2-methoxyphenyl)methanamine | 575.1 | 1.88 |
| 291 | 1-fluoro-3-methoxybenzene | 536.0 | 2.48 |
| 292 | N-(3-methoxyphenyl)acetamide | 575.4 | 2.21 |
| 293 | 1-fluoro-2-methoxybenzene | 536.0 | 2.39 |
| 294 | N,N-dimethyl-3-methoxyaniline | 561.1 | 1.82 |
| 295 | 1,3-difluoro-2-methoxybenzene | 554.2 | 2.45 |
| 296 | N-(2-methoxyphenyl)acetamide | 575.1 | 2.18 |
| 297 | N,N-diethyl-3-methoxyaniline | 589.1 | 1.89 |
| 298 | 6-methoxy-1,3-benzodioxole | 562.0 | 2.42 |

TABLE 12-continued

| Example | T12 | MS [M]+ | Rt (min) |
|---|---|---|---|
| 299 | (3-methoxyphenyl)-N-phenylsulfonamide | 673.2 | 2.26 |
| 300 | 1-acetyl-4-(4-methoxyphenyl)piperazine | 644.2 | 2.04 |
| 301 | 4-methoxyphenol | 534.0 | 2.13 |
| 302 | N-(2-methoxy-5-methylphenyl)acetamide | 589.1 | 2.30 |
| 303 | 2-methoxyphenyl methyl sulfone | 596.4 | 2.22 |
| 304 | 3-methoxyphenyl piperidine | 601.1 | 1.87 |
| 305 | 2-methoxyphenol | 534.3 | 2.30 |
| 306 | 3-methoxyphenol | 534.4 | 2.18 |
| 307 | 4-methoxy(trifluoromethyl)benzene | 586.1 | 2.57 |

(308) 5-[3-(1-pyrrolidinylmethyl)phenyl]-3-(1-{[3-(1-pyrrolidinyl)propyl]sulfonyl}-4-piperidinyl)-1H-indole-7-carboxamide To a solution of 5-(3-formylphenyl)-3-(1-{[3-(1-pyrrolidinyl)propyl]sulfonyl}-4-piperidinyl)-1H-indole-7-carboxamide (45.0 mg/0.086 mmol) in DCM/MeOH (1.0 ml/1.0 ml) was added pyrrolidine (0.043 mL, 0.517 mmol) and 1 drop of AcOH. The reaction mixture was stirred for 2 hr at r.t and then NaBH₄ (17.0 mg, 0.086 mmol) was added. The reaction mixture was stirred for 30 min and concentrated and redissolved in 1.5 ml of DMSO. The residue was purified by using a Gilson semi-preparative HPLC system, eluting with 10% B to 80% B, where A=H₂O (0.1% trifluoroacetic acid) and B=CH₃CN (0.1% trifluoroacetic acid) pumped at 25 mL/min to give the title compound (4 mg, 8%).

LC/MS: m/z 578.6 Rt 1.40 min.

Following the general procedure as described in example 308, but replacing pyrrolidine with the appropriate amine, compounds listed in Table 13 were prepared.

TABLE 13

| Example | T13 | MS [M]⁺ | Rt (min) |
|---|---|---|---|
| 309 | morpholinylmethyl | 594.4 | 1.35 |
| 310 | piperidinylmethyl | 592.4 | 1.32 |

(311) 5-phenyl-3-[1-(3-thienylsulfonyl)piperidin-4-yl]-1H-indole-7-carboxamide

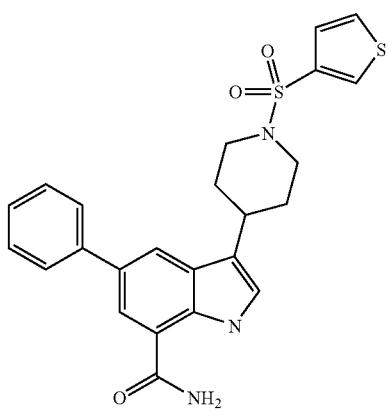

To a solution of 5-Phenyl-3-(4-piperidinyl)-1H-indole-7-carboxamide (31 mg/0.067 mmol) in CHCl₃ (1.0 ml) was added diisopropyl ethylamine (3 eq). The mixture was cooled to −10° C. and then added to 3-thiophenesulfonyl chloride. The solution was agitated for 1.5 h. Solid phase extraction (SPE) using an aminopropyl cartridge (500 mg) and elution with CHCl₃ followed by ethyl acetate provided the title compound (19 mg 61%). LC/MS: m/z 465 Rt 2.29 min.

Following the general procedure as described in example 311, but replacing 3-thiophenesulfonyl chloride with the appropriate sulfonyl chloride, compounds listed in Table 14 were prepared.

TABLE 14

| Example | T14 | MS [MH]⁺ | Rt (min) |
|---|---|---|---|
| 312 | 2,4-dimethylthiophene | 480 | 2.43 |
| 313 | 2,5-dimethylthiophene | 480 | 2.45 |
| 314 | benzothiophene | 515 | 2.54 |
| 315 | methyl 1,5-dimethylpyrrole-2-carboxylate | 520 | 2.28 |
| 316 | methyl 2,5-dimethylfuran-3-carboxylate | 521 | 2.47 |

Biological Data

IKK2 Assay

Recombinant human IKKβ (residues 1-737) was expressed in baculovirus as a C-terminal GST-tagged fusion protein, and its activity was assessed using a time-resolved fluorescence resonance energy transfer (TR-FRET) assay. Briefly, IKK2 (5 nM final) diluted in assay buffer (50 mM HEPES, 10 mM MgCl₂, 1 mM CHAPS pH 7.4 with 1 mM DTT and 0.01% w/v BSA) was added to wells containing various concentrations of compound or DMSO vehicle (3% final). The reaction was initiated by the addition of GST-IκBα substrate (25 nM final)/ATP (1 μM final), in a total volume of 30 μl. The reaction was incubated for 30 minutes at room temperature, then terminated by the addition of 15 μl of 50 mM EDTA. Detection reagent (15 μl) in buffer (100 mM HEPES pH 7.4, 150 mM NaCl and 0.1% w/v BSA) containing antiphosphoserine-IκBα-32/36 monoclonal antibody 12C2 (Cell Signalling Technology, Beverly Mass., USA) labelled with W-1024 europium chelate (Wallac OY, Turku, Finland), and an APC-labelled anti-GST antibody (Prozyme, San Leandro, Calif., USA) was added and the reaction was further incubated for 60 minutes at room temperature. The degree of phosphorylation of GST-IκBα was measured using a Packard Discovery plate reader (Perkin-Elmer Life Sciences, Pangbourne, UK) as a ratio of specific 665 nm energy transfer signal to reference europium 620 nm signal.

Results

The compounds of Examples 1-36, 38, 40-108, 110-173, 175-183, 185-198, 200, 202-204, 206-210, 213-247, 259-258, 262-280, 284-289, 291-306, and 308-316 were tested for activity against IKK2 and were found to be inhibitors of IKK2. These examples had a pIC$_{50}$ of 5.0 or greater. Example 249 was also tested for activity against IKK2 and was found to have a pIC$_{50}$ less than 4.6.

Monocyte Assay

Effect of IKK-β inhibition on human monocyte stimulated cytokine production was assessed as follows: Monocytes were isolated from heparinized whole blood by Ficoll gradient, followed by purification of CD14+ cells using MACS magnetic cell separation beads. Isolated monocytes were then adhered to 96-well culture plates at 1×10$^6$ cells/mL in RPMI 1640 10% FBS (JRH Biosciences, Lenexa Kans.) for 2 h. to further enrich the monocyte population. The media was then removed, cells washed once with RPMI 1640, and 0.125 mL RPMI 1640 10% FBS was added to the wells. Test compounds are added to the wells 30 minutes prior to stimulation with a final vehicle concentration of 0.1% DMSO. Monocytes were activated by the addition of 200 ng/mL endotoxin (LPS; E. coli serotype 026:B6) (Sigma, St. Louis, Mo.) and incubated for 24 hrs at 37 C. Cell-free supernates were analyzed by ELISA for TNF-α using Pharmingen matched pair Abs. Viability of the cells was determined by10% trypan blue exclusion.

Results

The compounds of Examples 1-26, 28-76, 80-81, 83-94, 96-116, 118-119, 122-151, 153-165, 167-183, 186-196, 198, 200, 202-204, 206-209, 213-226, 228-258, 262-265, 267-280, 283, 286, 290, 306-308, 310-312, and 314-316 were all tested in the monocyte assay. Examples 1-26, 28-37, 39-47, 49-55, 57-76, 81, 83-85, 91-92, 94, 96, 103, 105-106, 108-109, 110-116, 118-119, 122-130, 132-151, 153-158, 160, 164-165, 174-176, 178-183, 187-192, 194-195, 200, 202-204, 206-209, 213-226, 228-246, 251-256, 262-265, 267-268, 271-280, 290, 310-312, and 314-316 had an IC50 of less than 10 μM.

What is claimed is:

1. A compound according to formula (I):

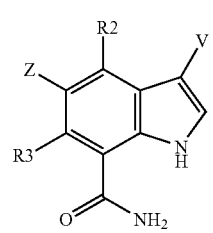

where:

R2 and R3 are both H, or one of R2 and R3 is H and the other is fluoro;

Z is optionally substituted aryl or optionally substituted heteroaryl,
where said aryl and heteroaryl are optionally substituted with one to three substituents independently selected from the group consisting of: halo, —CN, —N(Rb)SO$_2$Re, —N(Rb)C(O)Ra, —C(O)NRaRb, —C(O)NRfRg, —C(O)H, —SO$_2$Ri, —NRaRb, —SO$_2$NRaRb, —SO$_2$NRfRg, —ORc, —N(Rb)C(O)NRaRb, —N(Rb)C(O)NRfRg, —N(Rb)C(O)ORd, $C_1$-$C_6$ alkyl, $C_1$-$C_6$ alkyl substituted with one to three substituents independently selected from the group consisting of: —NRaRb, $C_3$-$C_6$ cycloalkyl, phenyl,
—ORc, heterocycloalkyl, and heterocycloalkyl substituted with OH, —C(O)NH$_2$, or one or two $C_1$-$C_6$ alkyl groups; $C_1$-$C_6$ haloalkyl, $C_1$-$C_6$ haloalkyl substituted with one to three substituents independently selected from the group consisting of —NRaRb, $C_3$-$C_6$ cycloalkyl, phenyl, heterocycloalkyl, and heterocycloalkyl substituted with one or two $C_1$-$C_6$ alkyl groups; heterocycloalkyl and heterocycloalkyl substituted with one or two $C_1$-$C_6$ alkyl groups;

V is piperidin-4-yl or 1,2,3,6-tetrahydropyridin-4-yl, each of which is substituted by —N(Rb)S(O)$_m$R4 or —S(O)$_m$R4;

m is 1 or 2;

R4 is the group —X—R5;

X is a bond, $C_1$-$C_6$ alkylene, $C_2$-$C_6$ alkenylene, $C_2$-$C_6$ alkynylene, heteroaryl, $C_1$-$C_6$ alkylene-heteroaryl, heterocycloalkyl, $C_1$-$C_6$ alkylene-heterocycloalkyl, $C_4$-$C_7$cycloalkyl, $C_1$-$C_6$ alkylene-$C_4$-$C_7$cycloalkyl, $C_5$-$C_7$cycloalkenyl, or $C_1$-$C_6$ alkylene-$C_5$-$C_7$cycloalkenyl;

R5 is —NRaRb, —ORj, optionally substituted heterocycloalkyl, or optionally substituted heteroaryl,
where said optionally substituted heterocycloalkyl and optionally substituted heteroaryl are optionally substituted with one to three substituents independently selected from the group consisting of: halo, heteroaryl, oxo, —CN, —C(O)Ra, —N(Rb)SO$_2$Re, —N(Rb)C(O)Ra, —NRaRb, —C(O)NRaRb, —C(O)NRfRg, —SO$_2$NRaRb, —SO$_2$NRfg, —ORc, —C(O)ORc, —N(Rb)C(O)NRaRb, —N(Rb)C(O)NRfRg, —N(Rb)C(O)ORd, $C_1$-$C_6$ alkyl, $C_1$-$C_6$ alkyl substituted with one to three substituents independently selected from the group consisting of: —NRaRb, —ORc, —C(O)NRaRb, —C(O)Rc, $C_3$-$C_6$ cycloalkyl, heterocycloalkyl, and phenyl; $C_1$-$C_6$ haloalkyl, $C_1$-$C_6$ haloalkyl substituted with one to three substituents independently selected from the group consisting of: —NRaRb, —ORc, —C(O)NRaRb, $C_3$-$C_6$ cycloalkyl, heterocycloalkyl, and phenyl; heterocycloalkyl, heterocycloalkyl substituted with one to three substituents independently selected from the group consisting of: $C_1$-$C_6$ alkyl, halo, —ORc, haloalkyl, CN, and —$SO_2$Ri; phenyl, and phenyl substituted with one to three substituents independently selected from the group consisting of: halo, —ORc, haloalkyl, —CN, and —$SO_2$Ri;

each Ra is independently selected from the group consisting of: H, —ORh, $C_2$-$C_6$ alkenyl, $C_2$-$C_6$ alkynyl, $C_1$-$C_6$ alkyl, $C_1$-$C_6$ alkyl substituted with one to three substituents independently selected from the group consisting of: halo, —CN, —C(O)$NH_2$, —NRkRk, —$SO_2$Ri, —N(Rb)$SO_2$Re, —C(O)ORb, —N(Rb)C(O)Rb, —ORc, —SRc, $C_3$-$C_7$ cycloalkyl, $C_1$-$C_6$ haloalkyl, heterocycloalkyl, phenyl, phenolyl, and heteroaryl; phenyl, phenyl substituted with one to three substituents independently selected from the group consisting of: halo, oxo, $C_1$-$C_6$ alkyl, $C_1$-$C_6$ haloalkyl, $NH_2$, heteroaryl, —ORc, and —NRfRg; heteroaryl, heteroaryl substituted with one to three substituents independently selected from the group consisting of: halo, oxo, $C_1$-$C_6$ alkyl, $C_1$-$C_6$ haloalkyl, $NH_2$, heteroaryl, —ORc, and —NRfRg; $C_3$-$C_7$ cycloalkyl, $C_3$-$C_7$ cycloalkyl substituted with one to three substituents independently selected from the group consisting of: halo, oxo, $C_1$-$C_6$ alkyl, $C_1$-$C_6$ haloalkyl, $NH_2$, heteroaryl, —ORc, and —NRfRg; heterocycloalkyl, and heterocycloalkyl substituted with one to three substituents independently selected from the group consisting of: halo, oxo, $C_1$-$C_6$ alkyl, —$CH_2$C(O)Rb, $C_1$-$C_6$ haloalkyl, —C(O)ORb, $NH_2$, heteroaryl, —ORc, and NRfRg;

each Rb is independently selected from the group consisting of: H, $C_1$-$C_6$ alkyl, $C_1$-$C_6$ alkyl substituted with one —ORc, and $C_3$-$C_7$ cycloalkyl;

each Rc is independently selected from the group consisting of: H, $C_1$-$C_6$ alkyl, $C_1$-$C_6$ alkyl substituted with one to three substituents independently selected from the group consisting of: OH, $C_3$-$C_6$ cycloalkyl, phenyl, heterocycloalkyl, and heteroaryl; $C_1$-$C_6$ haloalkyl, $C_1$-$C_6$ haloalkyl substituted with one to three substituents independently selected from the group consisting of: OH, $C_3$-$C_6$ cycloalkyl, phenyl, heterocycloalkyl, and heteroaryl; $C_3$-$C_7$ cycloalkyl, $C_3$-$C_7$ cycloalkyl substituted with one to three $C_1$-$C_3$ alkyl groups; heterocycloalkyl, heterocycloalkyl substituted with one to three $C_1$-$C_3$ alkyl groups; aryl, aryl substituted with one to three substituents independently selected from the group consisting of: halo, $C_1$-$C_3$ alkyl, $C_1$-$C_3$ haloalkyl, and OH; heteroaryl, and heteroaryl substituted with one to three substituents independently selected from the group consisting of: halo, $C_1$-$C_3$ alkyl, $C_1$-$C_3$ haloalkyl, and OH;

each Rd is independently an optionally substituted $C_1$-$C_3$ alkyl, where said $C_1$-$C_3$ alkyl is optionally substituted with one to three substituents selected from the group consisting of: $C_3$-$C_6$ cycloalkyl, heterocycloalkyl, optionally substituted phenyl, and optionally substituted heteroaryl; where said phenyl and heteroaryl are optionally substituted with one to three substituents selected from the group consisting of: halo, $C_1$-$C_6$ alkyl and $C_3$-$C_6$ cycloalkyl;

each Re is independently selected from the group consisting of: $C_1$-$C_6$ alkyl, $C_1$-$C_6$ alkyl substituted with one substituent selected from the group consisting of: phenyl, heteroaryl, heterocycloalkyl, and NRaRb; phenyl, phenyl substituted with one to three substituents selected from the group consisting of: halo, CN, $C_1$-$C_6$ alkyl, $C_1$-$C_6$ haloalkyl, and ORh; heteroaryl, heteroaryl substituted with one to three substituents selected from the group consisting of: halo, CN, $C_1$-$C_6$ alkyl, $C_1$-$C_6$ haloalkyl, and —ORh; $C_5$-$C_7$ cycloalkyl, $C_5$-$C_7$ cycloalkyl substituted with one to three substituents selected from the group consisting of: halo, $C_1$-$C_6$ alkyl, and $C_3$-$C_6$ cycloalkyl; heterocycloalkyl, and heterocycloalkyl substituted with one to three substituents selected from the group consisting of: halo, $C_1$-$C_6$ alkyl, and $C_3$-$C_6$ cycloalkyl;

Rf and Rg taken together with the nitrogen atom to which they are attached form a ring having from 5 to 7 member atoms wherein said ring optionally contains one additional heteroatom as a member atom, said ring is saturated or unsaturated but not aromatic, and said ring is optionally substituted with one or two $C_1$-$C_3$ alkyl substituents;

each Rh is independently selected from the group consisting of: H, $C_1$-$C_6$ alkyl, and $C_1$-$C_6$ haloalkyl;

each Ri is independently selected from the group consisting of: $C_1$-$C_3$ alkyl and phenyl;

Rj is selected from the group consisting of H, optionally substituted $C_1$-$C_6$ alkyl, $C_1$-$C_6$ haloalkyl, heteroaryl, and optionally substituted phenyl, where said optionally substituted $C_1$-$C_6$ alkyl is optionally substituted by one or two substituents each independently selected from the following: hydroxy, $C_1$-$C_6$ alkoxy, —$OCH_2CH_2N(CH_3)_2$, methylthio, $C_3$-$C_6$ cycloalkyl, $C_3$-$C_6$ cycloalkyl substituted by one $C_1$-$C_3$ alkyl group; heterocycloalkyl, heterocycloalkyl substituted by one $C_1$-$C_3$ alkyl, one oxo group, or one 4-fluorobenzyl group; —NRkRk, heteroaryl, —NHC(O)$CH_3$, and —$S(O)_2$Ri;

where said phenyl is optionally substituted by one to three substituents each independently selected from the following: $C_1$-$C_3$ alkoxy, —NHC(O)$CH_3$, —C(O)$NH_2$, halo, $CF_3$, —$S(O)_2$Ri, —$S(O)_2$NHRi, hydroxy, —$C_1$-$C_3$-alkyl-NRkRk, —NRkRk, $C_1$-$C_3$ alkyl, heterocycloalkyl, and heterocycloalkyl substituted with one —C(O)$CH_3$ group; and each Rk is independently selected from H, $C_1$-$C_6$ alkyl, $C_1$-$C_6$ alkyl substituted by one or two hydroxyl groups; phenyl, and phenyl substituted with one $C_1$-$C_3$ alkyl group;

or a pharmaceutically-acceptable salt thereof.

2. The compound according to claim 1 wherein R2 and R3 are both hydrogen, or a pharmaceutically acceptable salt thereof.

3. The compound according to claim 2 wherein V is

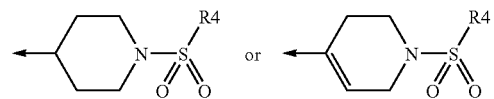

or a pharmaceutically acceptable salt thereof.

4. The compound according to claim 3 wherein V is

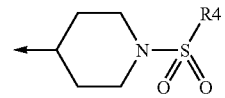

or a pharmaceutically acceptable salt thereof.

5. The compound according to claim 4 wherein X is a bond, $C_1$-$C_6$ alkylene, heteroaryl, or $C_1$-$C_6$ alkylene-heterocycloalkyl, or a pharmaceutically acceptable salt thereof.

6. The compound according to claim 5 wherein X is a bond or $C_1$-$C_6$ alkylene, or a pharmaceutically acceptable salt thereof.

7. The compound according to claim 6 wherein Z is optionally substituted phenyl or optionally substituted heteroaryl;
where said phenyl and heteroaryl are optionally substituted with one or two substituents selected from the group consisting of: halo, cyano, —N(Rb)SO$_2$Re, —N(Rb)C(O)Ra, $C_1$-$C_6$ alkyl, and $C_1$-$C_6$ alkyl substituted with one substituent selected from the group consisting of: —NRaRb, —ORc, heterocycloalkyl, and heterocycloalkyl substituted with one OH, —C(O)NH$_2$, or $C_1$-$C_3$ alkyl group; or a pharmaceutically acceptable salt thereof.

8. The compound according to claim 7 wherein
R5 is —NRaRb, optionally substituted heterocycloalkyl, or optionally substituted heteroaryl,
where said heterocycloalkyl and heteroaryl are optionally substituted with one to three substituents independently selected from the group consisting of: halo, —C(O)Ra, —NRaRb, heterocycloalkyl, heterocycloalkyl substituted with one $C_1$-$C_6$ alkyl group; phenyl, $C_1$-$C_6$ alkyl, $C_1$-$C_6$ alkyl substituted with one or two substituents selected from the group consisting of: —ORc, —C(O)Rc, —C(O)NRaRb, and phenyl; heteroaryl, oxo, N(Rb)C(O)Ra, —ORc, —C(O)NRaRb, and —C(O)ORc;
each Ra is independently selected from the group consisting of: H, —ORh, heterocycloalkyl, heterocycloalkyl substituted with one —C(O)ORb group; $C_2$-$C_6$ alkynyl, optionally substituted $C_1$-$C_6$ alkyl, $C_3$-$C_6$ cycloalkyl, $C_3$-$C_7$ cycloalkyl substituted with one —ORc group, and phenyl, where said optionally substituted $C_1$-$C_6$ alkyl is optionally substituted with one to three substituents selected from the group consisting of: halo, heteroaryl, heterocycloalkyl, —ORc, N(Rb)SO$_2$Re, —N(Rk)$_2$, $C_3$-$C_7$ cycloalkyl, phenyl, and phenolyl;
each Rb is independently selected from the group consisting of: H, $C_1$-$C_6$ alkyl, $C_1$-$C_6$ alkyl substituted with one —ORc group;
each Rc is independently selected from the group consisting of: H, $C_1$-$C_6$ alkyl, heterocycloalkyl, and aryl;
each Re is independently selected from the group consisting of: $C_1$-$C_6$ alkyl, phenyl, and phenyl substituted with one $C_1$-$C_6$ alkyl group;
each Rh is independently selected from the group consisting of: H, $C_1$-$C_6$ alkyl, and $C_1$-$C_6$ haloalkyl; and
each Rk is independently selected from the group consisting of H, $C_1$-$C_6$ alkyl; or a pharmaceutically-acceptable salt thereof.

9. The compound according to claim 8 wherein each Ra is independently selected from the group consisting of: H, optionally substituted $C_1$-$C_3$ alkyl, and phenyl, where said $C_1$-$C_3$ alkyl is optionally substituted with one to three substituents selected from the group consisting of: halo and phenyl;
each Rb is independently selected from the group consisting of: H and $C_1$-$C_3$ alkyl;
each Rc is independently selected from the group consisting of: H, $C_1$-$C_6$ alkyl, and aryl; and
each Re is independently selected from the group consisting of: $C_1$-$C_6$ alkyl and phenyl; or a pharmaceutically-acceptable salt thereof.

10. The compound according to claim 9 wherein R5 is —NRaRb or a pharmaceutically acceptable salt thereof.

11. The compound according to claim 10 wherein Z is optionally substituted phenyl, or a pharmaceutically acceptable salt thereof.

12. The compound according to claim 11 wherein Z is phenyl, or a pharmaceutically acceptable salt thereof.

13. The compound according to claim 10 wherein Z is optionally substituted heteroaryl, or a pharmaceutically acceptable salt thereof.

14. The compound according to claim 13 wherein Z is optionally substituted thienyl, or a pharmaceutically acceptable salt thereof.

15. The compound according to claim 9 wherein R5 is optionally substituted heterocycloalkyl or a pharmaceutically acceptable salt thereof.

16. The compound according to claim 15 wherein Z is optionally substituted phenyl, or a pharmaceutically acceptable salt thereof.

17. The compound according to claim 16 wherein Z is phenyl, or a pharmaceutically acceptable salt thereof.

18. The compound according to claim 15 wherein Z is optionally substituted heteroaryl, or a pharmaceutically acceptable salt thereof.

19. The compound according to claim 18 wherein Z is optionally substituted thienyl, or a pharmaceutically acceptable salt thereof.

20. The compound according to claim 9 wherein R5 is optionally substituted heteroaryl or a pharmaceutically acceptable salt thereof.

21. The compound according to claim 20 wherein Z is optionally substituted phenyl, or a pharmaceutically acceptable salt thereof.

22. The compound according to claim 21 wherein Z is phenyl, or a pharmaceutically acceptable salt thereof.

23. The compound according to claim 20 wherein Z is optionally substituted heteroaryl, or a pharmaceutically acceptable salt thereof.

24. The compound according to claim 23 wherein Z is optionally substituted thienyl, or a pharmaceutically acceptable salt thereof.

25. The compound according to claim 24 wherein R5 is —ORj;
each Ri is independently selected from the group consisting of: $C_1$-$C_3$ alkyl and phenyl;
Rj is selected from the group consisting of H, optionally substituted $C_1$-$C_6$ alkyl, $C_1$-$C_6$ haloalkyl, heteroaryl, and optionally substituted phenyl,
where said optionally substituted $C_1$-$C_6$ alkyl is optionally substituted by one or two substituents each independently selected from the following: hydroxy, $C_1$-$C_6$ alkoxy, —OCH$_2$CH$_2$N(CH$_3$)$_2$, methylthio, $C_3$-$C_6$ cycloalkyl, $C_3$-$C_6$ cycloalkyl substituted by one $C_1$-$C_3$ alkyl group; heterocycloalkyl, heterocycloalkyl substituted by one $C_1$-$C_3$ alkyl, one oxo group, or one 4-fluorobenzyl group; —NRkRk, heteroaryl, —NHC(O)CH$_3$, and —S(O)$_2$Ri;
where said phenyl is optionally substituted by one to three substituents each independently selected from the following: $C_1$-$C_3$ alkoxy, —NHC(O)CH$_3$, —C(O)NH$_2$, halo, CF$_3$, —S(O)$_2$Ri, —S(O)$_2$NHRi, hydroxy, —$C_1$-$C_3$-alkyl-NRkRk, —NRkRk, $C_1$-$C_3$ alkyl, heterocycloalkyl, and heterocycloalkyl substituted with one —C(O)CH$_3$ group; and each Rk is independently selected from H, $C_1$-$C_6$ alkyl, $C_1$-$C_6$ alkyl substituted by one or two hydroxyl groups; phenyl, and phenyl substituted with one $C_1$-$C_3$ alkyl group;

or a pharmaceutically-acceptable salt thereof.

26. The compound according to claim 25 wherein Z is optionally substituted phenyl, or a pharmaceutically acceptable salt thereof.

27. The compound according to claim 26 wherein Z is phenyl, or a pharmaceutically acceptable salt thereof.

28. The compound according to claim 25 wherein Z is optionally substituted heteroaryl, or a pharmaceutically acceptable salt thereof.

29. The compound according to claim 28 wherein Z is optionally substituted thienyl, or a pharmaceutically acceptable salt thereof.

30. The compound according to claim 1 which is:

3-(1-{[3-(dimethylamino)propyl]sulfonyl}-4-piperidinyl)-5-(2-thienyl)-1H-indole-7-carboxamide;

3-(1-{[3-(1-pyrrolidinyl)propyl]sulfonyl}-4-piperidinyl)-5-(2-thienyl)-1H-indole-7-carboxamide;

3-(1-{[3-(2-methyl-1-pyrrolidinyl)propyl]sulfonyl}-4-piperidinyl)-5-(2-thienyl)-1H-indole-7-carboxamide;

3-(1-{[3-(cyclopentylamino)propyl]sulfonyl}-4-piperidinyl)-5-(2-thienyl)-1H-indole-7-carboxamide;

3-(1-{[3-(4-hydroxy-1-piperidinyl)propyl]sulfonyl}-4-piperidinyl)-5-(2-thienyl)-1H-indole-7-carboxamide;

3-(1-{[2-(cyclopentylamino)ethyl]sulfonyl}-4-piperidinyl)-5-(2-thienyl)-1H-indole-7-carboxamide;

5-(5-chloro-2-thienyl)-3-(1-{[3-(1-pyrrolidinyl)propyl]sulfonyl}-4-piperidinyl)-1H-indole-7-carboxamide;

5-[5-(hydroxymethyl)-2-thienyl]-3-(1-{[3-(1-pyrrolidinyl)propyl]sulfonyl}-4-piperidinyl)-1H-indole-7-carboxamide;

5-[5-(1-pyrrolidinylmethyl)-2-thienyl]-3-(1-{[3-(1-pyrrolidinyl)propyl]sulfonyl}-4-piperidinyl)-1H-indole-7-carboxamide;

3-(1-{[3-(4-methyl-1-piperazinyl)propyl]sulfonyl}-4-piperidinyl)-5-(2-thienyl)-1H-indole-7-carboxamide;

3-(1-{[3-(4-morpholinyl)propyl]sulfonyl}-4-piperidinyl)-5-(2-thienyl)-1H-indole-7-carboxamide;

3-(1-{[3-(methyloxy)propyl]sulfonyl}-4-piperidinyl)-5-(2-thienyl)-1H-indole-7-carboxamide; or 3-(1-{[3-(ethyloxy)propyl]sulfonyl}-4-piperidinyl)-5-(2-thienyl)-1H-indole-7-carboxamide; or a pharmaceutically acceptable salt thereof.

31. The compound according to claim 1 which is:

3-(1-{[2-(dimethylamino)ethyl]sulfonyl}-4-piperidinyl)-5-(3-thienyl)-1H-indole-7-carboxamide;

3-(1-{[2-(cyclopentylamino)ethyl]sulfonyl}-4-piperidinyl)-5-(3-thienyl)-1H-indole-7-carboxamide;

3-(1-{[2-(4-hydroxy-1-piperidinyl)ethyl]sulfonyl}-4-piperidinyl)-5-(3-thienyl)-1H-indole-7-carboxamide;

3-(1-{[3-(4-methyl-1-piperazinyl)propyl]sulfonyl}-4-piperidinyl)-5-(3-thienyl)-1H-indole-7-carboxamide;

3-(1-{[3-(4-morpholinyl)propyl]sulfonyl}-4-piperidinyl)-5-(3-thienyl)-1H-indole-7-carboxamide; or 3-(1-{[3-(methyloxy)propyl]sulfonyl}-4-piperidinyl)-5-(3-thienyl)-1H-indole-7-carboxamide; or a pharmaceutically acceptable salt thereof.

32. A pharmaceutical composition comprising a compound according to claim 1, or a pharmaceutically acceptable salt thereof, and a pharmaceutically acceptable excipient.

* * * * *